(12) United States Patent
Porszasz-Reisz

(10) Patent No.: US 9,084,814 B2
(45) Date of Patent: Jul. 21, 2015

(54) CONDITIONAL MST OVEREXPRESSING CONSTRUCT AND CONDITIONAL MYOSTATIN OVEREXPRESSING TRANSGENIC MOUSE

(75) Inventor: Suzanne Porszasz-Reisz, Lakewood, CA (US)

(73) Assignee: CHARLES R. DREW UNIVERSITY OF MEDICINE AND SCIENCE, Los Angeles, CA (US)

( * ) Notice: Subject to any disclaimer, the term of this patent is extended or adjusted under 35 U.S.C. 154(b) by 352 days.

(21) Appl. No.: 13/542,741

(22) Filed: Jul. 6, 2012

(65) Prior Publication Data

US 2013/0219527 A1    Aug. 22, 2013

Related U.S. Application Data

(62) Division of application No. 12/398,994, filed on Mar. 5, 2009, now Pat. No. 8,222,478.

(60) Provisional application No. 61/034,083, filed on Mar. 5, 2008.

(51) Int. Cl.

| | |
|---|---|
| *G01N 33/00* | (2006.01) |
| *A61K 49/00* | (2006.01) |
| *C12N 15/85* | (2006.01) |
| *G01N 33/50* | (2006.01) |
| *G01N 33/68* | (2006.01) |
| *A01K 67/027* | (2006.01) |

(52) U.S. Cl.
CPC ........... *A61K 49/008* (2013.01); *A01K 67/0275* (2013.01); *C12N 15/8509* (2013.01); *G01N 33/5023* (2013.01); *G01N 33/5088* (2013.01); *G01N 33/6887* (2013.01); *A01K 2217/15* (2013.01); *A01K 2217/203* (2013.01); *A01K 2267/03* (2013.01); *G01N 2800/10* (2013.01)

(58) Field of Classification Search
None
See application file for complete search history.

(56) References Cited

PUBLICATIONS

BD Biosciences Tet-Off and Tet-On gene expression systems user manual. Cat. No. 630921, 630922 Published: Feb. 3, 2004.
Clontech: Tet-Off and Tet-On gene expression systems user manual. Cat. No. PT30001-1 Publisshed Jun. 25, 1999.
Fiers, et al., "Complete nucleotide sequence of SV40 DNA", Nature, 273(5658): 113-120, (1978).
Larochelle, et al., "Efficient muscle-specific transgene expression after adenovirus-mediated gene transfer in mice using a 1.35kb muscle creatine kinase promoter/enhancer", Gene Ther., 4: 465-472, (1997).
Lourenco, et al., "A cell-based bicistronic lentiviral reporter system for identification of inhibitors of the hepatitis C virus internal ribosome entry site", J. Virol. Methods, 158(1-2): 152-159, (2009).
McPherron, et al., Regulation of skeletal muscle mass in mice by a new TGF-β superfamily member, Nature, 387(6628): 83-90, (1997).

(Continued)

*Primary Examiner* — Valarie Bertoglio
(74) *Attorney, Agent, or Firm* — Arnold & Porter LLP

(57) ABSTRACT

Provided herein are novel nucleic acid sequences, vectors comprising such nucleic acid sequences, host cells comprising such vectors, and transgenic animals comprising such nucleic acid sequences, and related molecules and methods relating thereto. Such novel nucleic acid sequences, vectors comprising such nucleic acid sequences, host cells comprising such vectors, and transgenic animals comprising such nucleic acid sequences, and related molecules and methods provide conditional overexpression of genes, such as myostatin, and transgenic animals conditionally overexpression genes, such as myostatin.

6 Claims, 108 Drawing Sheets

(56) References Cited

PUBLICATIONS

Figures 1, 1A:
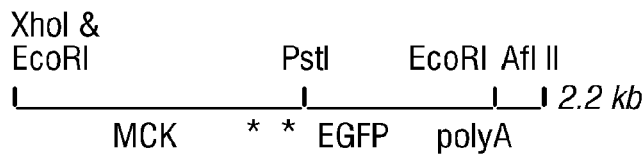

Mulligan, et al., "Expression of a bacteria gene in mammalian cells", Science, 209(4463): 1422-1427, (1980).

Pavlakis, et al., "Expresion of two human growth hormone genes in monkey cells infected by simian virus 40 recombinants", PNAS, 78(12): 7398-7402, (1981).

Shield, et al., "E-box sites and a proximal regulatory region of the muscle creatine kinase gene differentially regulate expression in diverse skeletal muscles and cardiac muscle of transgenic mice", Mol. Cell Biol., 16: 5058-5068, (1996).

Zimmers, et al., "Induction of cachexia in mice by systemically administered myostatin", Science, 296: 1486-1488, (2002).

Reisz-Porszasz, et al., "Lower skeletal muscle mass in male transgenic mice with muscle-specific overexpression of myostatin", Am J Physiol. Endocrinol . Metab., 285: pp. E876-E888, (2003).

Artaza, et al., "Alterations in myostatin expression are accoaited with changes in cardiac left ventricular mass but not ejection fraction in the mouse", Journal of Endocrinology, 194: 63-76, (2007).

Sigmund, "Viewpoint: Are studies in genetically altered mice out of control?", Arterioscler. Thromb. Vasc. Biol. 20: pp. 1425-1429, (2000).

Moens et al. 1993, Development 119: 485-499.

Lee, et al., "Regulation of muscle mass by myostatin", Annual Review of Cell and Developmental Biology, 20: pp. 61-86, (2004).

Petridou et al. 2003, Transgenic Research 12: 693-706.

*Myostatin transgenic mice*

- *Mst overexpressing construct*

- *Conditional Mst overexpressing construct*

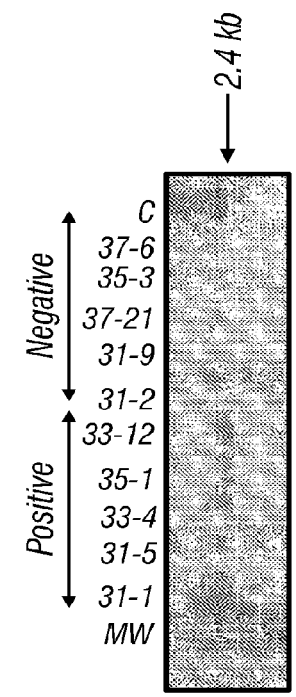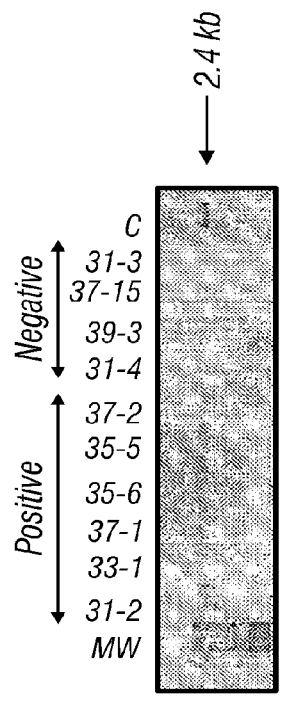
FIG. 3A    FIG. 3B
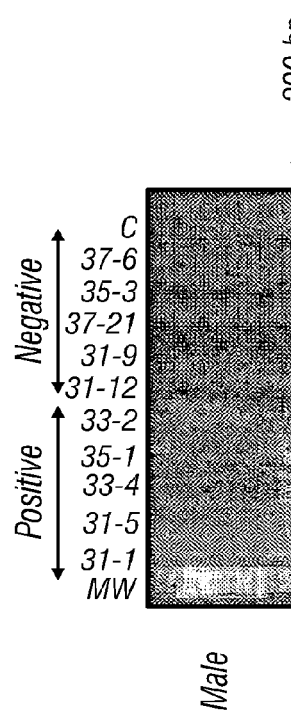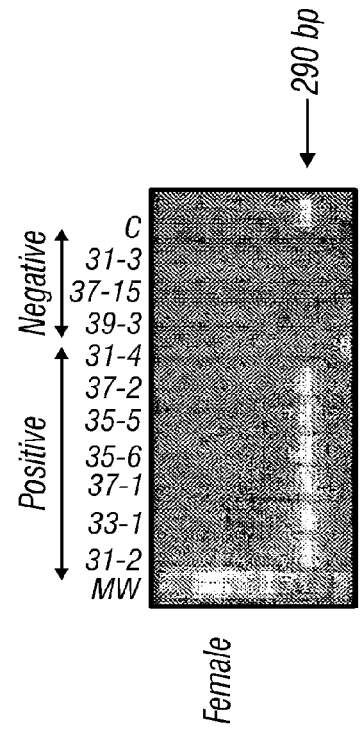

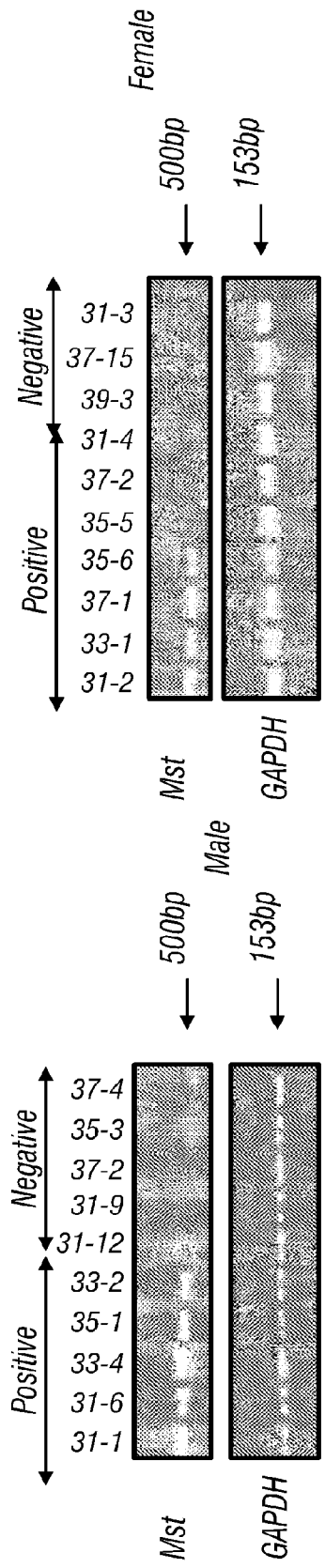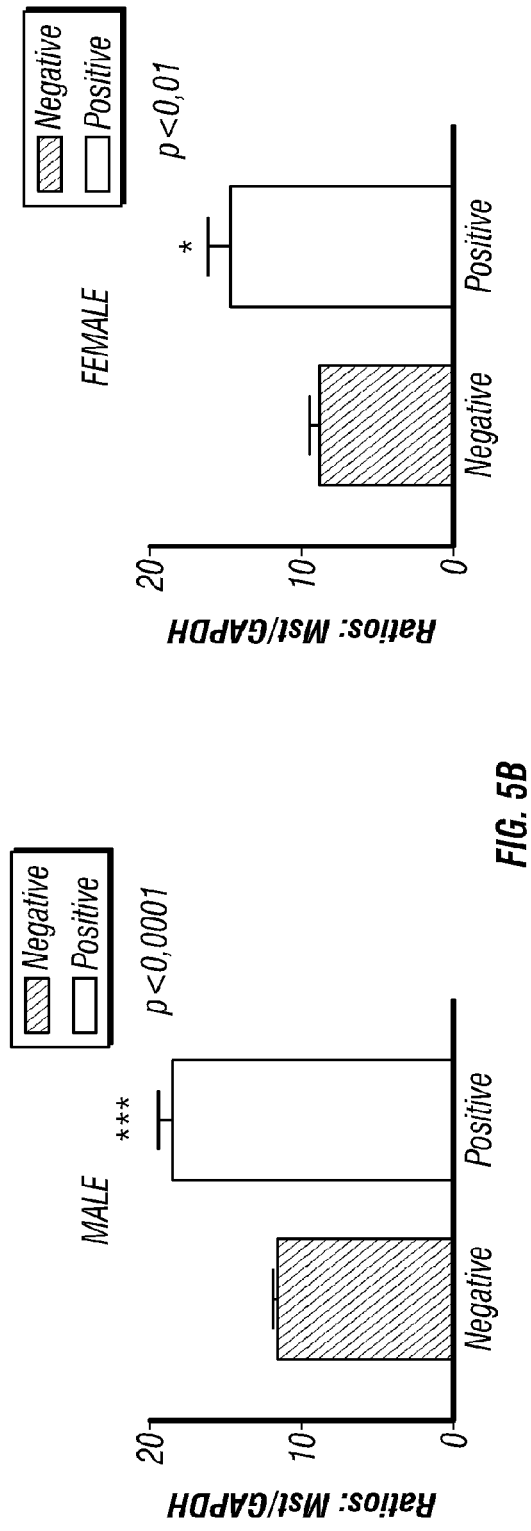
FIG. 5A
FIG. 5B

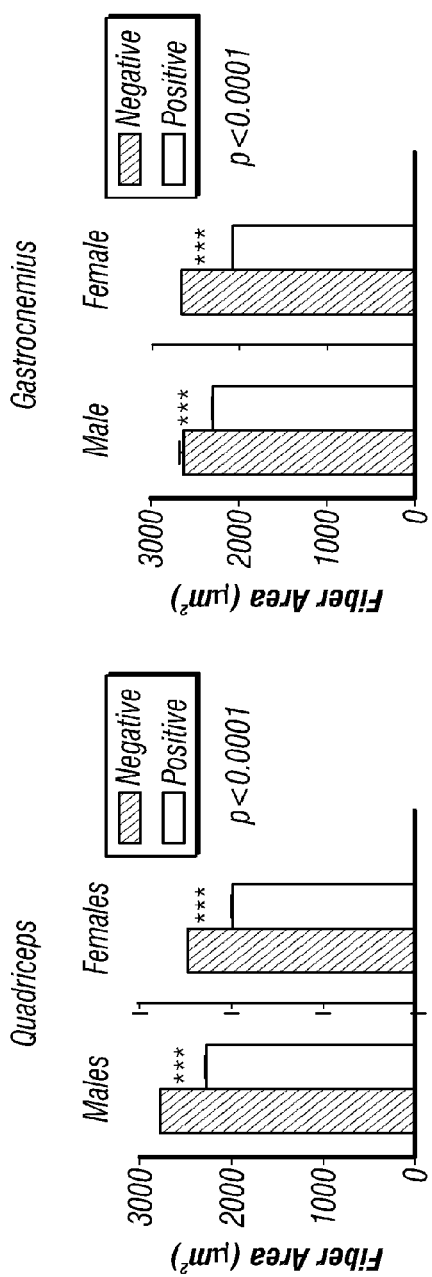
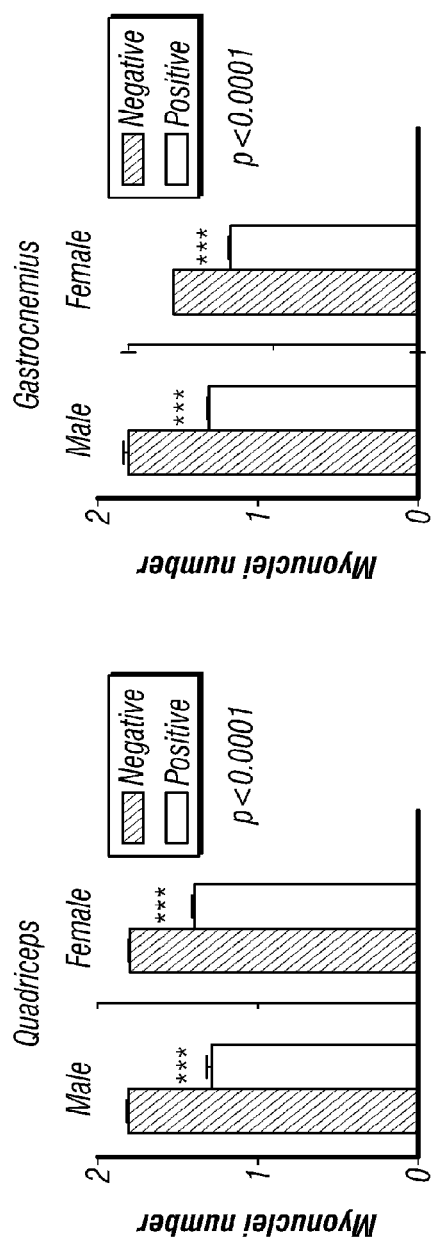
FIG. 7A
FIG. 7B

CMOT transgene

```
cttaagatacattgatgagtttggacaaaccacaactagaatgcagtgaaaaaaatgctttatttgtgaaatttgtg
atgctattgctttatttgtaaccattataagctgcaataaacaagttaacaacaacaattgcattcattttatgttt
caggttcaggggggaggtgtgggaggttttttaaagcaagtaaaacctctacaaatgtggtatggctgattatgatct
agagtcgcggccgctttacttgtacagctcgtccatgccgagagtgatcccggcggcggtcacgaactccagcagga
ccatgtgatcgcgcttctcgttgggtctttgctcagggcggactgggtgctcaggtagtggttgtcgggcagcagc
acggggccgtcgccgatggggtgttctgctggtagtggtcggcgagctgcacgctgccgtcctcgatgttgtggcg
gatcttgaagttcaccttgatgccgttcttctgcttgtcggccatgatatagacgttgtggctgttgtagttgtact
ccagcttgtgcccaggatgttgccgtcctccttgaagtcgatgcccttcagctcgatgcggttcaccaggtgtcg
ccctcgaacttcacctcggcgcgggtcttgtagttgccgtcgtccttgaagaagatggtgcgctcctggacgtagcc
ttcgggcatggcggacttgaagaagtcgtgctgcttcatgtggtcggggtagcggctgaagcactgcacgccgtagg
tcaggtggtcacgagggtgggccagggcacgggcagcttgccggtggtgcagatgaacttcagggtcagcttgccg
taggtggcatcgccctcgccctcgccggacacgctgaacttgtggccgtttacgtcgccgtccagctcgaccaggat
gggcaccacccggtgaacagctcctcgcccttgctcaccatggttgtggccatattatcatcgtgttttttcaaagg
aaaaccacgtcccgtggttcgggggggcctagacgttttttttaacctcgactaaacacatgtaaagcatgtgcaccg
aggccccagatcagatcccatacaatgggtaccttctgggcatccttcagccccttgttgaatacgcttgaggaga
gccatttgactcttccacaactatccaactcacaacgtggcactggggttgtgccgccttgcaggtgtatcttat
acacgtggcttttggccgcagaggcacctgtcgccaggtggggggttccgctgcctgcaaaggtcgctacagacgt
tgtttgtcttcaagaagcttccagaggaactgcttccttcacgacattcaacagaccttgcattcctttggcgagag
gggaaagaccccctaggaatgctcgtcaagaagacagggccaggtttccgggccctcacattgccaaaagacggcaat
atggtggaaaataacatatagacaaacgcacaccggccttattccaagcggcttcggccagtaacgttaggggggg
ggagggagaggggcggatcccgggcccgcggtaccgtcgactgcagaattcactagtgattaaattatattgtcgac
tcatgagcacccacagcggtctactaccatggctggaattttcccatatattatttgttctttgccattaaaatata
gcatattaatgggagacatttttgtcggagtgcagcaagggcctgctgagcctctgggtttgcttggtgcacaaga
tgagtatgcggatatttttgtaaaaacacaaattcacactctcctgagcagtaattggccttatatctttgggtgc
gataatccagtcccatccaaaggcttcaaaatcgaccgtgaggggtagcggcagcaccgggattccgtggagtgct
catcgcagtcaagcccaaagtctctccgggacctcttgggtgtgtctgtcaccttgacttctaaaaagggattcagc
ccatcttctcctggtcctgggaaggttacagcaagatcatggccattctcatccaaagctttgatttcaatgcctaa
gttggattcaggctgtttgagccaattttgcaacactgtcttcacatcaatactctgccaaataccagtgcctgggc
tcatgtcaagtttcagagatcggattccagtataccttgtaccgtctttcatgggtttgatgagtctcaggatttgc
acaaacactgttgtaggagtcttgacgggtctgagatatatccacagttgggcttttactactttgttgtactgtat
tttagagctaaatttaaaaaagcaacatttgggcttgccatccgcttgcattagaaagtcagactctgtaggcatgg
taatgattgtttccgtggtagcgtgataatcgtcatcttccaaagagccatcactgctgtcatccctctggacgtcg
tactgatcgatcagttcccggagtggaggcgctcttggcagaagttgtcttatagcatctttgctgatgttaggagc
tgtttccaggcgcagcttactgaggatttgaattttatggcttctattctggagtacctcgtgttttgtctccacg
cacatgcattacacagcccctcttttccacatttcttctctctcactgccctcatttagatccactgggccagca
gcaatcagcatgaacaggtaaatataaacatacatttgcagttttgcatcatggctggatccgggcccataagagc
gtaatctggaacatcgtatgggtacatggtgtctagctcgcgtcagctgactagaggatccccgggtaccgagctcg
aattcggggccgcggaggctggatcggtcccggtgtcttctatggaggtcaaaacagcgtggatggcgtctccaggc
gatctgacggttcactaaacgagctctgcttatataggcctccaccgtacacgcctactcgaccgggtaccgagc
tcgactttcacttttctctatcactgataggagtggtaaactcgactttcacttttctctatcactgataggagt
ggtaaactcgactttcacttttctctatcactgataggagtggtaaactcgactttcacttttctctatcactgat
agggagtggtaaactcgactttcacttttctctatcactgataggagtggtaaactcgactttcacttttctctat
cactgataggagtggtaaactcgactttcacttttctctatcactgataggagtggtaaactcgactttcacttt
tctctatcactgataggagtggtaaactcgagatctcgagctcaagcttcgaattatcgaattcctgcagcccgat
```

FIG. 18

```
ctcagctgaggtgcaaaaggctcctgtcatattgtgtcctgctctggtctgccttccacagcttgggggccacctag
cccacctctccctagggatgagagcagccactacgggtctaggctgcccatgtaaggaggcaaggcctggggacacc
cgagatgcctggttataattaacccagacatgtggctgcccccccccccccaacacctgctgcctgagcctcacccc
cacccggtgcctggtcttaggctctgtacaccatggaggagaagctcgctctaaaaataaccctgtccctggtgg
atccagggtgaggggcaggctgagggcggccacttccctcagccgcaggtttgttttcccaagaatggttttttctgc
ttctgtagcttttcctgtcaattctgccatggtggagcagcctgcactgggcttctgggagaaaccaaaccgggttc
taaccttttcagctacagttattgcctttcctgtagatgggcgactacagccccaccccaccccgtctcctgtatc
cttcctgggcctggggatcctaggcttcactggaaatttccccccaggtgctgtaggctagagtcacggctcccaa
gaacagtgcttgcctggcatgcatggttctgaacctccaactgcaaaaaatgacacataccttgaccttggaaggc
tgaggcaggggattgccatgagtgcaaagccagactgggtggcatagttagaccctgtctcaaaaaaccaaaaaca
attaaataactaaagtcaggcaagtaatcctactcgggagactgaggcagagggattgttacatgtctgaggccagc
ctggactacatagggtttcaggctagccctgtctacagagtaaggccctatttcaaaaacacaaacaaaatggttct
cccagctgctaatgctcaccaggcatgaagcctggtgagcattagcaatgaaggcaatgaaggagggtgctggctac
aatcaaggctgtgggggactgagggcaggctgtaacaggcttgggggccagggcttatacgtgcctgggactcccaa
agtattactgttccatgttcccggcgaagggccagctgtccccgccagctagactcagcacttagtttaggaacca
gtgagcaagtcagcccttgggcagcccatacaaggccatgggggctgggcaagctgcacgcctgggtccgggtggg
cacggtgcccgggcaacgagctgaaagctcatctgctctcaggggcccctccctggggacagcccctcctggctagt
cacacctgtaggctcctctatataacccaggggcacaggggctgcccccaagctggccgctctagaggatccccgg
gactagaattcaccatgtctagattagataaaagtaaagtgattaacagcgcattagagctgcttaatgaggtcgga
atcgaaggtttaacaacccgtaaactcgcccagaagcttggtgtagagcagcctacactgtattggcatgtaaaaaa
taagcgggctttgctcgacgccttagccattgagatgttagataggcaccatactcacttttgcccttaaaagggg
aaagctggcaagatttttacgcaataacgctaaaagttttagatgtgctttactaagtcatcgcaatggagcaaaa
gtacattcagatacacggcctacagaaaaacagtatgaaactctcgaaaatcaattagccttttatgccaacaagg
ttttttcactagagaacgcgttatatgcactcagcgctgtggggcatttttactttaggttgcgtattggaagatcaag
agcatcaagtcgctaaagaagaaagggaaacacctactactgatagtatgccgccattattacgacaagctatcgaa
ttatttgatcaccaaggtgcagagccagccttcttattcggccttgaattgatcatatgcggattagaaaaacaact
taaatgtgaaagtgggtccgcgtacagccgcgcgcgtacgaaaaacaattacgggtctaccatcgagggcctgctcg
atctcccggacgacgacgcccccgaagaggcggggctggcggctccgcgcctgtcctttctccccgcgggacacacg
cgcagactgtcgacggcccccccgaccgatgtcagcctgggggacgagctccacttagacggcgaggacgtggcgat
ggcgcatgccgacgcgctagacgatttcgatctggacatgttgggggacggggattccccgggtccgggatttaccc
cccacgactccgcccctacggcgctctggatatggccgacttcgagtttgagcagatgtttaccgatgcccttgga
attgacgagtacggtgggatggatccccgggtaccggtcgccaccatggtgagcaagggcgaggagctgttcaccgg
ggtggtgcccatcctggtcgagctggacggcgacgtaaacggccacaagttcagcgtgtccggcgagggcgagggcg
atgccacctacggcaagctgaccctgaagttcatctgcaccaccggcaagctgcccgtgccctggcccaccctcgtg
accaccctgacctggggcgtgcagtgcttcagccgctaccccgaccacatgaagcagcacgacttcttcaagtccgc
catgcccgaaggctacgtccaggagcgcaccatcttcttcaaggacgacggcaactacaagacccgcgccgaggtga
agttcgagggcgacaccctggtgaaccgcatcgagctgaagggcatcgacttcaaggaggacggcaacatcctgggg
cacaagctggagtacaactacatcagccacaacgtctatatcaccgccgacaagcagaagaacggcatcaaggccaa
cttcaagatccgccacaacatcgaggacggcagcgtgcagctcgccgaccactaccagcagaacacccccatcggcg
acggccccgtgctgctgcccgacaaccactacctgagcacccagtccgccctgagcaaagaccccaacgagaagcgc
gatcacatggtcctgctggagttcgtgaccgccgccgggatcactctcggcatggacgagctgtacaagtaaagcgg
ccgcgactctagatcataatcagccataccacatttgtagaggttttacttgctttaaaaaacctcccacacctccc
cctgaacctgaaacataaaatgaatgcaattgttgttgttaacttgtttattgcagcttataatggttacaaataaa
gcaatagcatcacaaatttcacaaataaagcatttttttcactgcattctagttgtggtttgtccaaactcatcaat
gtatcttaag
```

CMOT=pFin plasmid sequence
(pMCK/Tet-ON-BFP//TRE/HA-Mst/IRES-EGFP)

Bicistronic bridge:

```
ctcgactttc actttctct atcactgata gggagtggta aactcgagat ctcgagctca agcttcgaat
tatcgaattc ctgcagcccg atctcagctg aggtgcaaaa ggctcctgtc atattgtgtc ctgctctggt
ctgccttcca cagcttgggg gccacctagc ccacctctcc ctagggatga gagcagccac tacgggtcta
ggctgcccat gtaaggaggc aaggcctggg gacacccgag atgcctggtt ataattaacc cagacatgtg
gctgccccc ccccccaac acctgctgcc tgagcctcac ccccaccccg gtgcctgggt cttaggctct
gtacaccatg gaggagaagc tcgctctaaa aataaccctg tccctggtgg atccagggtg aggggcaggc
tgagggcggc cacttccctc agccgcaggt ttgttttccc aagaatggtt tttctgcttc tgtagcttt
cctgtcaatt ctgccatggt ggagcagcct gcactgggct tctgggagaa accaaaccgg gttctaacct
ttcagctaca gttattgcct ttcctgtaga tgggcgacta cagccccacc cccaccccg tctcctgtat
ccttcctggg cctggggatc ctaggctttc actggaaatt tcccccagg tgctgtaggc tagagtcacg
gctcccaaga acagtgcttg cctggcatgc atggttctga acctccaact gcaaaaaatg acacatacct
tgaccttgg aaggctgagg caggggatt gccatgagtg caaagccaga ctggtggca tagttagacc
ctgtctcaaa aaaccaaaaa caattaaata actaaagtca ggcaagtaat cctactcggg agactgaggc
agagggattg ttacatgtct gaggccagcc tggactacat agggtttcag gctagccctg tctacagagt
aaggccctat ttcaaaaaca caaacaaaat ggttctccca gctgctaatg ctcaccaggc atgaagcctg
gtgagcatta gcaatgaagg caatgaagga gggtgctggc tacaatcaag gctgtggggg actgagggca
ggctgtaaca ggcttggggg ccagggctta tacgtgcctg ggactcccaa agtattactg ttccatgttc
ccggcgaagg gccagctgtc ccccgccagc tagactcagc acttagttta ggaaccagtg agcaagtcag
cccttgggc agcccataca aggccatggg gctgggcaag ctgcacgcct gggtccgggg tgggcacggt
gcccggcaa cgagctgaaa gctcatctgc tctcagggc ccctccctgg ggacagcccc tcctggctag
tcacaccctg taggctcctc tatataaccc aggggcacag gggctgcccc caagctggcc gctctagagg
atccccggga ctagaattca ccatgtctag attagataaa agtaaagtga ttaacagcgc attagagctg
cttaatgagg tcggaatcga aggtttaaca acccgtaaac tcgcccagaa gcttggtgta gagcagccta
cactgtattg gcatgtaaaa aataagcggg ctttgctcga cgccttagcc attgagatgt tagataggca
ccatactcac ttttgccctt taaaagggga aagctggcaa gattttttac gcaataacgc taaaagtttt
agatgtgctt tactaagtca tcgcaatgga gcaaagtac attcagatac acggcctaca gaaaaacagt
atgaaactct cgaaaatcaa ttagcctttt tatgccaaca aggttttca ctagagaacg cgttatatgc
actcagcgct gtgggcatt ttactttagg ttgcgtattg gaagatcaag agcatcaagt cgctaaagaa
gaaagggaaa cacctactac tgatagtatg ccgccattat tacgacaagc tatcgaatta tttgatcacc
aaggtgcaga gccagccttc ttattcggcc ttgaattgat catatgcgga ttagaaaaac aacttaaatg
tgaaagtggg tccgcgtaca gccgcgcgcg tacgaaaaac aattacgggt ctaccatcga gggcctgctc
gatctcccgg acgacgacgc ccccgaagag gcgggctgg cggctccgcg cctgtccttt ctccccgcgg
gacacacgcg cagactgtcg acggcccccc cgaccgatgt cagcctgggg gacgagctcc acttagacgg
cgaggacgtg gcgatggcgc atgccgacgc gctagacgat ttcgatctgg acatgttggg ggacggggat
tccccgggtc cggatttac cccccacgac tccgcccct acggcgctct ggatatggcc gacttcgagt
ttgagcagat gtttaccgat gcccttggaa ttgacgagta cggtgggatg gatccccggg taccggtcgc
caccatggtg agcaagggcg aggagctgtt caccggggtg gtgcccatcc tggtcgagct ggacggcgac
gtaaacggcc acaagttcag cgtgtccggc gagggcgagg gcgatgccac ctacgcaag ctgaccctga
agttcatctg caccaccggc aagctgcccg tgccctggcc caccctcgtg accaccctga cctgggcgt
gcagtgcttc agccgctacc ccgaccacat gaagcagcac gacttcttca gtccgccat gcccgaaggc
tacgtccagg agcgcaccat cttcttcaag gacgacggca actacaagac ccgcgccgag gtgaagttcg
agggcgacac cctggtgaac cgcatcgagc tgaagggcat cgacttcaag gaggacggca acatcctggg
gcacaagctg gagtacaact acatcagcca caacgtctat atcaccgccg acaagcagaa gaacggcatc
aaggccaact tcaagatccg ccacaacatc gaggacggca gcgtgcagct cgccgaccac taccagcaga
acacccccat cggcgacggc cccgtgctgc tgcccgacaa ccactacctg agcacccagt ccgccctgag
```

*FIG. 19* caaagacccc aacgagaagc gcgatcacat ggtcctgctg gagttcgtga ccgccgccgg gatcactctc
ggcatggacg agctgtacaa g<u>taa</u>agcggc cgcagacatg ataag Tet-on polyA. a gcttcttaag
gcgtaaattg taagcgttaa tattttgtta aaattcgcgt taaattttg ttaaatcagc tcattttta
accaataggc cgaaatcggc aaaatccctt ataaatcaaa agaatägacc
gagatatggtcgatcggagtgctcacttgacccactctgcttatatagacctcccaccgtacacgcctacccgccat
ttgcgtcaatgggcggagttgttatgacattttggaaagtcccgttgattttggtgccaaaacaaactcccattga
cgtcaatggcgcgggggtcgttgggcggtcagccaggcgggccatttaccgtaagttatgtaacgcggaactccatat
atgggctatgaactaatgaccccgtaattgattactattaataacta
atgcatggcggtaatacggttatccacagaatcaggggataacgcaggaaagaacatgtgagcaaaaggccagcaaa
aggccaggaaccgtaaaaaggccgcgttgctggcgttttccataggctccgcccccctgacgagcatcacaaaaat
cgacgctcaagtcagaggtggcgaaacccgacaggactataaagataccaggcgtttccccctggaagctccctcgt
gcgctctcctgttccgaccctgccgcttaccggatacctgtccgcctttctcccttcgggaagcgtggcgctttctc
atagctcacgctgtaggtatctcagttcggtgtaggtcgttcgctccaagctgggctgtgtgcacgaaccccccgtt
cagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaact
acggctacactagaaggacagtatttggtatctgcgctctgctgaagccagttaccttcggaaaaagagttggtagc
tcttgatccggcaaacaaaccaccgctggtagcggtggtttttttgtttgcaagcagcagattacgcgcagaaaaaa
aggatctcaagaagatcctttgatcttttctacggggtctgacgctcagtggaacgaaaactcacgttaagggattt
tggtcatgagattatcaaaaaggatcttcacctagatccttttaaattaaaaatgaagttttaaatcaatctaaagt
atatatgagtaaacttggtctgacagttaccaatgcttaatcagtgaggcacctatctcagcgatctgtctatttcg
ttcatccatagttgcctgactccccgtcgtgtagataactacgatacgggagggcttaccatctggccccagtgctg
caatgataccgcgagacccacgctcaccggctccagatttatcagcaataaaccagccagccggaagggccgagcgc
agaagtggtcctgcaactttatccgcctccatccagtctattaattgttgccgggaagctagagtaagtagttcgcc
agttaatagtttgcgcaacgttgttgccattgctacaggcatcgtggtgtcacgctcgtcgtttggtatggcttcat
tcagctccggttcccaacgatcaaggcgagttacatgatcccccatgttgtgcaaaaaagcggttagctccttcggt
cctccgatcgttgtcagaagtaagttggccgcagtgttatcactcatggttatggcagcactgcataattctcttac
tgtcatgccatccgtaagatgcttttctgtgactggtgagtactcaaccaagtcattctgagaatagtgtatgcggc
gaccgagttgctcttgcccggcgtcaatacgggataataccgcgccacatagcagaactttaaaagtgctcatcatt
ggaaaacgttcttcggggcgaaaactctcaaggatcttaccgctgttgagatccagttcgatgtaacccactcgtgc
acccaactgatcttcagcatcttttactttcaccagcgtttctgggtgagcaaaaacaggaaggcaaaatgccgcaa
aaaagggaataagggcgacacggaaatgttgaatactcatactcttcctttttcaatattattgaagcatttatcag
ggttattgtctcatgagcggatacatatttgaatgtatttagaaaaataaacaaataggggttccgcgcacatttcc
ccgaaaagtgccacctgacgcgccctgtagcggcgcattaagcgcggcgggtgtggtggttacgcgcagcgtgaccg
ctacacttgccagcgccctagcgcccgctcctttcgctttcttcccttcctttctcgccacgttcgccggctttccc
cgtcaagctctaaatcgggggctccctttagggttccgatttagtgctttacggcacctcgaccccaaaaaacttga
ttagggtgatggttcacgtagtgggccatcgccctgatagacggtttttcgccctttgacgttggagtccacgttct
ttaatagtggactcttgttccaaactggaacaacactcaacctatctcggtctattcttttgatttataagggatt
ttgccgatttcggcctattggttaaaaaatgagctgatttaacaaaaatttaacgcgaattttaacaaaatattaac
gcttacaatttacgccttaagatacattgatgagtttggacaaaccacaactagaatgcagtgaaaaaaatgcttta
tttgtgaaatttgtgatgctattgctttatttgtaaccattataagctgcaataaacaagttaacaacaacaattgc
attcat

```
tttatgtttcaggttcagggggaggtgtgggaggtttttaaagcaagtaaaacctctacaaatgtggtatggctga
ttatgatctagagtcgcggccgctttacttgtacagctcgtccatgccgagagtgatcccggcggcggtcacgaact
ccagcaggaccatgtgatcgcgcttctcgttggggtctttgctcagggcggactgggtgctcaggtagtggttgtcg
ggcagcagcacggggccgtcgccgatgggggtgttctgctggtagtggtcggcgagctgcacgctgccgtcctcgat
gttgtggcggatcttgaagttcaccttgatgccgttcttctgcttgtcggccatgatatagacgttgtggctgttgt
agttgtactccagcttgtgccccaggatgttgccgtcctccttgaagtcgatgcccttcagctcgatgcggttcacc
agggtgtcgccctcgaacttcacctcggcgcgggtcttgtagttgccgtcgtccttgaagaagatggtgcgctcctg
gacgtagccttcgggcatggcggacttgaagaagtcgtgctgcttcatgtggtcggggtagcggctgaagcactgca
cgccgtaggtcagggtggtcacgagggtgggccagggcacgggcagcttgccggtggtgcagatgaacttcagggtc
agcttgccgtaggtggcatcgccctcgccctcgccggacacgctgaacttgtggccgtttacgtcgccgtccagctc
gaccaggatgggcaccaccccggtgaacagctcctcgcccttgctcaccatggttgtggccatattatcatcgtgtt
tttcaaaggaaaaccacgtccccgtggttcgggggcctagacgtttttttaacctcgactaaacacatgtaaagca
tgtgcaccgaggccccagatcagatcccatacaatggggtaccttctgggcatccttcagcccttgttgaatacgc
ttgaggagagccatttgactctttccacaactatccaactcacaacgtggcactgggttgtgccgcctttgcaggt
gtatcttatacacgtggcttttggccgcagaggcacctgtcgccaggtgggggttccgctgcctgcaaagggtcgc
tacagacgttgtttgtcttcaagaagcttccagaggaactgcttccttcacgacattcaacagaccttgcattcctt
tggcgagaggggaaagacccctaggaatgctcgtcaagaagacagggccaggtttccgggccctcacattgccaaaa
gacggcaatatggtggaaaataacatatagacaaacgcacaccggccttattccaagcggcttcggccagtaacgtt
agggggggggagggagaggggc
ggatcccgggcccgcggtaccgtcgactgcagaattcactagtgattaaattatattgtcgac
tcatgagcacccacagcggtctactaccatggctggaattttcccatatattatttgttctttgccattaaaatata
gcatattaatgggagacatttttgtcggagtgcagcaagggcctgctgagcctctgggttttgcttggtgcacaaga
tgagtatgcggatattttgtaaaaacacaaattcacactctcctgagcagtaattggcctttatatcttttgggtgc
gataatccagtcccatccaaaggcttcaaaatcgaccgtgaggggtagcggcagcaccgggattccgtggagtgct
catcgcagtcaagcccaaagtctctccgggacctcttgggtgtgtctgtcaccttgacttctaaaaagggattcagc
ccatcttctcctggtcctgggaaggttacagcaagatcatggccattctcatccaaagctttgatttcaatgcctaa
gttggattcaggctgtttgagccaattttgcaacactgtcttcacatcaatactctgccaaataccagtgcctgggc
tcatgtcaagtttcagagatcggattccagtataccttgtaccgtctttcatgggtttgatgagtctcaggatttgc
acaaacactgttgtaggagtcttgacgggtctgagatatatccacagttgggcttttactactttgttgtactgtat
tttagagctaaatttaaaaagcaacatttgggcttgccatccgcttgcattagaaagtcagactctgtaggcatgg
taatgattgtttccgtggtagcgtgataatcgtcatcttccaaagagccatcactgctgtcatccctctggacgtcg
tactgatcgatcagttcccggagtggaggcgctcttggcagaagttgtcttatagcatctttgctgatgttaggagc
tgtttccaggcgcagcttactgaggatttgaattttatggcttctattctggagtacctcgtgttttgtctccacg
cacatgcattacacagcccctcttttccacattttcttctctcactgccctcatttagatccactgggccagca
gcaatcagcatgaacaggtaaatataaacatacatttgcagttttgcatcatggctggatccgggcccat
aagagcgtaatctggaacatcgtatgggtacatggtgtctagctcgcgtcagctgactagaggatccccgggtaccg
agctcgaattcggggccgcggaggctggatcggtcccggtgtcttctatggaggtcaaaacagcgtggatggcgtct
ccaggcgatctgacggttcactaaacgagctctgcttatataggcctccaccgtacacgcctactcgacccgggta
ccgagctcgactttcacttttctctatcactgataggagtggtaaactcgactttcacttttctctatcactgata
gggagtggtaaactcgactttcacttttctctatcactgataggagtggtaaactcgactttcacttttctctatc
actgatagggagtggtaaactcgactttcacttttctctatcactgataggagtggtaaactcgactttcacttttt
ctctatcactgatagggagtggtaaactcgactttcacttttctctatcactgataggagtggtaaa
```

FIG. 19 (Cont'd)

CMOT plasmid

10273 base pairs

Graphic map | Table by enzyme name

```
                                       Eco88I BstYI Sau3AI Sfr274I BsoBI
                                       XhoI PaeR7I MboI BglII XhoI PaeR7I
  TthHB8I                 TspRI        Sfr274I DpnII MflI DpnI BcoI TaqI
ctcgactttcacttttctctatcactgatagggagtggtaaactcgagatctcgagctcaagcttcgaattatcg base pairs
gagctgaaagtgaaaagagatagtgactatccctcaccatttgagctctagagctcgagttcgaagcttaatagc 1 to 75
  TaqI                                    Ama87I TaqI NdeII XhoII Eco88I CviJI
                                          BcoI BsoBI BstX2I Kzo9I AvaI Ecl136II
                                          AvaI TthHB8I Bsp143I Ama87I TthHB8I EcoICRI Psp1241BI CviJI Bsp119I TaqI TspEI Fsp4HI NdeII BstDEI DdeI PspN4I
    SduI  Eco24I SstI TthHB8I NspV TthHB8I Tsp509I BbvI Sau3AI PvuII MnlI
   AluI Bbv12I Alw21I SfuI TaqI Sse9I AcsI SfcI PstI MboI DdeI NspBII NlaIV
aattcctgcagcccgatctcagctgaggtgcaaaaggctcctgtcatattgtgtcctgctctggtctgccttcca base pairs
ttaaggacgtcgggctagagtcgactccacgttttccgaggacagtataacacaggacgagaccagacggaaggt 76 to 150
   AspHI SacI BsiHKAI IspI Bpu14I Sse9I BstSFI CviJI Bsp143I MspA1I
     BmyI FriOI HindIII BstBI TspEI EcoRI BsoFI Bst71I DpnI CviJI CviJI
     Bsp1286I BanII AluI Csp45I Tsp509I ApoI ItaI DpnII Kzo9I AluI BstDEI BslI Cfr13I HaeIII     StyI EcoT14I ItaI                   BbvI  BsiYI
   AluI BsiYI AspS9I BsuRI    Eco130I BfaI BsoFI           CviJI   Hsp92II
  CviJI Esp1396I PalI BfaI  AvrII MaeI FokI CviJI       MaeI BsoFI  NlaIII
cagcttgggggccacctagcccacctctccctagggatgagagcagccactacgggtctaggctgcccatgtaag base pairs
gtcgaaccccggtggatcgggtggagagggatcccactctcgtcggtgatgcccagatccgacgggtacattc 151 to 225
   Bsc4I Van91I NlaIV MaeI MnlI BssT1I BstF5I  BbvI      BfaI Fsp4HI  Bsc4I
    AccB7I AsuI PspN4I CviJI  ErhI BsaJI   Fsp4HI          ItaI     BslI
   PflMI Sau96I CviJI         BlnI BseDI       Bst71I         Bst71I CviJI EcoRII MvaI BcoI SfaNI ScrFI TruII   Hsp92II Bst71I
       AatI BsuRI BstNI BsmFI EcoRII MvaI MseI AflIII CviJI
   MnlI Pme55I BsaJI MspR9I AvaI BstOI TspEI   BspLU11I BsoFI
gaggcaaggcctggggacacccgagatgcctggttataattaacccagacatgtggctgcccccccccccccaac base pairs
ctccgttccggaccctgtgggctctacggaccaatattaattgggtctgtacaccgacggggggggggggttg 226 to 300
        StuI Eco147I Bst2UI BsoBI MspR9I Tsp509I    BstXI Fsp4HI
        HaeIII BseDI ScrFI Eco88I Bst2UI Tru9I       NlaIII BbvI
        PalI SseBI BstOI Ama87I BstNI Sse9I          NspI ItaI BbvI           BsiYI MspI BshNI BseDI ScrFI SspBI Eco130I BstDSI
   BspMI MwoI MnlI  BseDI BcnI Eco64I BsaJI MspR9I Bsp1407I BssT1I NlaIII
   BsoFI BstDEI   HphI Bsc4I NciI MspR9I EccRII MvaI CviJI RsaI NcoI DsaI
acctgctgcctgagcctcaccccaccccggtgcctgggtcttaggctctgtacaccatggaggagaagctcgct base pairs
tggacgacggactcggagtgggggtggggccacggacccagaatccgagacatgtggtacctcctcttcgagcga 301 to 375
   Fsp4HI   CviJI     BsaJI MslI ScrFI NlaIV BstOI BstDEI AfaI BsaJI Bsp19I
   ItaI DdeI           BslI HpaII BanI PspN4I Bst2UI BsrGI ErhI EcoT14I
     Bst71I            BsiSI HapII AccB1I BstNI DdeI Csp6I StyI BseDI
```

FIG. 20

```
CviJI       BslI Bst2UI NdeII BstI DpnI BsaJI ScrFI MnlI FaeI HaeIII
   Cac8I    BseDI MspR9I DpnII MflI NlaIV AlwI Bst2UI Cac8I CfrI PalI
 BseRI      Bsc4I BstNI MvaI Sau3AI Kzo9I BseDI MvaI HphI BstDEI CviJI
ctaaaaataaccctgtccctggtggatccagggtgaggggcaggctgagggcggccacttccctcagccgcaggt base pairs
gattttattgggacagggaccacctaggtcccactccccgtccgactcccgccggtgaagggagtcggcgtcca 376 to 450
    AluI       BsaJI BstOI BstYI Bsp143I EcoRII MspR9I BsiYI MnlI ItaI AciI
 MnlI         EcoRII ScrFI BstX2I XhoII AclWI BstOI BslI CviJI Fsp4HI DdeI
Hsp92II        BsiYI BsmFI MboI BamHI PspN4I BstNI Bsc4I DdeI BsoFI BsuRI MnlI AciI                                      NcoI BstDSI Fsp4HI  BsgI
BstDEI      BsiYI        MwoI      Tsp509I StyI BseDI Hsp92II Bsc4I
 CviJI BspMI Bsc4I      SfcI CviJI    Sse9I Eco130I NlaIII BbvI BslI
ttgtttttcccaagaatggttttctgcttctgtagcttttcctgtcaattctgccatggtggagcagcctgcact base pairs
aacaaaagggttcttaccaaaaagacgaagacatcgaaaaggacagttaagacggtaccacctcgtcggacgtga 451 to 525
    Fsp4HI     BslI       BstSFI      TspEI  ErhI EcoT14I ItaI Cac8I
     ItaI                  AluI               BssT1I Bsp19I CviJI BsiYI
   BsoFI                                      BsaJI DsaI BsoFI Bst71I BsrI           NciI
   BseII         MspI MspR9I    SfcI                Bsc4I
   BseNI         BsiSI ScrFI    CviJI              SfcI BslI      SfcI
gggcttctggagaaaccaaaccgggttctaacctttcagctacagttattgcctttcctgtagatgggcgacta base pairs
cccgaagaccctctttggtttggcccaagattggaaagtcgatgtcaataacggaaaggacatctacccgctgat 526 to 600
   TspRI          HpaII         AluI                BstSFI        BstSFI
   CviJI          HapII         BstSFI              BsiYI
   BsrSI          BcnI BstOI Sau96I BsuRI BstNI BstYI Bsp143I
  MwoI           BsmBI        BseDI MvaI AspS9I EcoRII Bst2UI Sau3AI Kzo9I
  CviJI          Alw26I       EcoRII Bst2UI CviJI BslI BstOI DpnII BamHI
cagccccaccccaccccgtctcctgtatccttcctgggcctggggatcctaggctttcactggaaatttcccc base pairs
gtcggggtggggtgggggcagaggacataggaaggacccggaccccctaggatccgaaagtgacctttaaagggg 601 to 675
                 BsmAI        BsaJI ScrFI HaeIII BsiYI MspR9I MboI MflI
                 Esp3I        BstNI Cfr13I PalI BsaJI ScrFI NdeII BstI
                              MspR9I AsuI Bsc4I BseDI MvaI BstX2I XhoII NlaIV StyI EcoT14I BseNI Tsp509I Bst2UI BfaI PleI Cac8I ScrFI NlaIII EcoT22I
   ErhI BsaJI CviJI Sse9I EcoRII MvaI MaeI MaeIII BstOI MwoI BbuI Zso2I
 DpnI BlnI AlwI TspRI AcsI BseDI ScrFI CviJI CviJI EcoRII Cac8I NspI Mph1I
ccaggtgctgtaggctagagtcacggctcccaagaacagtgcttgcctggcatgcatggttctgaacctccaact base pairs
ggtccacgacatccgatctcagtgccgagggttcttgtcacgaacggaccgtacgtaccaagacttggaggttga 676 to 750
 PspN4I AclWI MaeI BseII BsaJI MspR9I BstSFI NlaIV BstNI MvaI Hsp92II NlaI
  AvrII BssT1I BfaI BsrI ApoI BstOI SfcI HinfI PspN4I MspR9I FpuI0I NsiI MnlI
   Eco130I BseDI BsrSI TspEI BstNI AlwNI Tsp45I TspRI Bst2UI PaeI SphI Hsp92II
```

FIG. 20 (Cont'd)

```
                      BsaJI BslI
                      StyI  Bsc4I                           MwoI                  BseII
C3I                   Eco130I  CviJI  MnlI          NlaIII        CviJI     BsrSI
gcaaaaaatgacacataccttgacccttggaaggctgaggcaggggattgccatgagtgcaaagccagactggg  base pairs
cgttttttactgtgtatggaactgggaaccttccgactccgtcccctaacggtactcacgtttcggtctgaccc  751 to 825
II                    ErhI BseDI BstDEI            Hsp92II                 BseNI
                      BssTlI BsiYI                                         BsrI
                      EcoT14I   DdeI MseI                       BsoBI
           AtsI   BsmAI              Tsp509I                      Eco88I
              Tth111I                 Sse9I                       Ama87I
tggcatagttagaccctgtctcaaaaaaccaaaaacaattaaataactaaagtcaggcaagtaatcctactcggg  base pairs
accgtatcaatctgggacagagttttttggttttgttaatttattgatttcagtccgttcattaggatgagccc  826 to 900
            AspI  Alw26I    TspEI                                  BcoI
                             Tru9I                                 AvaI
                             Tru1I NspI    PalI  CviJI ScrFI         BfaI
        BsmAI       AflIII  BstDEI Cac8I Bst2JI       PstNHI       BstSFI
    Alw26I   MnlI      BspLU11I  HaeIII BstOI             CviJI     AccI
agactgaggcagagggattgttacatgtctgaggccagcctggactacatagggtttcaggctagccctgtctac  base pairs
tctgactccgtctccctaacaatgtacagactccggtcggacctgatgtatcccaaagtccgatcgggacagatg  901 to 975

DdeI MnlI       MaeIII  NlaIII CviJI BstNI MvaI        NheI CviJI SfcI
      BstDEI                  Hsp92II BsuRI MspR9I            MaeI
                                DdeI MnlI EcoRII              Cac8I

DraII CviJI                    MspA1I MwoI     Bst2UI    EcoRII
         AsuI HaeIII                    AluI Fsp4HI     BstOI  Hsp92II
         Cfr13I PalI                    PvuII ItaI      EcoRII ScrFI   BstNI
agagtaaggccctatttcaaaaacacaaacaaaatggttctcccagctgctaatgctcaccaggcatgaagcctg  base pairs
tctcattccgggataaagttttgtgtttgttttaccaagagggtcgacgattacgagtggtccgtacttcggac  976 to
1050
         Sau96I BsuRI                   CviJI BbvI      BstNI NlaIII
         Eco0109I                       NspBII Bst71I   MspR9I     CviJI
         AspS9I                           BsoFI         HphI MvaI   BstOI MvaI
   Bst2UI                                                BstDEI       MaeIII
     MwoI      BsrDI    BsrDI  MnlI Cac8I       CviJI   DdeI MnlI CviJI
gtgagcattagcaatgaaggcaatgaaggagggtgctggctacaatcaaggctgtgggggactgagggcaggctg  base pairs
cactcgtaatcgttacttccgttacttcctcccacgaccgatgttagttccgacaccccctgactcccgtccgac  1051 to
1125
MspR9I         MwoI                  CviJI              BsmFI    Cac8I
   ScrFI
      HphI
```

FIG. 20 (Cont'd)

```
            NlaIV EcoRII Bst2UI BsaJI Bst2UI                    BcnI ScrFI
         AsuI HaeIII BstNI CviJI BstNI HinfI                    BsiST Bsc4I
    CviJI Cfr13I CviJI BstOI MaeII BstOI BsmFI              NlaIII MspI BsiYI
taacaggcttgggggccagggcttatacgtgcctgggactcccaaagtattactgttccatgttcccggcgaagg base pairs
attgtccgaaccccggtcccgaatatgcacggaccctgagggtttcataatgacaaggtacaaggccgcttcc 1126 to
1200
         Sau96I PalI BseDI MvaI BseDI MvaI                   Hsp92II HapII
         AspS9I BsuRI MspR9I BsaAI MspR9I PleI                   NciI MspR9I
         PspN4I BsaJI ScrFI EcoRII ScrFI                         HpaII BslI Sau96I Cac8I BsmFI     DdeI                        BsrI       BssTlI Fsp4HI
    AspS9I PvuII AciI BfaI                           BseNI        ErhI BseDI CviJI
     CviJI AluI FauI AluI  PleI DdeI       NlaIV BsrSI         CviJI EcoT14I Bst71I
gccagctgtcccccgccagctagactcagcacttagtttaggaaccagtgagcaagtcagcccttggggcagccc base pairs
cggtcgacaggggcggtcgatctgagtcgtgaatcaaatccttggtcactcgttcagtcgggaaccccgtcggg 1201 to
1275
Cfr13I BsuRI MspA1I MaeI      BstDEI    PspN4I TspRI        Eco130I BsoFI
  HaeIII CviJI  Cac8I HinfI                BscII              StyI HglI ItaI
  AsuI PalI NspBII CviJI BstDEI                             BsaJI MwoI BbvI CviJI BssT1I NlaIII CviJI Cac8I BstNI Cfr13I Eco47I BsiYI BseDI BmyI
    BslI Eco130I BseDI Hsp92II ItaI BsgI BstOI SinI AvaII BslI HapII ScrFI
       HaeIII NcoI DsaI BstXI Fsp4HI BsaJI ScrFI Sau96I PspN4I BsaJI SduI
atacaaggccatggggctgggcaagctgcacgcctgggtccggggtgggcacggtgcccgggcaacgagctgaaa base pairs
tatgttccggtaccccgacccgttcgacgtgcggacccaggccccaccgtgccacgggcccgttgctcgacttt 1276 to
1350
     Bsc4I BsuRI BsaJI Bsp19I Cac8I BbvI BseDI MvaI HgiEI Bsc4I HpaII MspR9I
       BsiYI ErhI EcoT14I CviJI AluI Bst71I MspR9I Bme18I AspS9I MspI NciI Bsp1286I
         PalI StyI BstDSI MwoI BsoFI EcoRII Bst2UI AsuI NlaIV BsiSI BcnI Eco64I NlaIV Eco88I SduI HpaII SrfI AluI Sau96I HaeIII BmyI Bsc4I BsiYI MvaI EcoRII
AccB1I Cfr9I BsoBI BcnI ScrFI CviJI PspOMI PspN4I Bsp1286I BsaJI BstOI CviJI
BanI Ama87I BseDI BmyI HapII CviJI Cfr13I DraII CviJI FriOI MnlI BstNI BsmFI
gctcatctgctctcaggggccctccctggggacagccctcctggctagtcacaccctgtaggctcctctatat base pairs
cgagtagacgagagtcccgggggagggaccctgtcggggaggaccgatcagtgtgggacatccgaggagatata 1351 to
1425
BshNI BcoI BsaJI BsiSI MspR9I AluI Bsp120I NlaIV BsuRI ApaI BseDI Bst2UI BstNI
   PspAI XmaI NciI MspI SmaI DdeI AsuI AspS9I SduI BanII EcoRII ScrFI BstOI
    PspN4I AvaI Bsp1286I PspALI BstDEI EcoC109I PalI Eco24I BslI MspR9I MnlI
```

FIG. 20 (Cont'd)

```
   MaeI BstSFI BseDI ScrFI BmyI ItaI CviJI HaeIII XbaI BstYI Sau3AI Kzo9I
  Bst2UI SfcI PspN4I BstOI Bsp1286I Bsc4I EaeI BsuRI AccBSI NdeII BstI NlaIV
 MspR9I Tsp45I MnlI BstNI SduI Fsp4HI BsiYI CviJI AciI BfaI MboI MflI MnlI
aacccaggggcacaggggctgcccccaagctggccgctctagaggatccccgggactagaattcaccatgtctag base pairs
ttgggtccccgtgtccccgacggggggttcgaccggcgagatctcctaggggccctgatcttaagtggtacagatc 1426 to
150C
    MvaI MaeIII BseRI MspR9I AlwNI BbvI AluI PalI ItaI MaeI BstX2I XhoII AclWI
     CviJI CviJI BsaJI Bst2UI CviJI Bst71I CfrI BsoFI BsrBI DpnII BamHI DpnI
  ScrFI BfaI NlaIV EcoRII MvaI BsoFI BslI Cac8I Fsp4HI BstD102I Bsp143I PspN4I BsaJI Eco88I HpaII MaeI TspEI XbaI Tru9I AspLEI BovI  HinfI
  Ama87I BsoBI HapII BfaI ApoI MaeI MseI HhaI Fsp4HI MnlI         Tru1I
  BseDI AvaI NciI ScrFI BsmFI Fsp5C9I HinP1I CviJI Tru9I FfiI     Tru9I
attagataaaagtaaagtgattaacagcgcattagagctgcttaatgaggtcggaatcgaaggtttaacaacccg base pairs
taatctattttcatttcactaattgtcgcgtaatctcgacgaattactccagccttagcttccaaattgttgggc 1501 to
1575
   BccI XmaI MspI SmaI AcsI HphI BfaI Hin6I BsoFI MseI TthHB8I MseI
  AlwI Cfr9I BcnI PspALI EcoRI Hsp92II HspAI AluI Bst71I TaqI
    PspAI BsiSI MspR9I Sse9I NlaIII Tru1I CfoI ItaI Tru1I BbvI                            MwoI
          AluI          ItaI          NspI              FauI
           HindIII       BsoFI    TspRI  NlaIII         Cac8I    TthHB8I
taaactcgcccagaagcttggtgtagagcagcctacactgtattggcatgtaaaaaataagcgggctttgctcga base pairs
atttgagcgggtcttcgaaccacatctcgtcggatgtgacataaccgtacattttttattcgcccgaaacgagct 1576 to
1650
          CviJI         Fsp4HI              Hsp92II     AciI    TaqI
           BstXI         CviJI                           CviJI
                         Bst71I BoiII DdeI              NlaIV                DraI
HinlI HgaI              BshNI                Tru1I              Cac8I
    AcyI    MslI        Eco64I               Tru9I BsiYI  CviJI
cgccttagccattgagatgttagataggcaccatactcactttgcccttaaaaggggaaagctggcaagattt base pairs
gcggaatcggtaactctacaatctatccgtggtatgagtgaaaacgggaaattttccccttttcgaccgttctaaa 1651 to
1725
  BsaHI CviJI        BanI              MseI BslI   AluI
Msp17I BstDEI        Acc31I            EcoNI
Hsp92I               PspN4I            Bsc4I AfaI
                   DdeI    MslI BsrDI  Csp6I
tttacgcaataacgctaaaagttttagatgtgctttactaagtcatcgcaatggagcaaaagtacattcagatac base pairs
aaatgcgttattgcgattttcaaaatctacacgaaatgattcagtagcgttacctcgttttcatgtaagtctatg 1726 to
1800
                                       BstDEI         RsaI
```

FIG. 20 (Cont'd)

```
SfcI
   PaII                              Tsp509I
     HaeIII                TthHB8I Sse9I CviJI                      MaeI
acggcctacagaaaaacagtatgaaactctcgaaaatcaattagccttttatgccaacaaggttttcactaga  base pairs
tgccggatgtcttttgtcatactttgagagcttttagttaatcggaaaaatacggttgttccaaaaagtgatct 1801 to
                                                                          1875
   CviJI              TaqI    TspEI                       BfaI
   BsuRI
     BstSFI BstUI          Hin6I AspLEI                  Bsp143I
   ThaI           HinP1I CfoI                   MboI DpnI AflIII   MwoI  DdeI Aor51HI HaeII            DpnII MboII  SfaNI
gaacgcgttatatgcactcagcgctgtggggcattttactttaggttgcgtattggaagatcaagagcatcaagt base pairs
cttgcgcaatatacgtgagtcgcgacaccccgtaaaatgaaatccaacgcataaccttctagttctcgtagttca 1876 to
                                                                          1950
   MluI Bsh1236I BstDEI AfcI Bsp143II           NdeII
     AccII       HspAI HhaI                     Sau3AI
     MvnI        Eco47III BstH2I                Kzo9I Tsp509I MboI
                                        ItaI         TthHB8I   BclI
       MboII                    BsoFI           CviJI Sse9I  FbaI
cgctaaagaagaaagggaaacacctactactgatagtatgccgccattattacgacaagctatcgaattatttga base pairs
gcgatttcttctttcccttgtggatgatgactatcatacggcggtaataatgctgttcgatagcttaataaact 1951 to
                                                                          2025
                                 Fsp4HI         AluI TspEI   DpnII
                                   AciI              TaqI    NdeII
                                                             Ksp22I Kzo9I BssT1I CviJI             TspEI MboI DpnI
   Bsp143I BscDI MwoI       PalI Sse9I NdeII FauNDI         TruII
   Sau3AI BsaJI BsgI        HaeIII FbaI Sau3AI AciI         Tru9I
tcaccaaggtgcagagccagccttcttattcggccttgaattgatcatatgcggattagaaaaacaacttaaatg base pairs
agtggttccacgtctcggtcggaagaataagccggaacttaactagtatacgcctaatcttttgttgaatttac 2026 to
                                                                          2100
   DpnI StyI MslI  CviJI        CviJI   DpnII Kzo9I         MseI
   Eco130I HphI Cac8I           BsuRI   BclI Bsp143I
   ErhI EcoT14I                     Tsp509I Ksp22I NdeI HgiEI AspS9I AciI BsoFI ThaI MvnI Cac8I Bsh1236I AfaI TaqI Eco0109I
       Fme18I PspN4I Csp6I Fsp4HI AccII HhaI AccII Pf123II Tsp509I DraII
         Cfr13I NlaIV Bsh1236I ItaI BsePI AciI ThaI PspLI RsaI TthHB8I AspS9I
tgaaagtgggtccgcgctacagccgcgcgcgtacgaaaaacaattacgggtctaccatcgagggcctgctcgatct base pairs
actttcacccaggcgcatgtcggcgcgcgcatgcttttttgttaatgcccagatggtagctcccggacgagctaga 2101 to
                                                                          2175
```

FIG. 20 (Cont'd)

```
       SinI AvaII AccII RsaI HinP1I BstUI CfoI BstUI SunI Sse9I Cfr13I HaeIII
       Sau96I ThaI BstJI CviJI BssHII Bsh1236I MvnI BsiWI TspEI Sau96I CviJI
       AsuI Eco47I MvnI AfaI HspAI Hin6I AspLEI SplI Csp6I AccI AsuI MnlI

Cac8I Sau3AI BcnI Hin1I HgaI Ksp632I BsoFI PspN4I BstUI   BseDI MvnI FauI
PalI NdeII BsiSI HapII Hsp92I Eam1104I Cac8I NlaIV Hin6I AspLEI AccII KspI
    TthHB8I Kzo9I MspI Msp17I BslI EarI CviJI AciI ThaI AciI BsaJI BstUI Sfr3
cccggacgacgacgcccccgaagaggcggggctggcggctccgcgcctgtcctttctccccgcgggacacacgcg base pairs
gggcctgctgctgcgggggcttctccgccccgaccgccgaggcgcggacaggaaagaggggcgccctgtgtgcgc 2176 to
                                                                          2250
     DpnII DpnI HpaII BbiII Bsc4I MnlI MwoI CviJI AccII HhaI BstDSI Bsh1236I
   TaqI Bsp143I MspR9I AcyI BsiYI AciI Tsp4HI HspAI Bsh1236I DsaI NspBII SstII
 BsuRI MboI NciI ScrFI BsaHI MboII FauI ItaI HinP1I MvnI CfoI ThaI MspAlI Cfr42I AciI AccII AspLEI HindII CviJI Bsh1285I BstOI Ecl136II BmyI SacI BsiHKAI
SacII ThaI MvnI TthHB8I AspS9I PspN4I CviJI MspR9I AluI AsoHI BanII BstDEI
 C3I HinP1I HhaI AccI Sau96I NlaIV PshAI BstNI BsmFI Bsp1286I FriOI DdeI
cagactgtcgacggccccccgaccgatgtcagcctgggggacgagctccacttagacggcgaggacgtggcgat base pairs
gtctgacagctgccgggggggctggctacagtcggaccccctgctcgaggtgaatctgccgctcctgcaccgcta 2251 to
                                                                           2325
 BsmFI BstUI SalI HincII HaeIII BstMCI BseDI MvaI CviJI Bov12I Alw21I
    HspAI Bsh1236I Cfr13I PalI BsiEI EcoRII Bst2UI SduI Eco24I SstI MaeII
    Hin6I CfoI TaqI AsuI BsuRI BsaOI BsaJI ScrFI EcoICRI Psp124BI MnlI AspLEI NspI AccII HhaI MamI Bse8I Bsp143I NspI         BcoI XmaI HpaII SmaI
  Hin6I PaeI SphI BstJI CfoI TthHB8I MboI AflIII     TfiI Ama87I NciI HapII
  HinP1I NlaIII ThaI Bsh1236I BsaBI DpnII DpnI    BsmFI  BsaJI Eco88I MspI
ggcgcatgccgacgcgctagacgatttcgatctggacatgttgggggacggggattccccgggtccgggatttac base pairs
ccgcgtacggctgcgcgatctgctaaagctagacctgtacaaccccctgccccctaaggggcccaggccctaaatg 2326 to
                                                                           2400
 HspAI Cac8I HinP1I HgaI BfaI TaqI NdeII BspLU11I   HinfI Cfr9I BsiSI ScrFI
   HhaI Hsp92II Hin6I AspLEI BsrBRI Sau3AI NlaIII        BseDI AvaI BcnI PspALI
   CfoI BbuI HspAI MvnI MaeI Bsh1365I Kzo9I Hsp92II     PspAI Bso3I MspR9I HgiEI PspN4I NciI PleI HspAI    CfrI                                BssT1I
  SinI AvaII BslI HapII AciI AspLEI  BaeI    TaqI                        ErhI
 Cfr13I Eco47I BsiYI BcnI HinP1I Bsp143II BsuRI                         SfaNI
ccccacgactccgcccctacggcgctctggatatggccgacttcgagtttgagcagatgtttaccgatgccct base pairs
ggggtgctgaggcgggggatgccgcgagacctataccggctgaagctcaaactcgtctacaaatggctacggga 2401 to
                                                                          2475
  Bme18I AspS9I HpaII HinfI HhaI HaeII CviJI TthHB8I                   Eco130I
    AsuI Bsc4I MspI MspR9I CfoI BstH2I PalI                             StyI
   Sau96I NlaIV BsiSI ScrFI Hin6I      HaeIII                           BsaJI Tsp509I         NdeII BamHI DpnI BseDI AvaI NciI ScrFI Acc65I RsaI
  BseDI      AfaI     DpnII Bsp143I AclWI PspAI BsiSI MspR9I Asp718I AfaI
  EcoT14I  Csp6I      BstYI Sau3AI PspN4I BcoI XmaI HpaII Eco64I NlaIV BslI
tggaattgacgagtacggtgggatggatccccgggtaccggtcgccaccatggtgagcaagggcgaggagctgtt base pairs
accttaactgctcatgccaccctacctaggggcccatggccagcggtggtaccactcgttcccgctcctcgacaa 2476 to
                                                                          2550
```

FIG. 20 (Cont'd)

```
              RsaI       BstF5I MflI Kzo9I AlwI Eco88I MspI SmaI BshNI Bsc4I
     Sse9I               BstX2I BstI NlaIV Ama87I BsoBI HapII BanI Csp6I AgeI
     TspEI               MboI FokI XhoII BsaJI Cfr9I BcnI PspALI AccB1I PspN4I

PinAI Cfr10I BsaOI BssT1I Bsp19I BseRI BsaJI ScrFI PspN4I BstOI TthHB8I HaeIII
  BsaWI HpaII Bsh1285I EcoT14I Hsp92II MspI MspR9I Acc31I BstF5I MvaI CviJI
     BsiYI HapII Eco130I BseDI NlaIII BsiSI NciI Eco64I Bsp1286I MspR9I AluI
 caccggggtggtgcccatcctggtcgagctggacggcgacgtaaacggccacaagttcagcgtgtccggcgaggg base pairs
 gtggcccccaccacgggtaggaccagctcgacctgccgctgcatttgccggtgttcaagtcgcacaggccgctccc 2551 to
 2625
   BssAI BsiSI BsiEI StyI BstDSI MnlI HpaII BcnI BanI SduI EcoRII ScrFI MaeII
     BsrFI MspI BstMCI NcoI DsaI HphI AluI BseDI MslI NlaIV BstNI Bst2UI EaeI
     Bse118I KpnI ErhI BsaJI MslI CviJI HapII HphI BshNI BmyI FokI TaqI CfrI MspI                                              Cfr10I MwoI ItaI  BsaJI BsiYI
 PalI HapII              AluI                         BsrFI HapII Fsp4HI EcoRII
 CviJI MwoI SfaNI        Cac8I         Eco57I         BsgI HpaII AluI Bst71I Bsp1286I
 cgagggcgatgccacctacggcaagctgacccctgaagttcatctgcaccaccggcaagctgcccgtgccctggcc base pairs
 gctcccgctacggtggatgccgttcgactgggacttcaagtagacgtggtggccgttcgacgggcacgggaccgg 2626 to
 2700
 HpaII        BcgI         CviJI                     BssAI MspI BsoFI  Bsc4I BslI
 BsuRI MnlI                                          Bse118I CviJI MwoI SduI BmyI
 BsiSI MnlI                                          BsiSI Cac8I BbvI BseDI BstNI MvaI AsuI MslI Bsc4I BstNI Cac8I       ItaI               ItaI
 BstOI Sau96I BsuRI BssSI BseDI MvaI      CviJI                BsoFI
     ScrFI AspS9I MaeIII BsaJI ScrFI TspRI BsoFI             NlaIII BbvI
 caccctcgtgaccaccctgacctggggcgtgcagtgcttcagccgctaccccgaccacatgaagcagcacgactt base pairs
 gtgggagcactggtgggactggaccccgcacgtcacgaagtcggcgatggggctggtgtacttcgtcgtgctgaa 2701 to
 2775
     MspR9I HaeIII BsiI BslI BstOI MwoI      Eco57I           Hsp92II
     Bst2UI CviJI MnlI EcoRII MspR9I BsgI    Fsp4HI           Fsp4HI
        Cfr13I PalI Tsp45I BsiYI Bst2UI              AciI             Bst71I MspR9I HhaI
              Hsp92II   BstNI HinP1I
    MboII   AciI        CviJI EcoRII MvaI CfoI    MboII
 cttcaagtccgccatgcccgaaggctacgtccaggagcgcaccatcttcttcaaggacgacggcaactacaagac base pairs
 gaagttcaggcggtacgggcttccgatgcaggtcctcgcgtggtagaagaagttcctgctgccgttgatgttctg 2776 to
 2850
              NlaIII       MaeII ScrFI Hin6I
                           BstOI HspAI
```

FIG. 20 (Cont'd)

```
                              Bst2JI AspLEI
   Hin6I AciI BsaJI TthHB8I        BstNI HphI           AluI
   ThaI MvnI CfoI MnlI            EcoRII ScrFI   TaqI         TaqI
   HinP1I AspLEI BslI    MnlI     BsaJI MspR9I AciI  CviJI Eco57I          MnlI
ccgcgccgaggtgaagttcgagggcgacaccctggtgaaccgcatcgagctgaaggcatcgacttcaaggagga base pairs
ggcgcggctccacttcaagctcccgctgtgggaccacttggcgtagctcgacttcccgtagctgaagttcctcct 2851 to
                                                                          2925
   HspAI Bsh1236I BsiYI         BseDI Bst2UI      TthHB8I          TthHB8I
   AccII FauI Bsc4I HphI        MslI MvaI        SfaNI            SfaNI
   BstUI HhaI BseDI TaqI        BstOI BstNI ScrFI       BpmI
       BseDI Bst2UI AluI Csp6I
    EcoRII FokI Bsp1286I           CviJI MaeII        HphI
cggcaacatcctggggcacaagctggagtacaactacatcagccacaacgtctatatcaccgccgacaagcagaa base pairs
gccgttgtaggaccccgtgttcgacctcatgttgatgtagtcggtgttgcagatatagtggcggctgttcgtctt 2926 to
                                                                          3000
   BsaJI MspR9I CviJI RsaI                                    AciI
   BstF5I SduI     GsuI
   BstOI MvaI BmyI   AfaI BsuRI       MboI Bsp143I                  Bst71I AluI
           CviJI       BstX2I DpnI     TthHB8I  ItaI  ItaI BbvI
  MboII   SfaNI        BstYI MflI AlwI       MnlI BsoFI BsoFI Bst71I
gaacggcatcaaggccaacttcaagatccgccacaacatcgaggacggcagcgtgcagctcgccgaccactacca base pairs
cttgccgtagttccggttgaagttctaggcggtgttgtagctcctgccgtcgcacgtcgagcggctggtgatggt 3001 to
                                                                          3075
           HaeIII    DpnII XhoII AciI       Fsp4HI Fsp4HI Cac8I
           PalI      NdeII Kzo9I    TaqI      BbvI  CviJI
                     Sau3AI AclWI                  Cac8I BsgI HaeIII  BsoFI                        BmyI BseNI BstDEI
            AsuI PalI ItaI                          Bsp1286I AciI
            Cfr13I BsuRI BbvI                 DdeI  SduI BsiHKAI
gcagaacacccccatcggcgacggccccgtgctgctgcccgacaaccactacctgagcacccagtccgccctgag base pairs
cgtcttgtgggggtagccgctgccggggcacgacgacgggctgttggtgatggactcgtgggtcaggcgggactc 3076 to
                                                                          3150
                    Sau96I NlaIV Bst71I            BstDEI Alw21I BsrI
                    AsoS9I PspN4I                  AspHI BsrSI DdeI
                    CviJI  Fsp4HI                  Bpv12I BscI ThaI Bsh1236I DpnI Hsp92II BpmI  Fsp4HI HapII NdeII AlwI
       Hin6I MvnI NdeII NlaIII AsuI GsuI  BsoFI MspI BcnI Sau3AI
       HinP1I AspLEI Bsp143I Sau96I AsoS9I ItaI HpaII ScrFI Bsp143I
caaagaccccaacgagaagcgcgatcacatggtcctgctggagttcgtgaccgccgcgggatcactctcggcat base pairs
gtttctggggttgctcttcgcgctagtgtaccaggacgacctcaagcactggcggcgccctagtgagagccgta 3151 to
                                                                          3225
```

FIG. 20 (Cont'd)

```
                        HspAI BstUI MboI Cfr13I HgiEI Tsp45I Bsc4I BsiYI MboI DpnI
                          HhaI CfoI Sau3AI SinI AvaII MaeIII  BslI NciI DpnII AclWI
                         AccII DpnII Kzo9I Bme18I Eco47I  AciI BsiSI MspR9I Kzo9I

Bsp1407I      BsoFI ItaI CviJI BsaOI Bsh1236I Sau3AI BsrBRI
  NlaIII SspBI           CfrI Fsp4HI BsuRI AccII HinfI DpnII MamI        MnlI
      CviJI AfaI         BaeI NotI HaeIII Bsh1285I PleI MboI DpnI CviJI
ggacgagctgtacaagtaaagcggccgcgactctagatcataatcagccataccacatttgtagaggttttactt base pairs
cctgctcgacatgttcatttcgccggcgctgagatctagtattagtcggtatggtgtaaacatctccaaaatgaa 3226 to
                                                                             3300
   Hsp92II Csp6I        BstZI EclXI PalI BstMCI AciI BfaI Kzo9I Bsh1365I
      AluI RsaI         CciNI Eco52I BsiEI BstUI XbaI NdeII BsaBI
         BsrGI          EagI XmaIII AciI ThaI MvnI MaeI Bsp143I Bse8I MunI          HincII
    TruiI                                              Mval269I      MseI
      Tru9I     MnlI       MnlI                        MfeI BsaMI     Tru9I
gctttaaaaaaacctcccacacctcccccctgaacctgaaacataaaatgaatgcaattgttgttgttaacttgtgttt base pairs
cgaaattttttggagggtgtggaggggggacttggactttgtattttacttacgttaacaacaacaattgaacaaa 3301 to
                                                                             3375
   MseI                                                  BsmI Tsp509I HpaI
     DraI                                                Sse9I        TruiI
                                                         TspEI        HindII AluI                            ApoI
   ItaI Bst71I                         AcsI
    BsoFI      MaeIII                  SfaNI                                TspRI
attgcagcttataatggttacaaataaagcaatagcatcacaaatttcacaaataaagcattttttcactgcat base pairs
taacgtcgaatattaccaatgtttatttcgttatcgtagtgtttaaagtgtttatttcgtaaaaaaagtgacgta 3376 to
                                                                             3450
     Fsp4HI                           Sse9I
       CviJI                          TspEI
        BbvI                          Tsp509I BsaMI                       MspCI    Tsp509I                     AcsI
   Mva1269I                     Bst98I   Sse9I      TruiI           TruiI
                                BspTI MseI          Tru9I           Tru9I Tsp5
tctagttgtggtttgtccaaactcatcaatgtatcttaaggcgtaaattgtaagcgttaatattttgttaaaatt base pairs
agatcaacaccaaacaggtttgagtagttacatagaattccgcatttaacattcgcaattataaaacaattttaa 3451 to
                                                                             3525
    BsmI                        AflII TruiI         MseI          MseI ApoI
    MaeI                        Vha464I   TspEI                   Sse9I
    BfaI                        BfrI Tru9I          SspI          TspEI BstUI AcsI     MseI
    ThaI MseI ApoI                         TruiI         PalI
     09I Tru9I Tsp509I    CviJI            Tru9I         HaeIII
cgcgttaaattttgttaaatcagctcattttttaaccaataggccgaaatcggcaaaatcccttataaatcaaa base pairs
gcgcaatttaaaaacaatttagtcgagtaaaaaattggttatccggctttagccgttttagggaatatttagttt 3526 to
                                                                             3600
```

FIG. 20 (Cont'd)

```
       Bsh1236I TspEI        AluI       MseI         CviJI
    AccII Sse9I   Tru9I                              BsuRI
    MvnI Tru1I    Tru1I

MaeI BstX2I AciI
              AluI  DpnII MflI DpnI                                          AfaI
              CviJI BstYI Bsp143I           CviJI              MnlI   Csp6I
    agaatagaccgagagctagcggatctgacggttcactaaaccagctctgcttatatagacctcccaccgtacacg base pairs
    tcttatctggctctcgatcgcctagactgccaagtgatttggtcgagacgaatatatctggagggtggcatgtgc 3601 to
                                                                                3675
              NhcI Cac8I Sau3AI AclWI        AluI                        RsaI
              PstNHI MboI XhoII AlwI
              BfaI NdeII Kzo9I NlaIV
                                                                       BshNI
           FauI      HgaI      AciI                    BsmFI           Eco64I
    cctacccgccatttgcgtcaatggggcggagttgttatgacattttggaaagtcccgttgattttggtgccaaaa base pairs
    ggatgggcggtaaacgcagttaccccgcctcaacaatactgtaaaacctttcagggcaactaaaaccacggtttt 3676 to
                                                                                3750
          AciI                                                           BanI
                                                                         AccB1I
                                                                         PspN4I MaeII                          MspR9I Cfr13I FauI
             BbiII AatII                    EcoRII MvaI AsuI CviJI
             HinlT AcyI   AciI         AciI BstNI BglI AspS9I       MaeIII
    caaactcccattgacgtcaatgggcggggtcgttgggcggtcagccaggcgggccatttaccgtaagttatgta base pairs
    gtttgagggtaactgcagttacccgcccccagcaacccgccagtcggtccgcccggtaaatggcattcaatacat 3751 to
                                                                                3825
             Msp17I      FauI        CviJI ScrFI Cac8I PalI
             Hsp92I                  BstOI MwoI AciI BsuRI
             BsaHI                   Bst2JI Sau96I HaeIII MvnI                                              AseI        Mph1103I
    AccII        BsiYI              Tsp509I    Tru9I             NsiI
       AciI      Bsc4I              Sse9I      AsnI Tru1I  Zsp2I AciI
    acgcggaactccatatatgggctatgaactaatgaccccgtaattgattactattaataactaatgcatggcggt base pairs
    tgcgccttgaggtatatacccgatacttgattactggggcattaactaatgataattattgattacgtaccgcca 3826 to
                                                                                3900
    ThaI         BslI                TspEI      VspI    Ppu10I Hsp92II
    BstUI        CviJI                          PshBI   EcoT22I
    Bsh1236I                                    MseI          NlaIII NspI        Cac8I    CviJI MspR9I
                                 NlaIII      PalI BsiYI BstNI
                      HinfI                  BspLU11I HaeIII BslI BsuRI
    aatacggttatccacagaatcaggggataacgcaggaaagaacatgtgagcaaaaggccagcaaaaggccaggaa base pairs
    ttatgccaataggtgtcttagtcccctattgcgtcctttcttgtacactcgttttccggtcgttttccggtcctt 3901 to
                                                                                3975
```

FIG. 20 (Cont'd)

```
                  TfiI                       AflIII        CviJI Bsc4I EcoRII
                                       Hsp92II    BsuRI        HaeIII
                                                                  PalI BstOI

CviJI ThaI MwoI
NlaIV BsiYI Fsp4HI Bsh1236I         PspN4I
Bst2UI BslI BsuRI AccII             CviJI AciI             SfaNI    TthHB8I
ccgtaaaaaggccgcgttgctggcgttttccataggctccgccccctgacgagcatcacaaaaatcgacgctc base pairs
ggcattttccggcgcaacgaccgcaaaaaggtatccgaggcggggggactgctcgtagtgttttttagctgcgag 3976 to
                                                                              4050
 MvaI Bsc4I BsoFI BstUI             NlaIV                     TagI   HgaI
 ScrFI    HaeIII MvnI Cac8I
   PspN4I PalI ItaI AciI Bst2UI        BstOI AluI        BssSI
                                    BstOI         EcoRII MvaI       HinP1I
DrdI       MnlI                     EcoRII MvaI   BsaJI Bst2UI   MnlI HhaI
aagtcagaggtggcgaaacccgacaggactataaagataccaggcgtttccccctggaagctccctcgtgcgctc base pairs
ttcagtctccaccgctttgggctgtcctgatatttctatggtccgcaaaggggggaccttcgagggagcacgcgag 4051 to
                                                                              4125
                                    BstNI         BseDI ScrFI       BsiI
                                    MspR9I        BstNI CviJI       HspAI
                                    ScrFI         MspR9I            Hin6I BsaWI                                    AspLEI
           ItaI Bsc4I HapII                              Hin6I HaeII
           BsoFI BslI MspI   AciI                        HinP1I BstH2I
tcctgttccgaccctgccgcttaccggatacctgtccgcctttctcccttcgggaagcgtggcgctttctcatag base pairs
aggacaaggctgggacggcgaatggcctatggacaggcggaaagagggaagcccttcgcaccgcgaaagagtatc 4126 to
                                                                              4200
AspLEI     Fsp4HI BsiSI                                  HspAI Bsp143II
 CfoI        AciI HpaII                                       HhaI
             BsiYI                                            CfoI Bsp1286I
CviJI                                                  VncI BmyI
      SfcI        DdeI                    CviJI        Alw44I Alw21I
ctcacgctgtaggtatctcagttcggtgtaggtcgttcgctccaagctgggctgtgtgcacgaacccccccgttca base pairs
gagtgcgacatccatagagtcaagccacatccagcaagcgaggttcgacccgacacacgtgcttgggggggcaagt 4201 to
                                                                              4275
      BstSFI      BstDEI                   AluI CviJI       SduI BsiHKAI
```

FIG. 20 (Cont'd)

```
    AluI                                            ApaII Bbv12I
                                                      AspHI

NspBII HinP1I CfoI HapII         MspI                BsrI
      BstMCI AciI BbvI BsaWI             BcnI ScrFI          BscNI
   CviJI BsiEI BscFI Hin6I BsiSI    HinfI  BsiSI             TspRI
   gcccgaccgctgcgccttatccggtaactatcgtcttgagtccaacccggtaagacacgacttatcgccactggc base pairs
   cgggctggcgacgcggaataggccattgatagcagaactcaggttgggccattctgtgctgaatagcggtgaccg 4276 to
   4350
        Bsh1285I ItaI HhaI HpaII        PleI NciI MspR9I      BsrSI
        BsaOI Fsp4HI Bst71I MspI             HpaII            BseII
          MspA1I HspAI AspLEI MaeIII         HapII ItaI   BseII
      Bst71I BsrSI                        BstSFI             PalI
      Fsp4HI TspRI          MnlI    AciI                     HaeIII
   agcagccactggtaacaggattagcagagcgaggtatgtaggcggtgctacagagttcttgaagtggtggcctaa base pairs
   tcgtcggtgaccattgtcctaatcgtctcgctccatacatccgccacgatgtctcaagaacttcaccaccggatt 4351 to
   4425
      BbvI   MaeIII                          SfcI             CviJI
      CviJI  BseNI                                            BsuRI
   BscFI   AlwNI BsrI AspLEI       BseNI
      BsiYI                   Hin6I        MaeIII
      BslI    MaeI            HinP1I       Eco57I
   ctacggctacactagaaggacagtatttggtatctgcgctctgctgaagccagttaccttcggaaaaagagttgg base pairs
   gatgccgatgtgatcttcctgtcataaaccatagacgcgagacgacttcggtcaatggaagccttttctcaacc 4426 to
   4500
   Bsc4I   BfaI             HspAI    CviJI BsrI
       CviJI                HhaI           BsrSI
                            CfoI           BseII Sau3AI HapII                               Bst71I  AccII
         NdeII HpaII        AciI                    Fsp4HI  HspAI
      CviJI Kzo9I MspI      NspBII  AciI        Cac8I BbvI MwoI BstUI
   tagctcttgatccggcaaacaaaccaccgctggtagcggtggttttttgtttgcaagcagcagattacgcgcag base pairs
   atcgagaactaggccgtttgtttggtggcgaccatcgccaccaaaaaaacaaacgttcgtcgtctaatgcgcgtc 4501 to
   4575
      AluI DpnII BsiSI     MspA1I                      BsoFI   HinP1I
         MboI DpnI AlwI                                ItaI    ThaI
         Bsp143I AclWI                                         Hin6I HhaI   NdeII Kzo9I BstX2I XhoII DpnII
   Bsh1236I Sau3AI AclWI MboI DpnI AlwI Kzo9I        BstDEI              MseI
         BstYI MflI AlwI Sau3AI MboII Sau3AI         HgaI  TspRI         MaeII
   aaaaaaaggatctcaagaagatcctttgatctttttctacggggtctgacgctcagtggaacgaaaactcacgtta base pairs
   ttttttttcctagagttcttctaggaaactagaaaagatgccccagactgcgagtcaccttgcttttgagtgcaat 4576 to
   4650
```

FIG. 20 (Cont'd)

```
   CfoI  DpnII XhoII BstYI Bsp143I MboI DpnI         DdeI                Tru9I
   MvnI  BstX2I DpnI DpnII MflI AclWI Bsp143I                            Tru1I
 AspLEI  MboI Bsp143I NdeII Kzo9I NdeII

MboI Bsp143I BfaI Sau3AI AclWI Ssc9I   Tru1I
              NlaIII   BstX2I DpnI MaeI BstX2I DpnI Tru1I Tru1I
        BspHI          BstYI MflI AlwI DpnII MflI AlwI TspEI  Tru9I
agggattttggtcatgagattatcaaaaaggatcttcacctagatcctttaaattaaaaatgaagttttaaatc base pairs
tccctaaaaccagtactctaatagttttcctagaagtggatctaggaaaatttaatttttacttcaaaatttag 4651 to
4725
        RcaI           DpnII XhoII MboII MboI XhoII MseI Tru9I DraI
            Hsp92II    NdeII Kzo9I HphI NdeII Kzo9I DraI MseI MseI
                       Sau3AI AclWI BstYI Bsp143I Tru9I Tsp509I CvnI CviJI   DraII CviJI Fsp4HI   BsoFI  BsaJI Eco24I
                  DdeI Bsu36I  AsuI HaeIII BsoFI BsiYI   Bst71I SduI
          MaeIII AocI MnlI    Cfr13I PalI Cac8I Bsc4I   BbvI EcoRII
aatctaaagtatatatgagtaacctgaggctatggcagggcctgccgccccgacgttggctgcgagccctgggcc base pairs
ttagatttcatatatactcattggactccgataccgtcccggacggcggggctgcaaccgacgctcgggaccccgg 4726 to
4800
             Eco81I        Sau96I BsuRI ItaI BslI ItaI CviJI BmyI
             Bse21I        Eco01091 MwoI   MaeII CviJI Cac8I Bsp1286I
             BstDEI        AspS9I AlwNI AciI    Fsp4HI BseDI FriOI ScrFI AspS9I BsiYI              MvnI FauI   HaeIII EslI
 BstNI Cfr13I PalI Bsc4I              AccII    AsuI PalI BsiYI BsaI
 BanII MvaI AsuI HohI               MboII Cac8I    Cfr13I BsuRI   Alw26I
ttcacccgaacttgggggtggggtggggaaaaggaagaaacgcgggcgtattggccccaatgggggtctcggtgg base pairs
aagtgggcttgaaccccccaccccacccctttccttctttgcgcccgcataaccgggggttaccccagagccacc 4801 to
4875
   BstOI Sau96I BsuRI              ThaI AciI  Sau96I NlaIV     Eco31I
      Bst2UI CviJI BslI             BstJI     AspS9I PspN4I    BsmAI
     MspR9I HaeIII                 Bsh1236I   CviJI Bsc4I EcoRII MspR9I Sau96I BsmFI MvnI
              BsaJI BstOI Cfr13I Eco47I AccII
     TthHB8I       Cac8I BslI ScrFI Bme18I NlaIV BstUI
ggtatcgacagagtgccagccctgggaccgaaccccgcgtttatgaacaaacgacccaacaccgtgcgttttatt base pairs
ccatagctgtctcacggtcgggaccctggcttggggcgcaaatacttgtttgctgggttgtggcacgcaaaataa 4876 to
4950
     TaqI         CviJI BstNI MvaI AsuI PspN4I FauI
                  BseDI BsiYI SinI AvaII ThaI AciI
                  Bsc4I Bst2UI HgiEI AspS9I Bsh1236I ThaI Bsh1236I MspI                    StyI
                 HspAI BstUI PspN4I                    Eco13
              MwoI HhaI AspLEI BsiSI     Alw26I     CviJI AvrII
ctgtcttttattgccgtcatagcgcgggttccttccggtattgtctccttccgtgtttcagttagcctcccccct base pairs
gacagaaaaataacggcagtatcgcgcccaaggaaggccataacagaggaaggcacaaagtcaatcggaggggga 4951 to
5025
```

FIG. 20 (Cont'd)

```
                    HinP1I CfoI NlaIV HapII  BsmAI              MnlI
                    Hin6I MvnI FauI HpaII                       ErhI
                    AccII AciI BsaWI                            ElnI

EcoT14I            BstX2I Kzo9I HspAI Bsh1236I CfoI Bsp143I MroNI Bse118I
   OI BfaI            NlaIII Bsp143I ThaI MvnI HhaI MboI GsuI AclWI CviJI
    MaeI BslI MboII  GsuI BstYI MboI DpnI AccII Bsc4I AspLEI Kzo9I FokI BsrFI
agggtgggcgaagaactccagcatgagatccccgcgctggaggatcatccagccggcgtcccggaaaacgattcc base pairs
tcccacccgcttcttgaggtcgtactctaggggcgcgacctcctagtaggtcggccgcagggccttttgctaagg 5026 to
                                                                             5100
BssT1I Bsc4I        BpmI DpnII Sau3AI AlwI BstJI BslI NdeII Mn1I BstF5I NgoAIV
  BsaJI BsiYI       Hsp92II XhoI HinP1I FauI BsiYI Sau3AI DpnI BssAI
  BseDI             NdeII MflI AclWI Hin6I AciI DpnII BpmI AlwI NgoMI Cac8I AcyI BcnI BsmFI ItaI                        BbiII
   HpaII BbiII BsiSI ScrFI BsoFI HinfI                  HinlI HgaI
    MspI Msp17I NciI MspR9I Fsp4HI TthHB8I    BsiI    BspMI BsaHI
gaagcccaacctttcatagaaggcggcggtggaatcgaaatctcgtgatggcaggttgggcgtcgcttggtcggt base pairs
cttcgggttggaaagtatcttccgccgccacccttagctttagagcactaccgtccaacccgcagcgaaccagcca 5101 to
                                                                             5175
    HapII Hsp92I HpaII TfiI AciI   TaqI      BssSI    MwoI AcyI
CfrlOI NaeI BsaHI MspI HinfI   TfiI                   Msp17I
BsiSI HinlI HgaI HapII CviJI                          Hsp92I BstBI Bpu14I     AciI                            HhaI BbvI
    LspI NspV        DdeI BstD102I                   Hin6I BsoFI TfiI
    TthHB8I    HinfI BsmFI BsrBI                     HinP1I Fsp4HI catttcgaaccccagagtcccgctcagaagaactcgtcaagaaggcgatagaaggcgatgcgctgcgaatcggga base pairs
gtaaagcttggggtctcagggcgagtcttcttgagcagttcttccgctatcttccgctacgcgacgcttagccct 5176 to
                                                                             5250
    SfuI TaqI    PleI AccBSI                          HspAI CfoI HinfI
    Csp45I       FauI     MboII                       SfaNI ItaI
    Bsp119I      BstDEI                               AspLEI Bst71I BsrBI                              MboII
    ItaI AciI     MnlI           ItaI  Ksp632I
    BsoFI         BsiI    AciI   BsoFI CviJI Eam1104I        CviJI
gcggcgataccgtaaagcacgaggaagcggtcagcccattcgccgccaagctcttcagcaatatcacgggtagcc base pairs
cgccgctatggcatttcgtgctccttcgccagtcgggtaagcggcggttcgagaagtcgttatagtgcccatcgg 5251 to
                                                                             5325
  Fsp4HI         BssSI      CviJI   Fsp4HI AluI  SapI
   AccBSI                           AciI   EarI
   BstD102I                                Eco57I CpoI AsuI AciI NgoMI BsiSI CfrI BsuRI    ItaI BsuRI
          BsiYI HgiEI AspS9I NgoAIV HapII CviJI Hinfl BsoFI AciI
          Bsc4I Bme18I AvaII MroNI Bse118I HaeIII TfiI  EaeI CviJI
aacgctatgtcctgatagcggtccgccacacccagccggccacagtcgatgaatccagaaaagcggccatttttcc base pairs
ttgcgatacaggactatcgccaggcggtgtgggtcggccggtgtcagctacttaggtcttttcgccggtaaaagg 5326 to
                                                                             5400
```

FIG. 20 (Cont'd)

```
                 BslI Sau96I Eco47I BsrFI MspI EaeI PalI       CfrI PalI
                   Cfr13I RsrII    BssAI Cfr10I NaeI TthHB8I    Fsp4HI
                    SinI CspI AciI CviJI HpaII Cac8I TaqI         HaeIII

ErhI EcoT14I MaeIII Sau3AI AlwI      BbuI
                       MslI BsaJI NlaIII BstX2I XhoII       NlaIII
         NlaIII    Cac8I   MwoI BssT1I BstDSI BstYI Bsp143I MnlI PaeI     CviJI
accatgatattcggcaagcaggcatcgccatggtcacgacgagatcctcgccgtcgggcatgctcgccttgagc   base pairs
tggtactataagccgttcgtccgtagcggtacccagtgctgctctaggagcggcagcccgtacgagcggaactcg 5401 to
                                                                           5475
       Hsp92II              SfaNI NcoI Bsp19I DpnII MflI AclWI Cac8I SphI   EcoRII
                              Eco130I DsaI Tsp45I MboI Kzo9I    Hsp92II
                               StyI BseDI Hsp92II NdeII DpnI     NspI MspR9I              Hin6I MvnI CviJI MwoI SapI NdeII  FokI Bsp143I Cfr10I
 BstNI                HinP1I CfoI SduI BanII MboII Sau3AI DpnII TthHB8I HpaII
   ScrFI    CviJI HhaI AspLEI BmyI SfaNI  DpnII DpnI MooI DpnI BsrFI HapII
ctggcgaacagttcggctggcgcgagcccctgatgctcttcgtccagatcatcctgatcgacaagaccggcttcc base pairs
gaccgcttgtcaagccgaccgcgctcggggactacgagaagcaggtctagtaggactagctgttctggccgaagg 5476 to
                                                                           5550
       MvaI          Cac8I AccII Cac8I Eco24I EarI MboI  BstF5I Kzo9I Bsel18I
 BstCI              HspAI BstUI Bsp1286I Eam1104I Bsp143I Sau3AI  BssAI MspI
 Bst2UI                ThaI Bsh1236I FriOI Ksp632I Kzo9I NdeII TaqI BsiSI CviJI AfaI    Bbv12I TaqI                              MspI MboI AclWI
         Csp6I   AspHI TthHB8I                             BsiSI Sau3AI
     BstF5I    SduI Alw21I          TthHB8I      BspMI DpnII DpnI  MwoI
atccgagtacgtgctcgctcgatgcgatgtttcgcttggtggtcgaatgggcaggtagccggatcaagcgtatgc base pairs
taggctcatgcacgagcgagctacgctacaaagcgaaccaccagcttacccgtccatcggcctagttcgcatacg 5551 to
                                                                           5625
       FokI MaeII Bsp1286I  SfaNI         TaqI         CviJI NdeII AlwI
         RsaI  BmyI BsiHKAI                             HpaII Bsp143I
          BsaAI Cac8I                                   HapII Kzo9I CviJI ItaI                                            MboI Bsp143I
 Fsp4HI AciI      CviJI                                   BstX2I DpnI
     Bst71I   BsrDI    NlaIII                    HphI     BstYI MflI
agccgccgcattgcatcagccatgatggatactttctcggcaggagcaaggtgagatgacaggagatcctgcccc base pairs
tcggcggcgtaacgtagtcggtactacctatgaaagagccgtcctcgttccactctactgtcctctaggacgggg 5626 to
```

FIG. 20 (Cont'd)

```
BsoFI BsoFI     SfaNI Hsp92II                                      DpnII XhoII
ItaI Fsp4HI                                                        NdeII Kzo9I
  BbvI                                                             Sau3AI AclWI

NciI ScrFI       BbvI   BsmFI              Tth111I  BmyI PvuII BsoFI FspI
BseDI HapII     ItaI Bse1I         Tsp45I AtsI      Bsp1286I MspA1I Hin6I
AlwI HpaII       BsoFI BsrSI        FauI Eco57I   TthHB8I Alw21I NspBII HspAI
ggcacttcgcccaatagcagccagtcccttcccgcttcagtgacaacgtcgagcacagctgcgcaaggaacgccc  base pairs
ccgtgaagcgggttatcgtcggtcagggaagggcgaagtcactgttgcagctcgtgtcgacgcgttccttgcggg  5701 to
                                                                              5775
BsaJI MspI       Fsp4HI BseNI     AciI  TspRI  TaqI    SduI BsiHKAI HinP1I
BsiSI MspR9I     CviJI BsrI       MaeIII MaeII    AspHI CviJI Fsp4HI AviII
  BcnI              Bst71I                AspI   Bbv12I AluI ItaI BbvI AspLEI PalI BalI   TtaI AccII HhaI ItaI          NlaIV BsiSI
  HhaI CfrI MluNI    CviJI ThaI AciI Fsp4HI        BshNI Bsp1286I
  Bst71I CviJI CviJI BsoFI Hin6I AspLEI MnlI       Eco64I BmyI HapII
gtcgtggccagccacgatagccgcgctgcctcgtcttgcagttcattcagggcaccggacaggtcggtcttgaca  base pairs
cagcaccggtcggtgctatcggcgcgacggagcagaacgtcaagtaagtcccgtggcctgtccagccagaactgt  5776 to
                                                                              5850
Acc16I EaeI MscI MwoI   HinP1I Bsh1236I BbvI       BanI SduI MspI
    MwoI BsuRI      Fsp4HI BstUI CfoI Bst71I       AccB1I BsaWI DrdI
  CfoI HaeIII Cac8I      HspAI MvnI BsoFI          PspN4I HpaII NciI KasI Hin1I HspAI EheI HaeII Hin6I HpaII Fsp4HI BbvI
       MspI MspR9I BbiII BsaHI HhaI BstH2I CfoI MspI BsoFI fsp4HI    BmyI
       BsiSI ScrFI Msp17I Hin6I CfoI BbeI HhaI BsiSI BsiYI BsoFI    SduI
aaaagaaccgggcgccctgcgctgacagccggaacacggcggcatcagagcagccgattgtctgttgtgcccag  base pairs
ttttcttggcccgcggggacgcgactgtcggccttgtgccgccgtagtctcgtcggctaacagacaacacgggtc  5851 to
                                                                              5925
        HpaII Eco64I Hsp92I NlaIV Bsp143II AspLEI HapII ItaI ItaI    Bsp1286I
        HapII BanI AccB1I NarI PspN4I HinP1I MwoI Bsc4I AciI CviJI
      BcnI BshNI HinP1I AcyI AspLEI HspAI CviJI BslI SfaNI Bst71I BseNI                     EagI Eco52I BsiSI BstMCI
                           CfrI EclXI BsuRI HapII
 BsrI         CviJI        EaeI XmaIII AciI MspI Cac8I            NlaIII
tcatagccgaatagcctctccacccaagcggccggagaacctgcgtgcaatccatcttgttcaatcatgcgaaac  base pairs
agtatcggcttatcggagaggtgggttcgccggcctcttggacgcacgttaggtagaacaagttagtacgctttg  5926 to
                                                                              6000
     CviJI          MnlI         BstZI ItaI PalI Bsh1285I                    Hsp92II
 BsrSI                           BsoFI HaeIII BsiEI BsaOI
 Bse1I                           Fsp4HI CviJI HpaII BspMI MboI DpnI AlwI     NdeII BanIII BscI DpnII CviJI BlnI MaeI AatI Sse8I
DpnII MamI Bse8I BsmAI Bsp143I BspXI ClaI Bsp143I BsaJI BfaI CviJI MnlI
  Bsp143I AclWI FokI MboI DpnI Bsp106I NdeII AvrII BssT1I StuI Eco147I
gatcctcatcctgtctcttgatcgatctttgcaaaagcctaggcctccaaaaaagcctcctcactacttctgaa  base pairs
ctaggagtaggacagagaactagctagaaacgttttcggatccggaggttttttcggaggagtgatgaagacctt  6001 to
                                                                              6075
```

FIG. 20 (Cont'd)

```
      Kzo9I Bsh1365I Alw26I Kzo9I Bsa29I BseCI Kzo9I StyI BseDI HaeIII CviJI
  NdeII BsaBI MnlI    DpnII TthH381 TaqI MboI DpnI Eco130I Pme55I BsuRI BseRI
  Sau3AI BsrBRI BstF5I Sau3AI BspDI Bsu15I Sau3AI ErhI EcoT14I PalI MnlI

BsuRI BglI CviJI BseDI                  BssT1I DsaI Bsc4I
    DdeI   PalI BseDI ItaI AciI PalI      Tsp509I  ErhI EcoT14I BsiYI
  CviJI  HaeIII MwoI PalI BsaJI BsuRI      Sse9I    CviJI BsaJI NlaIII
  tagctcagaggccgaggcggcctcggcctctgcataaataaaaaaaattagtcagccatggggcggagaatgggc base pairs
  atcgagtctccggctccgccggagccggagacgtatttattttttttaatcagtcggtaccccgcctcttacccg 6076 to
                                                                              6150
    AluI    CviJI SfiI Fsp4HI MnlI MnlI       TspEI      Eco130I Bsp19I AciI
     BstDEI MnlI  MnlI HaeIII HaeIII                      StyI BseDI Hsp92II
            BsaJI BsoFI BsuRI CviJI                       NcoI BstDSI Bs1I AciI         FokI                                      Cac8I
         Bse1I             MwoI              BsmFI       Tsp509I     Zsp2I
    AciI BsrSI         AciI    AciI      AciI         Ssc9I  Ppu10I
  ggaactgggcggagttaggggcgggatgggcggagttaggggcgggactatggttgctgactaattgagatgcat base pairs
  ccttgacccgcctcaatccccgccctacccgcctcaatccccgccctgataccaacgactgattaactctacgta 6151 to
                                                                              6225
       BseNI               FauI               FauI           TspEI    SfaNI
         BsrI              BstF5I                                     NsiI
                                                                      EcoT22I BbuI MwoI           BsaJI ScrFI       MspR9I                    Cac8I
       Hsp92II             CviJI MspR9I       BstNI        Tsp509I     Zsp2I
    Mph1103I    Cac8I    NlaIV BstNI BsmFI SexAI ScrFI    Sse9I  Ppu10I Mph11
  gctttgcatacttctgcctgctggggagcctggggacttccacacctggttgctgactaattgagatgcatgct base pairs
  cgaaacgtatgaagacggacgaccccctcggacccctgaaaggtgtggaccaacgactgattaactctacgtacga 6226 to
                                                                               6300
        PaeI SphI           PspN4I BstOI     EcoRII MvaI    TspEI      SfaNI
         NlaIII             EcoRII Bst2UI     BstCI                    NsiI
           NspI              BseDI MvaI       Bst2UI                   EcoT22I BbuI MwoI           BsaJI ScrFI                                MspA1I
       Hsp92II             CviJI MspR9I                                AluI
         03I     Cac8I    NlaIV BstNI BsmFI                            PvuII
  ttgcatacttctgcctgctggggagcctggggacttccacacctaactgacacacattccacagctggttctt base pairs
  aacgtatgaagacggacgaccccctcggacccctgaaaggtgtgggattgactgtgtgtaaggtgtcgaccaagaa 6301 to
                                                                               6375
    PaeI SphI              PspN4I BstOI                            CviJI
     NlaIII                EcoRII Bst2UI                           NspBII
      NspI                  BseDI MvaI CvnI MnlI   EarI                              NlaIII
       DdeI Bsu36I Eam1104I                         Alw26I BstD102I
         AciI AocI PleI       SspI                    BspHI   Acc3SI
  tccgcctcaggactcttcctttttcaatattattgaagcatttatcagggttattgtctcatgagcggatacata base pairs
  aggcggagtcctgagaaggaaaaagttataataacttcgtaaatagtcccaataacagagtactcgcctatgtat 6376 to
                                                                               6450
```

FIG. 20 (Cont'd)

```
        Eco81I HinfI                                               RcaI    BsrBI
     Bse21I    Ksp632I                                          BsmAI  AciI
     BstDEI    MboII                                               Hsp92II ThaI MvnI                        Hin6I
                                   HinP1I HhaI                         ThaI
                                NlaIV Hin6I AspLEI                     HinP1I
tttgaatgtatttagaaaaataaacaaatagggggttccgcgcacatttccccgaaaagtgccacctgacgcgccc base pairs
aaacttacataaatcttttatttgtttatccccaaggcgcgtgtaaaggggcttttcacggtggactgcgcggg 6451 to
6525
                                 PspN4I BstJI CfoI             HspAI
                                    HspAI Bsh1236I             AccII
                                    AccII AciI                 BstUI HhaI Bsc4I HinP1I Tru9I Hin6I CfoI AciI ThaI MvnI BsoFI Bst71I    HhaI MaeI
  MvnI SfcI Fsp4HI AspLEI HinP1I AspLEI FauI Hin6I CfoI BbvI        HspAI Bsp143II
    CfoI BslI ItaI HhaI MwoI ThaI Bsh1236I HinP1I HhaI ItaI AciI Cac8I CfoI BfaI
tgtagcggcgcattaagcgcggcggtgtggtggttacgcgcagcgtgaccgctacacttgccagcgccctagcg base pairs
acatcgccgcgtaattcgcgccgcccacaccaccaatgcgcgtcgcactggcgatgtgaacggtcgcgggatcgc 6526 to
6600
  Bsh1236I BsoFI AciI Tru1I AccII BsoFI MaeIII BstJI Fsp4HI MwoI   HinP1I BstH2I
  HgaI BstSFI HspAI CfoI HspAI BstUI ItaI HspAI Bsh1236I MaeIII    Hin6I HaeII
  AspLEI BsiYI Hin6I MseI HhaI MvnI Fsp4HI AccII AspLEI Tsp45I        AspLEI HinP1I Hin6I BstH2I MwoI                      BsrFI MspI NaeI
    CfoI FauI BstD102I                   BssAI BsiSI CviJI HhaI Cac8I BsrBI MboII        MaeII MroNI Cfr10I     CviJI
cccgctcctttcgctttcttcccttcctttctcgccacgttcgccggctttccccgtcaagctctaaatcggggg base pairs
gggcgaggaaagcgaaagaagggaaggaaagagcggtgcaagcggccgaaaggggcagttcgagatttagccccc 6601 to
6675
    AspLEI AciI                 MwoI Bse118I Cac8I   AluI
  HspAI HaeII AccBSI              NgoMI HpaII
    Bsp143II                      NgoAIV HapII Bsp1286I                   NlaIV
  PspN4I                     BshNI TaqI
CviJI Eco24I NlaIV           Eco64I MnlI                       HphI   MaeII
ctcccctttagggttccgatttagtgctttacggcacctcgaccccaaaaaacttgattagggtgatggttcacgt base pairs
gagggaaatcccaaggctaaatcacgaaatgccgtggagctggggttttttgaactaatcccactaccaagtgca 6676 to
6750
  NlaIV FriOI PspN4I           BanI TthHB8I                              BsaAI
    SduI BanII                 AccB1I
    BmyI                       PspN4I AspS9I
  DraIII CviJI                                                 Tru1I
    Cfr13I BsuRI              MaeII HinfI MaeII    Tru9I     HinfI
agtgggccatcgccctgatagacggttttttcgccctttgacgttggagtccacgttctttaatagtggactcttg base pairs
tcacccggtagcgggactatctgccaaaaagcgggaaactgcaacctcaggtgcaagaaattatcacctgagaac 6751 to
6825
```

FIG. 20 (Cont'd)

```
         Sau96I                              DrdI PleI     MseI       PleI
      AsuI PalI
         HaeIII

BseII              BsiYI                                    PalI
         BsrSI              Bsc4I                                    HaeIII
ttccaaactggaacaacactcaaccctatctcggtctattcttttgatttataagggattttgccgatttcggcc   base pairs
aaggtttgaccttgttgtgagttgggatagagccagataagaaaactaaatattccctaaaacggctaaagccgg   6826 to
                                                                              6900
         BseNI              BslI                                     CviJI
         BsrI                                                        BsuRI Tsp509I  BstUI Tsp509I
         TruII        TruII TspEI    AccII ApoI     MseI      Tsp509I
         Tru9I  CviJI Tru9I Sse9I    ThaI  AcsI MseI SspI     Sse9I
tattggttaaaaaaatgagctgatttaacaaaaattaacgcgaattttaacaaaatattaacgcttacaatttac   base pairs
ataaccaattttttactcgactaaattgttttaaattgcgcttaaaattgttttataattgcgaatgttaaatg    6901 to
                                                                              6975
         MseI   AluI  MseI  AcsI MseI MvnI TspEI    Tru9I      TspEI
                            ApoI TruII Sse9I Tru9I  TruII
                            Tru9I Bsh1236I TruII MspCI                                                       Tsp5
         Bst98I                              BsaMI                   TspEI
         BspTI MseI                  MaeI    BsmI                    Sse9I
gccttaagatacattgatgagtttggacaaaccacaactagaatgcagtgaaaaaaatgctttatttgtgaaatt   base pairs
cggaattctatgtaactactcaaacctgtttggtgttgatcttacgtcacttttttttacgaaataaacactttaa  6976 to
                                                                              7050
         AflII TruII                BfaI    Mva1269I                 AcsI
         Vha464I                             TspRI                   ApoI
         BfrI  Tru9I 09I                        ItaI     HincII Tsp509I
                           BsoFI    TruII  MunI     BsaMI
         SfaNI   MaeIII    CviJI    Tru9I  MfeI     BsmI
tgtgatgctattgctttatttgtaaccattataagctgcaataaacaagttaacaacaacaattgcattcatttt   base pairs
acactacgataacgaaataaacattggtaatattcgacgttatttgttcaattgttgttgttaacgtaagtaaaa   7051 to
                                                                              7125
                           AluI Bst71I    MseI      Sse9I    Mva1269I
                                Fsp4HI    HpaI      TspEI
                                BbvI      HindII TruII
                  MnlI MnlI Tru9I          MnlI              CviJI
atgtttcaggttcaggggggaggtgtgggaggttttttaaagcaagtaaaaacctctacaaatgtggtatggctgat  base pairs
tacaaagtccaagtcccccctccacaccctccaaaaaatttcgttcattttggagatgtttacaccataccgacta  7126 to
                                                                              7200
```

FIG. 20 (Cont'd)

```
                                        MseI
                                        DraI

Bse8I Sau3AI BfaI MvnI BsoFI Eco52I BsiEI Bsp1407I Hsp92II NciI AclWI Fsp4HI
   BsrBRI Bsp143I ThaI BstZI NotI HaeIII Bsh1285I CviJI MboI DpnI HpaII BscFI
    MamI NdeII XbaI AccII CfrI Fsp4HI CviJI BsaOI Csp6I NdeII Kzo9I MspI AlwI
tatgatctagagtcgcggccgcttacttgtacagctcgtccatgccgagagtgatcccggcggcggtcacgaac base pairs
atactagatctcagcgccggcgaaatgaacatgtcgagcaggtacggctctcactagggccgccgccagtgcttg 7201 to
7275
  BsaBI MboI MaeI BstUI CciNI XmaIII AciI AciI BsrGI AluI Sau3AI BcnI ScrFI
   Bsh1365I DpnI PleI Bsh1236I EclXI PalI BstMCI RsaI NlaIII BsiSI HapII Bsc4I
    DpnII Kzo9I HinfI EaeI EagI ItaI BsuRI SsoBI AfaI DpnII Bsp143I MspR9I ItaI MaeIII AsuI AspS9I Sau3AI Hin6I CfoI                   DdeI Bov12I
  AciI  SinI AvaII NdeII DpnI AccII AspLEI            BseII BmyI BsiHKAI
 BslI BpmI HgiEI NlaIII Kzo9I ThaI HhaI    DdeI    AciI BsrSI Bsp1286I
tccagcaggaccatgtgatcgcgcttctcgttggggtctttgctcagggcggactgggtgctcaggtagtggttg base pairs
aggtcgtcctggtacactagcgcgaagagcaaccccagaaacgagtcccgcctgacccacgagtccatcaccaac 7276 to
7350
 BsiYI  Cfr13I Eco47I MboI HspAI Bsh1236I BstDEI                BseNI AspHI
   Tsp45I Bme18I Hsp92II HinPlI MvnI                         BsrI SduI Alw21I
     GsuI Sau96I DpnII Bsp143I BstUI                              BstDEI Bst71I   NlaIV                                          Fsp4HI Fsp4HI
    ItaI     AsuI HaeIII                                        AluI Bst71I
    BsoFI    Cfr13I CviJI                                     Cac8I BbvI ItaI
tcgggcagcagcacggggccgtcgccgatgggggtgttctgctggtagtggtcggcgagctgcacgctgccgtcc base pairs
agcccgtcgtcgtgccccggcagcggctaccccacaagacgaccatcaccagccgctcgacgtgcgacggcagg 7351 to
7425
      Fsp4HI   Sau96I PalI                              CviJI Cac8I Bst71I
        BbvI    AspS9I BsuRI                              BsoFI  BsoFI
                PspN4I                                   ItaI BsgI BbvI MboI Bsp143I                             PalI
    TaqI     BstX2I AciI     HphI                 HaeIII
   TthHB8I    BstYI MflI AclWI MslI  SfaNI   MboII   EaeI    NlaIII MaeII
tcgatgttgtggcggatcttgaagttcaccttgatgccgttcttctgcttgtcggccatgatatagacgttgtgg base pairs
agctacaacaccgcctagaacttcaagtggaactacggcaagaagacgaacagccggtactatatctgcaacacc 7426 to
7500
           DpnII XhoII AlwI                       CfrI   Hsp92II
    MnlI    NdeII Kzo9I                            CviJI
            Sau3AI DpnI                            RsuRI BseDI Bst2UI                              TaqI
        AfaI  GsuI   BmyI BstCI FokI                      AluI
 CviJI  Csp6I CviJI   SduI BstNI BstF5I MnlI   TthHB8I   Eco57I
ctgttgtagttgtactccagcttgtgcccaggatgttgccgtcctccttgaagtcgatgcccttcagctcgatg base pairs
gacaacatcaacatgaggtcgaacacgggtcctacaacggcaggaggaacttcagctacgggaagtcgagctac 7501 to
7575
```

FIG. 20 (Cont'd)

```
         RsaI    AluI     Bsp1286I MvaI                    TaqI  SfaNI  CviJI
                 BpmI     BsaJI    MspR9I                                      TthHB8I

EcoRII   ScrFI

BstOI   MslI                      HinP1I MvnI AciI
         BseDI   ScrFI    MnlI              HphI  BslI HhaI  CfoI
SfaNI EcoRII Bst2UI       TthHB8I  BsaJI Bsc4I AccII FauI                MboII
cggttcaccagggtgtcgccctcgaacttcacctcggcgcgggtcttgtagttgccgtcgtccttgaagaagatg  base pairs
gccaagtggtcccacagcgggagcttgaagtggagccgcgcccagaacatcaacggcagcaggaacttcttctac  7576 to
                                                                              7650
  AciI  BsaJI  HphI    TaqI        BseDI  Hin6I  BstUI
        BstNI  MvaI                 MnlI  BsiYI  AspLEI
        MspR9I                            HspAI  ThaI  Bsh1236I AspLEI   ScrFI                               Bst71I
      Hin6I BstNI MvaI               AciI              ItaI               ItaI
      HinP1I BstOI MaeII    NlaIII         MboII     BsoFI   NlaIII      BsoFI
gtgcgctcctggacgtagccttcgggcatggcggacttgaagaagtcgtgctgcttcatgtggtcggggtagcgg  base pairs
cacgcgaggacctgcatcggaagcccgtaccgcctgaacttcttcagcacgacgaagtacaccagccccatcgcc  7651 to
                                                                              7725
  HspAI EcoRII     CviJI      Hsp92II               Fsp4HI  Hsp92II      Fsp4HI
        HhaI MspR9I                                 BbvI
        CfoI Bst2UI AciI                       Sau96I  EcoRII MvaI BsiYI ItaI  Cac8I
    MwoI       BsgI         BssSI HaeIII BstNI Bsc4I MwoI AluI BssAI
        Eco57I Cac8I         Tsp45I MslI Cfr13I BsuRI MspR9I SduI Fsp4HI BsrFI
ctgaagcactgcacgccgtaggtcagggtggtcacgagggtgggccagggcacgggcagcttgccggtggtgcag  base pairs
gacttcgtgacgtgcggcatccagtcccaccagtgctcccacccggtcccgtgcccgtcgaacggccaccacgtc  7726 to
                                                                              7800
         TspRI                MaeIII  BsiI AspS9I BsaJI Bst2UI BmyI CviJI Bse118I
CviJI                                  MnlI CviJI BseDI ScrFI Bsp1286I Bst71I
                                         AsuI PalI BstOI BslI BsoFI BbvI Cfr1

HpaII                                                     HapII           PalI
  MspI        AluI                                          HpaII           HaeIII
     HapII Eco57I Cac8I          SfaNI MnlI MnlI    MwoI    EaeI
atgaacttcagggtcagcttgccgtaggtggcatcgccctcgccctcgccggacacgctgaacttgtggccgttt  base pairs
tacttgaagtcccagtcgaacggcatcgccaccgtagcgggagcgggagcggcctgtgcgacttgaacaccggcaaa  7801 to
                                                                              7875
       BsgI          CviJI              Bcgl     BsiSI            CfrI
BsiSI                                            MspI             CviJI
 OI MwoI                                                          BsuRI MspR9I Eco64I Bsp1286I MspI  CviJI            NcoI BstDSI
            TthHB8I ScrFI BshNI BmyI MslI ScrFI  BseRI          StyI BseDI
 MaeII       CviJI  BstNI BstF5I SduI BsiSI HapII  MnlI         Eco130I HphI
acgtcgccgtccagctcgaccaggatgggcaccacccccggtgaacagctcctcgcccttgctcaccatggttgtg  base pairs
tgcagcggcaggtcgagctggtcctacccgtggtggggccacttgtcgaggagcgggaacgagtggtaccaacac  7876 to
                                                                              7950
```

FIG. 20 (Cont'd)

```
            AluI EcoRII MvaI AccB1I BsaJI BcnI HphI              ErhI EcoT14I
             TaqI BstOI FokI NlaIV BseDI HpaII AluI              BssT1I Bsp19I
                Bst2UI BanI PspN4I NciI MspR9I                   BsaJI DsaI

MslI HaeIII                             BsmFI      DraII PspN4I
 NlaIII PalI BalI                         BstDSI     AsuI NlaIV MaeI MseI
  BstXI BsuRI                 MaeII BsaJI BslI  Cfr13I HaeIII   Tru9I
gccatattatcatcgtgttttttcaaaggaaaaccacgtccccgtggttcgggggggcctagacgtttttttaacct  base pairs
cggtataatagtagcacaaaaagtttccttttggtgcaggggcaccaagccccccggatctgcaaaaaaattgga  7951 to
                                                                              8025
   EaeI CviJI                         BseDI BsiYI Sau96I CviJI MaeII
    CfrI MscI                          DsaI Bsc4I EcoO109I BsuRI TruII
 Hsp92II MluNI                                   AspS9I PalI BfaI NspI    VneI Bsp1286I Sau96I PalI NlaIV Bsp143I MflI AclWI BsiYI MnlI        NlaIII   Hsp92II Alw21I AsuI HaeIII NdeII DpnI BstX2I DpnI BslI
TthHB8I  BspLU11I     NlaIII BmyI BsaJI EcoO109I PspN4I BstYI Sau3AI AlwI
cgactaaacacatgtaaagcatgtgcaccgaggcccagatcagatcccatacaatggggtaccttctggcatc  base pairs
gctgatttgtgtacatttcgtacacgtggctccggggtctagtctagggtatgttacccccatggaagaccgtag  8026 to
                                                                              8100
TaqI      AflIII     Alw44I Bbv12I Cfr13I CviJI DpnII Kzo9I MboI XhoII AccB7I
            Hsp92II  NspI SduI BsiHKAI DraII MnlI MboI DpnII Bsp143I Bsc4I
                ApaLI AspHI BseDI AspS9I BsuRI Sau3AI NdeII Kzo9I PflMI Acc65I RsaI FokI
 Eco64I NlaIV SfaNI           CviJI
Esp1396I BshNI PspN4I    MnlI       HinfI                           MaeII
cttcagcccctkgttgaatacgcttgaggagagccatttgactctttccacaactatccaactcacaacgtggca  base pairs
gaagtcggggaacaacttatgcgaactcctctcggtaaactgagaaaggtgttgataggttgagtgttgcaccgt  8101 to
                                                                              8175
   Asp718I AflI Eco57I          BseRI      PleI                 DraIII
 Van91I Acc3lI BstF5I
   BanI Csp6I KpnI CviJI BsrI                             PmlI      PalI ItaI BshNI      MspR9I
   BseNI    ItaI MwoI              Eco72I   EaeI BsoFI Eco64I      BstOI
  TspRI   BsoFI      BspMI    AflIII BbrPI HaeIII MwoI NlaIV EcoRII MvaI
ctggggttgtgccgcctttgcaggtgtatcttatacacgtggcttttggccgcagaggcacctgtcgccaggtgg  base pairs
gaccccaacacggcggaaacgtccacatagaatatgtgcaccgaaaaccggcgtctccgtggacagcggtccacc  8176 to
                                                                              8250
   BsrSI  Fsp4HI                MaeII CviJI CviJI AciI AccB1I   BstNI
   BseII    AciI                 BsaAI  CfrI Fsp4HI BanI PspN4I ScrFI
                                   PmaCI    BsuRI BglI MnlI     Bst2UI
```

FIG. 20 (Cont'd)

```
         BsiYI    BsoFI    BslI                           MboII
    BslI PspN4I ItaI Bsc4I                          BbsI AluI              XmnI
       NlaIV AciI BbvI          SfcI  MaeII         BpuAI CviJI       MnlI
gggttccgctgcctgcaaagggtcgctacagacgttgtttgtcttcaagaagcttccagaggaactgcttcctt base pairs
cccccaaggcgacggacgtttcccagcgatgtctgcaacaaacagaagttcttcgaaggtctccttgacgaaggaa 8251 to
                                                                              8325
    Bsc4I    NspBII Bst71I     BstSFI             Bbv16II              Asp700I
            MspA1I Cac8I                          BpiI
         Fsp4HI   BsiYI                          HindIII BlnI BseDI             BpiI
                                   BsaMI         ErhI BsaJI BsaMI       Bbv16II
                                   BsmI    MnlI  AvrII MaeI Mva1269I    MboII
cacgacattcaacagaccttgcattcctttggcgagaggggaaagaccccctaggaatgctcgtcaagaagacagg base pairs
gtgctgtaagttgtctggaacgtaaggaaaccgctctccccttctggggatccttacgagcagttcttctgtcc 8326 to
                                                                              8400
              Mva1269I                           Eco130I   BsmI         BpuAI
                                                 StyI EcoT14I           BbsI
                                                 BssT1I BfaI            Cfr13I AspS9I BstNI MvaI BcnI Sau96I HaeIII BmyI ApaI BslI                 BsiSI
        CviJI MspR9I MspI Cfr13I Eco0109I Bsp1286I Bsc4I                Bse118I
    Sau96I EcoRII BsiSI MspR9I AspS9I PalI Eco24I BsrDI                 BssAI
gccaggtttccgggccctcacattgccaaaagacggcaatatggtggaaaataacatatagacaaacgcacaccg base pairs
cggtccaaaggcccgggagtgtaacggttttctgccgttataccaccttttattgtatatctgtttgcgtgtggc 8401 to
                                                                              8475
   HaeIII BstOI HpaII ScrFI AsuI CviJI SduI BanII             BsrFI
   AsuI BsuRI ScrFI NciI Bsp120I NlaIV PspN4I MnlI            Cfr1
       PalI Bst2JI HapII PspOMI DraII BsuRI FriOI BsiYI       HpaII CviJI      AciI  PalI BsrSI                    NdeII BstI NlaIV Eco88I
       BsuRI     ItaI MwoI BsuRI MaeII                DpnII MflI AciI PspAI
   MspI      BsoFI HaeI MaeIII Psp14061      MnlI MnlI Sau3AI Xzo9I BcoI
gccttattccaagcggcttcggccagtaacgttaggggggggggagggagaggggcggatcccgggcccgcggta base pairs
cggaataaggttcgccgaagccggtcattgcaatccccccccctccctctcccgcctagggcccgggcgccat  8476 to
                                                                              8550
   HapII    Fsp4HI HaeIII BsrI                    BstYI BamHI DpnI Cfr9I
   0I HaeIII  CviJI CviJI BseII                   BstX2I XhoII PspN4I
      PalI       Cfr1 BseNI                       MboI Bsp143I Ama87I XmaI MspI Cfr13I NlaIV SduI BsaJI DsaI MvnI FauI AciI Acc65I PspN4I SfcI
   BseDI HpaII SmaI AsuI HaeIII Eco24I BstDSI Bsh1236I Eco64I Csp6I SalI HindII
   AclWI BsoBI HapII Bsp12CI PalI Bsp1286I ApaI NspBII SstII BanI NlaIV TthHB8I
ccgtcgactgcagaattcactagtgattaaattatattgtcgactcatgagcacccacagcggtctactaccatg base pairs
ggcagctgacgtcttaagtgatcactaatttaatataacagctgagtactcgtgggtgtcgccagatgatggtac 8551 to
                                                                              8625
    AlwI BcnI PspALI AspS9I PspN4I BseDI ThaI MspA1I Cfr42I AccB1I KpnI HincII
    BsaJI NciI MspR9I Sau96I BsuRI Cac8I BanII BstUI Sfr303I Asp718I AfaI TaqI
    AvaI BsiSI ScrFI PspOMI CviJI BmyI FriOI AccII XspI SacII BshNI RsaI AccI
```

*FIG. 20 (Cont'd)*

```
      AcsI SpeI MseI TthHB8I PleI BmyI BsiHKAI StyI BseDI Hsp92II TruII PshBI
        TspEI BfaI Tsp509I HinfI SduI Bbv12I AccI BsaJI Bsp19I TspEI VspI TruII
     Sse9I AclNI TruII AccI BspHI Bsp1286I MspAlI BssT1I NlaIII ApoI AsnI MseI
  gctggaattttcccatatattatttgttctttgccattaaaatatagcatattaatgggagacatttttgtcgga base pairs
  cgaccttaaaagggtatataataaacaagaaacggtaattttatatcgtataattaccctctgtaaaaacagcct 8626 to
  8700
        EcoRI MaeI Sse9I TaqI RcaI AspHI MwoI AciI NcoI DsaI CviJI Tru9I Tru9I
      PstI ApoI Tru9I SalI HindII Hsp92II NspBII ErhI EcoT14I Sse9I MseI MslI Alw26I
    BstSFI Tsp509I TspEI HincII NlaIII Alw21I Eco130I BstDSI AcsI Tsp509I AseI DrdI  Bst71I DraII BsuRI Bsp1720I           Bsp1286I
     Fsp4HI Sau96I PalI CelII             ApaLI Bbv12I
       BsoFI Cfr13I CviJI DdeI CviJI        Alw44I Alw21I         AciI
  gtgcagcaagggcctgctgagcctctggggtttgcttggtgcacaagatgagtatgcggatatttttgtaaaaac base pairs
  cacgtcgttcccggacgactcggagaccccaaacgaaccacgtgttctactcatacgcctataaaaacattttg 8701 to
  8775
  BsmAI BbvI EcoO109I Cac8I BstDEI       VneI BmyI
      BsgI AsuI HaeIII BloI MnlI            SduI BsiHKAI
       ItaI MwoI AspS9I Bpu1102I            AspHI Tsp509I                  BsuRI                        BsmFI
     TspEI                    Tsp509I                      BseII  Bsc4I
     Sse9I         DdeI       Sse9I  HaeIII                BsrSI  BstF5I
  acaaattcacactctcctgagcagtaattggccttatatcttttgggtgcgataatccagtcccatccaaaggct base pairs
  tgtttaagtgtgagaggactcgtcattaaccggaatatagaaaacccacgctattaggtcagggtaggtttccga 8776 to
  8850
      AcsI         BstDEI  TspEI CviJI                    BseNI  FokI CviJI
      ApoI                       PalI                     BsrI   BslI
                                                                 BsiYI BstMCI MnlI           MspI MspR9I     Bbv12I
            BsiEI BsiYI    ItaI Bst71I BcnI BseDI AspHI
          TthHB8I Bsc4I    BsoFI BbvI NciI BsaJI  SduI BsiHKAI CviJI
  tcaaaatcgaccgtgaggggtagcggcagcaccgggattccgtggagtgctcatcgcagtcaagccccaaagtct base pairs
  agttttagctggcactcccccatcgccgtcgtggccctaaggcacctcacgagtagcgtcagttcgggtttcaga 8851 to
  8925
            TaqI        BslI    Fsp4HI  BsiSI ScrFI DsaI   Bsp1286I
                Bsh1285I          AciI  HpaII HinfI        BmyI
                BsaOI                   HapII TfiI BstDSI  Alw21I MspI MspR9I AsuI Psp5II MnlI                                MspR9I Bme18I
       BsiSI ScrFI HgiEI Eco47I Tsp45I                             BstNI Cfr13I
    Alw26I BcnI PpuMI DraII NlaIV HphI             HinfI CviJI    MboII ScrFI HgiEI
  ctccgggacctcttgggtgtgtctgtcaccttgacttctaaaaagggattcagcccatcttctcctggtcctggg base pairs
  gaggccctggagaacccacacagacagtggaactgaagattttccctaagtcgggtagaagaggaccaggaccc 8926 to
  9000
   BsmAI NciI Bme18I AvaII PspN4I                    TfiI            EcoRII MvaI
```

FIG. 20 (Cont'd)

```
        HpaII Cfr13I EcoO109I BsmFI                                      BstOI SinI
        HapII SinI Sau96I AspS9I MaeIII                                  Bst2UI Sau96I

AspS9I BstOI DpnII Kzo9I HaeIII FokI
    Eco47I BseDI MvaI Sau3AI NlaIII MluNI
       EcoRII MspR9I NdeII EaeI CviJI BalI AluI       DdeI    HinfI  CviJI MwoI
    aaggttacagcaagatcatggccattctcatccaaagctttgatttcaatgcctaagttggattcaggctgtttg base pairs
    ttccaatgtcgttctagtaccggtaagagtaggtttcgaaactaaagttacggattcaacctaagtccgacaaac 9001 to
                                                                                 9075
    AsuI BslI BsaJI ScrFI Bsp143I PalI MscI CviJI         BstDEI   TfiI
     AvaII BsiYI Bst2UI MooI CfrI BsuRI BstF5I
      Bsc4I BstNI MaeIII DpnI Hsp92II HindIII BpiI                    Bsc4I PflMI BstNI ScrFI
        TspEI             Bbv16II                 BseII BslI BsaJI MspR9I Bsp1286I
        Sse9I        TspRI                        BsrSI AlwNI Esp1396I SduI
    agccaattttgcaacactgtcttcacatcaatactctgccaaataccagtgcctgggctcatgtcaagtttcaga base pairs
    tcggttaaaacgttgtgacagaagtgtagttatgagacggtttatggtcacggacccgagtacagttcaaagtct 9076 to
                                                                                 9150
      CviJI              BpuAI                    BseNI AccB7I Van91I CviJI
        Tsp509I           BbsI                     BsrI EcoRII BseDI Bst2UI
                          MboII                     TspRI BsiYI BstOI MvaI BmyI FriOI DpnII DpnI BseNI                        BsmAI
         Bsp143I AccI  RsaI                        PleI
     BanII NdeII TfiI BseII        NlaIII    HinfI Alw26I              TspRI
    gatcggattccagtataccttgtaccgtctttcatgggtttgatgagtctcaggatttgcacaaacactgttgta base pairs
    ctagcctaaggtcatatggaacatggcagaaagtacccaaactactcagagtcctaaacgtgtttgtgacaacat 9151 to
                                                                                 9225
      NlaIII Sau3AI BsrSI  Csp6I          Hsp92II       DdeI
    Eco24I MboI Kzo9I BsrI AfaI                         BstDEI
      Hsp92II HinfI Bst1107I TspEI
                              BsiYI              AfaI                         Sse9I
        HinfI       DdeI      Bsc4I              Csp6I             CviJI
    ggagtcttgacgggtctgagatatatccacagttgggcttttactactttgttgtactgtatttagagctaaat base pairs
    cctcagaactgcccagactctatataggtgtcaacccgaaaatgatgaaacaacatgacataaaatctcgattta 9226 to
                                                                                 9300
         PleI      BstDEI       BslI                      RsaI         AluI Tsp509I
                                CviJI                                       AcsI
                                                                            ApoI BstSFI
         DraI               AciI            SfcI      MslI
      Tru9I      CviJI     BstF5I          HinfI     NlaIII
    ttaaaaaagcaacatttgggcttgccatccgcttgcattagaaagtcagactctgtaggcatggtaatgattgtt base pairs
    aattttttcgttgtaaacccgaacggtaggcgaacgtaatctttcagtctgagacatccgtaccattactaacaa 9301 to
                                                                                 9375
```

FIG. 20 (Cont'd)

```
              Cac8I   FokI                  AlwNI    Hsp92II
   MseI               Cac8I              PleI
   TruI
                                                Hsp92I  DpnII
                                              MnlI BsaHI AfaI Sau3AI
   BstDSI
   BsaJI              MboII  CviJI  MwoI      BstF5I Hin1I AcyI NdeII
   tccgtggtagcgtgataatcgtcatcttccaaagagccatcactgctgtcatccctctggacgtcgtactgatcg base pairs
   aggcaccatcgcactattagcagtagaaggtttctcggtagtgacgacagtagggagacctgcagcatgactagc 9376 to
                                                                              9450
   BscDI                                 TspRI    FokI    Msp17I RsaI  MboI
   DsaI                                                   BbiII AatII Bsp143I
                                                          MaeII Csp6I Kzo9I DpnI BspXI BseCI Kzo9I HpaII Hin6I HaeII
      Bsp106I ClaI Bsp143I MspR9I AspLEI
      TthH38I Bsu15I Sau3AI MspI HspAI CfoI         SfaNI          CviJI EcoRII
   atcagttcccggagtggaggcgctcttggcagaagttgtcttatagcatctttgctgatgttaggaggtgtttcc base pairs
   tagtcaagggcctcacctccgcgagaaccgtcttcaacagaatatcgtagaaacgactacaatcctcgacaaagg 9451 to
                                                                              9525
   BanIII BscI NdeII NciI HapII MnlI BstH2I                         AluI
      Bsa29I DpnII DpnI BcnI HinP1I Bsp143II
      BspDI TaqI MboI BsiSI ScrFI HhaI MwoI Bst2UI AspLEI AluI     TspEI              AfaI
   BstOI HspAI BsoFI DdeI AcsI                BpmI    BssSI         MslI
       MvaI CfoI BbvI   Sse9I      CviJI     Csp6I MnlI    Alw26I Ppu1
   aggcgcagcttactgaggatttgaattttatggcttctattctggagtacctcgtgttttgtctccacgcacat base pairs
   tccgcgtcgaatgactcctaaacttaaaaataccgaagataagacctcatggagcacaaaacagaggtgcgtgta 9526 to
                                                                              9600
   BstNI HinP1I CviJI BstDEI               GsuI    BsiI     BsmAI
   MspR9I HhaI Fsp4HI MnlI ApoI            RsaI
   ScrFI Hin6I ItaI Bst71I Tsp509I Zsp2I                                       MboI Bsp143I AsuI Bse1I
   Hsp92II                                        BstX2I DpnI Sau96I HaeIII
     01 EcoT22I   MnlI              MboII   TspRI   BstYI mflI AlwI BsrSI
   gcattacacagcccctcttttttccacattttcttctctctcactgccctcatttagatccactgggccagcagca base pairs
   cgtaatgtgtcgggagaaaaaggtgtaaaagaagagagagtgacgggagtaaatctaggtgaccggtcgtcgt 9601 to
                                                                              9675
   NlaIII   CviJI                         MnlI DpnII XhoII Cfr13I BsrI
   NspI Mph1103I                              NdeII Kzo9I TspRI BseNI
    NsiI                                      Sau3AI AclWI AspS9I BsoFI Hsp92II                           DpnII BamHI NlaIV AclWI
       Fsp4HI                                Hsp92II Sau3AI Kzo9I MspI
     PalI BbvI                     MwoI     SfaNI  BstYI Bsp143I BsiSI
   atcagcatgaacaggtaaatataaacatacatttgcagttttttgcatcatggctggatccgggcccataagagcg base pairs
   tagtcgtacttgtccatttatatttgtatgtaaacgtcaaaaacgtagtaccgacctaggcccgggtattctcgc 9676 to
                                                                              9750
```

FIG. 20 (Cont'd)

```
    BsuRI Bst71I                                       NlaIII NdeII XhoII HpaII
    Cac8I NlaIII                                        CviJI MboI BstI PspN4I
CviJI ItaI                                                  BstX2I MflI DpnI HapII

Cfr13I NlaIV SduI BanII Hsp92II     AccII AluI BfaI MboI Bsp143I Ac1WI BcoI
  MspR9I AsuI BsuRI FriOI RsaI   BfaI    ThaI  PvuII    BstX2I XhoII PspN4I
AlwI Bsp120I CviJI BmyI Csp6I   MaeI Cac8I HgaI MspA1I BstYI BamHI DpnI AlwI
taatctggaacatcgtatgggtacatggtgtctagctcgcgtcagctgactagaggatccccgggtaccgagctc  base pairs
attagaccttgtagcatacccatgtaccacagatcgagcgcagtcgactgatctcctaggggcccatggctcgag  9751 to
                                                                              9825
 BcnI Sau96I PalI Bsp1286I NlaIII   CviJI Bsh1236I MaeI DpnII MflI MnlI BseDI
NciI PspOMI HaeIII Eco24I AfaI      AluI MvnI CviJI   NdeII BstI NlaIV Ama87I
  ScrFI AspS9I PspN4I ApaI              BstUI NspBII  Sau3AI Kzo9I BsaJI PspAI BsoBI HapII BanI Csp6I Ecl136II Bbv12I BanII AcsI Cfr13I HaeIII BstDSI
Cfr9I NciI MspR9I Acc65I AfaI EcoICRI Eco24I Alw21I ApoI NlaIV BsuRI DsaI BstUI
  Eco88I HpaII Eco64I NlaIV CviJI Bsp1286I FriOI Sse9I Sau96I CviJI BseDI AccII
gaattcggggccgcggaggctggatcggtcccggtgtcttctatggaggtcaaaacagcgtggatggcgtctcca  base pairs
cttaagccccggcgcctccgacctagccagggccacagaagatacctccagttttgtcgcacctaccgcagaggt  9826 to
                                                                              9900
  AvaI BcnI PspALI BshNI RsaI AluI AspHI SacI SstI TspEI AspS9I BsoFI ItaI
    XmaI MspI SmaI AccB1I KpnI SduI BmyI TaqI BsiHKAI Tsp509I PalI Fsp4HI MvnI
    BsiSI ScrFI Asp718I PspN4I TthHB8I Psp124BI EcoRI AsuI PspN4I BsaJI ThaI MspA1I SacII MnlI Bsp143I AsuI Eco47I HpaII Bbv16II HinlI HgaI BstNI GsuI Sau3AI
     SstII BglI MboI AlwI Sau96I BsiSI HapII BbsI BstF5I AcyI BsmBI ScrFI MboI
       Sfr303I CviJI Kzo9I SinI AvaII NciI ScrFI MboII Msp17I EcoRII BstOI BpmI ggcgatctgacggttcactaaacgagctctgcttatataggcctcccaccgtacacgcctactcgacccgggtac  base pairs
ccgctagactgccaagtgatttgctcgagacgaatatatccggagggtggcatgtgcggatgagctgggcccatg  9901 to
                                                                              9975
NspBII Cfr42I DpnII DonI Bme18I NlaIV BcnI BsmFI MnlI BbiII Alw26I MspR9I NdeII
    KspI AciI NdeII AclWI HgiEI PspN4I MspR9I BpiI FokI BsaHI Eso3I MvaI DpnII
  Bsh1236I MwoI Sau3AI Cfr13I AspS9I MspI BpuAI MwoI Hsp92I BsmAI Bst2UI Bsp143I AluI BmyI SacI BsiHKAI Eco147I TaqI Eco88I NciI MspR9I BshNI RsaI AluI
     DpnI Bsp1286I BanII StuI PalI RsaI BcoI AvaI BsiSI PspALI AccB1I KpnI SduI
     Kzo9I SduI Eco24I SstI HaeIII MnlI Ama87I BseDI MspI SmaI Asp718I PspN4I
cgagctcgactttcacttttctctatcactgatagggagtggtaaactcgactttcacttttctctatcactgat  base pairs
gctcgagctgaaagtgaaaagagatagtgactatccctcaccatttgagctgaaagtgaaaagagatagtgacta  9976 to
                                                                              10050
       CviJI AspHI FriOI Pme55I SseBI TthHB8I BsaJI BcnI ScrFI Acc65I AfaI EcoICRI
     Ecl136II Bbv12I Alw21I CviJI Csp6I PsoAI XmaI HpaII Eco64I Csp6I Ecl136II
        EcoICRI Psp124BI AatI BsuRI AfaI Cfr9I Bso3I HapII BanI NlaIV CviJI AspHI SacI SstI TspRI
   Bbv12I BanII TthHB8I
Bsp1286I FriOI TspRI                    TspRI             TthHB8I
agggagtggtaaactcgactttcacttttctctatcactgatagggagtggtaaactcgactttcacttttctct  base pairs
tccctcaccatttgagctgaaagtgaaaagagatagtgactatccctcaccatttgagctgaaagtgaaaagaga  10051 to
                                                                              10125
```

FIG. 20 (Cont'd)

```
      Eco24I Alw21I TthHB8I                                      TaqI
   BmyI Psp124BI TaqI
TthHB8I TaqI BsiHKAI TaqI

TspRI          TthHB8I              TspRI          TthHB8I
atcactgatagggagtggtaaactcgactttcacttttctctatcactgatagggagtggtaaactcgactttca base pairs
tagtgactatccctcaccatttgagctgaaagtgaaaagagatagtgactatccctcaccatttgagctgaaagt 10126 to
                                                                             10200
                  TaqI                                             TaqI TspRI           TthHB8I             TspRI
cttttctctatcactgatagggagtggtaaactcgactttcacttttctctatcactgatagggagtggtaaa base pairs
gaaaagagatagtgactatccctcaccatttgagctgaaagtgaaaagagatagtgactatccctcaccattt 10201 to
                                                                          10273
                      TaqI
```

Table by Enzyme Name

| Enzyme name | No. cuts | Positions of sites | Recognition sequence |
|---|---|---|---|
| AatI | 3 | 234 6043 9941 | agg/cct |
| AatII | 2 | 3767 9439 | gacgt/c |
| Acc16I | 1 | 5762 | tgc/gca |
| Acc65I | 5 | 2509 8084 8547 9814 9971 | g/gtacc |
| AccB1I | 15 | 330 1328 1677 2509 2560 3741 5826 5861 6707 7903 8084 8232 8547 9814 9971 | g/gyrcc |
| AccB7I | 3 | 154 8079 9127 | ccannnn/ntgg |
| AccBSI | 5 | 1464 5200 5254 6443 6607 | gagcgg |
| AccI | 7 | 971 2150 2258 8554 8590 8614 | gt/mkac |

FIG. 20 (Cont'd)

```
                    9164
AccII      32       1880  2114  2124  2128  2218  2237        cg/cg
                    2248  2339  2853  3171  3252  3527
                    3828  3989  4570  4843  4912  4975
                    5059  5497  5798  6489  6520  6544
                    6564  6940  7215  7296  7614  8545
                    9789  9838
AciI       92       429   446   1216  1462  1639  1994  2079  ccgc
                    2115  2125  2204  2213  2219  2238
                    2415  2746  2787  2854  2893  2988
                    3031  3144  3204  3249  3253  3622
                    3684  3704  3777  3791  3803  3831
                    3899  3990  4018  4145  4164  4285
                    4395  4530  4539  4773  4846  4913
                    4978  5060  5126  5198  5254  5280
                    5296  5346  5351  5391  5631  5735
                    5799  5893  5956  6095  6141  6152
                    6162  6174  6183  6195  6380  6443
                    6490  6533  6547  6578  6605  7218
                    7222  7264  7327  7440  7578  7617
                    7684  7725  8190  8228  8260  8491
                    8533  8546  8613  8759  8877  9332
                    9839
AclNI      1        8569                                      a/ctagt
AclWI      26       403   650   1473  2504  3029  3214  3625  ggatc
                    4513  4587  4599  4684  4697  5056
                    5071  5448  5615  5694  6005  7258
                    7443  8073  8536  9660  9734  9809
                    9851
AcsI       15       75    666   1484  3417  3521  3532  6931  r/aatty
                    6942  7046  8563  8630  8778  9297
                    9548  9826
AcyI       8        1650  2187  3764  5081  5160  5862        gr/cgyc
                    9436  9892
AfaI       22       352   1788  2117  2131  2489  2511        gt/ac
                    2954  3236  3670  5558  7231  7513
                    8086  8549  9173  9280  9442  9574
                    9772  9816  9952  9973
AfeI       1        1897                                      agc/gct
AflII      2        3485  6978                                c/ttaag
AflIII     7        274   923   1878  2361  3942  8035  8210  a/crygt
AgeI       1        2512                                      a/ccggt
AluI       60       56    62    97    153   369   485   1021  ag/ct
                    1205  1219  1300  1344  1351  1454
                    1537  1591  1713  2009  2296  2545
                    2578  2650  2683  2899  2947  3058
                    3232  3382  3549  3615  3644  4110
```

FIG. 20 (Cont'd)

|         |    |                                              |           |
|---------|----|----------------------------------------------|-----------|
|         |    | 4200 4246 4503 5300 5758 6078                |           |
|         |    | 6366 6661 6918 7085 7235 7409                |           |
|         |    | 7520 7560 7784 7817 7889 7922                |           |
|         |    | 8303 9037 9294 9517 9533 9785                |           |
|         |    | 9795 9822 9926 9979                          |           |
| Alw21I  | 14 | 58 2298 3134 4260 5565 5755 7337             | gwgcw/c   |
|         |    | 8052 8603 8743 8902 9824 9928                |           |
|         |    | 9981                                         |           |
| Alw26I  | 12 | 624 847 904 4870 4998 6017 6435              | gtctc     |
|         |    | 8688 8926 9201 9591 9898                     |           |
| Alw44I  | 3  | 4256 8048 8739                               | g/tgcac   |
| AlwI    | 26 | 403 650 1473 2504 3029 3214 3625             | ggatc     |
|         |    | 4513 4587 4599 4684 4697 5056                |           |
|         |    | 5071 5448 5615 5694 6005 7258                |           |
|         |    | 7443 8073 8536 9660 9734 9809                |           |
|         |    | 9851                                         |           |
| AlwNI   | 6  | 682 1443 4358 4766 9127 9352                 | cagnnn/ctg|
| Ama87I  | 11 | 43 51 245 895 1332 1474 2383                 | c/ycgrg   |
|         |    | 2505 8536 9810 9967                          |           |
| AocI    | 2  | 4749 6381                                    | cc/tnagg  |
| Aor51HI | 1  | 1897                                         | agc/gct   |
| ApaI    | 4  | 1371 8416 8543 9740                          | gggcc/c   |
| ApaLI   | 3  | 4256 8048 8739                               | g/tgcac   |
| ApoI    | 15 | 75 666 1484 3417 3521 3532 6931              | r/aatty   |
|         |    | 6942 7046 8563 8630 8778 9297                |           |
|         |    | 9548 9826                                    |           |
| AseI    | 2  | 3879 8677                                    | at/taat   |
| AsnI    | 2  | 3879 8677                                    | at/taat   |
| Asp700I | 1  | 8317                                         | gaann/nnttc|
| Asp718I | 5  | 2509 8084 8547 9814 9971                     | g/gtacc   |
| AspHI   | 14 | 58 2298 3134 4260 5565 5755 7337             | qwgcw/c   |
|         |    | 8052 8603 8743 8902 9824 9928                |           |
|         |    | 9981                                         |           |
| AspI    | 2  | 840 5745                                     | gacn/nngtc|
| AspLEI  | 36 | 1529 1898 2126 2220 2250 2329                | gcg/c     |
|         |    | 2341 2426 2814 2855 3171 4122                |           |
|         |    | 4189 4289 4463 4572 4975 5061                |           |
|         |    | 5237 5497 5763 5800 5864 5872                |           |
|         |    | 6491 6522 6535 6544 6566 6592                |           |
|         |    | 6600 7298 7614 7655 9472 9530                |           |
| AspS9I  | 36 | 159 638 983 1138 1199 1312 1367              | g/gncc    |
|         |    | 2109 2161 2263 2387 2697 3098                |           |
|         |    | 3181 3802 4763 4796 4854 4900                |           |
|         |    | 5345 6754 7283 7366 7767 8003                |           |
|         |    | 8057 8399 8412 8539 8710 8931                |           |
|         |    | 8992 9664 9736 9833 9852                     |           |
| AsuI    | 36 | 159 638 983 1138 1199 1312 1367              | g/gncc    |
|         |    | 2109 2161 2263 2387 2697 3098                |           |
|         |    | 3181 3802 4763 4796 4854 4900                |           |

*FIG. 20 (Cont'd)*

|         |    |                                              |              |
|---------|----|----------------------------------------------|--------------|
|         |    | 5345 6754 7283 7366 7767 8003                |              |
|         |    | 8057 8399 8412 8539 8710 8931                |              |
|         |    | 8992 9664 9736 9833 9852                     |              |
| AtsI    | 2  | 840 5745                                     | gacn/nngtc   |
| AvaI    | 11 | 43 51 245 895 1332 1474 2383                 | c/ycgrg      |
|         |    | 2505 8536 9810 9967                          |              |
| AvaII   | 10 | 1312 2109 2387 3181 4900 5345                | g/gwcc       |
|         |    | 7283 8931 8992 9852                          |              |
| AviII   | 1  | 5762                                         | tgc/gca      |
| AvrII   | 5  | 180 650 5023 6038 8374                       | c/ctagg      |
| BalI    | 3  | 5782 7951 9021                               | tgg/cca      |
| BamHI   | 7  | 399 646 1469 2500 8532 9730 9805             | g/gatcc      |
| BanI    | 15 | 330 1328 1677 2509 2560 3741                 | g/gyrcc      |
|         |    | 5826 5861 6707 7903 8084 8232                |              |
|         |    | 8547 9814 9971                               |              |
| BanII   | 13 | 58 1371 2298 4793 5503 6677 8416             | grgcy/c      |
|         |    | 8543 9134 9740 9824 9928 9981                |              |
| BanIII  | 2  | 6022 9448                                    | at/cgat      |
| BbeI    | 1  | 5865                                         | ggcgc/c      |
| BbiII   | 8  | 1650 2187 3764 5081 5160 5862                | gr/cgyc      |
|         |    | 9436 9892                                    |              |
| BbrPI   | 1  | 8213                                         | cac/gtg      |
| BbsI    | 4  | 8297 8397 9099 9866                          | gaagac       |
| BbuI    | 5  | 729 2333 5463 6226 6298                      | gcatg/c      |
| Bbv12I  | 14 | 58 2298 3134 4260 5565 5755 7337             | gwgcw/c      |
|         |    | 8052 8603 8743 8902 9824 9928                |              |
|         |    | 9981                                         |              |
| Bbv16II | 4  | 8297 8397 9099 9866                          | gaagac       |
| BbvI    | 40 | 87 197 216 285 309 518 1025 1273             | gcagc        |
|         |    | 1304 1447 1541 1607 2687 2768                |              |
|         |    | 3052 3059 3110 3383 4288 4353                |              |
|         |    | 4562 4788 5241 5628 5721 5762                |              |
|         |    | 5804 5905 6570 7089 7359 7413                |              |
|         |    | 7420 7704 7785 8263 8707 8881                |              |
|         |    | 9534 9674                                    |              |
| BcgI    | 2  | 2637 7842                                    | cgannnnnntgc |
| BclI    | 2  | 2023 2067                                    | t/gatca      |
| BcnI    | 27 | 328 548 1191 1316 1333 1475 2177             | cc/sgg       |
|         |    | 2384 2391 2506 2554 3208 4322                |              |
|         |    | 5086 5699 5859 7258 7912 8411                |              |
|         |    | 8537 8884 8929 9459 9735 9811                |              |
|         |    | 9856 9968                                    |              |
| BcoI    | 11 | 43 51 245 895 1332 1474 2383                 | c/ycgrg      |
|         |    | 2505 8536 9810 9967                          |              |
| BfaI    | 28 | 166 181 208 651 690 962 1220                 | c/tag        |
|         |    | 1397 1464 1481 1497 1871 2342                |              |
|         |    | 3258 3452 3616 4437 4690 5024                |              |
|         |    | 6039 6595 7013 7207 8007 8375                |              |
|         |    | 8570 9782 9800                               |              |

*FIG. 20 (Cont'd)*

```
BfrI       2    3485 6978                                  c/ttaag
BglI       5    1266 3801 6092 8230 9841                   gccnnnn/nggc
BglII      1    47                                         a/gatct
BlnI       5    180 650 5023 6038 8374                     c/ctagg
BlpI       1    8717                                       gc/tnagc
Bme18I     10   1312 2109 2387 3181 4900 5345              g/gwcc
                7283 8931 8992 9852
BmyI       33   58 1326 1333 1371 1437 2298 2565           gdgch/c
                2694 2943 3134 4260 4793 5503
                5565 5755 5829 5922 6677 7337
                7528 7777 7906 8052 8416 8543
                8603 8743 8902 9134 9740 9824
                9928 9981
BpiI       4    8297 8397 9099 9866                        gaagac
BpmI       8    2953 3193 5046 5067 7280 7520              ctggag
                9573 9901
Bpu1102I   1    8717                                       gc/tnagc
Bpu14I     2    65 5180                                    tt/cgaa
BpuAI      4    8297 8397 9099 9866                        gaagac
Bsa29I     2    6022 9448                                  at/cgat
BsaAI      4    1153 5560 6748 8213                        yac/gtr
BsaBI      4    2352 3265 6005 7202                        gatnn/nnatc
BsaHI      8    1650 2187 3764 5081 5160 5862              gr/cgyc
                9436 9892
BsaI       1    4870                                       ggtctc
BsaJI      67   180 235 326 334 356 392 403 504            c/cnngg
                635 641 650 675 775 1141 1157
                1262 1284 1308 1315 1332 1375
                1428 1473 2029 2235 2284 2382
                2473 2504 2523 2553 2693 2721
                2856 2880 2935 4102 4792 4895
                5023 5428 5697 6038 6087 6096
                6131 6254 6326 7528 7583 7607
                7770 7910 7940 7991 8053 8374
                8536 8543 8621 8891 8995 9127
                9377 9809 9836 9967
BsaMI      6    3353 3452 7021 7120 8351 8384              gaatgc
BsaOI      7    2274 2517 3250 4282 5957 7219              cgry/cg
                8861
BsaWI      5    2512 4148 4295 4985 5829                   w/ccggw
Bsc4I      52   153 221 326 392 408 463 523 588            ccnnnn/nnngg
                640 779 1195 1278 1313 1375 1453
                1702 2196 2388 2511 2693 2720
                2856 3206 3841 3963 3981 4147
```

FIG. 20 (Cont'd)

| | | 4426 4779 4810 4861 4896 5027 | |
| | | 5060 5341 5885 6136 6528 6854 | |
| | | 7262 7612 7775 7996 8078 8248 | |
| | | 8268 8431 8843 8866 8994 9126 | |
| | | 9257 | |
| BscI | 2 | 6022 9448 | at/cgat |
| Bse118I | 8 | 2512 2675 5077 5360 5541 6643 | r/ccggy |
| | | 7788 8472 | |
| Bse1I | 19 | 527 665 824 1249 3140 4349 4362 | actgg |
| | | 4479 5725 5926 6158 6836 7332 | |
| | | 8179 8502 8836 9125 9164 9665 | |
| Bse21I | 2 | 4749 6381 | cc/tnagg |
| Bse8I | 4 | 2352 3265 6005 7202 | gatnn/nnatc |
| BseCI | 2 | 6022 9448 | at/cgat |
| BseDI | 67 | 180 235 326 334 356 392 403 504 | c/cnngg |
| | | 635 641 650 675 775 1141 1157 | |
| | | 1262 1284 1308 1315 1332 1375 | |
| | | 1428 1473 2029 2235 2284 2382 | |
| | | 2473 2504 2523 2553 2693 2721 | |
| | | 2856 2880 2935 4102 4792 4895 | |
| | | 5023 5428 5697 6038 6087 6096 | |
| | | 6131 6254 6326 7528 7583 7607 | |
| | | 7770 7910 7940 7991 8053 8374 | |
| | | 8536 8543 8621 8891 8995 9127 | |
| | | 9377 9809 9836 9967 | |
| BseNI | 19 | 527 665 824 1249 3140 4349 4362 | actgg |
| | | 4479 5725 5926 6158 6836 7332 | |
| | | 8179 8502 8836 9125 9164 9665 | |
| BsePI | 1 | 2124 | g/cgcgc |
| BseRI | 6 | 366 1420 2545 6062 7928 8131 | gaggag |
| BsgI | 10 | 524 1306 2039 2673 2734 3058 | gtgcag |
| | | 7415 7739 7800 8706 | |
| Bsh1236I | 32 | 1880 2114 2124 2128 2218 2237 | cg/cg |
| | | 2248 2339 2853 3171 3252 3527 | |
| | | 3828 3989 4570 4843 4912 4975 | |
| | | 5059 5497 5798 6489 6520 6544 | |
| | | 6564 6940 7215 7296 7614 8545 | |
| | | 9789 9838 | |
| Bsh1285I | 7 | 2274 2517 3250 4282 5957 7219 | cgry/cg |
| | | 8861 | |
| Bsh1365I | 4 | 2352 3265 6005 7202 | gatnn/nnatc |
| BshNI | 15 | 330 1328 1677 2509 2560 3741 | g/gyrcc |
| | | 5826 5861 6707 7903 8084 8232 | |
| | | 8547 9814 9971 | |
| BsiEI | 7 | 2274 2517 3250 4282 5957 7219 | cgry/cg |
| | | 8861 | |
| BsiHKAI | 14 | 58 2298 3134 4260 5565 5755 7337 | gwgcw/c |
| | | 8052 8603 8743 8902 9824 9928 | |
| | | 9981 | |
| BsiI | 6 | 2710 4120 5147 5273 7763 9582 | ctcgtg |

FIG. 20 (Cont'd)

```
BsiSI    45   328  547 1191 1315 1333 1475 2177   c/cgg
              2384 2390 2506 2513 2553 2616
              2676 3207 4149 4296 4322 4512
              4986 5078 5086 5361 5542 5609
              5699 5830 5858 5880 5957 6644
              7258 7789 7849 7912 8410 8473
              8537 8883 8928 9459 9734 9811
              9856 9968
BsiWI    1    2129                                 c/gtacg
BsiYI    52   154  222  327  393  409  464  524  589   ccnnnnn/nngg
              641  780 1196 1279 1314 1376 1454
              1703 2197 2389 2512 2694 2721
              2857 3207 3842 3964 3982 4148
              4427 4780 4811 4862 4897 5028
              5061 5342 5886 6137 6529 6855
              7263 7613 7776 7997 8079 8249
              8269 8432 8844 8867 8995 9127
              9258
BslI     52   154  222  327  393  409  464  524  589   ccnnnnn/nngg
              641  780 1196 1279 1314 1376 1454
              1703 2197 2389 2512 2694 2721
              2857 3207 3842 3964 3982 4148
              4427 4780 4811 4862 4897 5028
              5061 5342 5886 6137 6529 6855
              7263 7613 7776 7997 8079 8249
              8269 8432 8844 8867 8995 9127
              9258
BsmAI    12   624  847  904 4870 4998 6017 6435   gtctc
              8688 8926 9201 9591 9898
BsmBI    2    624 9898                             cgtctc
BsmFI    22   243  394 1112 1164 1212 1384 1481   gggac
              2243 2293 2374 3731 4903 5087
              5196 5728 6198 6262 6334 7991
              8839 8934 9857
BsmI     6    3353 3452 7021 7120 8351 8384       gaatgc
BsoBI    11   43   51  245  895 1332 1474 2383    c/ycgrg
              2505 8536 9810 9967
BsoFI    70   84  194  213  282  306  427  443  515   gc/ngc
              1022 1270 1301 1444 1459 1538
              1604 1991 2122 2211 2684 2743
              2765 3049 3056 3107 3204 3247
              3380 3987 4142 4285 4350 4559
              4770 4785 5124 5238 5252 5293
              5389 5625 5631 5718 5759 5796
              5801 5891 5902 5954 6093 6531
              6545 6567 7086 7216 7262 7356
              7410 7417 7701 7723 7782 8187
              8225 8260 8489 8704 8875 9531
              9671 9836
```

*FIG. 20 (Cont'd)*

| | | | |
|---|---|---|---|
| Bsp106I | 2 | 6022 9448 | at/cgat |
| Bsp119I | 2 | 65 5180 | tt/cgaa |
| Bsp120I | 4 | 1367 8412 8539 9736 | g/ggccc |
| Bsp1286I | 33 | 58 1326 1333 1371 1437 2298 2565 2694 2943 3134 4260 4793 5503 5565 5755 5829 5922 6677 7337 7528 7777 7906 8052 8416 8543 8603 8743 8902 9134 9740 9824 9928 9981 | gdgch/c |
| Bsp1407I | 3 | 350 3234 7229 | t/gtaca |
| Bsp143I | 48 | 47 89 399 646 1469 1933 2023 2067 2170 2353 2500 3024 3172 3210 3260 3621 4508 4583 4594 4602 4680 4692 5051 5067 5443 5521 5530 5611 5689 6000 6019 6023 7203 7253 7291 7439 8063 8068 8532 9013 9150 9445 9449 9655 9730 9805 9847 9903 | /gatc |
| Bsp143II | 7 | 1899 2427 4190 5865 6593 6601 9473 | rgcgc/y |
| Bsp1720I | 1 | 8717 | gc/tnagc |
| Bsp19I | 8 | 356 504 1284 2523 5428 6131 7940 8621 | c/catgg |
| BspDI | 2 | 6022 9448 | at/cgat |
| BspHI | 3 | 4662 6434 8595 | t/catga |
| BspLU11I | 5 | 274 923 2361 3942 8035 | a/catgt |
| BspMI | 6 | 306 450 5156 5606 5969 8200 | acctgc |
| BspTI | 2 | 3485 6978 | c/ttaag |
| BspXI | 2 | 6022 9448 | at/cgat |
| BsrBI | 5 | 1464 5200 5254 6443 6607 | gagcgg |
| BsrBRI | 4 | 2352 3265 6005 7202 | gatnn/nnatc |
| BsrDI | 5 | 1066 1075 1778 5639 8426 | gcaatg |
| BsrFI | 8 | 2512 2675 5077 5360 5541 6643 7788 8472 | r/ccggy |
| BsrGI | 3 | 350 3234 7229 | t/gtaca |
| BsrI | 19 | 527 665 824 1249 3140 4349 4362 4479 5725 5926 6158 6836 7332 8179 8502 8836 9125 9164 9665 | actgg |
| BsrSI | 19 | 527 665 824 1249 3140 4349 4362 4479 5725 5926 6158 6836 7332 8179 8502 8836 9125 9164 9665 | actgg |
| BssAI | 8 | 2512 2675 5077 5360 5541 6643 7788 8472 | r/ccggy |
| BssHII | 1 | 2124 | g/cgcgc |
| BssSI | 6 | 2710 4120 5147 5273 7763 9582 | ctcgtg |
| BssT1I | 17 | 180 356 504 650 775 1262 1284 2029 2473 2523 5023 5428 6038 6131 7940 8374 8621 | c/cwwgg |
| Bst1107I | 1 | 9165 | gta/tac |

*FIG. 20 (Cont'd)*

```
Bst2UI       47   236  255  335  394  404  636  642  677    cc/wgg
                  722  940  1036 1048 1142 1158 1309
                  1377 1393 1430 2285 2570 2695
                  2722 2807 2882 2936 3797 3970
                  4091 4104 4794 4897 5476 6255
                  6272 6327 7530 7584 7659 7771
                  7896 8244 8403 8990 8996 9128
                  9525 9899
Bst71I       40   87   197  216  285  309  518  1025 1273   gcagc
                  1304 1447 1541 1607 2687 2768
                  3052 3059 3110 3383 4288 4353
                  4562 4788 5241 5628 5721 5762
                  5804 5905 6570 7089 7359 7413
                  7420 7704 7785 8263 8707 8881
                  9534 9674
Bst98I       2    3485 6978                                 c/ttaag
BstBI        2    65 5180                                   tt/cgaa
BstD102I     5    1464 5200 5254 6443 6607                  gagcgg
BstDEI       33   93   98   310  341  420  438  785  904    c/tnag
                  929  1112 1225 1232 1362 1654
                  1763 1892 2302 3128 3146 4217
                  4626 4749 5198 6079 6381 7318
                  7336 8717 8792 9053 9199 9241
                  9538
BstDSI       14   356  504  1284 2235 2523 5428 6131        c/crygg
                  7940 7991 8543 8621 8891 9377
                  9836
BstF5I       17   189  2500 2570 2936 5075 5529             ggatg
                  5554 6011 6178 7536 7902 8101
                  8843 9033 9330 9429 9891
BstH2I       7    1899 2427 4190 5865 6593 6601             rgcgc/y
                  9473
BstI         7    399  646  1469 2500 8532 9730 9805        g/gatcc
BstMCI       7    2274 2517 3250 4282 5957 7219             cgry/cg
                  8861
BstNI        47   236  255  335  394  404  636  642  677    cc/wgg
                  722  940  1036 1048 1142 1158 1309
                  1377 1393 1430 2285 2570 2695
                  2722 2807 2882 2936 3797 3970
                  4091 4104 4794 4897 5476 6255
                  6272 6327 7530 7584 7659 7771
```

FIG. 20 (Cont'd)

|         |    |                                            |          |
|---------|----|--------------------------------------------|----------|
|         |    | 7896 8244 8403 8990 8996 9128              |          |
|         |    | 9525 9899                                  |          |
| BstOI   | 47 | 236 255 335 394 404 636 642 677            | cc/wgg   |
|         |    | 722 940 1036 1048 1142 1158 1309           |          |
|         |    | 1377 1393 1430 2285 2570 2695              |          |
|         |    | 2722 2807 2882 2936 3797 3970              |          |
|         |    | 4091 4104 4794 4897 5476 6255              |          |
|         |    | 6272 6327 7530 7584 7659 7771              |          |
|         |    | 7896 8244 8403 8990 8996 9128              |          |
|         |    | 9525 9899                                  |          |
| BstSFI  | 15 | 81 480 566 584 598 683 972 1408            | c/tryag  |
|         |    | 1806 4207 4398 6525 8277 8558              |          |
|         |    | 9353                                       |          |
| BstUI   | 32 | 1880 2114 2124 2128 2218 2237              | cg/cg    |
|         |    | 2248 2339 2853 3171 3252 3527              |          |
|         |    | 3828 3989 4570 4843 4912 4975              |          |
|         |    | 5059 5497 5798 6489 6520 6544              |          |
|         |    | 6564 6940 7215 7296 7614 8545              |          |
|         |    | 9789 9838                                  |          |
| BstX2I  | 20 | 47 399 646 1469 2500 3024 3621             | r/gatcy  |
|         |    | 4583 4594 4680 4692 5051 5443              |          |
|         |    | 5689 7439 8068 8532 9655 9730              |          |
|         |    | 9805                                       |          |
| BstXI   | 4  | 277 1291 1592 7947                         | ccannnnn/ntgg |
| BstYI   | 20 | 47 399 646 1469 2500 3024 3621             | r/gatcy  |
|         |    | 4583 4594 4680 4692 5051 5443              |          |
|         |    | 5689 7439 8068 8532 9655 9730              |          |
|         |    | 9805                                       |          |
| BstZI   | 3  | 3247 5954 7216                             | c/ggccg  |
| Bsu15I  | 2  | 6022 9448                                  | at/cgat  |
| Bsu36I  | 2  | 4749 6381                                  | cc/tnagg |
| BsuRI   | 61 | 161 234 429 640 934 984 1140               | gg/cc    |
|         |    | 1201 1283 1369 1458 1804 2058              |          |
|         |    | 2163 2264 2438 2598 2698 3014              |          |
|         |    | 3099 3249 3569 3804 3957 3968              |          |
|         |    | 3986 4420 4765 4798 4855 5364              |          |
|         |    | 5391 5782 5956 6043 6086 6095              |          |
|         |    | 6101 6756 6898 7218 7368 7480              |          |
|         |    | 7769 7869 7951 8005 8058 8224              |          |
|         |    | 8401 8414 8476 8497 8541 8712              |          |
|         |    | 8806 9021 9666 9738 9835 9941              |          |
| Cac8I   | 63 | 371 417 519 718 727 936 963 1087           | gcn/ngc  |
|         |    | 1120 1203 1217 1298 1305 1456              |          |
|         |    | 1638 1715 2043 2126 2165 2208              |          |
|         |    | 2331 2648 2681 2729 3053 3060              |          |
|         |    | 3617 3802 3959 3996 4556 4767              |          |
|         |    | 4789 4845 4892 5079 5362 5416              |          |
|         |    | 5461 5493 5499 5565 5784 5970              |          |
|         |    | 6224 6243 6296 6315 6588 6602              |          |

FIG. 20 (Cont'd)

|       |     |                                      |          |
|-------|-----|--------------------------------------|----------|
|       |     | 6645 7407 7414 7738 7786 7819        |          |
|       |     | 8264 8543 8714 9322 9333 9668        |          |
|       |     | 9787                                 |          |
| CciNI | 2   | 3247 7216                            | gc/ggccgc |
| CelII | 1   | 8717                                 | gc/tnagc |
| CfoI  | 36  | 1529 1898 2126 2220 2250 2329        | gcg/c    |
|       |     | 2341 2426 2814 2855 3171 4122        |          |
|       |     | 4189 4289 4463 4572 4975 5061        |          |
|       |     | 5237 5497 5763 5800 5864 5872        |          |
|       |     | 6491 6522 6535 6544 6566 6592        |          |
|       |     | 6600 7298 7614 7655 9472 9530        |          |
| Cfr10I | 8  | 2512 2675 5077 5360 5541 6643        | r/ccggy  |
|       |     | 7788 8472                            |          |
| Cfr13I | 36 | 159 638 983 1138 1199 1312 1367      | g/gncc   |
|       |     | 2109 2161 2263 2387 2697 3098        |          |
|       |     | 3181 3802 4763 4796 4854 4900        |          |
|       |     | 5345 6754 7283 7366 7767 8003        |          |
|       |     | 8057 8399 8412 8539 8710 8931        |          |
|       |     | 8992 9664 9736 9833 9852             |          |
| Cfr42I | 3  | 2238 8546 9839                       | ccgc/gg  |
| Cfr9I  | 7  | 1332 1474 2383 2505 8536 9810        | c/ccggg  |
|       |     | 9967                                 |          |
| CfrI  | 16  | 427 1456 2436 2596 3247 5362         | y/ggccr  |
|       |     | 5389 5780 5954 7216 7478 7867        |          |
|       |     | 7949 8222 8495 9019                  |          |
| ClaI  | 2   | 6022 9448                            | at/cgat  |
| CpoI  | 1   | 5345                                 | cg/gwccg |
| Csp45I | 2  | 65 5180                              | tt/cgaa  |
| Csp6I | 22  | 351 1787 2116 2130 2488 2510         | g/tac    |
|       |     | 2953 3235 3669 5557 7230 7512        |          |
|       |     | 8085 8548 9172 9279 9441 9573        |          |
|       |     | 9771 9815 9951 9972                  |          |
| CspI  | 1   | 5345                                 | cg/gwccg |
| CviJI | 231 | 56 62 86 97 112 153 161 169 196      | rg/cy    |
|       |     | 212 234 281 314 346 369 419 429      |          |
|       |     | 442 485 517 528 565 603 640 655      |          |
|       |     | 689 701 784 815 934 938 961 965      |          |
|       |     | 984 1021 1046 1089 1101 1122         |          |
|       |     | 1132 1140 1146 1201 1205 1219        |          |
|       |     | 1260 1272 1283 1291 1300 1344        |          |
|       |     | 1351 1369 1386 1396 1414 1443        |          |
|       |     | 1454 1458 1537 1591 1606 1640        |          |
|       |     | 1658 1713 1804 1844 2009 2041        |          |
|       |     | 2045 2058 2121 2163 2206 2213        |          |
|       |     | 2264 2283 2296 2438 2545 2578        |          |
|       |     | 2598 2650 2683 2698 2742 2799        |          |
|       |     | 2899 2947 2967 3014 3058 3099        |          |
|       |     | 3232 3249 3272 3382 3549 3569        |          |
|       |     | 3615 3644 3795 3804 3846 3957        |          |
|       |     | 3968 3986 4012 4110 4200 4246        |          |

FIG. 20 (Cont'd)

|  |  |  |  |  |  |  |  |
|---|---|---|---|---|---|---|---|
|  |  | 4251 | 4276 | 4355 | 4420 | 4431 | 4474 |
|  |  | 4503 | 4754 | 4765 | 4784 | 4791 | 4798 |
|  |  | 4855 | 4894 | 5016 | 5077 | 5104 | 5284 |
|  |  | 5300 | 5323 | 5360 | 5364 | 5391 | 5474 |
|  |  | 5491 | 5501 | 5545 | 5608 | 5627 | 5644 |
|  |  | 5720 | 5758 | 5782 | 5786 | 5795 | 5879 |
|  |  | 5904 | 5931 | 5939 | 5956 | 6037 | 6043 |
|  |  | 6055 | 6078 | 6086 | 6095 | 6101 | 6130 |
|  |  | 6253 | 6325 | 6366 | 6647 | 6661 | 6675 |
|  |  | 6756 | 6898 | 6918 | 7085 | 7195 | 7218 |
|  |  | 7235 | 7368 | 7409 | 7480 | 7500 | 7520 |
|  |  | 7568 | 7668 | 7725 | 7769 | 7784 | 7817 |
|  |  | 7869 | 7889 | 7922 | 7951 | 8005 | 8058 |
|  |  | 8106 | 8133 | 8217 | 8224 | 8303 | 8401 |
|  |  | 8414 | 8476 | 8491 | 8497 | 8541 | 8626 |
|  |  | 8712 | 8721 | 8806 | 8848 | 8915 | 8978 |
|  |  | 9021 | 9037 | 9068 | 9077 | 9132 | 9262 |
|  |  | 9294 | 9320 | 9411 | 9517 | 9533 | 9559 |
|  |  | 9611 | 9666 | 9727 | 9738 | 9785 | 9795 |
|  |  | 9822 | 9835 | 9844 | 9926 | 9941 | 9979 |
| CvnI | 2 | 4749 6381 |  |  |  |  | cc/tnagg |
| DdeI | 33 | 93 98 310 341 420 438 785 904 929 1112 1225 1232 1362 1654 1763 1892 2302 3128 3146 4217 4626 4749 5198 6079 6381 7318 7336 8717 8792 9053 9199 9241 9538 |  |  |  |  | c/tnag |
| DpnI | 48 | 49 91 401 648 1471 1935 2025 2069 2172 2355 2502 3026 3174 3212 3262 3623 4510 4585 4596 4604 4682 4694 5053 5069 5445 5523 5532 5613 5691 6002 6021 6025 7205 7255 7293 7441 8065 8070 8534 9015 9152 9447 9451 9657 9732 9807 9849 9905 |  |  |  |  | ga/tc |
| DpnII | 48 | 47 89 399 646 1469 1933 2023 2067 2170 2353 2500 3024 3172 3210 3260 3621 4508 4583 4594 4602 4680 4692 5051 5067 5443 5521 5530 5611 5689 6000 6019 6023 7203 7253 7291 7439 8063 8068 8532 9013 9150 9445 9449 9655 9730 9805 9847 9903 |  |  |  |  | /gatc |
| DraI | 6 | 1701 3305 4701 4720 7162 9302 |  |  |  |  | ttt/aaa |
| DraII | 9 | 983 1367 2161 4763 8003 8057 8413 8710 8931 |  |  |  |  | rg/gnccy |
| DraIII | 2 | 6751 8169 |  |  |  |  | cacnnn/gtg |
| DrdI | 4 | 4050 5839 6795 8692 |  |  |  |  | gacnnnn/nngtc |
| DsaI | 14 | 356 504 1284 2235 2523 5428 6131 7940 7991 8543 8621 8891 9377 |  |  |  |  | c/crygg |

*FIG. 20 (Cont'd)*

```
           9836
EaeI     16   427 1456 2436 2596 3247 5362    y/ggccr
              5389 5780 5954 7216 7478 7867
              7949 8222 8495 9019
EagI      3   3247 5954 7216                   c/ggccg
Eam1104I  4   2200 5306 5516 6393              ctcttc
EarI      4   2200 5306 5516 6393              ctcttc
Ecl136II  5   56 2296 9822 9926 9979           gag/ctc
EclXI     3   3247 5954 7216                   c/ggccg
Eco130I  17   180 356 504 650 775 1262 1284    c/cwwgg
              2029 2473 2523 5023 5428 6038
              6131 7940 8374 8621
Eco147I   3   234 6043 9941                    agg/cct
Eco24I   13   58 1371 2298 4793 5503 6677 8416 grgcy/c
              8543 9134 9740 9824 9928 9981
Eco31I    1   4870                             ggtctc
Eco47I   10   1312 2109 2387 3181 4900 5345    g/gwcc
              7283 8931 8992 9852
Eco47III  1   1897                             agc/gct
Eco52I    3   3247 5954 7216                   c/ggccg
Eco57I   10   2662 2742 2905 4474 5308 5740    ctgaag
              7568 7731 7811 8106
Eco64I   15   330 1328 1677 2509 2560 3741    g/gyrcc
              5826 5861 6707 7903 8084 8232
              8547 9814 9971
Eco72I    1   8213                             cac/gtg
Eco81I    2   4749 6381                        cc/tnagg
Eco88I   11   43 51 245 895 1332 1474 2383     c/ycgrg
              2505 8536 9810 9967
EcoICRI   5   56 2296 9822 9926 9979           gag/ctc
EcoNI     1   1701                             cctnn/nnnagg
Eco0109I  9   983 1367 2161 4763 8003 8057    rg/gnccy
              8413 8710 8931
EcoRI     4   75 1484 8563 9826                g/aattc
EcoRII   47   234 253 333 392 402 634 640 675  /ccwgg
              720 938 1034 1046 1140 1156 1307
              1375 1391 1428 2283 2568 2693
              2720 2805 2880 2934 3795 3968
              4089 4102 4792 4895 5474 6253
              6270 6325 7528 7582 7657 7769
```

FIG. 20 (Cont'd)

| | | | |
|---|---|---|---|
| | | 7894 8242 8401 8988 8994 9126 | |
| | | 9523 9897 | |
| EcoT14I | 17 | 180 356 504 650 775 1262 1284 | c/cwwgg |
| | | 2029 2473 2523 5023 5428 6038 | |
| | | 6131 7940 8374 8621 | |
| EcoT22I | 5 | 731 3893 6224 6296 9603 | atgca/t |
| EheI | 1 | 5863 | ggc/gcc |
| ErhI | 17 | 180 356 504 650 775 1262 1284 | c/cwwgg |
| | | 2029 2473 2523 5023 5428 6038 | |
| | | 6131 7940 8374 8621 | |
| Esp1396I | 3 | 154 8079 9127 | ccannnn/ntgg |
| Esp3I | 2 | 624 9898 | cgtctc |
| FauI | 20 | 1216 1640 2205 2238 2854 3684 | cccgc |
| | | 3778 3804 4847 4913 4979 5060 | |
| | | 5198 5735 6175 6196 6551 6605 | |
| | | 7618 8546 | |
| FauNDI | 1 | 2072 | ca/tatg |
| FbaI | 2 | 2023 2067 | t/gatca |
| FokI | 17 | 189 2500 2570 2936 5075 5529 | ggatg |
| | | 5554 6011 6178 7536 7902 8101 | |
| | | 8843 9033 9330 9429 9891 | |
| FriOI | 13 | 58 1371 2298 4793 5503 6677 8416 | grgcy/c |
| | | 8543 9134 9740 9824 9928 9981 | |
| Fsp4HI | 70 | 84 194 213 282 306 427 443 515 | gc/ngc |
| | | 1022 1270 1301 1444 1459 1538 | |
| | | 1604 1991 2122 2211 2684 2743 | |
| | | 2765 3049 3056 3107 3204 3247 | |
| | | 3380 3987 4142 4285 4350 4559 | |
| | | 4770 4785 5124 5238 5252 5293 | |
| | | 5389 5625 5631 5718 5759 5796 | |
| | | 5801 5891 5902 5954 6093 6531 | |
| | | 6545 6567 7086 7216 7262 7356 | |
| | | 7410 7417 7701 7723 7782 8187 | |
| | | 8225 8260 8489 8704 8875 9531 | |
| | | 9671 9836 | |
| FspI | 1 | 5762 | tgc/gca |
| GsuI | 8 | 2953 3193 5046 5067 7280 7520 | ctggag |
| | | 9573 9901 | |
| HaeII | 7 | 1899 2427 4190 5865 6593 6601 | rgcgc/y |
| | | 9473 | |
| HaeIII | 61 | 161 234 429 640 934 984 1140 | gg/cc |
| | | 1201 1283 1369 1458 1804 2058 | |
| | | 2163 2264 2438 2598 2698 3014 | |
| | | 3099 3249 3569 3804 3957 3968 | |
| | | 3986 4420 4765 4798 4855 5364 | |
| | | 5391 5782 5956 6043 6086 6095 | |
| | | 6101 6756 6898 7218 7368 7480 | |
| | | 7769 7869 7951 8005 8058 8224 | |
| | | 8401 8414 8476 8497 8541 8712 | |
| | | 8806 9021 9666 9738 9835 9941 | |

FIG. 20 (Cont'd)

```
HapII      45   328  547 1191 1315 1333 1475 2177   c/cgg
                2384 2390 2506 2513 2553 2616
                2676 3207 4149 4296 4322 4512
                4986 5078 5086 5361 5542 5609
                5699 5830 5858 5880 5957 6644
                7258 7789 7849 7912 8410 8473
                8537 8883 8928 9459 9734 9811
                9856 9968
HgaI       11  1653 2190 2340 3694 4048 4626        gacgc
                5085 5164 6521 9793 9896
HgiEI      10  1312 2109 2387 3181 4900 5345        g/gwcc
                7283 8931 8992 9852
HhaI       36  1529 1898 2126 2220 2250 2329        gcg/c
                2341 2426 2814 2855 3171 4122
                4189 4289 4463 4572 4975 5061
                5237 5497 5763 5800 5864 5872
                6491 6522 6535 6544 6566 6592
                6600 7298 7614 7655 9472 9530
Hin1I       8  1650 2187 3764 5081 5160 5862        gr/cgyc
                9436 9892
Hin6I      36  1527 1896 2124 2218 2248 2327        g/cgc
                2339 2424 2812 2853 3169 4120
                4187 4287 4461 4570 4973 5059
                5235 5495 5761 5798 5862 5870
                6489 6520 6533 6542 6564 6590
                6598 7296 7612 7653 9470 9528
HinP1I     36  1527 1896 2124 2218 2248 2327        g/cgc
                2339 2424 2812 2853 3169 4120
                4187 4287 4461 4570 4973 5059
                5235 5495 5761 5798 5862 5870
                6489 6520 6533 6542 6564 6590
                6598 7296 7612 7653 9470 9528
HincII      5  2259 3366 7101 8555 8591             gty/rac
HindII      5  2259 3366 7101 8555 8591             gty/rac
HindIII     4    60 1589 8301 9035                  a/agctt
HinfI      27   693 1162 1223 1554 2378 2408        g/antc
                3254 3917 4313 5095 5132 5190
                5242 5376 6386 6796 6818 7210
                8140 8592 8887 8972 9061 9156
                9195 9227 9349
HpaI        2  3366 7101                            gtt/aac
HpaII      45   328  547 1191 1315 1333 1475 2177   c/cgg
                2384 2390 2506 2513 2553 2616
                2676 3207 4149 4296 4322 4512
                4986 5078 5086 5361 5542 5609
                5699 5830 5858 5880 5957 6644
                7258 7789 7849 7912 8410 8473
                8537 8883 8928 9459 9734 9811
                9856 9968
HphI       21   321  411 1036 1054 1492 2030 2531   ggtga
```

FIG. 20 (Cont'd)

|          |    |                                           |          |
|----------|----|-------------------------------------------|----------|
|          |    | 2554 2864 2888 2986 4690 4806             |          |
|          |    | 5679 6740 7455 7584 7608 7918             |          |
|          |    | 7941 8955                                 |          |
| Hsp92I   | 8  | 1650 2187 3764 5081 5160 5862             | gr/cgyc  |
|          |    | 9436 9892                                 |          |
| Hsp92II  | 51 | 221 278 360 508 729 733 806 927           | catg/    |
|          |    | 1043 1187 1288 1495 1625 2333             |          |
|          |    | 2365 2527 2761 2791 3181 3226             |          |
|          |    | 3895 3946 4666 5050 5406 5432             |          |
|          |    | 5463 5649 5994 6135 6226 6298             |          |
|          |    | 6438 7245 7290 7485 7680 7710             |          |
|          |    | 7944 8039 8048 8599 8625 9020             |          |
|          |    | 9138 9186 9363 9601 9684 9726             |          |
|          |    | 9777                                      |          |
| HspAI    | 36 | 1527 1896 2124 2218 2248 2327             | g/cgc    |
|          |    | 2339 2424 2812 2853 3169 4120             |          |
|          |    | 4187 4287 4461 4570 4973 5059             |          |
|          |    | 5235 5495 5761 5798 5862 5870             |          |
|          |    | 6489 6520 6533 6542 6564 6590             |          |
|          |    | 6598 7296 7612 7653 9470 9528             |          |
| ItaI     | 70 | 84 194 213 282 306 427 443 515            | gc/ngc   |
|          |    | 1022 1270 1301 1444 1459 1538             |          |
|          |    | 1604 1991 2122 2211 2684 2743             |          |
|          |    | 2765 3049 3056 3107 3204 3247             |          |
|          |    | 3380 3987 4142 4285 4350 4559             |          |
|          |    | 4770 4785 5124 5238 5252 5293             |          |
|          |    | 5389 5625 5631 5718 5759 5796             |          |
|          |    | 5801 5891 5902 5954 6093 6531             |          |
|          |    | 6545 6567 7086 7216 7262 7356             |          |
|          |    | 7410 7417 7701 7723 7782 8187             |          |
|          |    | 8225 8260 8489 8704 8875 9531             |          |
|          |    | 9671 9836                                 |          |
| KasI     | 1  | 5861                                      | g/gcgcc  |
| KpnI     | 5  | 2513 8088 8551 9818 9975                  | ggtac/c  |
| Ksp22I   | 2  | 2023 2067                                 | t/gatca  |
| Ksp632I  | 4  | 2200 5306 5516 6393                       | ctcttc   |
| KspI     | 3  | 2238 8546 9839                            | ccgc/gg  |
| Kzo9I    | 48 | 47 89 399 646 1469 1933 2023              | /gatc    |
|          |    | 2067 2170 2353 2500 3024 3172             |          |
|          |    | 3210 3260 3621 4508 4583 4594             |          |
|          |    | 4602 4680 4692 5051 5067 5443             |          |
|          |    | 5521 5530 5611 5689 6000 6019             |          |
|          |    | 6023 7203 7253 7291 7439 8063             |          |
|          |    | 8068 8532 9013 9150 9445 9449             |          |
|          |    | 9655 9730 9805 9847 9903                  |          |
| LspI     | 2  | 65 5180                                   | tt/cgaa  |
| MaeI     | 28 | 166 181 208 651 690 962 1220              | c/tag    |
|          |    | 1397 1464 1481 1497 1871 2342             |          |
|          |    | 3258 3452 3616 4437 4690 5024             |          |
|          |    | 6039 6595 7013 7207 8007 8375             |          |

FIG. 20 (Cont'd)

```
MaeII     24   8570 9782 9800                           a/cgt
               1152 2316 2589 2802 2973 3764
               4645 4778 5559 5746 6637 6747
               6790 6802 7492 7663 7876 7985
               8011 8168 8212 8283 8504 9436
MaeIII    22   694 919 1124 1399 2707 3196 3391         /gtnac
               3822 4298 4361 4477 4743 5433
               5739 6558 6570 7071 7266 7755
               8500 8949 9003
MamI      4    2352 3265 6005 7202                      gatnn/nnatc
MboI      48   47 89 399 646 1469 1933 2023             /gatc
               2067 2170 2353 2500 3024 3172
               3210 3260 3621 4508 4583 4594
               4602 4680 4692 5051 5067 5443
               5521 5530 5611 5689 6000 6019
               6023 7203 7253 7291 7439 8063
               8068 8532 9013 9150 9445 9449
               9655 9730 9805 9847 9903
MboII     25   1935 1962 2199 2779 2824 3002            gaaga
               4596 4687 4839 5039 5206 5306
               5516 6393 6621 7470 7645 7693
               8297 8396 8987 9099 9404 9635
               9866
MfeI      2    3353 7110                                c/aattg
MflI      20   47 399 646 1469 2500 3024 3621           r/gatcy
               4583 4594 4680 4692 5051 5443
               5689 7439 8068 8532 9655 9730
               9805
MluI      1    1878                                     a/cgcgt
MluNI     3    5782 7951 9021                           tgg/cca
MnlI      87   103 177 229 318 364 413 425 440          cctc
               745 790 909 915 934 1082 1117
               1375 1392 1420 1470 1550 2162
               2201 2315 2543 2624 2630 2707
               2861 2873 2924 3044 3292 3315
               3324 3663 4060 4117 4384 4754
               5020 5068 5274 5450 5807 5943
               6007 6047 6059 6086 6092 6099
               6105 6383 6714 7147 7156 7179
               7427 7547 7598 7610 7764 7841
               7847 7928 8026 8058 8129 8233
               8313 8364 8419 8522 8528 8725
               8868 8937 9432 9470 9543 9579
               9617 9650 9806 9844 9874 9945
Mph1103I  5    731 3893 6224 6296 9603                  atgca/t
MroNI     3    5077 5360 6643                           g/ccggc
MscI      3    5782 7951 9021                           tgg/cca
MseI      35   265 864 1521 1542 1565 1700 2094         t/taa
               3304 3365 3486 3507 3518 3530
               3541 3558 3879 4648 4700 4705
```

*FIG. 20 (Cont'd)*

| | | | |
|---|---|---|---|
| | | 4719 6538 6809 6907 6924 6935 | |
| | | 6947 6958 6979 7100 7161 8019 | |
| | | 8577 8662 8677 9301 | |
| MslI | 17 | 328 1664 1773 2031 2525 2555 | caynn/nnrtg |
| | | 2705 2882 5427 7456 7585 7762 | |
| | | 7912 7945 8677 9364 9596 | |
| Msp17I | 8 | 1650 2187 3764 5081 5160 5862 | gr/cgyc |
| | | 9436 9892 | |
| MspA1I | 13 | 97 1021 1205 2237 4284 4529 5758 | cmg/ckg |
| | | 6366 8259 8545 8610 9795 9838 | |
| MspCI | 2 | 3485 6978 | c/ttaag |
| MspI | 45 | 328 547 1191 1315 1333 1475 2177 | c/cgg |
| | | 2384 2390 2506 2513 2553 2616 | |
| | | 2676 3207 4149 4296 4322 4512 | |
| | | 4986 5078 5086 5361 5542 5609 | |
| | | 5699 5830 5858 5880 5957 6644 | |
| | | 7258 7789 7849 7912 8410 8473 | |
| | | 8537 8883 8928 9459 9734 9811 | |
| | | 9856 9968 | |
| MspR9I | 74 | 236 255 328 335 394 404 548 636 | cc/ngg |
| | | 642 677 722 940 1036 1048 1142 | |
| | | 1158 1191 1309 1316 1333 1377 | |
| | | 1393 1430 1475 2177 2285 2384 | |
| | | 2391 2506 2554 2570 2695 2722 | |
| | | 2807 2882 2936 3208 3797 3970 | |
| | | 4091 4104 4322 4794 4897 5086 | |
| | | 5476 5699 5859 6255 6272 6327 | |
| | | 7258 7530 7584 7659 7771 7896 | |
| | | 7912 8244 8403 8411 8537 8884 | |
| | | 8929 8990 8996 9128 9459 9525 | |
| | | 9735 9811 9856 9899 9968 | |
| MunI | 2 | 3353 7110 | c/aattg |
| Mva1269I | 6 | 3353 3452 7021 7120 8351 8384 | gaatgc |
| MvaI | 47 | 236 255 335 394 404 636 642 677 | cc/wgg |
| | | 722 940 1036 1048 1142 1158 1309 | |
| | | 1377 1393 1430 2285 2570 2695 | |
| | | 2722 2807 2882 2936 3797 3970 | |
| | | 4091 4104 4794 4897 5476 6255 | |
| | | 6272 6327 7530 7584 7659 7771 | |
| | | 7896 8244 8403 8990 8996 9128 | |
| | | 9525 9899 | |
| MvnI | 32 | 1880 2114 2124 2128 2218 2237 | cg/cg |
| | | 2248 2339 2853 3171 3252 3527 | |
| | | 3828 3989 4570 4843 4912 4975 | |
| | | 5059 5497 5798 6489 6520 6544 | |
| | | 6564 6940 7215 7296 7614 8545 | |
| | | 9789 9838 | |
| MwoI | 53 | 311 482 600 722 807 1027 1052 | gcnnnnn/nngc |
| | | 1067 1266 1297 1642 1886 2042 | |

*FIG. 20 (Cont'd)*

|       |    |                                              |          |
|-------|----|----------------------------------------------|----------|
|       |    | 2207 2616 2676 2689 2733 3801                |          |
|       |    | 3995 4567 4766 4970 5157 5424                |          |
|       |    | 5507 5624 5769 5792 5876 6092                |          |
|       |    | 6177 6228 6300 6539 6583 6610                |          |
|       |    | 6640 7728 7781 7794 7854 8192                |          |
|       |    | 8230 8494 8607 8709 9074 9417                |          |
|       |    | 9476 9716 9841 9889                          |          |
| NaeI  | 3  | 5079 5362 6645                               | gcc/ggc  |
| NarI  | 1  | 5862                                         | gg/cgcc  |
| NciI  | 27 | 328 548 1191 1316 1333 1475 2177             | cc/sgg   |
|       |    | 2384 2391 2506 2554 3208 4322                |          |
|       |    | 5086 5699 5859 7258 7912 8411                |          |
|       |    | 8537 8884 8929 9459 9735 9811                |          |
|       |    | 9856 9968                                    |          |
| NcoI  | 8  | 356 504 1284 2523 5428 6131 7940             | c/catgg  |
|       |    | 8621                                         |          |
| NdeI  | 1  | 2072                                         | ca/tatg  |
| NdeII | 48 | 47 89 399 646 1469 1933 2023                 | /gatc    |
|       |    | 2067 2170 2353 2500 3024 3172                |          |
|       |    | 3210 3260 3621 4508 4583 4594                |          |
|       |    | 4602 4680 4692 5051 5067 5443                |          |
|       |    | 5521 5530 5611 5689 6000 6019                |          |
|       |    | 6023 7203 7253 7291 7439 8063                |          |
|       |    | 8068 8532 9013 9150 9445 9449                |          |
|       |    | 9655 9730 9805 9847 9903                     |          |
| NgoAIV| 3  | 5077 5360 6643                               | g/ccggc  |
| NgoMI | 3  | 5077 5360 6643                               | g/ccggc  |
| NheI  | 2  | 961 3615                                     | g/ctagc  |
| NlaIII| 51 | 221 278 360 508 729 733 806 927              | catg/    |
|       |    | 1043 1187 1288 1495 1625 2333                |          |
|       |    | 2365 2527 2761 2791 3181 3226                |          |
|       |    | 3895 3946 4666 5050 5406 5432                |          |
|       |    | 5463 5649 5994 6135 6226 6298                |          |
|       |    | 6438 7245 7290 7485 7680 7710                |          |
|       |    | 7944 8039 8048 8599 8625 9020                |          |
|       |    | 9138 9186 9363 9601 9684 9726                |          |
|       |    | 9777                                         |          |
| NlaIV | 55 | 113 160 332 401 648 702 1139                 | ggn/ncc  |
|       |    | 1243 1313 1330 1368 1415 1471                |          |
|       |    | 1679 2110 2214 2265 2388 2502                |          |
|       |    | 2511 2562 3100 3743 3974 4013                |          |
|       |    | 4856 4901 4980 5828 5863 6252                |          |
|       |    | 6324 6485 6676 6688 6709 7367                |          |
|       |    | 7905 8004 8059 8086 8234 8255                |          |
|       |    | 8414 8534 8541 8549 8932 9732                |          |
|       |    | 9738 9807 9816 9834 9854 9973                |          |
| NotI  | 2  | 3247 7216                                    | gc/ggccgc|
| NsiI  | 5  | 731 3893 6224 6296 9603                      | atgca/t  |
| NspBII| 13 | 97 1021 1205 2237 4284 4529 5758             | cmg/ckg  |
|       |    | 6366 8259 8545 8610 9795 9838                |          |

FIG. 20 (Cont'd)

```
NspI      13  278  729  927 1625 2333 2365 3946    rcatg/y
              5463 6226 6298 8039 8048 9601
NspV       2   65 5180                              tt/cgaa
PaeI       5  729 2333 5463 6226 6298               gcatg/c
PaeR7I     2   43   51                              c/tcgag
PalI      61  161  234  429  640  934  984 1140    gg/cc
             1201 1283 1369 1458 1804 2058
             2163 2264 2438 2598 2698 3014
             3099 3249 3569 3804 3957 3968
             3986 4420 4765 4798 4855 5364
             5391 5782 5956 6043 6086 6095
             6101 6756 6898 7218 7368 7480
             7769 7869 7951 8005 8058 8224
             8401 8414 8476 8497 8541 8712
             8806 9021 9666 9738 9835 9941
Pfl23II    1 2129                                   c/gtacg
PflMI      3  154 8079 9127                         ccannnn/ntgg
PinAI      1 2512                                   a/ccggt
PleI      16  697 1166 1227 2412 3258 4317          gagtc
             5194 6390 6800 6822 7214 8144
             8596 9199 9231 9353
PmaCI      1 8213                                   cac/gtg
Pmc55I     3  234 6043 9941                         agg/cct
PmlI       1 8213                                   cac/gtg
Ppu10I     5  727 3889 6220 6292 9599               a/tgcat
PpuMI      1 8931                                   rg/gwccy
PshAI      1 2276                                   gacnn/nngtc
PshBI      2 3879 8677                              at/taat
Psp124BI   5   58 2298 9824 9928 9981               gagct/c
Psp1406I   1 8504                                   aa/cgtt
Psp5II     1 8931                                   rg/gwccy
PspAI      7 1332 1474 2383 2505 8536 9810          c/ccggg
             9967
PspALI     7 1334 1476 2385 2507 8538 9812          ccc/ggg
             9969
PspLI      1 2129                                   c/gtacg
PspN4I    55  113  160  332  401  648  702 1139    ggn/ncc
             1243 1313 1330 1368 1415 1471
             1679 2110 2214 2265 2388 2502
             2511 2562 3100 3743 3974 4013
             4856 4901 4980 5828 5863 6252
             6324 6485 6676 6688 6709 7367
             7905 8004 8059 8086 8234 8255
             8414 8534 8541 8549 8932 9732
             9738 9807 9816 9834 9854 9973
PspOMI     4 1367 8412 8539 9736                    g/ggccc
PstI       2   85 8562                              ctgca/g
PstNHI     2  961 3615                              g/ctagc
PvuII      6   97 1021 1205 5758 6366 9795          cag/ctg
RcaI       3 4662 6434 8595                         t/catga8
```

*FIG. 20 (Cont'd)*

```
RsaI      22   352  1788 2117 2131 2489 2511    gt/ac
               2954 3236 3670 5558 7231 7513
               8086 8549 9173 9280 9442 9574
               9772 9816 9952 9973
RsrII     1    5345                              cg/gwccg
SacI      5    58 2298 9824 9928 9981            gagct/c
SacII     3    2238 8546 9839                    ccgc/gg
SalI      3    2257 8553 8589                    g/tcgac
SapI      2    5306 5516                         gctcttc
Sau3AI    48   47 89 399 646 1469 1933 2023      /gatc
               2067 2170 2353 2500 3024 3172
               3210 3260 3621 4508 4583 4594
               4602 4680 4692 5051 5067 5443
               5521 5530 5611 5689 6000 6019
               6023 7203 7253 7291 7439 8063
               8068 8532 9013 9150 9445 9449
               9655 9730 9805 9847 9903
Sau96I    36   159 638 983 1138 1199 1312 1367   g/gncc
               2109 2161 2263 2387 2697 3098
               3181 3802 4763 4796 4854 4900
               5345 6754 7283 7366 7767 8003
               8057 8399 8412 8539 8710 8931
               8992 9664 9736 9833 9852
ScrFI     74   236 255 328 335 394 404 548 636   cc/ngg
               642 677 722 940 1036 1048 1142
               1158 1191 1309 1316 1333 1377
               1393 1430 1475 2177 2285 2384
               2391 2506 2554 2570 2695 2722
               2807 2882 2936 3208 3797 3970
               4091 4104 4322 4794 4897 5086
               5476 5699 5859 6255 6272 6327
               7258 7530 7584 7659 7771 7896
               7912 8244 8403 8411 8537 8884
               8929 8990 8996 9128 9459 9525
               9735 9811 9856 9899 9968
SduI      33   58 1326 1333 1371 1437 2298 2565  gdgch/c
               2694 2943 3134 4260 4793 5503
               5565 5755 5829 5922 6677 7337
               7528 7777 7906 8052 8416 8543
               8603 8743 8902 9134 9740 9824
               9928 9981
SexAI     1    6270                              a/ccwggt
SfaNI     25   254 1946 2472 2637 2896 2911      gcatc
               3010 3414 4034 5236 5426 5511
               5575 5642 5897 6223 6295 7058
               7462 7561 7576 7835 8100 9500
               9723
SfcI      15   81 480 566 584 598 683 972 1408   c/tryag
               1806 4207 4398 6525 8277 8558
               9353
```

FIG. 20 (Cont'd)

```
SfiI      1   6092                                              ggccnnnn/nggcc
Sfr274I   2   43  51                                            c/tcgag
Sfr303I   3   2238 8546 9839                                    ccgc/gg
SfuI      2   65  5180                                          tt/cgaa
SinI     10   1312 2109 2387 3181 4900 5345                     g/gwcc
              7283 8931 8992 9852
SmaI      7   1334 1476 2385 2507 8538 9812                     ccc/ggg
              9969
SpeI      1   8569                                              a/ctagt
SphI      5   729 2333 5463 6226 6298                           gcatg/c
SplI      1   2129                                              c/gtacg
SrfI      1   1334                                              gccc/gggc
Sse9I    36   67  75  262 496 666 861 1484 1838                 /aatt
              2015 2063 2140 2478 3353 3417
              3495 3521 3532 3866 4702 6120
              6212 6284 6931 6942 6968 7046
              7110 8563 8579 8630 8778 8800
              9079 9297 9548 9826
SseBI     3   234 6043 9941                                     agg/cct
SspBI     3   350 3234 7229                                     t/gtaca
SspI      3   3511 6403 6956                                    aat/att
SstI      5   58  2298 9824 9928 9981                           gagct/c
SstII     3   2238 8546 9839                                    ccgc/gg
StuI      3   234 6043 9941                                     agg/cct
StyI     17   180 356 504 650 775 1262 1284                     c/cwwgg
              2029 2473 2523 5023 5428 6038
              6131 7940 8374 8621
SunI      1   2129                                              c/gtacg
TaqI     49   2  44  52  65  73 1557 1647 1830                  t/cga
              2013 2157 2169 2258 2352 2445
              2574 2868 2895 2910 3039 4042
              4880 5135 5180 5371 5533 5569
              5593 5749 6022 6713 7426 7555
              7570 7597 7891 8025 8554 8590
              8857 9448 9824 9963 9981 10023
              10065 10107 10149 10191 10233
TfiI     11   1554 2378 3917 5095 5132 5242                     g/awtc
              5376 8887 8972 9061 9156
ThaI     32   1880 2114 2124 2128 2218 2237                     cg/cg
              2248 2339 2853 3171 3252 3527
              3828 3989 4570 4843 4912 4975
              5059 5497 5798 6489 6520 6544
              6564 6940 7215 7296 7614 8545
              9789 9838
Tru1T    35   265 864 1521 1542 1565 1700 2094                  t/taa
              3304 3365 3486 3507 3518 3530
              3541 3558 3879 4648 4700 4705
              4719 6538 6809 6907 6924 6935
              6947 6958 6979 7100 7161 8019
              8577 8662 8677 9301
```

*FIG. 20 (Cont'd)*

```
Tru9I       35   265  864  1521 1542 1565 1700 2094  t/taa
                 3304 3365 3486 3507 3518 3530
                 3541 3558 3879 4648 4700 4705
                 4719 6538 6809 6907 6924 6935
                 6947 6958 6979 7100 7161 8019
                 8577 8662 8677 9301
Tsp45I      10   694  1399 2707 3196 5433 5739       /gtsac
                 6570 7266 7755 8949
Tsp509I     36   67   75   262  496  666  861  1484 1838  /aatt
                 2015 2063 2140 2478 3353 3417
                 3495 3521 3532 3866 4702 6120
                 6212 6284 6931 6942 6968 7046
                 7110 8563 8579 8630 8778 8800
                 9079 9297 9548 9826
TspEI       36   67   75   262  496  666  861  1484 1838  /aatt
                 2015 2063 2140 2478 3353 3417
                 3495 3521 3532 3866 4702 6120
                 6212 6284 6931 6942 6968 7046
                 7110 8563 8579 8630 8778 8800
                 9079 9297 9548 9826
TspRI       28   27   526  664  716  1250 1615 2736  cagtg
                 3447 4348 4361 4632 5742 7025
                 7736 8178 9094 9126 9220 9420
                 9645 9664 10006 10048 10090
                 10132 10174 10216 10258
Tth111I     2    840  5745                           gacn/nngtc
TthHB8I     49   2    44   52   65   73   1557 1647 1830  t/cga
                 2013 2157 2169 2258 2352 2445
                 2574 2868 2895 2910 3039 4042
                 4880 5135 5180 5371 5533 5569
                 5593 5749 6022 6713 7426 7555
                 7570 7597 7891 8025 8554 8590
                 8857 9448 9824 9963 9981 10023
                 10065 10107 10149 10191 10233
Van91I      3    154  8079 9127                      ccannnn/ntgg
Vha464I     2    3485 6978                           c/ttaag
VneI        3    4256 8048 8739                      g/tgcac
VspI        2    3879 8677                           at/taat
XbaI        4    1463 1496 3257 7206                 t/ctaga
XhoI        2    43   51                             c/tcgag
XhoII       20   47   399  646  1469 2500 3024 3621  r/gatcy
                 4583 4594 4680 4692 5051 5443
                 5689 7439 8068 8532 9655 9730
                 9805
XmaI        7    1332 1474 2383 2505 8536 9810       c/ccggg
                 9967
XmaIII      3    3247 5954 7216                      c/ggccg
XmnI        1    8317                                gaann/nnttc
Zsp2I       5    731  3893 6224 6296 9603            atgca/t
```

FIG. 20 (Cont'd)

The following endonucleases were selected but don't cut this sequence:

Acc113I, AccIII, AhdI, AscI, AspEI, BseAI, BsiMT, Bsp13I, Bsp68I, BspCI, BspEI, BstEII, BstPI, BstSNI, Eam1105I, EclHKI, Eco105I, Eco255I, Eco32I, Eco91I, EcoO65I, EcoRV, FseI, Kpn2I, MroI, NruI, PacI, Ple19I, PmeI, PspEI, PvuI, SbfI, ScaI, SgfI, SgrAI, SmiI, SnaBI, Sse8387I, SwaI, XcmI

FIG. 20 (Cont'd)

pMCK/Tet-ON-BFP/TRE/HA-Mst/IRES-EGFP ㉓

(pFinal)

1.) Open both pBlue$_{MNN}$ and pLong with Bgl II. Get the 6.3 kb and 6.6 kb plasmid opened and ligate them. Search for the 13 kb fusion plasmid which has the opposite orientation.

pfusion 13.4 kb test : EcoR I  0.5
                1.1
                1.3
               10.5
              13.4 kb 2.) Restriction digest the pfusion with NheI enzyme : get the ≈3.3 kb and ≈10.1 kb fragment. Cut the 10.1 kb fragment and self-ligate.

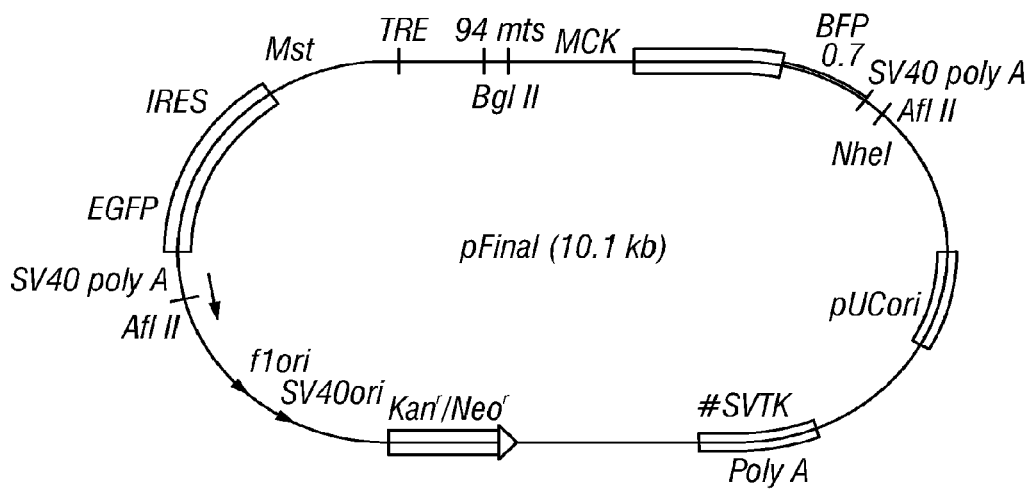

Constructed by Suzanne Porszasz - Reisz

Test: Afl II → 6.5 kb
              3.6 kb

* unique sit to release:
cut out the
construct with
Afl II

FIG. 21

CMOT transgene

6786 base pairs

Graphic map | Table by enzyme name

```
MspCI                                                                    Tsp509I
Bst98I                              BsaMI                                TspEI
BspTI MseI              MaeI        BsmI                                 Sse9I
cttaagatacattgatgagtttggacaaaccacaactagaatgcagtgaaaaaaatgctttatttgtgaaatttg base pairs
gaattctatgtaactactcaaacctgtttggtgttgatcttacgtcactttttttacgaaataaacactttaaac 1 to 75
AflII TruII                         BfaI   Mva1269I                      AcsI
Vha464I                                    TspRI                         ApoI
BfrI Tru9I ItaI       HincII Tsp509I
                              BsoFI      TruII  MunI     BsaMI
   SfaNI       MaeIII         CviJI      Tru9I  MfeI     BsmI
tgatgctattgctttatttgtaaccattataagctgcaataaacaagttaacaacaacaattgcattcattttat base pairs
actacgataacgaaataaacattggtaatattcgacgttatttgttcaattgttgttgttaacgtaagtaaaata 76 to 150
                    AluI Bst71I   MseI       Sse9I    Mva1269I
                    Fsp4HI         HpaI      TspEI
                      BbvI        HindII TruII
             MnlI    MnlI Tru9I                 MnlI           CviJI
gtttcaggttcagggggaggtgtgggaggttttttaaagcaagtaaaacctctacaaatgtggtatggctgatta base pairs
caaagtccaagtccccctccacaccctccaaaaaatttcgttcattttggagatgtttacaccataccgactaat 151 to 225
                             MseI
                             DraI Bse8I Sau3AI BfaI MvnI BsoFI Eco52I BsiEI Bsp1407I Hsp92II NciI AclWI Fsp4HI
BsrBRI Bsp143I ThaI BstZI NotI HaeIII Bsh1285I CviJI MboI DpnI HpaII BsoFI
MamI NdeII XbaI AccII CfrI Fsp4HI CviJI BsaOI Csp6I NdeII Kzo9I MspI AlwI BslI
tgatctagagtcgcggccgctttacttgtacagctcgtccatgccgagagtgatcccggcggcggtcacgaactc base pairs
actagatctcagcgccggcgaaatgaacatgtcgagcaggtacggctctcactagggccgccgccagtgcttgag 226 to 300
BsaBI MboI MaeI BstUI CciNI XmaIII AciI AciI BsrGI AluI Sau3AI BcnI ScrFI BsiYI
Bsh1365I DpnI PleI Bsh1236I EclXI PalI BstMCI RsaI NlaIII BsiSI HapII Bsc4I
 DpnII Kzo9I HinfI EaeI EagI ItaI BsuRI SspBI AfaI DpnII Bsp143I MspR9I ItaI MaeIII AsuI AspS9I Sau3AI Hin6I CfoI               DdeI Bbv12I
AciI  SinI AvaII NdeII DpnI AccII AspLEI              BseII BmyI BsiHKAI
    BpmI HgiEI NlaIII Kzo9I ThaI HhaI      DdeI    AciI BsrSI Bsp1286I
cagcaggaccatgtgatcgcgcttctcgttgggtctttgctcagggcggactgggtgctcaggtagtggttgtc base pairs
gtcgtcctggtacactagcgcgaagagcaacccagaaacgagtcccgcctgacccacgagtccatcaccaacag 301 to 375
       Cfr13I Eco47I MboI HspAI Bsh1236I BstDEI       BseNI AspHI
Tsp45I Bmc18I Hsp92II HinP1I MvnI                     BsrI SduI Alw21I
   GsuI Sau96I DpnII Bsp143I BstJI                    BstDEI
```

*FIG. 22*

```
              Bst71I  NlaIV                                          Fsp4HI Fsp4HI
    ItaI      AsuI    HaeIII                                  AluI  Bst71I         TaqI
    BsoFI     Cfr13I  CviJI                                   Cac8I BbvI   ItaI    TthHB8I
    gggcagcagcacgggccgtcgccgatgggggtgttctgctggtagtggtcggcgagctgcacgctgccgtcctc  base pairs
    cccgtcgtcgtgccccggcagcggctaccccccacaagacgaccatcaccagccgctcgacgtgcgacggcaggag  376 to 450
    Fsp4HI    Sau96I  PalI                                         CviJI  Cac8I  Bst71I
      BbvI    AspS9I  BsuRI                                               BsoFI  BsoFI
              PspN4I                                                      ItaI   BsgI BbvI MboI  Bsp143I                                       PalI
           BstX2I AciI      HphI                               HaeIII
           BstYI MflI AclWI MslI      SfaNI      MboII    EaeI NlaIII MaeII     CviJI
    gatgttgtggcggatcttgaagttcaccttgatgccgttcttctgcttgtcggccatgatatagacgttgtggct  base pairs
    ctacaacaccgcctagaacttcaagtggaactacggcaagaagacgaacagccggtactatatctgcaacaccga  451 to 525
           DpnII  XhoII AlwI                                   CfrI   Hsp92II
    MnlI   NdeII  Kzo9I                                        CviJI
           Sau3AI DpnI                                         BsuRI BseDI  Bst2UI                                    TaqI
           AfaI  GsuI   BmyI   BstOI  FokI                               AluI
    Csp6I  CviJI       SduI  BstNI  Bst75I   MnlI     TthHB8I     Eco57I SfaNI
    gttgtagttgtactccagcttgtgccccaggatgttgccgtcctccttgaagtcgatgcccttcagctcgatgcg  base pairs
    caacatcaacatgaggtcgaacacggggtcctaccaggcaggaggaacttcagctacgggaagtcgagctacgc  526 to 600
           RsaI  AluI   Bsp1286I MvaI                          TaqI   SfaNI  CviJI
                 BpmI   BsaJI  MspR9I                                        TthHB8I
                        EcoRII ScrFI BstOI  MslI                HinP1I  MvnI  AciI
    BseDI  ScrFI      MnlI    HphI    BslI    HhaI  CfoI
    EcoRII Bst2UI TthHB8I     BsaJI   Bsc4I AccII FauI                    MboII
    gttcaccagggtgtcgccctcgaacttcacctcggcgcgggtcttgtagttgccgtcgtccttgaagaagatggt  base pairs
    caagtggtcccacagcgggagcttgaagtggagccgcgcccagaacatcaacggcagcaggaacttcttctacca  601 to 675
    AciI BsaJI HphI    TaqI      BseDI Hin6I BstUI
         BstNI MvaI               MnlI BsiYI AspLEI
         MspR9I                   HspAI ThaI Bsh1236I AspLEI ScrFI                                     Bst71I                 AciI
    Hin6I BstNI MvaI                           AciI    ItaI                   ItaI
    HinP1I  BstOI MaeII             NlaIII     MboII   BsoFI     NlaIII       BsoFI
    gcgctcctggacgtagccttcgggcatggcggacttgaagaagtcgtgctgcttcatgtggtcggggtagcggct  base pairs
    cgcgaggacctgcatcggaagcccgtaccgcctgaacttcttcagcacgacgaagtacaccagccccatcgccga  676 to 750
    HspAI EcoRII  CviJI       Hsp92II            Fsp4HI       Hsp92II         Fsp4HI
      HhaI MspR9I                                  BbvI                       CviJI
    CfoI  Bst2UI Sau96I EcoRII MvaI  BsiYI ItaI  Cac8I
                                     BssSI HaeIII BstNI Bsc4I Mwol AluI  BssAI
    MwoI   BsgI           Tsp45I MslI Cfr13I BsuRI MspR9I SduI Fsp4HI BsrFI
      Eco57I Cac8I
    gaagcactgcacgccgtaggtcagggtggtcacgagggtgggccagggcacgggcagcttgccggtggtgcagat  base pairs
```

FIG. 22 (Cont'd)

```
cttcgtgacgtgcggcatccagtcccaccagtgctcccacccggtcccgtgccgtcgaacggccaccacgtcta 751 to 825
     TspRI           MaeIII  BsiI AspS9I BsaJI Bst2UI BmyI CviJI Bse118I
                             MnlI CviJI BseDI ScrFI Bsp1286I Bst71I
                             AsuI PalI BstOI BslI BsoFI BbvI Cfr1

HpaII                                     HapII          PalI
  MspI         AluI                        HpaII         HaeIII
     HapII Eco57I  Cac8I         SfaNI MnlI MnlI   MwoI     EaeI    MaeII
gaacttcagggtcagcttgccgtaggtggcatcgccctcgccctcgccggacacgctgaacttgtggccgtttac base pairs
cttgaagtcccagtcgaacggcatccaccgtagcgggagcgggagcggcctgtgcgacttgaacaccggcaaatg 826 to 900
      BsgI       CviJI                  BcgI   BsiSI            CfrI
BsiSI                                           MspI            CviJI
0I MwoI                                                         BsuRI MspR9I Eco64I Bsp1286I MspI CviJI        NcoI BstDSI
        TthHB8I ScrFI BshNI BmyI MslI ScrFI   BseRI   StyI BseDI NlaIII
     CviJI  BstNI BstF5I SduI BsiSI HapII  MnlI       Eco130I HphI
gtcgccgtccagctcgaccaggatgggcaccaccccggtgaacagctcctcgcccttgctcaccatggttgtggc base pairs
cagcggcaggtcgagctggtcctacccgtggtggggccacttgtcgaggagcgggaacgagtggtaccaacaccg 901 to 975
     AluI EcoRII MvaI AccB1I BsaJI BcnI HphI              ErhI EcoT14I
          TaqI BstOI FokI NlaIV BseDI HpaII AluI          BssT1I Bsp19I
          Bst2JI BanI PspN4I NciI MspR9I                  BsaJI DsaI Hsp92II MslI HaeIII                       BsmFI   DraII PspN4I
  PalI BalI                       BstDSI  AsuI NlaIV MaeI MseI   MnlI
BstXI BsuRI              MaeII BsaJI BslI  Cfr13I HaeIII  Tru9I TthHB8I
catattatcatcgtgtttttcaaaggaaaaccacgtccccgtggttcgggggggcctagacgtttttttaacctcg base pairs
gtataatagtagcacaaaaagtttccttttggtgcagggggcaccaagcccccggatctgcaaaaaaattggagc 976 to 1050
EaeI CviJI                   BseDI BsiYI Sau96I CviJI MaeII    TaqI
  CfrI MscI                  DsaI Bsc4I  Eco0109I BsuRI Tru1I
    MluNI                                AspS9I PalI BfaI NspI    VneI Bsp1286I Sau96I PalI NlaIV Bsp143I MflI AclWI BsiYI
        NlaIII  Hsp92II Alw21I AsuI HaeIII NdeII DpnI BstX2I DpnI BslI
     BspLU11I   NlaIII BmyI BsaJI EcoO109I PspN4I BstYI Sau3AI AlwI Esp1396I
actaaacacatgtaaagcatgtgcaccgaggcccagatcagatcccatacaatggggtaccttctgggcatcct base pairs
tgatttgtgtacatttcgtacacgtggctccgggtctagtctagggtatgttacccccatggaagacccgtagga 1051 to 1125
       AflIII    Alw44I Bbv12I Cfr13I CviJI DpnI Kzo9I MboI XhoII AccB7I
          Hsp92II NspI SduI BsiHKAI DraII MnlI MboI DpnII Bsp143I Bsc4I
                  ApaLI AspHI BseDI AspS9I BsuRI Sau3AI NdeII Kzo9I PflMI Acc65I RsaI FokI
Eco64I NlaIV SfaNI              CviJI
   BshNI PspN4I         MnlI       HinfI                  MaeII
tcagcccttgttgaatacgcttgaggagagccatttgactctttccacaactatccaactcacaacgtggcact base pairs
agtcggggaacaacttatgcgaactcctctcggtaaactgagaaaggtgttgataggttgagtgttgcaccgtga 1126 to 1200
```

FIG. 22 (Cont'd)

```
     Asp718I AfaI Eco57I        BseRI          PleI                       DraIII
Van91I AccBII BstF5I
  BanI Csp6I KpnI CviJI

BsrI                                PmlI     PalI ItaI BshNI       MspR9I BsiYI
   BseNI   ItaI MwoI                  Eco72I   EaeI BsoFI Eco64I       BstOI BslI
TspRI    BsoFI       BsoMI   AflIII BbrPI  HaeIII MwoI NlaIV  EcoRII MvaI
ggggttgtgccgcctttgcaggtgtatcttatacacgtggcttttggccgcagaggcacctgtcgccaggtgggg  base pairs
ccccaacacggcggaaacgtccacatagaatatgtgcaccgaaaaccggcgtctccgtggacagcggtccacccc  1201 to
                                                                            1275
  EsrSI     Fsp4HI               MaeII CviJI CviJI AciI AccBII   BstNI Bsc4I
  BseII     AciI                 BsaAI   CfrI Fsp4HI BanI PspN4I ScrFI
                                 PmaCI      BsuRI BglI MnlI        Bst2UI BsoFI   BslI                      MboII
   PspN4I ItaI Bsc4I                    BbsI  AluI           XmnI
  NlaIV AciI BbvI       SfcI MaeII     BpuAI CviJI      MnlI
ggttccgctgcctgcaaagggtcgctacagacgttgtttgtcttcaagaagcttccagaggaactgcttccttca  base pairs
ccaaggcgacggacgtttcccagcgatgtctgcaacaaacagaagttcttcgaaggtctccttgacgaaggaagt  1276 to
                                                                             1350
     Nsp3II Bst71I       BstSFI              Bbv16II         Asp700I
     MspA1I Cac8I                            BpiI
       Fsp4HI   BsiYI                          HindIII BlnI BseDI          BpiI
                             BsaMI     ErhI BsaJI BsaMI    Bbv16II
                             BsmI         MnlI   AvrII MaeI Mva1269I    MboII cgacattcaacagaccttgcattcctttggcgagaggggaaagacccctaggaatgctcgtcaagaagacagggc  base pairs
gctgtaagttgtctggaacgtaaggaaaccgctctccccttctggggatccttacgagcagttcttctgtcccg  1351 to
                                                                            1425
                     Mva1269I                 Eco130I    BsmI          BpuAI
                                               StyI  EcoT14I           BbsI
                                                BssT1I BfaI              Cfr13I AspS9I BstNI MvaI BcnI Sau96I HaeIII BmyI ApaI BslI                    BsiSI
  CviJI MspR9I MspI Cfr13I EcoO109I Bsp1286I Bsc4I                      Bse118I
Sau96I EcoRII BsiSI MspR9I AspS9I PalI Eco24I BsrDI                     BssAI
caggtttccgggccctcacattgccaaaagacggcaatatggtggaaaataacatatagacaaacgcacaccggc  base pairs
gtccaaaggcccgggagtgtaacggttttctgccgttataccacctttattgtatatctgtttgcgtgtggccg  1426 to
                                                                            1500
 HaeIII BstOI HpaII ScrFI AsuI CviJI SduI BanII                        BsrFI
AsuI BsuRI ScrFI NciI Bsp1201 NlaIV PspN4I MnlI                        Cfr10I
    PalI Bst2JI HapII PspOMI DraII BsuRI FriOI BsiYI                    HpaII CviJI    AciI  PalI BsrSI               NceII BstI NlaIV Eco88I
   BsuRI   ItaI MwoI BsuRI MaeII            DpnII MflI AciI PspAI
  MspI     BsoFI EaeI MaeIII Psp1406I    MnlI MnlI Sau3AI Kzo9I BcoI AclWI
cttattccaagcggcttcggccagtaacgttaggggggggggagggagagggggcggatcccggccccgcggtacc  base pairs
gaataaggttcgccgaagccggtcattgcaatcccccccccctccctctcccgcctagggccgggcgccatgg   1501 to
```

FIG. 22 (Cont'd)

1575

| | | | | | |
|---|---|---|---|---|---|
| HapII | Fsp4HI | HaeIII | BsrI | BstYI BamHI DpnI Cfr9I | |
| HaeIII | CviJI | CviJI | BseII | BstX2I XhoII PspN4I | |
| PalI | | CfrI | BseNI | MboI Bsp143I Ama87I | |

```
   XmaI MspI Cfr13I NlaIV SduI BsaJI DsaI MvnI FauI AciI Acc65I PspN4I SfcI
BseDI HpaII SmaI AsuI HaeIII Eco24I BstDSI Bsh1236I Eco64I Csp6I SalI HindII
  BsoBI HapII Bsp120I PalI Bsp1286I ApaI NspBII SstII BanI NlaIV TthHB8I
gtcgactgcagaattcactagtgattaaattatattgtcgactcatgagcacccacagcggtctactaccatggc base pairs
cagctgacgtcttaagtgatcactaatttaatataacagctgagtactcgtgggtgtcgccagatgatggtaccg 1576 to
1650
   AlwI BcnI PspALI AspS9I PspN4I BseDI ThaI MspA1I Cfr42I AccB1I KpnI HincII
BsaJI NciI MspR9I Sau96I BsuRI Cac8I BanII BstJI Sfr303I Asp718I AfaI TaqI
AvaI BsiSI ScrFI PspOMI CviJI BmyI FriOI AccII KspI SacII BshNI RsaI AccI BstSFI AcsI SpeI MseI TthHB8I PleI BmyI BsiHKAI StyI BseDI Hsp92II Tru1I PshBI DrdI
    TspEI BfaI Tsp509I HinfI SduI Bbv12I AccI BsaJI Bsp19I TspEI VspI Tru1I
     Sse9I AclNI Tru1I AccI BspHI Bsp1286I MspA1I BssT1I NlaIII ApoI AsnI MseI
tggaattttcccatatattatttgttctttgccattaaaatatagcatattaatgggagacattttttgtcggagt base pairs
accttaaaagggtatataataaacaagaaacggtaatttatatcgtataattacctctgtaaaacagcctca 1651 to
1725
   EcoRI MaeI Sse9I TaqI RcaI AspHI MwoI AciI NcoI DsaI CviJI Tru9I Tru9I BsmAI
PstI ApoI Tru9I SalI HindII Hsp92II NspBII ErhI EcoT14I Sse9I MseI MslI Alw26I
      Tsp509I TspEI HincII NlaIII Alw21I Eco130I BstDSI AcsI Tsp509I AseI Bst71I DraII BsuRI Bsp172CI       Bsp1286I
  Fsp4HI Sau96I PalI CelII           ApaLI Bbv12I
   BsoFI Cfr13I CviJI DdeI CviJI      Alw44I Alw21I       AciI
gcagcaagggcctgctgagcctctgggttttgcttggtgcacaagatgagtatgcggatatttttgtaaaaacac base pairs
cgtcgttcccggacgactcggagaccccaaacgaaccacgtgttctactcatacgcctataaaaacatttttgtg 1726 to
1800
     BbvI EcoC109I Cac8I BstDEI       VneI BmyI
     BsgI AsuI HaeIII BlpI MnlI         SduI BsiHKAI
     ItaI MwoI AspS9I Bpu1102I          AspHI Tsp509I                BsuRI                     BsmFI
   TspEI                  Tsp509I                   BseII  Bsc4I
   Sse9I       DdeI       Sse9I HaeIII              BsrSI  BstF5I
aaattcacactctcctgagcagtaattggcctatatctttgggtgcgataatccagtcccatccaaaggcttc base pairs
tttaagtgtgagaggactcgtcattaaccggaatatagaaacccacgctattaggtcagggtaggttccgaag 1801 to
1875

AcsI         BstDEI  TspEI CviJI                   BseNI  FokI CviJI
    ApoI                       PalI                    BsrI   BslI
                                                              BsiYI

BstMCI MnlI          MspI MspR9I     Bbv12I
         BsiEI BsiYI    ItaI Bst71I BcnI BseDI AspHI
   TthHB8I Bsc4I   BsoFI BbvI NciI BsaJI      SduI BsiHKAI CviJI    Alw26I
aaaatcgaccgtgagggggtagcggcagcaccgggattccgtggagtgctcatcgcagtcaagcccaaagtctct base pairs
```

*FIG. 22 (Cont'd)*

```
ttttagctggcactcccccatcgccgtcgtggccctaaggcacctcacgagtagcgtcagttcgggtttcagaga 1876 to
                                                                             1950
     TaqI      BslI      Fsp4HI  BsiSI ScrFI DsaI    Bsp1286I              BsmAI
        Bsh1285I          AciI   HpaII HinfI         BmyI
     BsaOI                       HapII TfiI BstDSI   Alw21I MspI MspR9I AsuI Psp5II MnlI                               MspR9I Bme18I
   BsiSI ScrFI HgiEI Eco47I Tsp45I                            BstNI Cfr13I
         BcnI PpuMI DraII NlaIV HphI         HinfI CviJI   MboII ScrFI HgiEI
ccgggacctcttgggtgtgtctgtcaccttgacttctaaaaagggattcagcccatcttctcctggtcctgggaa base pairs
ggccctggagaacccacacagacagtggaactgaagattttttccctaagtcgggtagaagaggaccaggaccctt 1951 to
                                                                             2025
     NciI Bme18I AvaII PspN4I                 TfiI           EcoRII MvaI AsuI
   HpaII Cfr13I EcoO109I BsmFI                               BstOI SinI AvaII
   HapII SinI Sau96I AspS9I MaeIII                           Bst2UI Sau96I AspS9I BstOI DpnII Kzo9I HaeIII FokI
 Eco47I BseDI MvaI Sau3AI NlaIII MluNI
     EcoRII MspR9I NdeII EaeI CviJI BalI AluI           DdeI    HinfI CviJI MwoI
ggttacagcaagatcatggccattctcatccaaagctttgatttcaatgcctaagttggattcaggctgtttgag base pairs
ccaatgtcgttctagtaccggtaagagtaggtttcgaaactaaagttacggattcaacctaagtccgacaaactc 2026 to
                                                                             2100
   BslI BsaJI ScrFI Bsp143I PalI MscI CviJI           BstDEI  TfiI
      BsiYI Bst2UI MboI CfrI BsuRI BstF5I
   Bsc4I BstNI MaeIII DpnI Hsp92II HindIII BpiI                      Bsc4I PflMI BstNI ScrFI FriOI
   TspEI               Bbv16II                  BseII BslI BsaJI MspR9I Bsp1286I
   Sse9I       TspRI                            PsrSI AlwNI Esp1396I SduI BanII
ccaattttgcaacactgtcttcacatcaatactctgccaaataccagtgcctgggctcatgtcaagtttcagaga base pairs
ggttaaaacgttgtgacagaagtgtagttatgagacggtttatggtcacggacccgagtacagttcaaagtctct 2101 to
                                                                             2175
 CviJI                  BpuAI                   BseNI Acc37I Van91I CviJI NlaIII
    Tsp509I             BbsI                    BsrI EcoRII BseDI Bst2UI Eco24I
                        MboII                         TspRI BsiYI BstOI MvaI BmyI DpnII DpnI BseNI                            BsmAI
      Bsp143I AccI   RsaI                      PleI
     NdeII TfiI BseII              NlaIII  HinfI Alw26I             TspRI
tcggattccagtataccttgtaccgtctttcatgggtttgatgagtctcaggatttgcacaaacactgttgtagg base pairs
agcctaaggtcatatggaacatggcagaaagtacccaaactactcagagtcctaaacgtgtttgtgacaacatcc 2176 to
                                                                             2250
        Sau3AI BsrSI  Csp6I        Hsp92II       DdeI
           MboI Kzo9I BsrI AfaI                  BstDEI
     Hsp92II HinfI Bst1107I TspEI
                         BsiYI              AfaI                     Sse9I
   HinfI       DdeI          Bsc4I              Csp6I        CviJI Tru9I
agtcttgacgggtctgagatatatccacagttgggcttttactactttgttgtactgtattttagagctaaattt base pairs
```

*FIG. 22 (Cont'd)*

```
                                                                                  2251 to
tcagaactgcccagactctatataggtgtcaacccgaaaatgatgaaacaacatgacataaaatctcgatttaaa
                                                                                  2325
      PleI      BstDEI          BslI                     RsaI          AluI Tsp509I
                               CviJI                                         AcsI
                                                                             ApoI BstSFI
  DraI                Acil                SfcI          MslI
            CviJI  BstF5I                 HinfI       NlaIII
aaaaaagcaacatttgggcttgccatccgcttgcattagaaagtcagactctgtaggcatggtaatgattgtttc   base pairs
ttttttcgttgtaaacccgaacggtaggcgaacgtaatctttcagtctgagacatccgtaccattactaacaaag   2326 to
                                                                                2400
            Cac8I   FokI                    AlwNI       Hsp92II
  MseI              Cac8I                   PleI
  TruII Hsp92I   DpnII  DpnI
BstDSI                                                    MnlI  BsaHI AfaI Sau3AI
BsaJI                MboII   CviJI  MwoI           BstF5I  HinlI AcyI NdeII
cgtggtagcgtgataatcgtcatcttccaaagagccatcactgctgtcatccctctggacgtcgtactgatcgat base pairs
gcaccatcgcactattagcagtagaaggtttctcggtagtgacgacagtagggagacctgcagcatgactagcta 2401 to
                                                                               2475
BseDI                                    TspRI        FokI  Msp17I RsaI  MboI
DsaI                                                         BbiII AatII Bsp143I
                                                             MaeII Csp6I Kzo9I BspXI  BseCI Kzo9I  HpaII  Hin6I  HaeII                                 Bst2UI
      Bso106I ClaI Bsp143I MspR9I AspLEI                                      BstOI
    TthHB8I Bsu15I Sau3AI MspI HspAI CfoI        SfaNI           CviJI  EcoRII
cagttcccggagtggaggcgctcttggcagaagttgtcttatagcatctttgctgatgttaggagctgtttccag   base pairs
gtcaagggcctcacctccgcgagaaccgtcttcaacagaatatcgtagaaacgactacaatcctcgacaaaggtc   2476 to
                                                                                 2550
  BanIII  BscI  NdeII  NciI HapII MnlI  BstH2I                      AluI     BstNI
      Bsa29I DpnII DpnI BcnI HinP1I Bsp143II                                 MspR9I
      BspDI TaqI MboI BsiSI ScrFI HhaI MwoI                                  ScrFI AspLEI AluI        TspEI                    AfaI
      HspAI BsoFI DdeI     AcsI                     BpmI    BssSI          MslI Hsp92II
      MvaI CfoI BbvI     Sse9I        CviJI         Csp6I MnlI          Alw26I  Ppu1
gcgcagcttactgaggatttgaattttatggcttctattctggagtacctcgtgttttgtctccacgcacatgc   base pairs
cgcgtcgaatgactcctaaacttaaaatacccgaagataagacctcatggagcacaaaacagaggtgcgtgtacg  2551 to
                                                                                2625
      HinP1I CviJI BstDEI                   CsuI     BsiI    BsmAI        NI
      HhaI Fsp4HI MnlI  ApoI                RsaI                          NspI
      Hin6I ItaI Bst71I Tsp509I Zsp2I                                             MboI Bsp143I AsuI Bse1I
                                                    BstX2I DpnI Sau96I HaeIII
OI EcoT22I   MnlI              MboII        TspRI  BstYI MflI AlwI BsrSI
attacacagcccctcttttttccacatttttcttctctctcactgccctcatttagatccactgggccagcagcaat base pairs
```

*FIG. 22 (Cont'd)*

```
taatgtgtcggggagaaaaaggtgtaaaagaagagagagtgacgggagtaaatctaggtgacccggtcgtcgtta 2626 to
                                                                              2700
    aIII    CviJI                         MnlI DpnII XhoII Cfr13I BsrI
      Mph1103I                                 NdeII Kzo9I TspRI BseNI
  NsiI                                         Sau3AI AclWI AspS9I CviJI BscFI Hsp92II                              DpnII BamHI NlaIV AclWI
     Fsp4HI                                   Hsp92II Sau3AI Kzo9I MspI
  PalI BbvI                          MwoI  SfaNI  BstYI Bsp143I BsiSI AlwI
cagcatgaacaggtaaatataaacatacatttgcagtttttgcatcatggctggatccgggcccataagagcgta base pairs
gtcgtacttgtccatttatatttgtatgtaaacgtcaaaaacgtagtaccgacctaggccgggtattctcgcat 2701 to
                                                                              2775
    BsuRI Bst71I                             NlaIII NdeII XhoII HpaII BcnI
    Cac8I NlaIII                             CviJI MboI BstI PspN4I NciI
       ItaI                                        BstX2I MflI DpnI HapII Cfr13I NlaIV SduI BanII Hsp92II    AccII AluI BfaI MboI Bsp143I AclWI BcoI
 MspR9I AsuI BsuRI FriOI RsaI  BfaI     ThaI  PvuII    BstX2I XhoII PspN4I Cfr9I Bsp120I CviJI BmyI Csp6I    MacI Cac8I HgaI MspA1I BstYI BamHI DpnI AlwI
atctggaacatcgtatgggtacatggtgtctagctcgcgtcagctgactagaggatccccgggtaccgagctcga base pairs
tagaccttgtagcatacccatgtaccacagatcgagcgcagtcgactgatctcctaggggcccatggctcgagct 2776 to
                                                                               2850
     Sau96I PalI Bsp1286I NlaIII  CviJI Bsh1236I MaeI DpnII MflI MnlI BseDI
    PspOMI HaeIII Eco24I AfaI    AluI MvnI CviJI     NdeII BstI NlaIV Ama87I
  ScrFI AspS9I PspN4I ApaI               BstUI NspBII     Sau3AI Kzo9I BsaJI PspAI BsoBI HaeII BanI Csp6I Ecl136II Bbv12I BanII AcsI Cfr13I HaeIII BstDSI MspA1I
     NciI MspR9I Acc65I AfaI EcoICRI Eco24I Alw21I ApoI NlaIV BsuRI DsaI BstUI
  Eco88I HpaII Eco64I NlaIV CviJI Bsp1286I FriOI Sse9I Sau96I CviJI BseDI AccII
attcggggccgcggaggctggatcggtcccggtgtcttctatggaggtcaaaacagcgtggatggcgtctccagg base pairs
taagccccggcgcctccgacctagccagggccacagaagatacctccagttttgtcgcacctaccgcagaggtcc 2851 to
                                                                               2925
Aval BcnI PspALI BshNI RsaI AluI AspHI SacI SstI TspEI AspS9I BsoFI ItaI NspBII
  XmaI MspI SmaI AccB1I KpnI SduI BmyI TaqI BsiHKAI Tsp509I PalI Fsp4HI MvnI
    BsiSI ScrFI Asp718I PspN4I TthHB8I Psp124BI EcoRI AsuI PspN4I BsaJI ThaI SacII MnlI Bsp143I AsuI Eco47I HpaII Bbv16II HinII HgaI BstNI GsuI Sau3AI
     SstII BglI MboI AlwI Sau96I BsiSI HapII BosI BstF5I AcyI BsmBI ScrFI MboI
      Sfr303I CviJI Kzo9I SinI AvaII NciI ScrFI MboII Msp17I EcoRII BstOI BpmI
cgatctgacggttcactaaacgagctctgcttatatataggcctcccaccgtacacgcctactcgacccgggtaccg base pairs
gctagactgccaagtgatttgctcgagacgaatatatccggagggtggcatgtgcggatgagctgggcccatggc 2926 to
                                                                                3000
     Cfr42I DpnII DpnI Bme18I NlaIV BcnI BsmFI MnlI BbiII Alw26I MspR9I NdeII
   XspI AciI NdeII AclWI HgiEI PspN4I MspR9I BoiI FokI BsaJI Esp3I MvaI DpnII
    Bsh1236I MwoI Sau3AI Cfr13I AspS9I MspI BpuAI MwoI Hsp92II BsmAI Bst2UI Bsp143I AluI BmyI SacI BsiHKAI Eco47I TaqI Eco88I NciI MspR9I BshNI RsaI AluI
    DpnI Bsp1286I BanII StuI PalI RsaI BcoI AvaI BsiSI PspALI Acc31I KpnI SduI
   Kzo9I SduI Eco24I SstI HaeIII MnlI Ama87I BseDI MspI SmaI Asp718I PspN4I Bsp1286I
```

*FIG. 22 (Cont'd)*

```
agctcgactttcacttttctctatcactgatagggagtggtaaactcgactttcacttttctctatcactgatag  base pairs
tcgagctgaaagtgaaaagagatagtgactatccctcaccatttgagctgaaagtgaaaagagatagtgactatc  3001 to
                                                                             3075
   CviJI AspHI FriOI Pmc55I SsoBI TthHB8I BsaJI BcnI ScrFI Acc65I AfaI EcoICRI
   Ecl136II Bbv12I Alw21I CviJI Csp6I PspAI XmaI HpaII Eco64I Csp6I Ecl136II
      EcoICRI Psp124BI AatI BsuRI AfaI Cfr9I BsoBI HapII BanI NlaIV CviJI TthHB8I AspHI SacI SstI TspRI
  Bbv12I BanII TthHB8I
      FriOI TspRI              TspRI           TthHB8I
ggagtggtaaactcgactttcacttttctctatcactgatagggagtggtaaactcgactttcacttttctctat  base pairs
cctcaccatttgagctgaaagtgaaaagagatagtgactatccctcaccatttgagctgaaagtgaaaagagata  3076 to
                                                                             3150
    Eco24I Alw21I TthHB8I                              TaqI
  BmyI Psp124BI TaqI
     TaqI BsiHKAI TaqI TspRI           TthHB8I              TspRI           TthHB8I
cactgatagggagtggtaaactcgactttcacttttctctatcactgatagggagtggtaaactcgactttcact  base pairs
gtgactatccctcaccatttgagctgaaagtgaaaagagatagtgactatccctcaccatttgagctgaaagtga  3151 to
                                                                             3225
               TaqI                                TaqI TspRI           TthHB8I              TspRI           TthHB8I
tttctctatcactgatagggagtggtaaactcgactttcacttttctctatcactgatagggagtggtaaactcg  base pairs
aaagagatagtgactatccctcaccatttgagctgaaagtgaaaagagatagtgactatccctcaccatttgagc  3226 to
                                                                             3300
                   TaqI                                      TaqI Eco88I BstYI Sau3AI Sfr274I BsoBI EcoICRI
                                     XhoI PaeR7I MboI BglII XhoI PaeR7I SduI
              TspRI                  Sfr274I DpnII MflI DpnI BcoI TaqI AluI
actttcacttttctctatcactgatagggagtggtaaactcgagatctcgagctcaagcttcgaattatcgaatt  base pairs
tgaaagtgaaaagagatagtgactatccctcaccatttgagctctagagctcgagttcgaagcttaatagcttaa  3301 to
                                                                             3375
                                     Ama87I TaqI NdeII XhoII Eco88I CviJI
                                     BcoI BsoBI BstX2I Kzo9I AvaI Ecl136II
                                     AvaI TthHB8I Bsp143I Ama87I TthHB8I Psp124BI CviJI Bsp119I TaqI TspEI Fsp4HI NdeII BstDEI DdeI PspN4I
  Eco24I SstI TthHB8I NspV TthHB8I Tsp509I BbvI Sau3AI PvuII MnlI      AluI
   Bbv12I Alw21I SfuI TaqI Sse9I AcsI SfcI PstI MboI DdeI NspBII NlaIV   CviJI
cctgcagcccgatctcagctgaggtgcaaaaggctcctgtcatattgtgtcctgctctggtctgccttccacagc  base pairs
```

FIG. 22 (Cont'd)

```
ggacgtcgggctagagtcgactccacgttttccgaggacagtataacacaggacgagaccagacggaaggtgtcg 3376 to
                                                                               3450
 AspHI SacI BsiHKAI LspI Bpu14I Sse9I BstSFI CviJI Bsp143I MspA1I          Bsc4I
  BmyI FriOI HindIII BstBI TspEI EcoRI BsoFI Bst71I DpnI CviJI CviJI
Bsp1286I BanII AluI Csp45I Tsp509I ApoI ItaI DpnII Kzo9I AluI BstDEI BslI Cfr13I HaeIII       StyI EcoT14I ItaI              BbvI  BsiYI
    BsiYI AspS9I BsuRI    Eco130I BfaI  BsoFI           CviJI  Hsp92II
     Esp1396I PalI BfaI   AvrII MaeI FokI CviJI     MaeI BsoFI  NlaIII
ttgggggccacctagcccacctctccctagggatgagagcagccactacgggtctaggctgcccatgtaaggagg base pairs
aaccccccggtggatcgggtggagagggatccctactctcgtcggtgatgcccagatccgacgggtacattcctcc 3451 to
                                                                               3525
    Van91I NlaIV MaeI MnlI BssT1I BstF5I BbvI       BfaI Fsp4HI  Bsc4I
Acc37I AsuI PspN4I CviJI   ErhI BsaJI    Fsp4HI          ItaI    BslI
PflMI Sau96I CviJI         BlnI BseDI    Bst71I          Bst71I CviJI EcoRII MvaI BcoI SfaNI ScrFI TruI   Hsp92II Bst71I
   AatI BsuRI BstNI BsmFI EcoRII MvaI MseI AflIII CviJI
MnlI Pme55I BsaJI MspR9I AvaI BstOI TspEI  BspLU11I BsoFI
caaggcctggggacacccgagatgcctggttataattaacccagacatgtggctgccccccccccccccaacacct base pairs
gttccggacccctgtgggctctacggaccaatattaattgggtctgtacaccgacggggggggggggggttgtgga 3526 to
                                                                               3600
    StuI Eco147I Bst2UI BsoBI MspR9I Tsp509I    BstXI Fsp4HI
    HaeIII BseDI ScrFI Eco88I Bst2UI Tru9I       NlaIII BbvI
    PalI SseBI BstOI Ama87I BstNI Sse9I          NspI ItaI BbvI          BsiYI MspI BshNI BseDI ScrFI Ssp3I Eco130I BstDSI CviJI
 BspMI MwoI  MnlI    BscDI BcnI Eco64I BsaJI MspR9I Bsp1407I BssT1I NlaIII
  BsoFI BstDEI   HphI Bsc4I NciI MspR9I EcoRII MvaI CviJI RsaI NcoI DsaI BseRI
gctgcctgagcctcaccccccaccccggtgcctgggtcttaggctctgtacaccatggaggagaagctcgctctaa base pairs
cgacggactcggagtgggggtgggccacggacccagaatccgagacatgtggtacctcctcttcgagcgagatt 3601 to
                                                                               3675
   Fsp4HI CviJI      BsaJI MslI ScrFI NlaIV BstOI BstDEI AfaI BsaJI Bsp19I
   ItaI DdeI         BslI HpaII BanI PspN4I Bst2UI BsrGI ErhI EcoT14I MnlI
      Bst71I           BsiSI HapII AccBII BstNI DdeI Csp6I StyI BseDI Hsp92II BslI Bst2UI NdeII BstI DpnI BsaJI ScrFI MnlI EaeI HaeIII MnlI
 Cac8I    BseDI MspR9I DpnII MflI NlaIV AlwI Bst2UI Cac8I CfrI PalI BstDEI
          Bsc4I BstNI MvaI Sau3AI Kzo9I BseDI MvaI HphI BstDEI CviJI CviJI
aaataaccctgtccctggtggatccagggtgaggggcaggctgagggcggccacttccctcagccgcaggttttgt base pairs
tttattgggacagggaccacctaggtcccactccccgtccgactcccgccggtgaagggagtcggcgtccaaaca 3676 to
                                                                               3750
   AluI       BsaJI BstOI BstYI Bsp143I EcoRII MspR9I BsiYI MnlI ItaI AciI Fsp4HI
            EcoRII ScrFI BstX2I XhoII AclWI BstOI BslI CviJI Fsp4HI DdeI ItaI
```

FIG. 22 (Cont'd)

```
                       BsiYI BsmFI MboI BamHI PspN4I BstNI Bsc4I DdeI BsoFI BsuRI BsoFI
 AciI                                                 NcoI BstDSI Fsp4HI BsgI
         BsiYI                MwoI           Tsp509I StyI BseDI Hsp92II Bsc4I
   BspMI Bsc4I             SfcI CviJI          Sse9I Eco130I NlaIII BbvI BslI
tttcccaagaatggttttttctgcttctgtagcttttcctgtcaattctgccatggtggagcagcctgcactgggc base pairs
aaagggttcttaccaaaaagacgaagacatcgaaaaggacagttaagacggtaccacctcgtcggacgtgacccg 3751 to
                                                                               3825
         BslI               BstSFI           TspEI      ErhI EcoT14I ItaI Cac8I TspRI
                              AluI                      BssT1I Bsp19I CviJI BsiYI
                                                        BsaJI DsaI BsoFI Bst71I BsrSI BsrI            NciI
 BseII           MspI MspR9I     SfcI                    Bsc4I          MwoI
 BseNI           BsiSI ScrFI     CviJI                 SfcI BslI    SfcI CviJI
ttctgggagaaaccaaaccgggttctaacctttcagctacagttattgcctttcctgtagatgggcgactacagc base pairs
aagaccctctttggtttggcccaagattggaaagtcgatgtcaataacggaaaggacatctacccgctgatgtcg 3826 to
                                                                               3900
                 HpaII           AluI                 BstSFI          BstSFI
 CviJI           HapII          BstSFI                 BsiYI
                 BcnI BstOI Sau96I BsuRI BstNI BstYI Bsp143I NlaIV
            BsmBI        BseDI MvaI AspS9I EcoRII Bst2UI Sau3AI Kzo9I
            Alw26I     EcoRII Bst2UI CviJI BslI BstOI DpnII BamHI DpnI
cccacccccaccccgtctcctgtatccttcctgggcctggggatcctaggctttcactggaaatttccccccag base pairs
gggtggggtgggggcagaggacataggaaggacccggaccccctaggatccgaaagtgacctttaaagggggtc 3901 to
                                                                               3975
                BsmAI        BsaJI ScrFI HaeIII BsiYI MspR9I MboI MflI PspN4I
                Esp3I         BstNI Cfr13I PalI BsaJI ScrFI NdeII BstI AvrII
                              MspR9I AsuI Bsc4I BseDI MvaI BstX2I XhoII Eco13

StyI EcoT14I BseNI Tsp509I Bst2UI BfaI PleI Cac8I ScrFI NlaIII EcoT22I
 ErhI BsaJI CviJI Sse9I EcoRII MvaI MaeI MaeIII BstOI MwoI BbuI Zsp2I
    BlnI AlwI TspRI AcsI BseDI ScrFI CviJI CviJI EcoRII Cac8I NspI Mph1103I
gtgctgtaggctagagtcacggctcccaagaacagtgcttgcctggcatgcatggttctgaacctccaactgcaa base pairs
cacgacatccgatctcagtgccgagggttcttgtcacgaacggaccgtacgtaccaagacttggaggttgacgtt 3976 to
                                                                               4050
     AclWI MaeI BseII BsaJI MspR9I BstSFI NlaIV BstNI MvaI Hsp92II NlaIII
     BssT1I BfaI BsrI ApoI BstOI SfcI HinfI PspN4I MspR9I Ppu10I NsiI MnlI
     CI BseDI BsrSI TspEI BstNI AlwNI Tsp45I TspRI Bst2UI PaeI SphI Hsp92II BsaJI BslI
                 StyI Bsc4I
                 Eco130I CviJI MnlI            MwoI                  BseII
                                           NlaIII    CviJI           BsrSI
aaaatgacacataccttgacccttggaaggctgaggcaggggattgccatgagtgcaaagccagactgggtggc base pairs
ttttactgtgtatggaactgggaaccttccgactccgtcccctaacggtactcacgtttcggtctgacccaccg 4051 to
                                                                             4125
                 ErhI BseDI BstDEI             Hsp92II              BseNI
                 BssT1I BsiYI                                        BsrI
```

FIG. 22 (Cont'd)

```
                    EcoT14I   DdeI
                                MseI                                          BsoBI
          AtsI   BsmAI        Tsp509I                                         Eco88I
         Tth111I               Sse9I                                          Ana87I
atagttagaccctgtctcaaaaaaccaaaaacaattaaataactaaagtcaggcaagtaatcctactcgggagac base pairs
tatcaatctgggacagagttttttggttttgttaatttattgatttcagtccgttcattaggatgagccctctg 4126 to
4200
          AspI   Alw26I        TspEI                                          BcoI
                                Tru9I                                         AvaI
                                Tru1I NspI    PalI  CviJI ScrFI              BfaI BsmAI           AflIII BstDEI Cac8I Bst2JI             PstNHI   BstSFI
Alw26I    MnlI   BspLU11I  HaeIII BstOI                CviJI    AccI
tgaggcagagggattgttacatgtctgaggccagcctggactacatagggtttcaggctagccctgtctacagag base pairs
actccgtctccctaacaatgtacagactccggtcggacctgatgtatcccaaagtccgatcgggacagatgtctc 4201 to
4275
DdeI MnlI     MaeIII  NlaIII CviJI BstNI MvaI          NheI CviJI SfcI
BstDEI                Hsp92II BsuRI MspR9I                  MaeI
                      DdeI MnlI EcoRII                      Cac8I DraII CviJI                    MspA1I MwoI     Bst2UI   EcoRII MvaI
    AsuI HaeIII                    AluI Fsp4HI     BstOI Hsp92II Bst2UI
    Cfr13I PalI                    PvuII ItaI     EcoRII ScrFI   BstNI
taaggccctatttcaaaaacacaaacaaaatggttctcccagctgctaatgctcaccaggcatgaagcctggtga base pairs
attccgggataaagttttgtgtttgttttaccaagagggtcgacgattacgagtggtccgtacttcggaccact 4276 to
4350
    Sau96I BsuRI                   CviJI BbvI      PstNI NlaIII MspR9I
    Eco0109I                       NspBII Bst71I   MspR9I   CviJI ScrFI
    AspS9I                         BsoFI           HphI Mval    BstOI BstDEI     MaeIII
MwoI      BsrDI   BsrDI MnlI Cac8I        CviJI    DdeI MnlI CviJI
gcattagcaatgaaggcaatgaaggagggtgctggctacaatcaaggctgtgggggactgagggcaggctgtaac base pairs
cgtaatcgttacttccgttacttcctcccacgaccgatgttagttccgacaccccctgactcccgtccgacattg 4351 to
4425
          MwoI                 CviJI               BsmFI   Cac8I HphI NlaIV EcoRII Bst2UI BsaJI Bst2UI              BcnI ScrFI Sau96I
      AsuI HaeIII BstNI CviJI BstNI HinfI             BsiSI Bsc4I AspS9I
   CviJI Cfr13I CviJI BstOI MaeII BstOI BsmFI         NlaIII MspI BsiYI
aggcttgggggccagggcttatacgtgcctggactcccaaagtattactgttccatgttcccggcgaagggcca base pairs
tccgaaccccggtcccgaatatgcacggaccctgaggggtttcataatgacaaggtacaagggccgcttcccggt 4426 to
4500
         Sau96I PalI BseDI MvaI BseDI Mval           Hsp92II HpaII Cfr13I
```

FIG. 22 (Cont'd)

```
      AspS9I BsuRI MspR9I BsaAI MspR9I PleI              NciI MspR9I HaeIII
     PspN4I BsaJI ScrFI EcoRII ScrFI                    HpaII BslI AsuI

Cac8I BsmFI      DdeI                   BsrI         BssT1I Fsp4HI
      PvuII AciI BfaI                      BseNI        ErhI BseDI CviJI
 CviJI AluI FauI AluI  PleI DdeI      NlaIV BsrSI       CviJI EcoT14I Bst71I
gctgtcccccgccagctagactcagcacttagtttaggaaccagtgagcaagtcagcccttggggcagcccatac base pairs
cgacagggggcggtcgatctgagtcgtgaatcaaatccttggtcactcgttcagtcgggaacccccgtcgggtatg 4501 to
4575
    BsuRI MspA1I MaeI       BstDEI    PspN4I TspRI       Eco130I BsoFI   Bsc4I
       CviJI  Cac8I Hinfl                   BseII        StyI BglI ItaI
    PalI Nsp3II CviJI BstDEI                             BsaJI MwoI BbvI CviJI BssT1I NlaIII CviJI Cac8I BstNI Cfr13I Eco47I BsiYI BseDI BmyI NlaIV
 BslI Eco13CI BseDI Hsp92II ItaI BsgI BstOI SinI AvaII BslI HapII ScrFI AccB1I
     HaeIII NcoI DsaI BstXI Fsp4HI BsaJI ScrFI Sau96I PspN4I BsaJI SduI BanI
aaggccatggggctgggcaagctgcacgcctgggtccggggtgggcacggtgcccgggcaacgagctgaaagctc base pairs
ttccggtaccccgacccgttcgacgtgcggacccaggccccaccccgtgccacgggcccgttgctcgactttcgag 4576 to
4650
     BsuRI BsaJI Bsp19I Cac8I BbvI BseDI MvaI HgiEI Bsc4I HpaII MspR9I BshNI
 BsiYI ErhI EcoT14I CviJI AluI Bst71I MspR9I Bme18I AspS9I MspI NciI Bsp1286I
    PalI StyI BstDSI MwoI BsoFI EcoRII Bst2UI AsuI NlaIV BsiSI BcnI Eco64I Eco88I SduI HpaII SrfI AluI Sau96I HaeIII BmyI Bsc4I BsiYI MvaI EcoRII
    Cfr9I BsoBI BcnI ScrFI CviJI PspOMI PspN4I Bsp1286I BsaJI BstOI CviJI Bst2UI
 Ama87I BseDI BmyI HapII CviJI Cfr13I DraII CviJI FriOI MnlI BstNI BsmFI MspR9I
atctgctctcaggggcccctccctggggacagcccctcctggctagtcacaccctgtaggctcctctatataacc base pairs
tagacgagagtccccggggagggaccccctgtcggggaggaccgatcagtgtgggacatccgaggagatatattgg 4651 to
4725
    BcoI BsaJI BsiSI MspR9I AluI Bsp120I NlaIV BsuRI ApaI BseDI Bst2UI BstNI
    PspAI XmaI NciI MspI SmaI DdeI AsuI AspS9I SduI BanII EcoRII ScrFI BstOI
 PspN4I AvaI Bsp1286I PspALI BstDEI Eco0109I PalI Eco24I BslI MspR9I MnlI ScrFI MaeI BstSFI BseDI ScrFI BmyI ItaI CviJI HaeIII XbaI BstYI Sau3AI Kzo9I BsaJI
      SfcI PspN4I BstOI Bsp1286I Bsc4I EaeI BsuRI AccBSI NdeII BstI NlaIV Ama87I
      Tsp45I MnlI BstNI SduI Fsp4HI BsiYI CviJI AciI BfaI MboI MflI MnlI BseDI
cagggcacaggggctgcccccaagctggccgctctagaggatccccgggactagaattcaccatgtctagatta base pairs
gtccccgtgtccccgacggggttcgaccggcgagatctcctaggggccctgatcttaagtggtacagatctaat 4726 to
4800
 MvaI MaeIII BseRI MspR9I AlwNI BbvI AluI PalI ItaI MaeI BstX2I XhoII AclWI
 CviJI CviJI BsaJI Bst2JI CviJI Bst71I CfrI BsoFI BsrBI DpnII BamHI DpnI AlwI
     BfaI NlaIV EcoRII MvaI BsoFI BslI Cac8I Fsp4HI BstD102I Bsp143I PspN4I Eco88I HpaII MaeI TspEI XbaI Tru9I AspLEI BbvI  Hinfl
      BsoBI HapII BfaI ApoI MaeI MseI HhaI Fsp4HI MnlI        Tru1I
     AvaI NciI ScrFI BsmFI Tsp509I HinP1I CviJI Tru9I TfiI    Tru9I
gataaaagtaaagtgattaacagcgcattagagctgcttaatgaggtcggaatcgaaggtttaacaacccgtaaa base pairs
ctattttcatttcactaattgtcgcgtaatctcgacgaattactccagccttagcttccaaattgttgggcattt 4801 to
4875
 BcoI XmaI MspI SmaI AcsI HphI BfaI Hin6I BsoFI MseI  TthH38I MseI
```

FIG. 22 (Cont'd)

```
    Cfr9I BcnI PspALI EcoRI Hsp92II HspAI AluI Bst71I  TaqI
PspAI BsiSI MspR9I Sse9I NlaIII Tru1I CfoI ItaI Tru1I
                        BbvI                            MwoI     BbiII
         AluI           ItaI          NspI              FauI     HinlI
         HindIII        BsoFI   TspRI NlaIII            Cac8I    TthHB8I
ctcgcccagaagcttggtgtagagcagcctacactgtattggcatgtaaaaaataagcgggctttgctcgacgcc base pairs
gagcgggtcttcgaaccacatctcgtcggatgtgacataaccgtacattttttattcgcccgaaacgagctgcgg 4876 to
                                                                             4950
         CviJI          Fsp4HI                Hsp92II   AciI     TaqI BsaHI
         BstXI          CviJI                           CviJI    Msp17I
                        Bst71I                                   Hsp92I DdeI                   NlaIV                 DraI
 HgaI                   BshNI                 Tru1I     Cac8I
 AcyI    MslI           Eco64I                Tru9I BsiYI CviJI
ttagccattgagatgttagataggcaccatactcacttttgccctttaaaaggggaaagctggcaagatttttta base pairs
aatcggtaactctacaatctatccgtggtatgagtgaaaacgggaaattttcccctttcgaccgttctaaaaaat 4951 to
                                                                             5025
 CviJI                  BanI                  MseI BslI AluI
 BstDEI                 AccB1I                EcoNI
                        PspN4I                Bsc4I AfaI
                                      DdeI    MslI BsrDI Csp6I
cgcaataacgctaaaagttttagatgtgctttactaagtcatcgcaatggagcaaaagtacattcagatacacgg base pairs
gcgttattgcgattttcaaaatctacacgaaatgattcagtagcgttacctcgttttcatgtaagtctatgtgcc 5026 to
                                                                             5100
                                      BstDEI                   RsaI SfcI
 PalI                                 Tsp509I
 HaeIII                 TthHB8I Sse9I CviJI                     MaeI    AflIII
cctacagaaaaacagtatgaaactctcgaaaatcaattagccttttatgccaacaaggttttttcactagagaac base pairs
ggatgtcttttgtcatactttgagagctttagttaatcggaaaaatacggttgttccaaaaagtgatctcttg 5101 to
                                                                             5175
CviJI                   TaqI          TspEI                     BfaI    MluI
```

FIG. 22 (Cont'd)

```
BsuRI
  BstSFI

BstUI         Hin6I AspLEI                       Bsp143I
ThaI          HinP1I CfoI                        MboI DpnI
    MwoI  DdeI Aor51HI HaeII                     DpnII MboII  SfaNI
gcgttatatgcactcagcgctgtggggcattttactttaggttgcgtattggaagatcaagagcatcaagtcgct base pairs
cgcaatatacgtgagtcgcgacaccccgtaaaatgaaatccaacgcataaccttctagttctcgtagttcagcga 5176 to
5250
     Bsh1236I BstDEI AfeI Bsp143II                  NdeII
AccII         HspAI HhaI                            Sau3AI
MvnI          Eco47III BstH2I                       Kzo9I Tsp509I MboI Kzo9I
                                    ItaI               TthHB8I BclI Bsp143I
      MboII                         BscFI              CviJI Sse9I  FbaI Sau3AI
aaagaagaaagggaaacacctactactgatagtatgccgccattattacgacaagctatcgaattatttgatcac base pairs
tttcttctttccctttgtggatgatgactatcatacggcggtaataatgctgttcgatagcttaataaactagtg 5251 to
5325
                                    Fsp4HI         AluI  TspEI    DpnII
                                      AciI              TaqI      NdeII
                                                                  Ksp22I BssT1I CviJI              TspEI MboI DpnI
      BseDI MvnI         PalI Sse9I NdeII FauNDI            TruII
    BsaJI BsgI           HaeIII   FbaI Sau3AI AciI          Tru9I
caaggtgcagagccagccttcttattcggccttgaattgatcatatgcggattagaaaaacaacttaaatgtgaa base pairs
gttccacgtctcggtcggaagaataagccggaacttaactagtatacgcctaatcttttgttgaatttacactt 5326 to
5400
DpnI StyI MslI  CviJI    CviJI    DpnII Kzo9I                      MseI
Eco13CI HphI Cac8I       BsuRI    BclI Bsp143I
  ErhI EcoT14I                    Tsp509I Ksp22I NdeI HgiEI AspS9I AciI BsoFI ThaI MvnI Cac8I Bsh1236I AfaI TaqI EcoO109I Cac8I
   Bme18I PspN4I Csp6I Fsp4HI AccII HhaI AccII Pf123II Tsp509I DraII PalI
   Cfr13I NlaIV Bsh1236I ItaI BsePI AciI ThaI PspLI RsaI TthHB8I AspS9I TthHB8I
agtgggtccgcgtacagccgcgcgcgtacgaaaaacaattacgggtctaccatcgagggcctgctcgatctcccg base pairs
tcacccaggcgcatgtcggcgcgcgcatgcttttttgttaatgcccagatggtagctcccggacgagctagagggc 5401 to
5475
    SinI AvaII AccII RsaI HinP1I BstUI CfoI BstUI SunI Sse9I Cfr13I HaeIII
    Sau96I ThaI BstUI CviJI BssHII Bsh1236I MvnI BsiWI TspEI Sau96I CviJI
    AsuI Eco47I MvnI AfaI HspAI Hin6I AspLEI SplI Csp6I AccI AsuI MnlI BsuRI Sau3AI BcnI Hin1I HgaI Ksp632I BsoFI PspN4I BstUI   BseDI MvnI FauI AciI
 NdeII BsiSI HapII Hsp92I Eam1104I Cac8I NlaIV Hin6I AspLEI AccII KspI SacII
     Kzo9I MspI Msp17I BslI EarI CviJI AciI ThaI AciI BsaJI BstUI Sfr303I
gacgacgacgcccccgaagaggcggggctggcggctccgcgcctgtcctttctccccgcgggacacacgcgcaga base pairs
ctgctgctgcgggggcttctccgccccgaccgccgaggcgcggacaggaaagaggggcgccctgtgtgcgcgtct 5476 to
5550
 DpnII DpnI HpaII BbiII Bsc4I MnlI MwoI CviJI AccII HhaI BstDSI Bsh1236I BsmFI
```

FIG. 22 (Cont'd)

```
TaqI Bsp143I MspR9I AcyI BsiYI AciI Fsp4HI HspAI Bsh1236I DsaI NspBII SstII
  MboI NciI ScrFI BsaHI MboII FauI ItaI HinP1I MvnI CfoI ThaI MspA1I Cfr42I

AccII AspLEI HindII CviJI Bsh1285I BstOI Ecl136II BmyI SacI BsiHKAI
   ThaI MvnI TthHB8I AspS9I PspN4I CviJI MspR9I AluI AspHI BanII BstDEI    Hin6I
 HinP1I HhaI AccI Sau96I NlaIV PshAI BstNI BsmFI Bsp1286I FriOI DdeI       HinP1I
ctgtcgacggccccccgaccgatgtcagcctgggggacgagctccacttagacggcgaggacgtggcgatggcg base pairs
gacagctgccgggggggctggctacagtcggaccccctgctcgaggtgaatctgccgctcctgcaccgctaccgc 5551 to
5625
    BstUI SalI HincII HaeIII BstMCI BseDI MvaI CviJI Bbv12I Alw21I        HspAI
 HspAI Bsh1236I Cfr13I PalI BsiEI EcoRII Bst2UI SduI Eco24I SstI MaeII
   Hin6I CfoI TaqI AsuI BsuRI BsaOI BsaJI ScrFI EcoICRI Psp124BI MnlI AspLEI NspI AccII HhaI MamI Bse8I Bsp143I NspI      BcoI XmaI HpaII SmaI
    PaeI SphI BstUI CfoI TthHB8I MboI AflIII     TfiI Ama87I NciI HapII SinI
       NlaIII ThaI Bsh1236I BsaBI DpnII DpnI   BsmFI  BsaJI Eco88I MspI Cfr13I
catgccgacgcgctagacgatttcgatctggacatgttgggggacggggattccccgggtccgggatttaccccc base pairs
gtacggctgcgcgatctgctaaagctagacctgtacaaccccctgccccttaaggggccaggccctaaatggggg 5626 to
5700
    Cac8I HinP1I HgaI BfaI TaqI NdeII BspLU11I  HinfI Cfr9I BsiSI ScrFI Bme18I
 HhaI Hsp92II Hin6I AspLEI BsrBRI Sau3AI NlaIII      BseDI AvaI BcnI PspALI
 CfoI BbuI HspAI MvnI MaeI Bsh1365I Kzo9I Hsp92II     PspAI BsoBI MspR9I Sau96I HgiEI PspN4I NciI PleI HspAI    CfrI                            BssTlI
  AvaII BslI HapII AciI AspLEI  EaeI    TaqI                    ErhI BseDI
   Eco47I BsiYI BcnI HinP1I Bsp143II BsuRI                      SfaNI EcoT14I
cacgactccgcccctacggcgctctggatatggccgacttcgagtttgagcagatgtttaccgatgcccttgga base pairs
gtgctgaggcggggatgccgcgagacctataccggctgaagctcaaactcgtctacaaatggctacgggaacct 5701 to
5775
    AspS9I HpaII HinfI HhaI HaeII CviJI TthHB8I                 Eco130I
 AsuI Bsc4I MspI MspR9I CfoI BstH2I PalI                        StyI Sse9I
   NlaIV BsiSI ScrFI Hin6I    HaeIII                            BsaJI Tsp509I         NdeII BamHI DpnI BseDI AvaI NciI ScrFI Acc65I RsaI PinAI
         AfaI    DpnII Bsp143I AclWI PspAI BsiSI MspR9I Asp718I AfaI BsaWI
         Csp6I   BstYI Sau3AI PspN4I BcoI XmaI HpaII Eco64I NlaIV BslI
attgacgagtacggtgggatggatccccgggtaccggtcgccaccatggtgagcaaggcgaggagctgttcacc base pairs
taactgctcatgccaccctacctaggggcccatggccagcggtggtaccactcgttcccgctcctcgacaagtgg 5776 to
5850
         RsaI    BstF5I MflI Kzo9I AlwI Eco88I MspI SmaI BshNI Bsc4I BssAI
                 BstX2I BstI NlaIV Ama87I BsoBI HapII BanI Csp6I AgeI BsrFI
 TspEI           MboI FokI XhoII BsaJI Cfr9I BcnI PspALI AccBlI PspN4I Cfr10I BsaOI BssT1I Bsp19I BseRI BsaJI ScrFI PspN4I BstOI TthHB8I HaeIII
    HpaII Bsh1285I EcoT14I Hsp92II MspI MspR9I Acc3I BstF5I MvaI CviJI PalI
 BsiYI HapII Eco130I BseDI NlaIII BsiSI NciI Eco64I Bsp1286I MspR9I AluI CviJI
ggggtggtgcccatcctggtcgagctggacgcgacgtaaacggccacaagttcagcgtgtccggcgagggcgag base pairs
ccccaccacgggtaggaccagctcgacctgccgctgcatttgccggtgttcaagtcgcacaggccgctcccgctc 5851 to
5925
    BsiSI BsiEI StyI BstDSI MnlI HpaII BcnI BanI SduI EcoRII ScrFI MaeII HpaII
```

*FIG. 22 (Cont'd)*

```
      MspI BstMCI NcoI DsaI HphI AluI BseDI MslI NlaIV BstNI Bst2UI EaeI BsuRI
Bse118I KpnI ErhI BsaJI MslI CviJI HapII HphI BshNI BmyI FokI TaqI CfrI BsiSI

MspI                                    Cfr10I MwoI ItaI  BsaJI BsiYI
  HapII           AluI                    BsrFI HapII Fsp4HI EcoRII BstOI
  MwoI SfaNI    Cac8I        Eco57I       BsgI HpaII AluI Bst71I Bsp1286I
ggcgatgccacctacggcaagctgaccctgaagttcatctgcaccaccggcaagctgcccgtgccctggcccacc base pairs
ccgctacggtggatgccgttcgactgggacttcaagtagacgtggtggccgttcgacgggcacgggaccgggtgg 5926 to
                                                                               6000
     BcgI          CviJI                  BssAI MspI BsoFI Bsc4I BslI
   MnlI                                 Bse118I CviJI MwoI SduI BmyI
   MnlI                                   BsiSI Cac8I BbvI BseDI BstNI MvaI AsuI MslI Bsc4I BstNI Cac8I     ItaI             ItaI
    Sau96I BsuRI BssSI BseDI Mval     CviJI             BsoFI
  ScrFI AspS9I MaeIII BsaJI ScrFI TspRI BsoFI        NlaIII BbvI
ctcgtgaccaccctgacctgggcgtgcagtgcttcagccgctaccccgaccacatgaagcagcacgacttcttc base pairs
gagcactggtgggactggaccccgcacgtcacgaagtcggcgatggggctggtgtacttcgtcgtgctgaagaag 6001 to
                                                                               6075
MspR9I HaeIII BsiI BslI BstOI MwoI    Eco57I              Hsp92II
Bst2UI CviJI MnlI EcoRII MspR9I BsgI   Fsp4HI             Fsp4HI
  Cfr13I PalI Tsp45I BsiYI Bst2UI       AciI               Bst71I MspR9I HhaI                                Hin6I
         Hsp92II       BstNI HinP1I                            ThaI
MboII  AciI     CviJI EcoRII MvaI CfoI  MboII                HinP1I
aagtccgccatgcccgaaggctacgtccaggagcgcaccatcttcttcaaggacgacggcaactacaagacccgc base pairs
ttcaggcggtacgggcttccgatgcaggtcctcgcgtggtagaagaagttcctgctgccgttgatgttctgggcg 6076 to
                                                                               6150
           NlaIII       MaeII ScrFI Hin6I                        HspAI
                              BstOI HspAI                        AccII
                              Bst2UI AspLEI                      BstUI AciI BsaJI TthHB8I       BstNI HphI       AluI
  MvnI CfoI MnlI            EcoRII ScrFI  TaqI        TaqI
   AspLEI BslI  MnlI    BsaJI MspR9I AciI  CviJI Eco57I          MnlI
gccgaggtgaagttcgagggcgacaccctggtgaaccgcatcgagctgaagggcatcgacttcaaggaggacggc base pairs
cggctccacttcaagctcccgctgtgggaccacttggcgtagctcgacttcccgtagctgaagttcctcctgccg 6151 to
                                                                               6225
  Bsh1236I BsiYI      BseDI Bst2UI    TthHB8I      TthHB8I
  FauI Bsc4I HphI      MslI Mval       SfaNI        SfaNI
  HhaI BscDI TaqI      BstOI BstNI ScrFI      BpmI
   BseDI Bst2UI AluI Csp6I
   EcoRII FokI Bsp1286I         CviJI MaeII       HphI       MboII
aacatcctggggcacaagctggagtacaactacatcagccacaacgtctatatcaccgccgacaagcagaagaac base pairs
ttgtaggacccccgtgttcgacctcatgttgatgtagtcggtgttgcagatatagtggcggctgttcgtcttcttg 6226 to
                                                                               6300
```

FIG. 22 (Cont'd)

```
           BsaJI MspR9I CviJI RsaI                                 AciI
              BstF5I SduI      GsuI
              BstOI MvaI BmyI   AfaI

BsuRI       MboI Bsp143I                 Bst71I AluI
              CviJI       BstX2I DpnI    TthHB8I  ItaI  ItaI BbvI
    SfaNI                 BstYI MflI AlwI     MnlI BsoFI BsoFI Bst71I
ggcatcaaggccaacttcaagatccgccacaacatcgaggacggcagcgtgcagctcgccgaccactaccagcag base pairs
ccgtagttccggttgaagttctaggcggtgttgtagctcctgccgtcgcacgtcgagcggctggtgatggtcgtc 6301 to
                                                                             6375
              HaeIII     DpnII XhoII AciI         Fsp4HI Fsp4HI Cac8I
              PalI       NdeII Kzo9I    TaqI       BbvI   CviJI
                         Sau3AI AclWI                 Cac8I BsgI HaeIII  BsoFI                    BmyI  BseNI BstDEI
                     AsuI PalI ItaI                   Bsp1286I  AciI
                     Cfr13I BsuRI BbvI          DdeI  SduI  BsiHKAI
aacaccccatcggcgacggccccgtgctgctgcccgacaaccactacctgagcacccagtccgccctgagcaaa base pairs
ttgtgggggtagccgctgccggggcacgacgacgggctgttggtgatggactcgtgggtcaggcgggactcgttt 6376 to
                                                                             6450
              Sau961 NlaIV Bst71I        BstDEI Alw21I Bsrl
              AspS9I PspN4I              AspHI BsrSI DdeI
              CviJI  Fsp4HI              Bbv12I Bse1I ThaI Bsh1236I DpnI Hsp92II BpmI Fsp4HI HapII NdeII AlwI
       Hin6I MvnI NdeII NlaIII AsuI GsuI  BsoFI MspI BcnI Sau3AI NlaIII
       HinP1I AspLEI Bsp143I Sau961 AspS9I ItaI HpaII ScrFI Bsp143I
gaccccaacgagaagcgcgatcacatggtcctgctggagttcgtgaccgccgccgggatcactctcggcatggac base pairs
ctggggttgctcttcgcgctagtgtaccaggacgacctcaagcactggcggcggccctagtgagagccgtacctg 6451 to
                                                                             6525
             HspAI BstUI MboI Cfr13I HgiEI Tsp45I Bsc4I BsiYI MboI DpnI Hsp92II
             HhaI CfoI Sau3AI SinI AvaII MaeIII Bsl NciI DpnII AclWI
             AccII DpnII Kzo9I Bme18I Eco47I  AciI BsiSI MspR9I Kzo9I Bsp1407I      BsoFI ItaI CviJI BsaOI Bsh1236I Sau3AI BsrBRI
      SspBI       CfrI Fsp4HI BsuRI AccII HinfI DpnII MamI    MnlI
    CviJI AfaI    EaeI NotI HaeIII Bsh1285I PleI MboI DpnI CviJI
gagctgtacaagtaaagcggccgcgactctagatcataatcagccataccacatttgtagaggttttacttgctt base pairs
ctcgacatgttcatttcgccggcgctgagatctagtattagtcggtatggtgtaaacatctccaaaatgaacgaa 6526 to
                                                                             6600
       Csp6I     BstZI EclXI PalI BstMCI AciI BfaI Kzo9I Bsh1365I
    AluI RsaI    CciNI Eco52I BsiEI BstUI XbaI NdeII BsaBI
       BsrGI     EagI XmaIII AciI ThaI MvnI MaeI Bsp143I Bse8I MunI       HincII
    TruI                                      Mva1269I   MseI
    Tru9I      MnlI    MnlI                   MfeI BsaMI Tru9I
taaaaaacctcccacacctcccctgaacctgaaacataaaatgaatgcaattgttgttgttaacttgtttattg base pairs
attttttggagggtgtggagggggacttggactttgtattttacttacgttaacaacaacaattgaacaaataac 6601 to
                                                                             6675
```

FIG. 22 (Cont'd)

```
    MseI                                    BsmI Tsp509I HpaI
     DraI                                    Sse9I        TruII
                                             TspEI        HindII AluI                        ApoI                      BsaMI
   ItaI Bst71I                   AcsI                     Mva1269I
  BsoFI       MaeIII            SfaNI                      TspRI
cagcttataatggttacaaataaagcaatagcatcacaaatttcacaaataaagcattttttttcactgcattcta base pairs
gtcgaatattaccaatgtttatttcgttatcgtagtgtttaaagtgtttatttcgtaaaaaaagtgacgtaagat 6676 to
                                                                              6750
  Fsp4HI                        Sse9I                      BsmI
   CviJI                         TspEI                     MaeI
    BovI                         Tsp509I                   BfaI
                            MspCI
                            Bst98I
                            BspTI MseI
gttgtggtttgtccaaactcatcaatgtatcttaag  base pairs
caacaccaaacaggtttgagtagttacatagaattc  6751 to 6786
                            AflII TruII
                            Vha464I
                            BfrI Tru9I
```

FIG. 22 (Cont'd)

Table by Enzyme Name

| Enzyme name | No. cuts | Positions of sites | Recognition sequence |
|---|---|---|---|
| AatI | 2 | 2964 3530 | agg/cct |
| AatII | 1 | 2462 | gacgt/c |
| Acc65I | 5 | 1107 1570 2837 2994 5805 | g/gtacc |
| AccB1I | 11 | 926 1107 1255 1570 2837 2994 3626 4624 4973 5805 5856 | g/gyrcc |
| AccB7I | 3 | 1102 2150 3450 | ccannnn/ntgg |
| AccBSI | 1 | 4760 | gagcgg |
| AccI | 7 | 1577 1613 1637 2187 4267 5446 5554 | gt/mkac |
| AccII | 17 | 238 319 637 1568 2812 2861 5176 5410 5420 5424 5514 5533 5544 5635 6149 6467 6548 | cg/cg |
| AciI | 44 | 241 245 287 350 463 601 640 707 748 1213 1251 1283 1514 1556 1569 1636 1782 1900 2355 2862 3725 3742 4512 4758 4935 5290 5375 5411 5421 5500 5509 5515 5534 5711 6042 6083 6150 6189 6284 6327 6440 6500 6545 6549 | ccgc |
| AclNI | 1 | 1592 | a/ctagt |
| AclWI | 14 | 281 466 1096 1559 2683 2757 2832 2874 3699 3946 4769 5800 6325 6510 | ggatc |
| AcsI | 11 | 69 1586 1653 1801 2320 2571 2849 3371 3962 4780 6713 | r/aatty |
| AcyI | 4 | 2459 2915 4946 5483 | gr/cgyc |
| AfaI | 20 | 254 536 1109 1572 2196 2303 2465 2597 2795 2839 2975 2996 3648 5084 5413 5427 5785 5807 6250 6532 | gt/ac |
| AfeI | 1 | 5193 | agc/gct |
| AflII | 2 | 1 6781 | c/ttaag |
| AflIII | 6 | 1058 1233 3570 4219 5174 5657 | a/crygt |
| AgeI | 1 | 5808 | a/ccggt |
| AluI | 47 | 108 258 432 543 591 807 840 912 945 1326 2060 2317 2540 2556 2808 2818 2845 2949 3002 3352 3358 3393 3449 3665 3781 3861 4317 4501 4515 4596 4640 4647 4750 4833 4887 5009 5305 5592 5841 5874 5946 5979 6195 6243 6354 6528 6678 | ag/ct |
| Alw21I | 11 | 360 1075 1626 1766 1925 2847 2951 3004 3354 5594 6430 | gwgcw/c |
| Alw26I | 8 | 1711 1949 2224 2614 2921 3920 | gtctc |

FIG. 22 (Cont'd)

|  |  |  |  |
|---|---|---|---|
| | | 4143 4200 | |
| Alw44I | 2 | 1071 1762 | g/tgcac |
| AlwI | 14 | 281 466 1096 1559 2683 2757 2832 2874 3699 3946 4769 5800 6325 6510 | ggatc |
| AlwNI | 4 | 2150 2375 3978 4739 | cagnnn/ctg |
| Ama87I | 11 | 1559 2833 2990 3339 3347 3541 4191 4628 4770 5679 5801 | c/ycgrg |
| Aor51HI | 1 | 5193 | agc/gct |
| ApaI | 4 | 1439 1566 2763 4667 | gggcc/c |
| ApaLI | 2 | 1071 1762 | g/tgcac |
| ApoI | 11 | 69 1586 1653 1801 2320 2571 2849 3371 3962 4780 6713 | r/aatty |
| AseI | 1 | 1700 | at/taat |
| AsnI | 1 | 1700 | at/taat |
| Asp700I | 1 | 1340 | gaann/nnttc |
| Asp718I | 5 | 1107 1570 2837 2994 5805 | g/gtacc |
| AspHI | 11 | 360 1075 1626 1766 1925 2847 2951 3004 3354 5594 6430 | gwgcw/c |
| AspI | 1 | 4136 | gacn/nngtc |
| AspLEI | 16 | 321 637 678 2495 2553 4825 5194 5422 5516 5546 5625 5637 5722 6110 6151 6467 | gcg/c |
| AspS9I | 29 | 306 389 790 1026 1080 1422 1435 1562 1733 1954 2015 2687 2759 2856 2875 3455 3934 4279 4434 4495 4608 4663 5405 5457 5559 5683 5993 6394 6477 | g/gncc |
| AsuI | 29 | 306 389 790 1026 1080 1422 1435 1562 1733 1954 2015 2687 2759 2856 2875 3455 3934 4279 4434 4495 4608 4663 5405 5457 5559 5683 5993 6394 6477 | g/gncc |
| AtsI | 1 | 4136 | gacn/nngtc |
| AvaI | 11 | 1559 2833 2990 3339 3347 3541 4191 4628 4770 5679 5801 | c/ycgrg |
| AvaII | 8 | 306 1954 2015 2875 4608 5405 5683 6477 | g/gwcc |
| AvrII | 3 | 1397 3476 3946 | c/ctagg |
| BalI | 2 | 974 2044 | tgg/cca |
| BamHI | 7 | 1555 2753 2828 3695 3942 4765 5796 | g/gatcc |
| BanI | 11 | 926 1107 1255 1570 2837 2994 3626 4624 4973 5805 5856 | g/gyrcc |
| BanII | 10 | 1439 1566 2157 2763 2847 2951 3004 3354 4667 5594 | grgcy/c |
| BanIII | 1 | 2471 | at/cgat |
| BbiII | 4 | 2459 2915 4946 5483 | gr/cgyc |
| BbrPI | 1 | 1236 | cac/gtg |
| BbsI | 4 | 1320 1420 2122 2889 | gaagac |

*FIG. 22 (Cont'd)*

| | | | |
|---|---|---|---|
| BbuI | 2 | 4025 5629 | gcatg/c |
| Bbv12I | 11 | 360 1075 1626 1766 1925 2847 2951 3004 3354 5594 6430 | gwgcw/c |
| Bbv16II | 4 | 1320 1420 2122 2889 | gaagac |
| BbvI | 29 | 112 382 436 443 727 808 1286 1730 1904 2557 2697 3383 3493 3512 3581 3605 3814 4321 4569 4600 4743 4837 4903 5983 6064 6348 6355 6406 6679 | gcagc |
| BcgI | 2 | 865 5933 | cgannnnnntgc |
| BclI | 2 | 5319 5363 | t/gatca |
| BcnI | 23 | 281 935 1434 1560 1907 1952 2482 2758 2834 2879 2991 3624 3844 4487 4612 4629 4771 5473 5680 5687 5802 5850 6504 | cc/sgg |
| BcoI | 11 | 1559 2833 2990 3339 3347 3541 4191 4628 4770 5679 5801 | c/ycgrg |
| BfaI | 22 | 36 230 1030 1398 1593 2805 2823 3462 3477 3504 3947 3986 4258 4516 4693 4760 4777 4793 5167 5638 6554 6748 | c/tag |
| BfrI | 2 | 1 6781 | c/ttaag |
| BglI | 3 | 1253 2864 4562 | gccnnnn/nggc |
| BglII | 1 | 3343 | a/gatct |
| BlnI | 3 | 1397 3476 3946 | c/ctagg |
| BlpI | 1 | 1740 | gc/tnagc |
| Bme18I | 8 | 306 1954 2015 2875 4608 5405 5683 6477 | g/gwcc |
| BmyI | 25 | 360 551 800 929 1075 1439 1566 1626 1766 1925 2157 2763 2847 2951 3004 3354 4622 4629 4667 4733 5594 5861 5990 6239 6430 | gdgch/c |
| BpiI | 4 | 1320 1420 2122 2889 | gaagac |
| BpmI | 6 | 303 543 2596 2924 6249 6489 | ctggag |
| Bpu1102I | 1 | 1740 | gc/tnagc |
| Bpu14I | 1 | 3361 | tt/cgaa |
| BpuAI | 4 | 1320 1420 2122 2889 | gaagac |
| Bsa29I | 1 | 2471 | at/cgat |
| BsaAI | 2 | 1236 4449 | yac/gtr |
| BsaBI | 3 | 225 5648 6561 | gatnn/nnatc |
| BsaHI | 4 | 2459 2915 4946 5483 | gr/cgyc |
| BsaJI | 55 | 551 606 630 793 933 963 1014 1076 1397 1559 1566 1644 1914 2018 2150 2400 2832 2859 2990 3476 3531 3622 3630 3652 3688 3699 3800 3931 3937 3946 3971 4071 4437 4453 4558 4580 4604 4611 4628 4671 4724 4769 5325 5531 5580 5678 5769 5800 5819 5849 5989 6017 6152 6176 6231 | c/cnngg |

*FIG. 22 (Cont'd)*

| | | | |
|---|---|---|---|
| BsaMI | 6 | 44 143 1374 1407 6649 6748 | gaatgc |
| BsaOI | 5 | 242 1884 5570 5813 6546 | cgry/cg |
| BsaWI | 1 | 5808 | w/ccggw |
| Bsc4I | 36 | 285 635 798 1019 1101 1271 1291 1454 1866 1889 2017 2149 2280 3449 3517 3622 3688 3704 3759 3819 3884 3936 4075 4491 4574 4609 4671 4749 4998 5492 5684 5807 5989 6016 6152 6502 | ccnnnn/nnngg |
| BscI | 1 | 2471 | at/cgat |
| Bse118I | 4 | 811 1495 5808 5971 | r/ccggy |
| Bse1I | 12 | 355 1202 1525 1859 2148 2187 2688 3823 3961 4120 4545 6436 | actgg |
| Bse8I | 3 | 225 5648 6561 | gatnn/nnatc |
| BseCI | 1 | 2471 | at/cgat |
| BseDI | 55 | 551 606 630 793 933 963 1014 1076 1397 1559 1566 1644 1914 2018 2150 2400 2832 2859 2990 3476 3531 3622 3630 3652 3688 3699 3800 3931 3937 3946 3971 4071 4437 4453 4558 4580 4604 4611 4628 4671 4724 4769 5325 5531 5580 5678 5769 5800 5819 5849 5989 6017 6152 6176 6231 | c/cnngg |
| BseNI | 12 | 355 1202 1525 1859 2148 2187 2688 3823 3961 4120 4545 6436 | actgg |
| BsePI | 1 | 5420 | g/cgcgc |
| BseRI | 5 | 951 1154 3662 4716 5841 | gaggag |
| BsgI | 10 | 438 762 823 1729 3820 4602 5335 5969 6030 6354 | gtgcag |
| Bsh1236I | 17 | 238 319 637 1568 2812 2861 5176 5410 5420 5424 5514 5533 5544 5635 6149 6467 6548 | cg/cg |
| Bsh1285I | 5 | 242 1884 5570 5813 6546 | cgry/cg |
| Bsh1365I | 3 | 225 5648 6561 | gatnn/nnatc |
| BshNI | 11 | 926 1107 1255 1570 2837 2994 3626 4624 4973 5805 5856 | g/gyrcc |
| BsiEI | 5 | 242 1884 5570 5813 6546 | cgry/cg |
| BsiHKAI | 11 | 360 1075 1626 1766 1925 2847 2951 3004 3354 5594 6430 | gwgcw/c |
| BsiI | 3 | 786 2605 6006 | ctcgtg |
| BsiSI | 29 | 281 812 872 935 1433 1496 1560 1906 1951 2482 2757 2834 2879 2991 3624 3843 4487 4611 4629 4771 5473 5680 5686 5802 5809 5849 5912 5972 6503 | c/cgg |
| BsiWI | 1 | 5425 | c/gtacg |
| BsiYI | 36 | 286 636 799 1020 1102 1272 1292 1455 1867 1890 2018 2150 2281 3450 3518 3623 3689 3705 3760 | ccnnnnn/nnngg |

*FIG. 22 (Cont'd)*

|  |  |  |  |
|---|---|---|---|
|  |  | 3820 3885 3937 4076 4492 4575 |  |
|  |  | 4610 4672 4750 4999 5493 5685 |  |
|  |  | 5808 5990 6017 6153 6503 |  |
| BslI | 36 | 286 636 799 1020 1102 1272 1292 | ccnnnnn/nngg |
|  |  | 1455 1867 1890 2018 2150 2281 |  |
|  |  | 3450 3518 3623 3689 3705 3760 |  |
|  |  | 3820 3885 3937 4076 4492 4575 |  |
|  |  | 4610 4672 4750 4999 5493 5685 |  |
|  |  | 5808 5990 6017 6153 6503 |  |
| BsmAI | 8 | 1711 1949 2224 2614 2921 3920 | gtctc |
|  |  | 4143 4200 |  |
| BsmBI | 2 | 2921 3920 | cgtctc |
| BsmFI | 14 | 1014 1862 1957 2880 3539 3690 | gggac |
|  |  | 4408 4460 4508 4680 4777 5539 |  |
|  |  | 5589 5670 |  |
| BsmI | 6 | 44 143 1374 1407 6649 6748 | gaatgc |
| BsoBI | 11 | 1559 2833 2990 3339 3347 3541 | c/ycgrg |
|  |  | 4191 4628 4770 5679 5801 |  |
| BsoFI | 45 | 109 239 285 379 433 440 724 746 | gc/ngc |
|  |  | 805 1210 1248 1283 1512 1727 |  |
|  |  | 1898 2554 2694 2859 3380 3490 |  |
|  |  | 3509 3578 3602 3723 3739 3811 |  |
|  |  | 4318 4566 4597 4740 4755 4834 |  |
|  |  | 4900 5287 5418 5507 5980 6039 |  |
|  |  | 6061 6345 6352 6403 6500 6543 |  |
|  |  | 6676 |  |
| Bsp106I | 1 | 2471 | at/cgat |
| Bsp119I | 1 | 3361 | tt/cgaa |
| Bsp120I | 4 | 1435 1562 2759 4663 | g/ggccc |
| Bsp1286I | 25 | 360 551 800 929 1075 1439 1566 | gdgch/c |
|  |  | 1626 1766 1925 2157 2763 2847 |  |
|  |  | 2951 3004 3354 4622 4629 4667 |  |
|  |  | 4733 5594 5861 5990 6239 6430 |  |
| Bsp1407I | 3 | 252 3646 6530 | t/gtaca |
| Bsp143I | 31 | 226 276 314 462 1086 1091 1555 | /gatc |
|  |  | 2036 2173 2468 2472 2678 2753 |  |
|  |  | 2828 2870 2926 3343 3385 3695 |  |
|  |  | 3942 4765 5229 5319 5363 5466 |  |
|  |  | 5649 5796 6320 6468 6506 6556 |  |
| Bsp143II | 3 | 2496 5195 5723 | rgcgc/y |
| Bsp1720I | 1 | 1740 | gc/tnagc |
| Bsp19I | 6 | 963 1644 3652 3800 4580 5819 | c/catgg |
| BspDI | 1 | 2471 | at/cgat |
| BspHI | 1 | 1618 | t/catga |
| BspLU11I | 4 | 1058 3570 4219 5657 | a/catgt |
| BspMI | 3 | 1223 3602 3746 | acctgc |
| BspTI | 2 | 1 6781 | c/ttaag |
| BspXI | 1 | 2471 | at/cgat |
| BsrBI | 1 | 4760 | gagcgg |
| BsrBRI | 3 | 225 5648 6561 | gatnn/nnatc |

*FIG. 22 (Cont'd)*

```
BsrDI       4    1449 4362 4371 5074                      gcaatg
BsrFI       4    811 1495 5808 5971                       r/ccggy
BsrGI       3    252 3646 6530                            t/gtaca
BsrI        12   355 1202 1525 1859 2148 2187             actgg
                 2688 3823 3961 4120 4545 6436
BsrSI       12   355 1202 1525 1859 2148 2187             actgg
                 2688 3823 3961 4120 4545 6436
BssAI       4    811 1495 5808 5971                       r/ccggy
BssHII      1    5420                                     g/cgcgc
BssSI       3    786 2605 6006                            ctcgtg
BssT1I      13   963 1397 1644 3476 3652 3800             c/cwwgg
                 3946 4071 4558 4580 5325 5769
                 5819
Bst1107I    1    2188                                     gta/tac
Bst2UI      37   553 607 682 794 919 1267 1426            cc/wgg
                 2013 2019 2151 2548 2922 3532
                 3551 3631 3690 3700 3932 3938
                 3973 4018 4236 4332 4344 4438
                 4454 4605 4673 4689 4726 5581
                 5866 5991 6018 6103 6178 6232
Bst71I      29   112 382 436 443 727 808 1286             gcagc
                 1730 1904 2557 2697 3383 3493
                 3512 3581 3605 3814 4321 4569
                 4600 4743 4837 4903 5983 6064
                 6348 6355 6406 6679
Bst98I      2    1 6781                                   c/ttaag
BstBI       1    3361                                     tt/cgaa
BstD102I    1    4760                                     gagcgg
BstDEI      27   341 359 1740 1815 2076 2222 2264         c/tnag
                 2561 3389 3394 3606 3637 3716
                 3734 4081 4200 4225 4408 4521
                 4528 4658 4950 5059 5188 5598
                 6424 6442
BstDSI      12   963 1014 1566 1644 1914 2400             c/crygg
                 2859 3652 3800 4580 5531 5819
BstF5I      12   559 925 1124 1866 2056 2353 2452         ggatg
                 2914 3485 5796 5866 6232
BstH2I      3    2496 5195 5723                           rgcgc/y
BstI        7    1555 2753 2828 3695 3942 4765            g/gatcc
                 5796
BstMCI      5    242 1884 5570 5813 6546                  cgry/cg
BstNI       37   553 607 682 794 919 1267 1426            cc/wgg
                 2013 2019 2151 2548 2922 3532
                 3551 3631 3690 3700 3932 3938
                 3973 4018 4236 4332 4344 4438
                 4454 4605 4673 4689 4726 5581
                 5866 5991 6018 6103 6178 6232
BstOI       37   553 607 682 794 919 1267 1426            cc/wgg
                 2013 2019 2151 2548 2922 3532
                 3551 3631 3690 3700 3932 3938
```

*FIG. 22 (Cont'd)*

|         |    |                                              |              |
|---------|----|----------------------------------------------|--------------|
|         |    | 3973 4018 4236 4332 4344 4438               |              |
|         |    | 4454 4605 4673 4689 4726 5581               |              |
|         |    | 5866 5991 6018 6103 6178 6232               |              |
| BstSFI  | 12 | 1300 1581 2376 3377 3776 3862               | c/tryag      |
|         |    | 3880 3894 3979 4268 4704 5102               |              |
| BstUI   | 17 | 238 319 637 1568 2812 2861 5176             | cg/cg        |
|         |    | 5410 5420 5424 5514 5533 5544               |              |
|         |    | 5635 6149 6467 6548                         |              |
| BstX2I  | 12 | 462 1091 1555 2678 2753 2828                | r/gatcy      |
|         |    | 3343 3695 3942 4765 5796 6320               |              |
| BstXI   | 4  | 970 3573 4587 4888                          | ccannnnn/ntgg|
| BstYI   | 12 | 462 1091 1555 2678 2753 2828                | r/gatcy      |
|         |    | 3343 3695 3942 4765 5796 6320               |              |
| BstZI   | 2  | 239 6543                                    | c/ggccg      |
| Bsu15I  | 1  | 2471                                        | at/cgat      |
| BsuRI   | 42 | 241 391 503 792 892 974 1028                | gg/cc        |
|         |    | 1081 1247 1424 1437 1499 1520               |              |
|         |    | 1564 1735 1829 2044 2689 2761               |              |
|         |    | 2858 2964 3457 3530 3725 3936               |              |
|         |    | 4230 4280 4436 4497 4579 4665               |              |
|         |    | 4754 5100 5354 5459 5560 5734               |              |
|         |    | 5894 5994 6310 6395 6545                    |              |
| Cac8I   | 38 | 430 437 761 809 842 1287 1566               | gcn/ngc      |
|         |    | 1737 2345 2356 2691 2810 3667               |              |
|         |    | 3713 3815 4014 4023 4232 4259               |              |
|         |    | 4383 4416 4499 4513 4594 4601               |              |
|         |    | 4752 4934 5011 5339 5422 5461               |              |
|         |    | 5504 5627 5944 5977 6025 6349               |              |
|         |    | 6356                                        |              |
| CciNI   | 2  | 239 6543                                    | gc/ggccgc    |
| CelII   | 1  | 1740                                        | gc/tnagc     |
| CfoI    | 16 | 321 637 678 2495 2553 4825 5194             | gcg/c        |
|         |    | 5422 5516 5546 5625 5637 5722               |              |
|         |    | 6110 6151 6467                              |              |
| Cfr10I  | 4  | 811 1495 5808 5971                          | r/ccggy      |
| Cfr13I  | 29 | 306 389 790 1026 1080 1422 1435             | g/gncc       |
|         |    | 1562 1733 1954 2015 2687 2759               |              |
|         |    | 2856 2875 3455 3934 4279 4434               |              |
|         |    | 4495 4608 4663 5405 5457 5559               |              |
|         |    | 5683 5993 6394 6477                         |              |
| Cfr42I  | 3  | 1569 2862 5534                              | ccgc/gg      |
| Cfr9I   | 7  | 1559 2833 2990 4628 4770 5679               | c/ccggg      |
|         |    | 5801                                        |              |
| CfrI    | 12 | 239 501 890 972 1245 1518 2042              | y/ggccr      |
|         |    | 3723 4752 5732 5892 6543                    |              |
| ClaI    | 1  | 2471                                        | at/cgat      |
| Csp45I  | 1  | 3361                                        | tt/cgaa      |
| Csp6I   | 20 | 253 535 1108 1571 2195 2302 2464            | g/tac        |
|         |    | 2596 2794 2838 2974 2995 3647               |              |
|         |    | 5083 5412 5426 5784 5806 6249               |              |

```
                6531
CviJI    160    108  218  241  258  391  432  503  523    rg/cy
                543  591  691  748  792  807  840  892
                912  945  974  1028 1081 1129 1156
                1240 1247 1326 1424 1437 1499
                1514 1520 1564 1649 1735 1744
                1829 1871 1938 2001 2044 2060
                2091 2100 2155 2285 2317 2343
                2434 2540 2556 2582 2634 2689
                2750 2761 2808 2818 2845 2858
                2867 2949 2964 3002 3352 3358
                3382 3393 3408 3449 3457 3465
                3492 3508 3530 3577 3610 3642
                3665 3715 3725 3738 3781 3813
                3824 3861 3899 3936 3951 3985
                3997 4080 4111 4230 4234 4257
                4261 4280 4317 4342 4385 4397
                4418 4428 4436 4442 4497 4501
                4515 4556 4568 4579 4587 4596
                4640 4647 4665 4682 4692 4710
                4739 4750 4754 4833 4887 4902
                4936 4954 5009 5100 5140 5305
                5337 5341 5354 5417 5459 5502
                5509 5560 5579 5592 5734 5841
                5874 5894 5946 5979 5994 6038
                6095 6195 6243 6263 6310 6354
                6395 6528 6545 6568 6678
DdeI     27     341  359  1740 1815 2076 2222 2264        c/tnag
                2561 3389 3394 3606 3637 3716
                3734 4081 4200 4225 4408 4521
                4528 4658 4950 5059 5188 5598
                6424 6442
DpnI     31     228  278  316  464  1088 1093 1557        ga/tc
                2038 2175 2470 2474 2680 2755
                2830 2872 2928 3345 3387 3697
                3944 4767 5231 5321 5365 5468
                5651 5798 6322 6470 6508 6558
DpnII    31     226  276  314  462  1086 1091 1555        /gatc
                2036 2173 2468 2472 2678 2753
                2828 2870 2926 3343 3385 3695
                3942 4765 5229 5319 5363 5466
                5649 5796 6320 6468 6506 6556
DraI     4      185  2325 4997 6601                       ttt/aaa
DraII    8      1026 1080 1436 1733 1954 4279             rg/gnccy
                4663 5457
DraIII   1      1192                                      cacnnn/gtg
DrdI     1      1715                                      gacnnnn/nngtc
DsaI     12     963  1014 1566 1644 1914 2400             c/crygg
                2859 3652 3800 4580 5531 5819
EaeI     12     239  501  890  972  1245 1518 2042        y/ggccr
```

FIG. 22 (Cont'd)

|  |  |  |  |
|---|---|---|---|
|  |  | 3723 4752 5732 5892 6543 |  |
| EagI | 2 | 239 6543 | c/ggccg |
| Eam1104I | 1 | 5496 | ctcttc |
| EarI | 1 | 5496 | ctcttc |
| Ecl136II | 5 | 2845 2949 3002 3352 5592 | gag/ctc |
| EclXI | 2 | 239 6543 | c/ggccg |
| Eco130I | 13 | 963 1397 1644 3476 3652 3800 3946 4071 4558 4580 5325 5769 5819 | c/cwwgg |
| Eco147I | 2 | 2964 3530 | agg/cct |
| Eco24I | 10 | 1439 1566 2157 2763 2847 2951 3004 3354 4667 5594 | grgcy/c |
| Eco47I | 8 | 306 1954 2015 2875 4608 5405 5683 6477 | g/gwcc |
| Eco47III | 1 | 5193 | agc/gct |
| Eco52I | 2 | 239 6543 | c/ggccg |
| Eco57I | 7 | 591 754 834 1129 5958 6038 6201 | ctgaag |
| Eco64I | 11 | 926 1107 1255 1570 2837 2994 3626 4624 4973 5805 5856 | g/gyrcc |
| Eco72I | 1 | 1236 | cac/gtg |
| Eco88I | 11 | 1559 2833 2990 3339 3347 3541 4191 4628 4770 5679 5801 | c/ycgrg |
| EcoICRI | 5 | 2845 2949 3002 3352 5592 | gag/ctc |
| EcoNI | 1 | 4997 | cctnn/nnnagg |
| EcoO109I | 8 | 1026 1080 1436 1733 1954 4279 4663 5457 | rg/gnccy |
| EcoRI | 4 | 1586 2849 3371 4780 | g/aattc |
| EcoRII | 37 | 551 605 680 792 917 1265 1424 2011 2017 2149 2546 2920 3530 3549 3629 3688 3698 3930 3936 3971 4016 4234 4330 4342 4436 4452 4603 4671 4687 4724 5579 5864 5989 6016 6101 6176 6230 | /ccwgg |
| EcoT14I | 13 | 963 1397 1644 3476 3652 3800 3946 4071 4558 4580 5325 5769 5819 | c/cwwgg |
| EcoT22I | 2 | 2626 4027 | atgca/t |
| ErhI | 13 | 963 1397 1644 3476 3652 3800 3946 4071 4558 4580 5325 5769 5819 | c/cwwgg |
| Esp1396I | 3 | 1102 2150 3450 | ccannnn/ntgg |
| Esp3I | 2 | 2921 3920 | cgtctc |
| FauI | 7 | 641 1569 4512 4936 5501 5534 6150 | cccgc |
| FauNDI | 1 | 5368 | ca/tatg |
| FbaI | 2 | 5319 5363 | t/gatca |
| FokI | 12 | 559 925 1124 1866 2056 2353 2452 2914 3485 5796 5866 6232 | ggatg |
| FriOI | 10 | 1439 1566 2157 2763 2847 2951 3004 3354 4667 5594 | grgcy/c |

*FIG. 22 (Cont'd)*

```
Fsp4HI      45   109  239  285  379  433  440  724  746     gc/ngc
                 805  1210 1248 1283 1512 1727
                 1898 2554 2694 2859 3380 3490
                 3509 3578 3602 3723 3739 3811
                 4318 4566 4597 4740 4755 4834
                 4900 5287 5418 5507 5980 6039
                 6061 6345 6352 6403 6500 6543
                 6676
GsuI        6    303  543  2596 2924 6249 6489              ctggag
HaeII       3    2196 5195 5723                             rgcgc/y
HaeIII      42   241  391  503  792  892  974  1028         gg/cc
                 1081 1247 1424 1437 1499 1520
                 1564 1735 1829 2044 2689 2761
                 2858 2964 3457 3530 3725 3936
                 4230 4280 4436 4497 4579 4665
                 4754 5100 5354 5459 5560 5734
                 5894 5994 6310 6395 6545
HapII       29   281  812  872  935  1433 1496 1560         c/cgg
                 1906 1951 2482 2757 2834 2879
                 2991 3624 3843 4487 4611 4629
                 4771 5473 5680 5686 5802 5809
                 5849 5912 5972 6503
HgaI        5    2816 2919 4949 5486 5636                   gacgc
HgiEI       8    306  1954 2015 2875 4608 5405              g/gwcc
                 5683 6477
HhaI        16   321  637  678  2495 2553 4825 5194         gcg/c
                 5422 5516 5546 5625 5637 5722
                 6110 6151 6467
Hin1I       4    2459 2915 4946 5483                        gr/cgyc
Hin6I       16   319  635  676  2493 2551 4823 5192         g/cgc
                 5420 5514 5544 5623 5635 5720
                 6108 6149 6465
HinP1I      16   319  635  676  2493 2551 4823 5192         g/cgc
                 5420 5514 5544 5623 5635 5720
                 6108 6149 6465
HincII      5    124  1578 1614 5555 6662                   gty/rac
HindII      5    124  1578 1614 5555 6662                   gty/rac
HindIII     4    1324 2058 3356 4885                        a/agctt
HinfI       17   233  1163 1615 1910 1995 2084              g/antc
                 2179 2218 2250 2372 3989 4458
                 4519 4850 5674 5704 6550
HpaI        2    124  6662                                  gtt/aac
HpaII       29   281  812  872  935  1433 1496 1560         c/cgg
                 1906 1951 2482 2757 2834 2879
                 2991 3624 3843 4487 4611 4629
                 4771 5473 5680 5686 5802 5809
                 5849 5912 5972 6503
HphI        17   478  607  631  941  964  1978 3617         ggtga
                 3707 4332 4350 4788 5326 5827
                 5850 6160 6184 6282
```

FIG. 22 (Cont'd)

```
Hsp92I      4    2459 2915 4946 5483                      gr/cgyc
Hsp92II     38   268  313  508  703  733  967  1062       catg/
                 1071 1622 1648 2043 2161 2209
                 2386 2624 2707 2749 2800 3517
                 3574 3656 3804 4025 4029 4102
                 4223 4339 4483 4584 4791 4921
                 5629 5661 5823 6057 6087 6477
                 6522
HspAI       16   319  635  676  2493 2551 4823 5192       g/cgc
                 5420 5514 5544 5623 5635 5720
                 6108 6149 6465
ItaI        45   109  239  285  379  433  440  724  746   gc/ngc
                 805  1210 1248 1283 1512 1727
                 1898 2554 2694 2859 3380 3490
                 3509 3578 3602 3723 3739 3811
                 4318 4566 4597 4740 4755 4834
                 4900 5287 5418 5507 5980 6039
                 6061 6345 6352 6403 6500 6543
                 6676
KpnI        5    1111 1574 2841 2998 5809                 ggtac/c
Ksp22I      2    5319 5363                                t/gatca
Ksp632I     1    5496                                     ctcttc
KspI        3    1569 2862 5534                           ccgc/gg
Kzo9I       31   226  276  314  462  1086 1091 1555       /gatc
                 2036 2173 2468 2472 2678 2753
                 2828 2870 2926 3343 3385 3695
                 3942 4765 5229 5319 5363 5466
                 5649 5796 6320 6468 6506 6556
LspI        1    3361                                     tt/cgaa
MaeI        22   36   230  1030 1398 1593 2805 2823       c/tag
                 3462 3477 3504 3947 3986 4258
                 4516 4693 4760 4777 4793 5167
                 5638 6554 6748
MaeII       15   515  686  899  1008 1034 1191 1235       a/cgt
                 1306 1527 2459 4448 5612 5885
                 6098 6269
MaeIII      13   94   289  778  1523 1972 2026 3990       /gtnac
                 4215 4420 4695 6003 6492 6687
MamI        3    225  5648 6561                           gatnn/nnatc
MboI        31   226  276  314  462  1086 1091 1555       /gatc
                 2036 2173 2468 2472 2678 2753
                 2828 2870 2926 3343 3385 3695
                 3942 4765 5229 5319 5363 5466
                 5649 5796 6320 6468 6506 6556
MboII       16   493  668  716  1320 1419 2010 2122       gaaga
                 2427 2658 2889 5231 5258 5495
                 6075 6120 6298
MfeI        2    133  6649                                c/aattg
MflI        12   462  1091 1555 2678 2753 2828            r/gatcy
                 3343 3695 3942 4765 5796 6320
```

*FIG. 22 (Cont'd)*

```
MluI      1   5174                                        a/cgcgt
MluNI     2   974 2044                                    tgg/cca
MnlI      67  170 179 202 450 570 621 633 787             cctc
              864 870 951 1049 1081 1152 1256
              1336 1387 1442 1545 1551 1748
              1891 1960 2455 2493 2566 2602
              2640 2673 2829 2867 2897 2968
              3399 3473 3525 3614 3660 3709
              3721 3736 4041 4086 4205 4211
              4230 4378 4413 4671 4688 4716
              4766 4846 5458 5497 5611 5839
              5920 5926 6003 6157 6169 6220
              6340 6588 6611 6620
Mph1103I  2   2626 4027                                   atgca/t
MscI      2   974 2044                                    tgg/cca
MseI      18  2 123 184 1042 1600 1685 1700               t/taa
              2324 3561 4160 4817 4838 4861
              4996 5390 6600 6661 6782
MslI      16  479 608 785 935 968 1700 2387               caynn/nnrtg
              2619 3624 4960 5069 5327 5821
              5851 6001 6178
Msp17I    4   2459 2915 4946 5483                         gr/cgyc
MspA1I    9   1282 1568 1633 2818 2861 3393               cmg/ckg
              4317 4501 5533
MspCI     2   1 6781                                      c/ttaag
MspI      29  281 812 872 935 1433 1496 1560              c/cgg
              1906 1951 2482 2757 2834 2879
              2991 3624 3843 4487 4611 4629
              4771 5473 5680 5686 5802 5809
              5849 5912 5972 6503
MspR9I    60  281 553 607 682 794 919 935 1267            cc/ngg
              1426 1434 1560 1907 1952 2013
              2019 2151 2482 2548 2758 2834
              2879 2922 2991 3532 3551 3624
              3631 3690 3700 3844 3932 3938
              3973 4018 4236 4332 4344 4438
              4454 4487 4605 4612 4629 4673
              4689 4726 4771 5473 5581 5680
              5687 5802 5850 5866 5991 6018
              6103 6178 6232 6504
MunI      2   133 6649                                    c/aattg
Mva1269I  6   44 143 1374 1407 6649 6748                  gaatgc
MvaI      37  553 607 682 794 919 1267 1426               cc/wgg
              2013 2019 2151 2548 2922 3532
              3551 3631 3690 3700 3932 3938
              3973 4018 4236 4332 4344 4438
              4454 4605 4673 4689 4726 5581
              5866 5991 6018 6103 6178 6232
MvnI      17  238 319 637 1568 2812 2861 5176             cg/cg
              5410 5420 5424 5514 5533 5544
```

FIG. 22 (Cont'd)

|         |    |                                              |           |
|---------|----|----------------------------------------------|-----------|
|         |    | 5635 6149 6467 6548                          |           |
| MwoI    | 33 | 751 804 817 877 1215 1253 1517               | gcnnnnn/nngc |
|         |    | 1630 1732 2097 2440 2499 2739                |           |
|         |    | 2864 2912 3607 3778 3896 4018                |           |
|         |    | 4103 4323 4348 4363 4562 4593                |           |
|         |    | 4938 5182 5338 5503 5912 5972                |           |
|         |    | 5985 6029                                    |           |
| NciI    | 23 | 281 935 1434 1560 1907 1952 2482             | cc/sgg    |
|         |    | 2758 2834 2879 2991 3624 3844                |           |
|         |    | 4487 4612 4629 4771 5473 5680                |           |
|         |    | 5687 5802 5850 6504                          |           |
| NcoI    | 6  | 963 1644 3652 3800 4580 5819                 | c/catgg   |
| NdeI    | 1  | 5368                                         | ca/tatg   |
| NdeII   | 31 | 226 276 314 462 1086 1091 1555               | /gatc     |
|         |    | 2036 2173 2468 2472 2678 2753                |           |
|         |    | 2828 2870 2926 3343 3385 3695                |           |
|         |    | 3942 4765 5229 5319 5363 5466                |           |
|         |    | 5649 5796 6320 6468 6506 6556                |           |
| NheI    | 1  | 4257                                         | g/ctagc   |
| NlaIII  | 38 | 268 313 508 703 733 967 1062                 | catg/     |
|         |    | 1071 1622 1648 2043 2161 2209                |           |
|         |    | 2386 2624 2707 2719 2800 3517                |           |
|         |    | 3574 3656 3804 4025 4029 4102                |           |
|         |    | 4223 4339 4483 4584 4791 4921                |           |
|         |    | 5629 5661 5823 6057 6087 6477                |           |
|         |    | 6522                                         |           |
| NlaIV   | 41 | 390 928 1027 1082 1109 1257 1278             | ggn/ncc   |
|         |    | 1437 1557 1564 1572 1955 2755                |           |
|         |    | 2761 2830 2839 2857 2877 2996                |           |
|         |    | 3409 3456 3628 3697 3944 3998                |           |
|         |    | 4435 4539 4609 4626 4664 4711                |           |
|         |    | 4767 4975 5406 5510 5561 5684                |           |
|         |    | 5798 5807 5858 6396                          |           |
| NotI    | 2  | 239 6543                                     | gc/ggccgc |
| NsiI    | 2  | 2626 4027                                    | atgca/t   |
| NspBII  | 9  | 1282 1568 1633 2818 2861 3393                | cmg/ckg   |
|         |    | 4317 4501 5533                               |           |
| NspI    | 9  | 1062 1071 2624 3574 4025 4223                | rcatg/y   |
|         |    | 4921 5629 5661                               |           |
| NspV    | 1  | 3361                                         | tt/cgaa   |
| PaeI    | 2  | 4025 5629                                    | gcatg/c   |
| PaeR7I  | 2  | 3339 3347                                    | c/tcgag   |
| PalI    | 42 | 241 391 503 792 892 974 1028                 | gg/cc     |
|         |    | 1081 1247 1424 1437 1499 1520                |           |
|         |    | 1564 1735 1829 2044 2689 2761                |           |
|         |    | 2858 2964 3457 3530 3725 3936                |           |
|         |    | 4230 4280 4436 4497 4579 4665                |           |
|         |    | 4754 5100 5354 5459 5560 5734                |           |
|         |    | 5894 5994 6310 6395 6545                     |           |
| Pf123II | 1  | 5425                                         | c/gtacg   |

FIG. 22 (Cont'd)

```
PflMI      3   1102 2150 3450                          ccannnn/ntgg
PinAI      1   5808                                    a/ccggt
PleI       11  237 1167 1619 2222 2254 2376            gagtc
               3993 4462 4523 5708 6554
PmaCI      1   1236                                    cac/gtg
Pme55I     2   2964 3530                               agg/cct
PmlI       1   1236                                    cac/gtg
Ppu10I     2   2622 4023                               a/tgcat
PpuMI      1   1954                                    rg/gwccy
PshAI      1   5572                                    gacnn/nngtc
PshBI      1   1700                                    at/taat
Psp124BI   5   2847 2951 3004 3354 5594                gagct/c
Psp1406I   1   1527                                    aa/cgtt
Psp5II     1   1954                                    rg/gwccy
PspAI      7   1559 2833 2990 4628 4770 5679           c/ccggg
               5801
PspALI     7   1561 2835 2992 4630 4772 5681           ccc/ggg
               5803
PspLI      1   5425                                    c/gtacg
PspN4I     41  390 928 1027 1082 1109 1257 1278        ggn/ncc
               1437 1557 1564 1572 1955 2755
               2761 2830 2839 2857 2877 2996
               3409 3456 3628 3697 3944 3998
               4435 4539 4609 4626 4664 4711
               4767 4975 5406 5510 5561 5684
               5798 5807 5858 6396
PspOMI     4   1435 1562 2759 4663                     g/ggccc
PstI       2   1585 3381                               ctgca/g
PstNHI     1   4257                                    g/ctagc
PvuII      4   2818 3393 4317 4501                     cag/ctg
RcaI       1   1618                                    t/catga
RsaI       20  254 536 1109 1572 2196 2303 2465        gt/ac
               2597 2795 2839 2975 2996 3648
               5084 5413 5427 5785 5807 6250
               6532
SacI       5   2847 2951 3004 3354 5594                gagct/c
SacII      3   1569 2862 5534                          ccgc/gg
SalI       3   1576 1612 5553                          g/tcgac
Sau3AI     31  226 276 314 462 1086 1091 1555          /gatc
               2036 2173 2468 2472 2678 2753
               2828 2870 2926 3343 3385 3695
               3942 4765 5229 5319 5363 5466
               5649 5796 6320 6468 6506 6556
Sau96I     29  306 389 790 1026 1080 1422 1435         g/gncc
               1562 1733 1954 2015 2687 2759
               2856 2875 3455 3934 4279 4434
               4495 4608 4663 5405 5457 5559
               5683 5993 6394 6477
ScrFI      60  281 553 607 682 794 919 935 1267        cc/ngg
               1426 1434 1560 1907 1952 2013
```

*FIG. 22 (Cont'd)*

|  |  |  |  |
|---|---|---|---|
|  |  | 2019 2151 2482 2548 2758 2834 | |
|  |  | 2879 2922 2991 3532 3551 3624 | |
|  |  | 3631 3690 3700 3844 3932 3938 | |
|  |  | 3973 4018 4236 4332 4344 4438 | |
|  |  | 4454 4487 4605 4612 4629 4673 | |
|  |  | 4689 4726 4771 5473 5581 5680 | |
|  |  | 5687 5802 5850 5866 5991 6018 | |
|  |  | 6103 6178 6232 6504 | |
| SduI | 25 | 360 551 800 929 1075 1439 1566 | gdgch/c |
|  |  | 1626 1766 1925 2157 2763 2847 | |
|  |  | 2951 3004 3354 4622 4629 4667 | |
|  |  | 4733 5594 5861 5990 6239 6430 | |
| SfaNI | 16 | 81 485 584 599 858 1123 2523 | gcatc |
|  |  | 2746 3550 5242 5768 5933 6192 | |
|  |  | 6207 6306 6710 | |
| SfcI | 12 | 1300 1581 2376 3377 3776 3862 | c/tryag |
|  |  | 3880 3894 3979 4268 4704 5102 | |
| Sfr274I | 2 | 3339 3347 | c/tcgag |
| Sfr303I | 3 | 1569 2862 5534 | ccgc/gg |
| SfuI | 1 | 3361 | tt/cgaa |
| SinI | 8 | 306 1954 2015 2875 4608 5405 | g/gwcc |
|  |  | 5683 6477 | |
| SmaI | 7 | 1561 2835 2992 4630 4772 5681 | ccc/ggg |
|  |  | 5803 | |
| SpeI | 1 | 1592 | a/ctagt |
| SphI | 2 | 4025 5629 | gcatg/c |
| SplI | 1 | 5425 | c/gtacg |
| SrfI | 1 | 4630 | gccc/gggc |
| Sse9I | 25 | 69 133 1586 1602 1653 1801 1823 | /aatt |
|  |  | 2102 2320 2571 2849 3363 3371 | |
|  |  | 3558 3792 3962 4157 4780 5134 | |
|  |  | 5311 5359 5436 5774 6649 6713 | |
| SseBI | 2 | 2964 3530 | agg/cct |
| SspBI | 3 | 252 3646 6530 | t/gtaca |
| SstI | 5 | 2847 2951 3004 3354 5594 | gagct/c |
| SstII | 3 | 1569 2862 5534 | ccgc/gg |
| StuI | 2 | 2964 3530 | agg/cct |
| StyI | 13 | 963 1397 1644 3476 3652 3800 | c/cwwgg |
|  |  | 3946 4071 4558 4580 5325 5769 | |
|  |  | 5819 | |
| SunI | 1 | 5425 | c/gtacg |
| TaqI | 38 | 449 578 593 620 914 1048 1577 | t/cga |
|  |  | 1613 1880 2471 2847 2986 3004 | |
|  |  | 3046 3088 3130 3172 3214 3256 | |
|  |  | 3298 3340 3348 3361 3369 4853 | |
|  |  | 4943 5126 5309 5453 5465 5554 | |
|  |  | 5648 5741 5870 6164 6191 6206 | |
|  |  | 6335 | |
| TfiI | 6 | 1910 1995 2084 2179 4850 5674 | g/awtc |
| ThaI | 17 | 238 319 637 1568 2812 2861 5176 | cg/cg |

FIG. 22 (Cont'd)

|         |    |                                                                 |              |
|---------|----|-----------------------------------------------------------------|--------------|
|         |    | 5410 5420 5424 5514 5533 5544                                   |              |
|         |    | 5635 6149 6467 6548                                             |              |
| Tru1I   | 18 | 2 123 184 1042 1600 1685 1700                                   | t/taa        |
|         |    | 2324 3561 4160 4817 4838 4861                                   |              |
|         |    | 4996 5390 6600 6661 6782                                        |              |
| Tru9I   | 18 | 2 123 184 1042 1600 1685 1700                                   | t/taa        |
|         |    | 2324 3561 4160 4817 4838 4861                                   |              |
|         |    | 4996 5390 6600 6661 6782                                        |              |
| Tsp45I  | 7  | 289 778 1972 3990 4695 6003 6492                                | /gtsac       |
| Tsp509I | 25 | 69 133 1586 1602 1653 1801 1823                                 | /aatt        |
|         |    | 2102 2320 2571 2849 3363 3371                                   |              |
|         |    | 3558 3792 3962 4157 4780 5134                                   |              |
|         |    | 5311 5359 5436 5774 6649 6713                                   |              |
| TspEI   | 25 | 69 133 1586 1602 1653 1801 1823                                 | /aatt        |
|         |    | 2102 2320 2571 2849 3363 3371                                   |              |
|         |    | 3558 3792 3962 4157 4780 5134                                   |              |
|         |    | 5311 5359 5436 5774 6649 6713                                   |              |
| TspRI   | 24 | 48 759 1201 2117 2149 2243 2443                                 | cagtg        |
|         |    | 2668 2687 3029 3071 3113 3155                                   |              |
|         |    | 3197 3239 3281 3323 3822 3960                                   |              |
|         |    | 4012 4546 4911 6032 6743                                        |              |
| Tth111I | 1  | 4136                                                            | gacn/nngtc   |
| TthHB8I | 38 | 449 578 593 620 914 1048 1577                                   | t/cga        |
|         |    | 1613 1880 2471 2847 2986 3004                                   |              |
|         |    | 3046 3088 3130 3172 3214 3256                                   |              |
|         |    | 3298 3340 3348 3361 3369 4853                                   |              |
|         |    | 4943 5126 5309 5453 5465 5554                                   |              |
|         |    | 5648 5741 5870 6164 6191 6206                                   |              |
|         |    | 6335                                                            |              |
| Van91I  | 3  | 1102 2150 3450                                                  | ccannnn/ntgg |
| Vha464I | 2  | 1 6781                                                          | c/ttaag      |
| VneI    | 2  | 1071 1762                                                       | g/tgcac      |
| VspI    | 1  | 1700                                                            | at/taat      |
| XbaI    | 4  | 229 4759 4792 6553                                              | t/ctaga      |
| XhoI    | 2  | 3339 3347                                                       | c/tcgag      |
| XhoII   | 12 | 462 1091 1555 2678 2753 2828                                    | r/gatcy      |
|         |    | 3343 3695 3942 4765 5796 6320                                   |              |
| XmaI    | 7  | 1559 2833 2990 4628 4770 5679                                   | c/ccggg      |
|         |    | 5801                                                            |              |
| XmaIII  | 2  | 239 6543                                                        | c/ggccg      |
| XmnI    | 1  | 1340                                                            | gaann/nnttc  |
| Zsp2I   | 2  | 2626 4027                                                       | atgca/t      |

FIG. 22 (Cont'd)

The following endonucleases were selected but don't cut this sequence:

Acc113I, Acc16I, AccIII, AhdI, AocI, AscI, AspEI, AviII, BbeI, BsaI, Bse21I, BseAI, BsiMI, Bsp13I, Bsp68I, BspCI, BspEI, BstEII, BstPI, BstSNI, Bsu36I, CpoI, CspI, CvnI, Eam1105I, EclHKI, Eco105I, Eco255I, Eco31I, Eco32I, Eco81I, Eco91I, EcoO65I, EcoRV, EheI, FseI, FspI, KasI, Kpn2I, MroI, MroNI, NaeI, NarI, NgoAIV, NgoMI, NruI, PacI, Ple19I, PmeI, PspEI, PvuI, RsrII, SapI, SbfI, ScaI, SexAI, SfiI, SgfI, SgrAI, SmiI, SnaBI, Sse8387I, SspI, SwaI, XcmI

FIG. 22 (Cont'd)

SEQUENCE LISTING

<160> NUMBER OF SEQ ID NOS: 23

<210> SEQ ID NO 1
<211> LENGTH: 6786
<212> TYPE: DNA
<213> ORGANISM: Mus Musculus

```
<400> SEQUENCE: 1
cttaagatac attgatgagt ttggacaaac cacaactaga atgcagtgaa aaaaatgctt      60
tatttgtgaa atttgtgatg ctattgcttt atttgtaacc attataagct gcaataaaca     120
agttaacaac aacaattgca ttcattttat gtttcaggtt caggggggagg tgtgggaggt    180 tttttaaagc aagtaaaacc tctacaaatg tggtatggct gattatgatc tagagtcgcg    240
gccgctttac ttgtacagct cgtccatgcc gagagtgatc ccggcggcgg tcacgaactc    300
cagcaggacc atgtgatcgc gcttctcgtt ggggtctttg ctcagggcgg actgggtgct    360
caggtagtgg ttgtcgggca gcagcacggg gccgtcgccg atgggggtgt tctgctggta    420
gtggtcggcg agctgcacgc tgccgtcctc gatgttgtgg cggatcttga agttcacctt    480
gatgccgttc ttctgcttgt cggccatgat atagacgttg tggctgttgt agttgtactc    540
cagcttgtgc cccaggatgt tgccgtcctc cttgaagtcg atgcccttca gctcgatgcg    600
gttcaccagg gtgtcgccct cgaacttcac ctcggcgcgg tcttgtagt tgccgtcgtc    660 cttgaagaag atggtgcgct cctggacgta gccttcgggc atgcggact  tgaagaagtc    720 gtgctgcttc atgtggtcgg ggtagcggct gaagcactgc acgccgtagg tcagggtggt    780
cacgagggtg ggccagggca cgggcagctt gccggtggtg cagatgaact tcagggtcag    840
cttgccgtag gtggcatcgc cctcgccctc gccggacacg ctgaacttgt ggccgtttac    900
gtcgccgtcc agctcgacca ggatgggcac caccccggtg aacagctcct cgcccttgct    960
caccatggtt gtggccatat tatcatcgtg tttttcaaag gaaaaccacg tccccgtggt   1020 tcgggggggcc tagacgtttt tttaacctcg actaaacaca tgtaaagcat gtgcaccgag   1080
gccccagatc agatcccata caatgggta ccttctgggc atccttcagc cccttgttga     1140
atacgcttga ggagagccat ttgactcttt ccacaactat ccaactcaca acgtggcact   1200
ggggttgtgc cgcctttgca ggtgtatctt atacacgtgg cttttggccg cagaggcacc   1260
tgtcgccagg tgggggttc cgctgcctgc aaagggtcgc tacagacgtt gtttgtcttc    1320
aagaagcttc cagaggaact gcttccttca cgacattcaa cagaccttgc attcctttgg   1380
cgagagggga aagaccccta ggaatgctcg tcaagaagac agggccaggt ttccgggccc   1440
tcacattgcc aaaagacggc aatatggtgg aaaataacat atagacaaac gcacaccggc   1500
cttattccaa gcggcttcgg ccagtaacgt tagggggggg ggaggggagag gggcggatcc   1560 cgggcccgcg gtaccgtcga ctgcagaatt cactagtgat taaattatat tgtcgactca   1620
tgagcaccca cagcggtcta ctaccatggc tggaattttc ccatatatta tttgttcttt   1680
gccattaaaa tatagcatat taatgggaga cattttttgtc ggagtgcagc aagggcctgc   1740
tgagcctctg ggggtttgctt ggtgcacaag atgagtatgc ggatattttt gtaaaaacac   1800
aaattcacac tctcctgagc agtaattggc cttatatctt ttgggtgcga taatccagtc   1860
ccatccaaag gcttcaaaat cgaccgtgag ggggtagcgg cagcaccggg attccgtgga   1920
gtgctcatcg cagtcaagcc caaagtctct ccgggacctc ttgggtgtgt ctgtcacctt   1980
gacttctaaa aagggattca gcccatcttc tcctggtcct gggaaggtta cagcaagatc   2040
atggccattc tcatccaaag ctttgatttc aatgcctaag ttggattcag ctgtttgag    2100 ccaatttgc aacactgtct tcacatcaat actctgccaa ataccagtgc ctgggctcat    2160
gtcaagtttc agagatcgga ttccagtata ccttgtaccg tctttcatgg gtttgatgag   2220
tctcaggatt tgcacaaaca ctgttgtagg agtcttgacg ggtctgagat atatccacag   2280
ttgggctttt actactttgt tgtactgtat tttagagcta aatttaaaaa agcaacattt   2340
```

```
gggcttgcca tccgcttgca ttagaaagtc agactctgta ggcatggtaa tgattgtttc   2400
cgtggtagcg tgataatcgt catcttccaa agagccatca ctgctgtcat ccctctggac   2460
gtcgtactga tcgatcagtt cccggagtgg aggcgctctt ggcagaagtt gtcttatagc   2520
atctttgctg atgttaggag ctgtttccag gcgcagctta ctgaggattt gaattttat    2580 ggcttctatt ctggagtacc tcgtgttttg tctccacgca catgcattac acagcccctc   2640
tttttccaca ttttcttctc tctcactgcc ctcatttaga tccactgggc agcagcaat    2700 cagcatgaac aggtaaatat aaacatacat ttgcagtttt tgcatcatgg ctggatccgg   2760
gcccataaga gcgtaatctg gaacatcgta tgggtacatg gtgtctagct cgcgtcagct   2820
gactagagga tccccgggta ccgagctcga attcggggcc gcggaggctg gatcggtccc   2880
ggtgtcttct atggaggtca aaacagcgtg atggcgtct ccaggcgatc tgacggttca    2940
ctaaacgagc tctgcttata taggcctccc accgtacacg cctactcgac ccgggtaccg   3000
agctcgactt tcactttct ctatcactga tagggagtgg taaactcgac tttcactttt    3060
ctctatcact gatagggagt ggtaaactcg actttcactt ttctctatca ctgataggga   3120
gtggtaaact cgactttcac ttttctctat cactgatagg gagtggtaaa ctcgactttc   3180
acttttctct atcactgata gggagtggta aactcgactt tcacttttct ctatcactga   3240
tagggagtgg taaactcgac tttcactttt ctctatcact gatagggagt ggtaaactcg   3300
actttcactt ttctctatca ctgataggga gtggtaaact cgagatctcg agctcaagct   3360
tcgaattatc gaattcctgc agcccgatct cagctgaggt gcaaaaggct cctgtcatat   3420
tgtgtcctgc tctggtctgc cttccacagc ttgggggcca cctagcccac ctctccctag   3480
ggatgagagc agccactacg ggtctaggct gcccatgtaa ggaggcaagg cctggggaca   3540
cccgagatgc ctggttataa ttaacccaga catgtggctg cccccccccc cccaacacct   3600
gctgcctgag cctcaccccc accccggtgc ctggtctta ggctctgtac accatggagg    3660
agaagctcgc tctaaaaata accctgtccc tggtggatcc agggtgaggg gcaggctgag   3720
ggcggccact tccctcagcc gcaggtttgt ttcccaaga atggttttc tgcttctgta     3780 gcttttcctg tcaattctgc catggtggag cagcctgcac tgggcttctg ggagaaacca   3840
aaccgggttc taacctttca gctacagtta ttgccttttcc tgtagatggg cgactacagc  3900
cccaccccca ccccgtctc ctgtatcctt cctgggcctg gggatcctag gctttcactg    3960
gaaatttccc cccaggtgct gtaggctaga gtcacggctc ccaagaacag tgcttgcctg   4020
gcatgcatgg ttctgaacct ccaactgcaa aaaatgacac ataccttgac ccttggaagg   4080
ctgaggcagg gggattgcca tgagtgcaaa gccagactgg gtggcatagt tagaccctgt   4140
ctcaaaaaac caaaaacaat taaataacta aagtcaggca agtaatccta ctcgggagac   4200
tgaggcagag ggattgttac atgtctgagg ccagcctgga ctacatagg tttcaggcta    4260 gccctgtcta cagagtaagg ccctatttca aaaacacaaa caaatggtt ctcccagctg    4320 ctaatgctca ccaggcatga agcctggtga gcattagcaa tgaaggcaat gaaggagggt   4380
gctggctaca atcaaggctg tggggactg agggcaggct gtaacaggct gggggccag    4440 ggcttatacg tgcctgggac tcccaaagta ttactgttcc atgttcccgg cgaagggcca   4500
gctgtccccc gccagctaga ctcagcactt agtttaggaa ccagtgagca agtcagccct   4560
tggggcagcc catacaaggc catggggctg gcaagctgc acgcctgggt ccggggtggg    4620
cacggtgccc gggcaacgag ctgaaagctc atctgctctc aggggcccct ccctggggac   4680
```

| | |
|---|---|
| agcccctcct ggctagtcac accctgtagg ctcctctata taacccaggg gcacagggc | 4740 |
| tgccccaag ctggccgctc tagaggatcc ccgggactag aattcaccat gtctagatta | 4800 |
| gataaaagta aagtgattaa cagcgcatta gagctgctta atgaggtcgg aatcgaaggt | 4860 |
| ttaacaaccc gtaaactcgc ccagaagctt ggtgtagagc agcctacact gtattggcat | 4920 |
| gtaaaaaata agcgggcttt gctcgacgcc ttagccattg agatgttaga taggcaccat | 4980 |
| actcactttt gcccttaaaa aggggaaagc tggcaagatt ttttacgcaa taacgctaaa | 5040 |
| agttttagat gtgctttact aagtcatcgc aatggagcaa aagtacattc agatacacgg | 5100 |
| cctacagaaa aacagtatga aactctcgaa aatcaattag cctttttatg ccaacaaggt | 5160 |
| ttttcactag agaacgcgtt atatgcactc agcgctgtgg ggcattttac tttaggttgc | 5220 |
| gtattggaag atcaagagca tcaagtcgct aaagaagaaa gggaaacacc tactactgat | 5280 |
| agtatgccgc cattattacg acaagctatc gaattatttg atcaccaagg tgcagagcca | 5340 |
| gccttcttat tcggccttga attgatcata tgcggattag aaaaacaact taaatgtgaa | 5400 |
| agtgggtccg cgtacagccg cgcgcgtacg aaaaacaatt acgggtctac catcgagggc | 5460 |
| ctgctcgatc tcccggacga cgacgccccc gaagaggcgg ggctggcggc tccgcgcctg | 5520 |
| tcctttctcc ccgcgggaca cacgcgcaga ctgtcgacgg ccccccgac cgatgtcagc | 5580 |
| ctgggggacg agctccactt agacggcgag gacgtggcga tggcgcatgc cgacgcgcta | 5640 |
| gacgatttcg atctggacat gttggggac ggggattccc cgggtccggg atttaccccc | 5700 |
| cacgactccg cccctacgg cgctctggat atggccgact tcgagtttga gcagatgttt | 5760 |
| accgatgccc ttggaattga cgagtacggt gggatggatc cccgggtacc ggtcgccacc | 5820 |
| atggtgagca agggcgagga gctgttcacc ggggtggtgc ccatcctggt cgagctggac | 5880 |
| ggcgacgtaa acggccacaa gttcagcgtg tccggcgagg gcgagggcga tgccacctac | 5940 |
| ggcaagctga ccctgaagtt catctgcacc accggcaagc tgcccgtgcc ctggcccacc | 6000 |
| ctcgtgacca ccctgacctg gggcgtgcag tgcttcagcc gctaccccga ccacatgaag | 6060 |
| cagcacgact tcttcaagtc cgccatgccc gaaggctacg tccaggagcg caccatcttc | 6120 |
| ttcaaggacg acggcaacta caagacccgc gccgaggtga agttcgaggg cgacaccctg | 6180 |
| gtgaaccgca tcgagctgaa gggcatcgac ttcaaggagg acggcaacat cctggggcac | 6240 |
| aagctggagt acaactacat cagccacaac gtctatatca ccgccgacaa gcagaagaac | 6300 |
| ggcatcaagg ccaacttcaa gatccgccac aacatcgagg acggcagcgt gcagctcgcc | 6360 |
| gaccactacc agcagaacac ccccatcggc gacggccccg tgctgctgcc cgacaaccac | 6420 |
| tacctgagca cccagtccgc cctgagcaaa gaccccaacg agaagcgcga tcacatggtc | 6480 |
| ctgctggagt tcgtgaccgc cgccgggatc actctcggca tggacgagct gtacaagtaa | 6540 |
| agcggccgcg actctagatc ataatcagcc ataccacatt tgtagaggtt ttacttgctt | 6600 |
| taaaaaacct cccacacctc cccctgaacc tgaaacataa aatgaatgca attgttgttg | 6660 |
| ttaacttgtt tattgcagct tataatggtt acaaataaag caatagcatc acaaatttca | 6720 |
| caaataaagc attttttca ctgcattcta gttgtggttt gtccaaactc atcaatgtat | 6780 |
| cttaag | 6786 |

<210> SEQ ID NO 2
<211> LENGTH: 3131
<212> TYPE: DNA
<213> ORGANISM: Mus Musculus

```
<400> SEQUENCE: 2
atgcatggcg gtaatacggt tatccacaga atcaggggat aacgcaggaa agaacatgtg    60
agcaaaaggc cagcaaaagg ccaggaaccg taaaaaggcc gcgttgctgg cgttttttcca   120 taggctccgc cccctgacg agcatcacaa aaatcgacgc tcaagtcaga ggtggcgaaa    180
cccgacagga ctataaagat accaggcgtt tccccctgga agctccctcg tgcgctctcc   240
tgttccgacc ctgccgctta ccggatacct gtccgccttt ctcccttcgg aagcgtggc    300 gctttctcat agctcacgct gtaggtatct cagttcggtg taggtcgttc gctccaagct   360
gggctgtgtg cacgaacccc ccgttcagcc cgaccgctgc gccttatccg gtaactatcg    420
tcttgagtcc aacccggtaa gacacgactt atcgccactg gcagcagcca ctggtaacag   480
gattagcaga gcgaggtatg taggcggtgc tacagagttc ttgaagtggt ggcctaacta    540
cggctacact agaaggacag tatttggtat ctgcgctctg ctgaagccag ttaccttcgg   600
aaaaagagtt ggtagctctt gatccggcaa acaaaccacc gctggtagcg gtggttttt    660 tgtttgcaag cagcagatta cgcgcagaaa aaaggatcc aagaagatc ctttgatctt    720 ttctacgggg tctgacgctc agtggaacga aaactcacgt taagggattt tggtcatgag   780
attatcaaaa aggatcttca cctagatcct tttaaattaa aaatgaagtt ttaaatcaat    840
ctaaagtata tatgagtaac ctgaggctat ggcagggcct gccgccccga cgttggctgc    900
gagccctggg ccttcacccg aacttggggg gtggggtggg gaaaaggaag aaacgcgggc   960
gtattggccc caatggggtc tcggtggggt atcgacagag tgccagccct gggaccgaac   1020
cccgcgttta tgaacaaacg acccaacacc gtgcgtttta ttctgtcttt ttattgccgt   1080
catagcgcgg gttccttccg gtattgtctc cttccgtgtt tcagttagcc tcccctagg   1140 gtgggcgaag aactccagca tgagatcccc gcgctggagg atcatccagc cggcgtcccg   1200
gaaaacgatt ccgaagccca acctttcata gaaggcggcg gtggaatcga atctcgtga   1260 tggcaggttg ggcgtcgctt ggtcggtcat ttcgaacccc agagtccgc tcagaagaac   1320 tcgtcaagaa ggcgatagaa ggcgatgcgc tgcgaatcgg gagcggcgat accgtaaagc   1380
acgaggaagc ggtcagccca ttcgccgcca agctcttcag caatatcacg ggtagccaac   1440
gctatgtcct gatagcggtc cgccacaccc agccggccac agtcgatgaa tccagaaaag   1500
cggccatttt ccaccatgat attcggcaag caggcatcgc catgggtcac gacgagatcc   1560
tcgccgtcgg gcatgctcgc cttgagcctg gcgaacagtt cggctggcgc gagccctga   1620 tgctcttcgt ccagatcatc ctgatcgaca agaccggctt ccatccgagt acgtgctcgc   1680
tcgatgcgat gtttcgcttg gtggtcgaat gggcaggtag ccggatcaag cgtatgcagc   1740
cgccgcattg catcagccat gatggatact ttctcggcag gagcaaggtg agatgacagg   1800
agatcctgcc ccggcacttc gcccaatagc agccagtccc ttcccgcttc agtgacaacg   1860
tcgagcacag ctgcgcaagg aacgcccgtc gtggccagcc acgatagccg cgctgcctcg   1920
tcttgcagtt cattcagggc accggacagg tcggtcttga caaaaagaac cgggcgcccc   1980
tgcgctgaca gccggaacac ggcggcatca gagcagccga ttgtctgttg tgcccagtca   2040
tagccgaata gcctctccac ccaagcgcc ggagaacctg cgtgcaatcc atcttgttca   2100
atcatgcgaa acgatcctca tcctgtctct tgatcgatct ttgcaaaagc ctaggcctcc   2160
aaaaaagcct cctcactact tctggaatag ctcagaggcc gaggcggcct cggcctctgc   2220
ataaataaaa aaaattagtc agccatgggg cggagaatgg gcggaactgg gcggagttag   2280
gggcgggatg gccggagtta ggggcgggac tatggttgct gactaattga gatgcatgct   2340
```

```
ttgcatactt ctgcctgctg gggagcctgg ggactttcca cacctggttg ctgactaatt    2400
gagatgcatg ctttgcatac ttctgcctgc tggggagcct gggactttc cacaccctaa     2460 ctgacacaca ttccacagct ggttctttcc gcctcaggac tcttcctttt tcaatattat    2520
tgaagcattt atcagggtta ttgtctcatg agcggataca tatttgaatg tatttagaaa    2580
aataaacaaa taggggttcc gcgcacattt ccccgaaaag tgccacctga cgcgccctgt    2640
agcggcgcat taagcgcggc gggtgtggtg gttacgcgca gcgtgaccgc tacacttgcc    2700
agcgccctag cgcccgctcc tttcgctttc ttcccttcct ttctcgccac gttcgccggc    2760 tttcccgtc aagctctaaa tcggggctc cctttagggt tccgatttag tgctttacgg      2820
cacctcgacc ccaaaaaact tgattagggt gatggttcac gtagtgggcc atcgccctga    2880
tagacggttt ttcgcccttt gacgttggag tccacgttct ttaatagtgg actcttgttc    2940
caaactggaa caacactcaa ccctatctcg gtctattctt ttgatttata agggattttg    3000
ccgatttcgg cctattggtt aaaaaatgag ctgatttaac aaaaatttaa cgcgaatttt    3060
aacaaaatat taacgcttac aatttacgcc ttaagataca ttgatgagtt tggacaaacc    3120
acaactagaa t                                                         3131

<210> SEQ ID NO 3
<211> LENGTH: 51
<212> TYPE: DNA
<213> ORGANISM: Mus Musculus

<400> SEQUENCE: 3
gcagtgaaaa aaatgcttta tttgtgaaat ttgtgatgct attgctttat t             51

<210> SEQ ID NO 4
<211> LENGTH: 1308
<212> TYPE: DNA
<213> ORGANISM: Mus Musculus

<400> SEQUENCE: 4
ttacttgtac agctcgtcca tgccgagagt gatcccggcg gcggtcacga actccagcag      60
gaccatgtga tcgcgcttct cgttggggtc tttgctcagg gcggactggg tgctcaggta     120
gtggttgtcg ggcagcagca cggggccgtc gccgatgggg tgttctgct ggtagtggtc      180 ggcgagctgc acgctgccgt cctcgatgtt gtggcggatc ttgaagttca ccttgatgcc     240
gttcttctgc ttgtcggcca tgatatagac gttgtggctg ttgtagttgt actccagctt     300
gtgccccagg atgttgccgt cctccttgaa gtcgatgccc ttcagctcga tgcggttcac     360
cagggtgtcg ccctcgaact tcacctcggc gcgggtcttg tagttgccgt cgtccttgaa     420
gaagatggtg cgctcctgga cgtagccttc gggcatggcg gacttgaaga agtcgtgctg     480
cttcatgtgg tcggggtagc ggctgaagca ctgcacgccg taggtcaggg tggtcacgag     540
ggtgggccag ggcacgggca gcttgccggt ggtgcagatg aacttcaggg tcagcttgcc     600
gtaggtggca tcgccctcgc cctcgccgga cacgctgaac ttgtggccgt ttacgtcgcc     660
gtccagctcg accaggatgg gcaccaccc ggtgaacagc tcctcgccct tgctcaccat      720
ggttgtggcc atattatcat cgtgtttttc aaaggaaaac cacgtccccg tggttcgggg     780
ggcctagacg ttttttttaac ctcgactaaa cacatgtaaa gcatgtgcac cgaggcccca    840
gatcagatcc catacaatgg ggtaccttct gggcatcctt cagccccttg ttgaatacgc     900
ttgaggagag ccatttgact ctttccacaa ctatccaact cacaacgtgg cactgggagtt    960 gtgccgcctt tgcaggtgta tcttatacac gtggcttttg gccgcagagg cacctgtcgc   1020
```

```
caggtggggg gttccgctgc ctgcaaaggg tcgctacaga cgttgtttgt cttcaagaag    1080
cttccagagg aactgcttcc ttcacgacat tcaacagacc ttgcattcct tttggcgagag    1140 gggaaagacc cctaggaatg ctcgtcaaga agacagggcc aggtttccgg gccctcacat    1200
tgccaaaaga cggcaatatg gtggaaaata acatatagac aaacgcacac cggccttatt    1260
ccaagcggct tcggccagta acgttagggg gggggagggg agaggggc                  1308

<210> SEQ ID NO 5
<211> LENGTH: 1131
<212> TYPE: DNA
<213> ORGANISM: Mus Musculus

<400> SEQUENCE: 5
tcatgagcac ccacagcggt ctactaccat ggctggaatt ttcccatata ttatttgttc      60
tttgccatta aaatatagca tattaatggg agacattttt gtcggagtgc agcaagggcc     120
tgctgagcct ctggggtttg cttggtgcac aagatgagta tgcggatatt tttgtaaaaa     180
cacaaattca cactctcctg agcagtaatt ggccttatat ctttttgggtg cgataatcca    240 gtcccatcca aaggcttcaa aatcgaccgt gaggggtag cggcagcacc gggattccgt     300
ggagtgctca tcgcagtcaa gcccaaagtc tctccgggac ctcttgggtg tgtctgtcac    360
cttgacttct aaaaagggat tcagcccatc ttctcctggt cctgggaagg ttacagcaag    420
atcatggcca ttctcatcca aagctttgat ttcaatgcct aagttggatt caggctgttt    480
gagccaattt tgcaacactg tcttcacatc aatactctgc caaataccag tgcctgggct    540
catgtcaagt tcagagatc ggattccagt ataccttgta ccgtctttca tgggtttgat     600
gagtctcagg atttgcacaa acactgttgt aggagtcttg acgggtctga atatatcca     660 cagttgggct tttactactt tgttgtactg tattttagag ctaaatttaa aaaagcaaca    720
tttgggcttg ccatccgctt gcattagaaa gtcagactct gtaggcatgg taatgattgt    780
ttccgtggta gcgtgataat cgtcatcttc caaagagcca tcactgctgt catccctctg    840
gacgtcgtac tgatcgatca gttcccggag tggaggcgct cttggcagaa gttgtcttat    900
agcatctttg ctgatgttag gagctgtttc caggcgcagc ttactgagga tttgaatttt    960
tatggcttct attctggagt acctcgtgtt ttgtctccac gcacatgcat tacacagccc   1020 ctcttttttcc acattttctt ctctctcact gcccctcatt tagatccactg gccagcagc   1080 aatcagcatg aacaggtaaa tataaacata catttgcagt ttttgcatca t            1131

<210> SEQ ID NO 6
<211> LENGTH: 30
<212> TYPE: DNA
<213> ORGANISM: Mus Musculus

<400> SEQUENCE: 6
aagagcgtaa tctggaacat cgtatgggta                                      30

<210> SEQ ID NO 7
<211> LENGTH: 432
<212> TYPE: DNA
<213> ORGANISM: Mus Musculus

<400> SEQUENCE: 7
aggctggatc ggtcccggtg tcttctatgg aggtcaaaac agcgtggatg gcgtctccag      60
gcgatctgac ggttcactaa acgagctctg cttatatagg cctcccaccg tacacgccta    120
ctcgacccgg gtaccgagct cgactttcac ttttctctat cactgatagg gagtggtaaa    180
```

```
ctcgactttc acttttctct atcactgata gggagtggta aactcgactt tcactttttct      240 ctatcactga tagggagtgg taaactcgac tttcactttt ctctatcact gatagggagt      300
ggtaaactcg actttcactt ttctctatca ctgatacggg gtggtaaact cgactttcac      360
ttttctctat cactgatagg gagtggtaaa ctcgactttc acttttctct atcactgata      420
gggagtggta aa                                                          432

<210> SEQ ID NO 8
<211> LENGTH: 1357
<212> TYPE: DNA
<213> ORGANISM: Mus Musculus

<400> SEQUENCE: 8
cagctgaggt gcaaaaggct cctgtcatat tgtgtcctgc tctggtctgc cttccacagc       60
ttgggggcca cctagcccac ctctccctag ggatgagagc agccactacg ggtctaggct      120
gcccatgtaa ggaggcaagg cctggggaca cccgagatgc ctggttataa ttaacccaga      180
catgtggctg cccccccccc cccaacacct gctgcctgag cctcaccccc accccggtgc      240
ctgggtctta ggctctgtac accatggagg agaagctcgc tctaaaaata accctgtccc      300
tggtggatcc agggtgaggg gcaggctgag ggcggccact tccctcagcc gcaggtttgt      360
tttcccaaga atggttttc tgcttctgta gcttttcctg tcaattctgc catggtggag       420
cagcctgcac tgggcttctg ggagaaacca accgggttc taacctttca gctacagtta       480
ttgcctttcc tgtagatggg cgactacagc cccacccccca ccccgtctc ctgtatcctt      540 cctgggcctg gggatcctag gctttcactg gaaatttccc ccaggtgct gtaggctaga      600 gtcacggctc ccaagaacag tgcttgcctg gcatgcatgg ttctgaacct ccaactgcaa      660
aaaatgacac ataccttgac ccttggaagg ctgaggcagg gggattgcca tgagtgcaaa      720
gccagactgg gtggcatagt tagaccctgt ctcaaaaaac caaaaacaat taaataacta      780
aagtcaggca agtaatccta ctcgggagac tgaggcagag ggattgttac atgtctgagg      840
ccagcctgga ctacataggg tttcaggcta gccctgtcta cagagtaagg ccctatttca      900
aaaacacaaa caaatggttt ctcccagctg ctaatgctca ccaggcatga agcctggtga      960
gcattagcaa tgaaggcaat gaaggagggt gctggctaca atcaaggctg tggggactg     1020 agggcaggct gtaacaggct gggggccag ggcttatacg tgcctgggac tcccaaagta     1080
ttactgttcc atgttcccgg cgaagggcca gctgtccccc gccagctaga ctcagcactt     1140
agtttaggaa ccagtgagca agtcagccct tggggcagcc catacaaggc catgggctg     1200 ggcaagctgc acgcctgggt ccggggtggg cacggtgccc gggcaacgag ctgaaagctc     1260
atctgctctc aggggcccct ccctggggac agccctcct ggctagtcac accctgtagg     1320
ctcctctata taacccaggg gcacagggc tgccccc                               1357

<210> SEQ ID NO 9
<211> LENGTH: 1005
<212> TYPE: DNA
<213> ORGANISM: Mus Musculus

<400> SEQUENCE: 9
atgtctagat tagataaaag taaagtgatt aacagcgcat tagagctgct taatgaggtc       60
ggaatcgaag gtttaacaac ccgtaaactc gcccagaagc ttggtgtaga gcagcctaca      120
ctgtattggc atgtaaaaaa taagcggggct ttgctcgacg ccttagccat tgagatgtta      180
gataggcacc atactcactt tgcccctta aaaggggaaa gctggcaaga ttttttacgc      240
```

| | | |
|---|---|---|
| aataacgcta aaagttttag atgtgcttta ctaagtcatc gcaatggagc aaaagtacat | 300 | |
| tcagatacac ggcctacaga aaaacagtat gaaactctcg aaaatcaatt agccttttta | 360 | |
| tgccaacaag gttttcact agagaacgcg ttatatgcac tcagcgctgt ggggcatttt | 420 | |
| actttaggtt gcgtattgga agatcaagag catcaagtcg ctaaagaaga agggaaaca | 480 | |
| cctactactg atagtatgcc gccattatta cgacaagcta tcgaattatt tgatcaccaa | 540 | |
| ggtgcagagc cagccttctt attcggcctt gaattgatca tatgcggatt agaaaaacaa | 600 | |
| cttaaatgtg aaagtgggtc cgcgtacagc cgcgcgcgta cgaaaaacaa ttacgggtct | 660 | |
| accatcgagg gcctgctcga tctcccggac gacgacgccc ccgaagaggc ggggctggcg | 720 | |
| gctccgcgcc tgtcctttct ccccgcggga cacacgcgca gactgtcgac ggccccccg | 780 | |
| accgatgtca gctggggga cgagctccac ttagacggcg aggacgtggc gatgcgcat | 840 | |
| gccgacgcgc tagacgattt cgatctggac atgttggggg acggggattc cccgggtccg | 900 | |
| ggatttaccc cccacgactc cgcccccta ggcgctctgg atatggccga cttcgagttt | 960 | |
| gagcagatgt ttaccgatgc ccttggaatt gacgagtacg gtggg | 1005 | |

<210> SEQ ID NO 10
<211> LENGTH: 720
<212> TYPE: DNA
<213> ORGANISM: Mus Musculus

<400> SEQUENCE: 10

| | | |
|---|---|---|
| atggtgagca agggcgagga gctgttcacc ggggtggtgc ccatcctggt cgagctggac | 60 | |
| ggcgacgtaa acggccacaa gttcagcgtg tccggcgagg gcgagggcga tgccacctac | 120 | |
| ggcaagctga ccctgaagtt catctgcacc accggcaagc tgcccgtgcc ctggcccacc | 180 | |
| ctcgtgacca ccctgacctg gggcgtgcag tgcttcagcc gctaccccga ccacatgaag | 240 | |
| cagcacgact tcttcaagtc cgccatgccc gaaggctacg tccaggagcg caccatcttc | 300 | |
| ttcaaggacg acggcaacta caagacccgc gccgaggtga agttcgaggg cgacaccctg | 360 | |
| gtgaaccgca tcgagctgaa gggcatcgac ttcaaggagg acggcaacat cctggggcac | 420 | |
| aagctggagt acaactacat cagccacaac gtctatatca ccgccgacaa gcagaagaac | 480 | |
| ggcatcaagg ccaacttcaa gatccgccac aacatcgagg acggcagcgt gcagctcgcc | 540 | |
| gaccactacc agcagaacac ccccatcggc gacggccccg tgctgctgcc cgacaaccac | 600 | |
| tacctgagca cccagtccgc cctgagcaaa gaccccaacg agaagcgcga tcacatggtc | 660 | |
| ctgctggagt tcgtgaccgc cgccgggatc actctcggca tggacgagct gtacaagtaa | 720 | |

<210> SEQ ID NO 11
<211> LENGTH: 51
<212> TYPE: DNA
<213> ORGANISM: Mus Musculus

<400> SEQUENCE: 11

| | | |
|---|---|---|
| aataaagcaa tagcatcaca aatttcacaa ataaagcatt ttttcactg c | 51 | |

<210> SEQ ID NO 12
<211> LENGTH: 6
<212> TYPE: DNA
<213> ORGANISM: Mus Musculus

<400> SEQUENCE: 12

| | | |
|---|---|---|
| cttaag | 6 | |

<210> SEQ ID NO 13
<211> LENGTH: 10273
<212> TYPE: DNA
<213> ORGANISM: Mus Musculus

<400> SEQUENCE: 13

| | | | | | |
|---|---|---|---|---|---|
| ctcgactttc | acttttctct | atcactgata | gggagtggta | aactcgagat | ctcgagctca | 60 |
| agcttcgaat | tatcgaattc | ctgcagcccg | atctcagctg | aggtgcaaaa | ggctcctgtc | 120 |
| atattgtgtc | ctgctctggt | ctgccttcca | cagcttgggg | gccacctagc | ccacctctcc | 180 |
| ctagggatga | gagcagccac | tacgggtcta | ggctgcccat | gtaaggaggc | aaggcctggg | 240 |
| gacacccgag | atgcctggtt | ataattaacc | cagacatgtg | gctgccccc | ccccccaac | 300 |
| acctgctgcc | tgagcctcac | ccccaccccg | gtgcctgggt | cttaggctct | gtacaccatg | 360 |
| gaggagaagc | tcgctctaaa | aataaccctg | tccctggtgg | atccagggtg | aggggcaggc | 420 |
| tgagggcggc | cacttccctc | agccgcaggt | ttgttttccc | aagaatggtt | tttctgcttc | 480 |
| tgtagctttt | cctgtcaatt | ctgccatggt | ggagcagcct | gcactgggct | tctgggagaa | 540 |
| accaaaccgg | gttctaacct | ttcagctaca | gttattgcct | ttcctgtaga | tgggcgacta | 600 |
| cagccccacc | cccaccccg | tctcctgtat | ccttcctggg | cctggggatc | ctaggctttc | 660 |
| actggaaatt | tccccccagg | tgctgtaggc | tagagtcacg | gctcccaaga | acagtgcttg | 720 |
| cctggcatgc | atggttctga | acctccaact | gcaaaaaatg | acacatacct | tgacccttgg | 780 |
| aaggctgagg | caggggatt | gccatgagtg | caaagccaga | ctgggtggca | tagttagacc | 840 |
| ctgtctcaaa | aaaccaaaaa | caattaaata | actaaagtca | ggcaagtaat | cctactcggg | 900 |
| agactgaggc | agagggattg | ttacatgtct | gaggccagcc | tggactacat | agggtttcag | 960 |
| gctagccctg | tctacagagt | aaggcccctat | ttcaaaaaca | caaacaaaat | ggttctccca | 1020 |
| gctgctaatg | ctcaccaggc | atgaagcctg | gtgagcatta | gcaatgaagg | caatgaagga | 1080 |
| gggtgctggc | tacaatcaag | gctgtggggg | actgagggca | ggctgtaaca | ggcttggggg | 1140 |
| ccagggctta | tacgtgcctg | ggactcccaa | agtattactg | ttccatgttc | ccggcgaagg | 1200 |
| gccagctgtc | ccccgccagc | tagactcagc | acttagttta | ggaaccagtg | agcaagtcag | 1260 |
| cccttggggc | agcccataca | aggccatggg | gctgggcaag | ctgcacgcct | gggtccgggg | 1320 |
| tgggcacggt | gcccgggcaa | cgagctgaaa | gctcatctgc | tctcaggggc | ccctccctgg | 1380 |
| ggacagcccc | tcctggctag | tcacaccctg | taggctcctc | tatataaccc | aggggcacag | 1440 |
| gggctgcccc | caagctggcc | gctctagagg | atccccggga | ctagaattca | ccatgtctag | 1500 |
| attagataaa | agtaaagtga | ttaacagcgc | attagagctg | cttaatgagg | tcggaatcga | 1560 |
| aggtttaaca | acccgtaaac | tcgcccagaa | gcttggtgta | gagcagccta | cactgtattg | 1620 |
| gcatgtaaaa | aataagcggg | ctttgctcga | cgccttagcc | attgagatgt | tagataggca | 1680 |
| ccatactcac | ttttgccctt | taaaggggga | aagctggcaa | gattttttac | gcaataacgc | 1740 |
| taaaagtttt | agatgtgctt | tactaagtca | tcgcaatgga | gcaaaagtac | attcagatac | 1800 |
| acggcctaca | gaaaaacagt | atgaaactct | cgaaaatcaa | ttagcctttt | tatgccaaca | 1860 |
| aggttttca | ctagagaacg | cgttatatgc | actcagcgct | gtggggcatt | ttactttagg | 1920 |
| ttgcgtattg | gaagatcaag | agcatcaagt | cgctaaagaa | gaagggaaa | cacctactac | 1980 |
| tgatagtatg | ccgccattat | tacgacaagc | tatcgaatta | tttgatcacc | aaggtgcaga | 2040 |
| gccagccttc | ttattcggcc | ttgaattgat | catatgcgga | ttagaaaaac | aacttaaatg | 2100 |
| tgaaagtggg | tccgcgtaca | gccgcgcgcg | tacgaaaaac | aattacgggt | ctaccatcga | 2160 |

| | |
|---|---|
| gggcctgctc gatctcccgg acgacgacgc ccccgaagag gcggggctgg cggctccgcg | 2220 |
| cctgtcctttt ctccccgcgg gacacacgcg cagactgtcg acggcccccc cgaccgatgt | 2280 |
| cagcctgggg gacgagctcc acttagacgg cgaggacgtg gcgatggcgc atgccgacgc | 2340 |
| gctagacgat ttcgatctgg acatgttggg ggacggggat tccccgggtc cgggatttac | 2400 |
| cccccacgac tccgcccct acggcgctct ggatatggcc gacttcgagt ttgagcagat | 2460 |
| gtttaccgat gcccttggaa ttgacgagta cggtgggatg gatccccggg taccggtcgc | 2520 |
| caccatggtg agcaagggcg aggagctgtt caccggggtg gtgcccatcc tggtcgagct | 2580 |
| ggacggcgac gtaaacggcc acaagttcag cgtgtccggc gagggcgagg gcgatgccac | 2640 |
| ctacggcaag ctgaccctga agttcatctg caccaccggc aagctgcccg tgccctggcc | 2700 |
| caccctcgtg accaccctga cctggggcgt gcagtgcttc agccgctacc ccgaccacat | 2760 |
| gaagcagcac gacttcttca gtccgccat gcccgaaggc tacgtccagg agcgcaccat | 2820 |
| cttcttcaag gacgacggca actacaagac ccgcgccgag gtgaagttcg agggcgacac | 2880 |
| cctggtgaac cgcatcgagc tgaagggcat cgacttcaag gaggacggca acatcctggg | 2940 |
| gcacaagctg gagtacaact acatcagcca caacgtctat atcaccgccg acaagcagaa | 3000 |
| gaacggcatc aaggccaact tcaagatccg ccacaacatc gaggacggca gcgtgcagct | 3060 |
| cgccgaccac taccagcaga acacccccat cggcgacggc cccgtgctgc tgcccgacaa | 3120 |
| ccactacctg agcacccagt ccgccctgag caaagacccc aacgagaagc gcgatcacat | 3180 |
| ggtcctgctg gagttcgtga ccgccgccgg gatcactctc ggcatggacg agctgtacaa | 3240 |
| gtaaagcggc cgcgactcta gatcataatc agccatacca catttgtaga ggttttactt | 3300 |
| gctttaaaaa acctcccaca cctccccctg aacctgaaac ataaaatgaa tgcaattgtt | 3360 |
| gttgttaact tgtttattgc agcttataat ggttacaaat aaagcaatag catcacaaat | 3420 |
| ttcacaaata aagcattttt ttcactgcat tctagttgtg gtttgtccaa actcatcaat | 3480 |
| gtatcttaag gcgtaaattg taagcgttaa tattttgtta aaattcgcgt taaattttg | 3540 |
| ttaaatcagc tcatttttta accaataggc cgaaatcggc aaaatccctt ataaatcaaa | 3600 |
| agaatagacc gagagctagc ggatctgacg gttcactaaa ccagctctgc ttatatagac | 3660 |
| ctcccaccgt acacgcctac ccgccatttg cgtcaatggg gcggagttgt tatgacattt | 3720 |
| tggaaagtcc cgttgatttt ggtgccaaaa caaactccca ttgacgtcaa tgggcggggg | 3780 |
| tcgttgggcg gtcagccagg cgggccattt accgtaagtt atgtaacgcg gaactccata | 3840 |
| tatgggctat gaactaatga cccgtaatt gattactatt aataactaat gcatggcggt | 3900 |
| aatacggtta tccacagaat caggggataa cgcaggaaag aacatgtgag caaaaggcca | 3960 |
| gcaaaaggcc aggaaccgta aaaaggccgc gttgctggcg ttttccata ggctccgccc | 4020 |
| ccctgacgag catcacaaaa atcgacgctc aagtcagagg tggcgaaacc cgacaggact | 4080 |
| ataaagatac caggcgtttc ccctggaag ctccctcgtg cgctctcctg ttccgaccct | 4140 |
| gccgcttacc ggatacctgt ccgcctttct cccttcggga agcgtggcgc tttctcatag | 4200 |
| ctcacgctgt aggtatctca gttcggtgta ggtcgttcgc tccaagctgg gctgtgtgca | 4260 |
| cgaaccccc gttcagcccg accgctgcgc cttatccggt aactatcgtc ttgagtccaa | 4320 |
| cccggtaaga cacgacttat cgccactggc agcagccact ggtaacagga ttagcagagc | 4380 |
| gaggtatgta ggcggtgcta cagagttctt gaagtggtgg cctaactacg gctacactag | 4440 |
| aaggacagta tttggtatct gcgctctgct gaagccagtt accttcggaa aaagagttgg | 4500 |
| tagctcttga tccggcaaac aaaccaccgc tggtagcggt ggtttttttg tttgcaagca | 4560 |

```
gcagattacg cgcagaaaaa aaggatctca agaagatcct tgatctttt ctacggggtc    4620
tgacgctcag tggaacgaaa actcacgtta agggattttg gtcatgagat tatcaaaaag   4680
gatcttcacc tagatccttt taaattaaaa atgaagtttt aaatcaatct aaagtatata   4740
tgagtaacct gaggctatgg cagggcctgc cgccccgacg ttggctgcga gccctgggcc   4800
ttcacccgaa cttgggggt ggggtgggga aaggaagaa acgcgggcgt attggcccca    4860
atggggtctc ggtgggtat cgacagagtg ccagccctgg gaccgaaccc cgcgtttatg    4920
aacaaacgac ccaacaccgt gcgttttatt ctgtcttttt attgccgtca tagcgcgggt   4980
tccttccggt attgtctcct tccgtgtttc agttagcctc cccctagggt gggcgaagaa   5040
ctccagcatg agatccccgc gctggaggat catccagccg gcgtcccgga aaacgattcc   5100
gaagcccaac ctttcataga aggcggcggt ggaatcgaaa tctcgtgatg gcaggttggg   5160
cgtcgcttgg tcggtcattt cgaaccccag agtcccgctc agaagaactc gtcaagaagg   5220
cgatagaagg cgatgcgctg cgaatcggga gcggcgatac cgtaaagcac gaggaagcgg   5280
tcagcccatt cgccgccaag ctcttcagca atatcacggg tagccaacgc tatgtcctga   5340
tagcggtccg ccacacccag ccggccacag tcgatgaatc cagaaaagcg gccattttcc   5400
accatgatat tcggcaagca ggcatcgcca tgggtcacga cgagatcctc gccgtcgggc   5460
atgctcgcct tgagcctggc gaacagttcg gctggcgcga ccccctgatg ctcttcgtcc   5520
agatcatcct gatcgacaag accggcttcc atccgagtac gtgctcgctc gatgcgatgt   5580
ttcgcttggt ggtcgaatgg gcaggtagcc ggatcaagcg tatgcagccg ccgcattgca   5640
tcagccatga tggatacttt ctcggcagga gcaaggtgag atgacaggag atcctgcccc   5700
ggcacttcgc ccaatagcag ccagtccctt cccgcttcag tgacaacgtc gagcacagct   5760
gcgcaaggaa cgcccgtcgt ggccagccac gatagccgcg ctgcctcgtc ttgcagttca   5820
ttcagggcac cggacaggtc ggtcttgaca aaaagaaccg ggcgcccctg cgctgacagc   5880
cggaacacgg cggcatcaga gcagccgatt gtctgttgtg cccagtcata gccgaatagc   5940
ctctccaccc aagcggccgg agaacctgcg tgcaatccat cttgttcaat catgcgaaac   6000
gatcctcatc ctgtctcttg atcgatcttt gcaaaagcct aggcctccaa aaaagcctcc   6060
tcactacttc tggaatagct cagaggccga ggcggcctcg gcctctgcat aaataaaaaa   6120
aattagtcag ccatggggcg gagaatgggc ggaactgggc ggagttaggg gcgggatggg   6180
cggagttagg ggcgggacta tggttgctga ctaattgaga tgcatgcttt gcatacttct   6240
gcctgctggg gagcctgggg actttccaca cctggttgct gactaattga gatgcatgct   6300
ttgcatactt ctgcctgctg gggagcctgg ggactttcca caccctaact gacacacatt   6360
ccacagctgg ttctttccgc ctcaggactc ttccttttc aatattattg aagcatttat   6420
cagggttatt gtctcatgag cggatacata tttgaatgta tttagaaaaa taaacaaata   6480
ggggttccgc gcacatttcc ccgaaaagtg ccacctgacg cgcccgtag cggcgcatta    6540
agcgcggcg gtgtggtggt tacgcgcagc gtgaccgcta cacttgccag cgccctagcg   6600
cccgctcctt tcgctttctt cccttccttt ctcgccacgt tcgccggctt tccccgtcaa   6660
gctctaaatc gggggctccc tttagggttc cgatttagtg ctttacgca cctcgacccc    6720
aaaaaacttg attagggtga tggttcacgt agtgggccat cgccctgata cggtttttt    6780
cgcccttga cgttggagtc cacgttcttt aatagtggac tcttgttcca aactggaaca   6840
acactcaacc ctatctcggt ctattctttt gatttataag ggattttgcc gatttcggcc   6900
tattggttaa aaaatgagct gatttaacaa aaatttaacg cgaatttta caaaatatta   6960
```

```
acgcttacaa tttacgcctt aagatacatt gatgagtttg acaaaccac aactagaatg    7020 cagtgaaaaa aatgctttat ttgtgaaatt tgtgatgcta ttgctttatt tgtaaccatt    7080
ataagctgca ataaacaagt taacaacaac aattgcattc attttatgtt tcaggttcag    7140
ggggaggtgt gggaggtttt ttaaagcaag taaaacctct acaaatgtgg tatggctgat    7200
tatgatctag agtcgcggcc gctttacttg tacagctcgt ccatgccgag agtgatcccg    7260
gcggcggtca cgaactccag caggaccatg tgatcgcgct tctcgttggg gtctttgctc    7320
agggcggact gggtgctcag gtagtggttg tcgggcagca gcacggggcc gtcgccgatg    7380
ggggtgttct gctggtagtg gtcggcgagc tgcacgctgc cgtcctcgat gttgtggcgg    7440
atcttgaagt tcaccttgat gccgttcttc tgcttgtcgg ccatgatata gacgttgtgg    7500
ctgttgtagt tgtactccag cttgtgcccc aggatgttgc cgtcctcctt gaagtcgatg    7560
cccttcagct cgatgcggtt caccagggtg tcgccctcga acttcacctc ggcgcgggtc    7620
ttgtagttgc cgtcgtcctt gaagaagatg gtgcgctcct ggacgtagcc ttcgggcatg    7680
gcggacttga agaagtcgtg ctgcttcatg tggtcggggt agcggctgaa gcactgcacg    7740
ccgtaggtca gggtggtcac gagggtgggc cagggcacgg gcagcttgcc ggtggtgcag    7800
atgaacttca gggtcagctt gccgtaggtg gcatcgccct cgccctcgcc ggacacgctg    7860
aacttgtggc cgtttacgtc gccgtccagc tcgaccagga tgggcaccac cccggtgaac    7920
agctcctcgc ccttgctcac catggttgtg gccatattat catcgtgttt ttcaaaggaa    7980
aaccacgtcc ccgtggttcg gggggcctag acgttttttt aacctcgact aaacacatgt    8040
aaagcatgtg caccgaggcc ccagatcaga tcccatacaa tggggtacct tctgggcatc    8100
cttcagcccc ttgttgaata cgcttgagga gagccatttg actctttcca caactatcca    8160
actcacaacg tggcactggg gttgtgccgc ctttgcaggt gtatcttata cacgtggctt    8220
ttggccgcag aggcacctgt cgccaggtgg ggggttccgc tgcctgcaaa gggtcgctac    8280
agacgttgtt tgtcttcaag aagcttccag aggaactgct tccttcacga cattcaacag    8340
accttgcatt cctttggcga gaggggaaag acccctagga atgctcgtca agaagacagg    8400
gccaggtttc cgggccctca cattgccaaa agacggcaat atggtggaaa ataacatata    8460
gacaaacgca caccggcctt attccaagcg gcttcggcca gtaacgttag gggggggga    8520 gggagagggg cggatcccgg gcccgcggta ccgtcgactg cagaattcac tagtgattaa    8580
attatattgt cgactcatga gcacccacag cggtctacta ccatggctgg aattttccca    8640
tatattattt gttctttgcc attaaaatat agcatattaa tgggagacat ttttgtcgga    8700
gtgcagcaag ggcctgctga gcctctgggg tttgcttggt gcacaagatg agtatgcgga    8760 tattttgta aaaacacaaa ttcacactct cctgagcagt aattggcctt atatcttttg    8820
ggtgcgataa tccagtccca tccaaaggct tcaaaatcga ccgtgagggg gtagcggcag    8880
caccgggatt ccgtggagtg ctcatcgcag tcaagcccaa agtctctccg ggacctcttg    8940
ggtgtgtctg tcaccttgac ttctaaaaag ggattcagcc catcttctcc tggtcctggg    9000
aaggttacag caagatcatg gccattctca tccaaagctt tgatttcaat gcctaagttg    9060
gattcaggct gtttgagcca attttgcaac actgtcttca catcaatact ctgccaaata    9120
ccagtgcctg ggctcatgtc aagtttcaga gatcggattc cagtatacct tgtaccgtct    9180
ttcatgggtt tgatgagtct caggatttgc acaaacactg ttgtaggagt cttgacgggt    9240
ctgagatata tccacagttg ggcttttact actttgttgt actgtatttt agagctaaat    9300
ttaaaaaagc aacatttggg cttgccatcc gcttgcatta gaaagtcaga ctctgtaggc    9360
```

-continued

```
atggtaatga ttgtttccgt ggtagcgtga taatcgtcat cttccaaaga gccatcactg    9420
ctgtcatccc tctggacgtc gtactgatcg atcagttccc ggagtggagg cgctcttggc    9480
agaagttgtc ttatagcatc tttgctgatg ttaggagctg tttccaggcg cagcttactg    9540
aggatttgaa ttttatggc ttctattctg gagtacctcg tgttttgtct ccacgcacat     9600
gcattacaca gcccctcttt ttccacattt tcttctctct cactgccctc atttagatcc    9660
actgggccag cagcaatcag catgaacagg taaatataaa catacatttg cagttttgc     9720 atcatggctg gatccgggcc cataagagcg taatctggaa catcgtatgg gtacatggtg    9780
tctagctcgc gtcagctgac tagaggatcc ccgggtaccg agctcgaatt cggggccgcg    9840
gaggctggat cggtcccggt gtcttctatg gaggtcaaaa cagcgtggat ggcgtctcca    9900
ggcgatctga cggttcacta aacgagctct gcttatatag gcctcccacc gtacacgcct    9960
actcgacccg ggtaccgagc tcgactttca cttttctcta tcactgatag ggagtggtaa   10020
actcgacttt cacttttctc tatcactgat agggagtggt aaactcgact ttcacttttc   10080
tctatcactg atagggagtg gtaaactcga ctttcacttt tctctatcac tgataggag   10140 tggtaaactc gactttcact tttctctatc actgataggg agtggtaaac tcgactttca   10200
cttttctcta tcactgatag ggagtggtaa actcgacttt cacttttctc tatcactgat   10260
agggagtggt aaa                                                      10273
```

<210> SEQ ID NO 14
<211> LENGTH: 6
<212> TYPE: DNA
<213> ORGANISM: Mus musculus
<220> FEATURE:
<221> NAME/KEY: misc_feature
<222> LOCATION: (2)..(2)
<223> OTHER INFORMATION: x = any nucleotide

<400> SEQUENCE: 14 cncaat                                                                    6

<210> SEQ ID NO 15
<211> LENGTH: 6
<212> TYPE: DNA
<213> ORGANISM: Mus musculus

<400> SEQUENCE: 15 aataaa                                                                    6

<210> SEQ ID NO 16
<211> LENGTH: 24
<212> TYPE: DNA
<213> ORGANISM: Mus Musculus

<400> SEQUENCE: 16
atgatgcaaa aactgcaaat gtat                                               24

<210> SEQ ID NO 17
<211> LENGTH: 15
<212> TYPE: DNA
<213> ORGANISM: Mus Musculus

<400> SEQUENCE: 17
tcatgagcac ccaca                                                         15

```
<210> SEQ ID NO 18
<211> LENGTH: 20
<212> TYPE: DNA
<213> ORGANISM: Mus Musculus

<400> SEQUENCE: 18
aaccagtgag caagtcagcc                                                   20

<210> SEQ ID NO 19
<211> LENGTH: 18
<212> TYPE: DNA
<213> ORGANISM: Mus Musculus

<400> SEQUENCE: 19
gccagcagca atcagcat                                                     18

<210> SEQ ID NO 20
<211> LENGTH: 20
<212> TYPE: DNA
<213> ORGANISM: Mus Musculus

<400> SEQUENCE: 20
agacaaaaca cgaggtactc                                                   20

<210> SEQ ID NO 21
<211> LENGTH: 20
<212> TYPE: DNA
<213> ORGANISM: Mus Musculus

<400> SEQUENCE: 21
tggattcagg ctgtttgagc                                                   20

<210> SEQ ID NO 22
<211> LENGTH: 20
<212> TYPE: DNA
<213> ORGANISM: Mus Musculus

<400> SEQUENCE: 22
gtctcccatt aatatgctat                                                   20

<210> SEQ ID NO 23
<211> LENGTH: 20
<212> TYPE: DNA
<213> ORGANISM: Mus Musculus

<400> SEQUENCE: 23
atcataccct cctaactcag                                                   20
```

CONDITIONAL MST OVEREXPRESSING CONSTRUCT AND CONDITIONAL MYOSTATIN OVEREXPRESSING TRANSGENIC MOUSE

CROSS-REFERENCE TO RELATED APPLICATIONS

This application is a divisional application claiming the benefit of, and priority under 35 U.S.C. §120 to, U.S. application Ser. No. 12/398,994, filed Mar. 5, 2009, now U.S. Pat. No. 8,222,478, issued Jul. 17, 2012, which claims the benefit of, and claims priority under 35 U.S.C. §119(e) from U.S. Provisional Application Ser. No. 61/034,083 filed Mar. 5, 2008, the contents of all of which applications are hereby incorporated by reference in their entirety.

GOVERNMENT SUPPORT

This work was made possible, in part, with support from the United States government, NIH/MBRS Score Program Grant: 506 GM 0685510-01 and NIH/NIASMD grant 1R21AR0541010-01A2. The United States government may have certain rights in this invention.

A Sequence Listing is provided in electronic form in the text file named "CDU-0001US.txt" and being 37.45 kB in size, which was filed with the United States Patent and Trademark Office on Mar. 12, 2010, the contents of which are hereby incorporated by reference in their entirety.

FIELD OF THE INVENTION

The instant invention relates to the field of molecular genetics, in particular to the generation of transgenic mice, and most particularly to the generation of conditional transgenic mice which allows for the study of myostatin gene expression at different stages of development.

BACKGROUND OF THE INVENTION

Myostatin a Member of the (TGF)-13 Superfamily

Myostatin (Mst), a member of the transforming growth factor (TGF)-13 superfamily, is thought to be a negative regulatory protein of skeletal muscle mass during embryological development (McPherron et al. Nature 387:83-90 1997) and to be a genetic determinant of skeletal muscle mass in mice, cattle, and humans. Mst is also referred to as growth and differentiation factor-8 (GDF-8). Specifically, Mst is thought to be a negative regulator of skeletal muscle mass; to modulate transcription of muscle-specific genes; to keep muscle progenitor (satellite) cells in a quiescent state; to inhibit muscle regeneration; to inhibit proliferation and differentiation of myoblast; and to downregulate DNA and protein synthesis. All members of the (TGF)-β superfamily share a common structure including a short peptide signal for secretion and an N-terminal peptide fragment that is separated from the bioactive carboxy-terminal fragment by proteolytic cleavage at a highly conserved proteolytic cleavage site.

Since myostatin belongs to the TGF-β superfamily, it is likely to share many features to different members of this family. The biologically active forms of TGF-β are dimers and have been shown to signal by binding receptors followed by activation of Smad proteins. The myostatin gene is composed of three exons. Mst is a 376 amino acid long protein including a signal sequence for secretion, a proteolytic processing site and a C-terminal cysteine residue, like other Members of TGF-β superfamily. The biological activation mechanism includes a proteolytic process yielding a 110 amino acid at the C-terminal region, capable of forming a disulfide-linked dimer. The bioactive carboxy-terminal domain is encoded by the third exon and is characterized by cysteine residues at highly conserved positions which are involved in intra- and intermolecular disulfide bridges. Functional myostatin protein molecules are covalently linked (via a S—S bond) dimers of the carboxy-terminal domain.

Myostatin is expressed in skeletal muscle and its precursors from early embryonic stages until adulthood. Myostatin expression is also observed at a lower level in adipose tissue (MePherron et al Nature 387:83-90 1997). Myostatin mRNA has also been observed in the mammary gland (Ji et al. American Journal of Physiology 275: part 2, R1265-1273, 1998) and in cardiac muscle (Sharma et al. Journal of Cell Physiology 180:1-9 1999).

MHC Isoforms

The pathomechanism of muscle wasting is not completely understood, but it is characterized, among other things, by the derangement in size and number of muscle fibers. Muscle function depends on fiber numbers and size, and its myosin heavy chain (MHC) isoform composition. Mst has an effect on these muscle determinants, although data are contradictory. Myosin, the most abundant protein expressed in striated muscle cells, was first isolated by Kuhne in 1864. Years later, its central role in the contractile process was elucidated. Myosin comprises ~25% of the total protein pool and exists as a complex molecule. An important feature concerning muscle structural/functional properties is the existence of the MHC gene family of motor proteins in which specific genes encode MHC protein isoforms. These isoforms have distinctly different ATPase (and shortening velocity) properties, which impact the intrinsic functional properties of the individual myofibers in which they are expressed, and provide the molecular basis of a muscle fiber's functional diversity. Four different fiber types, each with different mechanical properties, have been reported in rodent muscle: slow type I, and fast types IIA, IIX and IIB. It is well recognized that muscles are capable of undergoing significant transition in MHC isoform expression, and several animal models have been developed to determine this plastic feature during different mechanical conditions. After endurance exercise training, MHC type I and IIA increase, and MHC IIX decreases. Mechanical unloading upregulates the fast MHC protein isoform content while concomitantly downregulating the content of the slow MHC protein isoform. In contrast, mechanical overloading produces a significant reduction in the relative proportion of the fast type IIB MHC isoform and a concomitant increase in the slow type I MHC isoform. Removal of load bearing via hindlimb unloading results in similar changes.

Overloading and Unloading the Muscle

In skeletal muscle, interventions that unload or reduce the weight-bearing activity of the muscle cause slow-to-fast MHC conversions, whereas fast-to-slow conversions are seen when the muscles become either chronically overloaded or subjected to intermittent loading, as occurs during resistance training and endurance exercise. How physiological conditions change muscle function and muscle composition has been investigated. Overloading muscle in wild type rats by removing almost all muscle in the hind limb except the plantaris, and then unloading that muscle by casting the animal's limb in order to immobilize it, yields unexpected results. Over time, the plantaris fast muscle, which originally contains 65% MHC isoform IIB type MHC isoform, shifted to slow type muscle. Using antibodies against all 4 different MHC isoforms, it was possible to identify a shift in MHC isoform composition. Prior to overloading, the muscle contained 60-65% fast type JIB fibers, but after six weeks of overloading, the ratio of the IIB:IIX had increased. During those six weeks it was found that the concentration of the type IIB isoform gradually decreased, the ratio of the IIB:IIX increased, and thereafter, the rate of IIX:IIA also increased. By the end of experiment, the majority of the muscle contained isoform type I (slow type). These findings demonstrate a partial shift toward a slower phenotype; however, the high degree of polymorphism found in the plantaris muscle represents a unique design that appears to minimize the functional consequences of these MHC transitions, and could be a characteristic of fibers with high adaptive potential, i.e., hybrid fibers are more suitable to switch phenotype to meet new functional demands.

Shifting Myosin Heavy Chain (MHC) Isoform

It has also been shown that Mst knockout mice lose more muscle mass after hindlimb suspension, and it is not clear whether this is a consequence of the modified muscle development during embryogenesis or a consequence of an Mst-independent mechanism. To date, there is no direct evidence that Mst can influence muscle plasticity in adulthood. The effect of Mst on fiber type alterations had been investigated by comparing adult muscles from the Mst knockout mice with wild-type controls. Based on myofibrillar ATPase staining, the soleus of Mst knockout mice displays a larger proportion of fast type II fibers and a reduced proportion of slow type I fibers, compared with wild-type animals. Using a staining for succinate dehydrogenase (SDH) activity, a larger proportion of glycolytic (fast) fibers and a reduced proportion of oxidative (slow) fibers occur in the extensor digitorum longus (EDL) of Mst knockouts. These differences in distribution of fiber types are accompanied by differences in the expression of MHC isoforms. In both Mst knockout soleus and EDL, larger numbers of faster MHC isoforms are expressed at the expense of slower isoforms, when compared with wild-type littermates. Proteomic analysis supported these findings. The differences in the proportion of fiber types in Compact mice (natural Mst mutant strain) vs. WT are similar to differences observed between double-muscled and normal cattle. Hypermuscularity seems to be associated with a shift in the metabolic pathway of energy production toward glycolysis, and lower capillary density which could have negative consequences for physical fitness. Another study with similar results compared MHC composition in normal- and double-muscled animals during prenatal development. It was concluded that Mst downregulates the fast type MHC isoform expression and is associated with changes in both skeletal muscle fiber type and fiber size during muscle development. This muscle phenotype is likely a consequence of developmental processes. It is not known for certain whether inhibition of Mst in adults drives the shift towards a glycolytic (faster) phenotype or not.

Embryogenesis

Myostatin plays a critical role during embryogenesis. The ontogeny of Mst coincides with the periods of the primary and secondary muscle fiber formation. Since myofiber number is mostly completed by the end of embryogenesis, the reduction of Mst prior to this stage could be due to the reduction in myogenic and mytogenic events. Skeletal myogenesis is a precisely orchestrated process by which committed but proliferating myoblasts irreversibly exit from the cell cycle, and differentiate to multinucleated myotubes. Myofibers are permanently differentiated after birth and cannot undergo mitotic division. Satellite cells (muscle stem cells) are the probable source of new myonuclei, and their proliferation is required to support muscle hypertrophy, while inhibition of satellite cell proliferation maintains muscle atrophy. Several studies indicate that Mst acts to keep muscle progenitor cells in a quiescent state, and when Mst levels are reduced, these progenitor cells are released from growth arrest.

Adult Skeletal Muscle Atrophy

Regulation of muscle size and number is essential for proper development and homeostasis of adult musculature. A number of genetic factors, growth factors, hormones, nutritional factors, and a network of signal transduction pathways are important in the regulation of skeletal muscle mass. However, their precise role in the integrated, in vivo regulation of skeletal muscle homeostasis and its pathology, muscle wasting, remains poorly understood. It can cause generalized weakness and debilitation and, when respiratory muscles are involved, asphyxia and even death. Pathological atrophy or muscle wasting is a characteristic of a number of diseases, including cancer, cachexia, sepsis, HIV-infection, diabetes, and end-stage kidney, heart and pulmonary disease. Both serum and intramuscular concentrations of Mst are increased in HIV-infected men with weight loss, and correlate inversely with fat-free mass index. Chronic disuse, prolonged bed rest, cachexia, spaceflight, glucocorticoid treatment are all coupled with elevated levels of Mst, and as a consequence, with muscle atrophy. These data support the hypothesis that Mst diminishes adult skeletal muscle growth and contributes to adult muscle wasting. The changes in Mst expression in conditions associated with skeletal muscle loss in adult animals and humans, although suggesting an inverse correlation between myostatin levels and muscle mass, have not established a clear cause/effect relationship. Therefore, the precise functional role of Mst protein in regulating muscle growth in adult animals remains poorly understood.

Mst Knock-Out Mice

Homozygous Mst-null mice have 30 to 50% more muscle mass than the wild type mice, and have larger cross-sectional fiber area (hypertrophy) and higher fiber number (hyperplasia). Similarly, the dominant negative transgenic mice which express an Mst precursor mutated at its cleavage site under the control of a muscle specific promoter, results in myofiber hypertrophy, but not hyperplasia. However, these studies do not clarify the role of Mst in the adult wild type animal.

Transgenic Animal Models

In the last decade transgenic animals have become a powerful research tool for studying the molecular mechanisms underlying cellular and physiological processes such as cell growth, differentiation, and regulation of specific gene expression. Transgenic mice (McPherron et al. Nature 387: 83-90 1997) previously disclosed have been used to exhibit reduced or completely disrupted expression of Mst. However, it is possible that Mst protein plays an important role in regulating skeletal muscle mass and function in postnatal life, by reducing the number and size of muscle fibers, and decreasing muscle function even further than what could be expected from the loss of muscle mass. This role has not been elucidated by using regular transgenic mice because changes in Mst expression and/or function in these animals may be compensated by ancillary pathways that may obscure results obtained in adult animals.

Constitutive loss of Mst function results in a dramatic increase in skeletal muscle mass as a result of combined muscle hyperplasia and hypertrophy. Both myostatin knockout mice along as well as mice (McPherron et al. Nature 387:83-90 1997; Szabo et al. Mammalian Genome 9:671-672 1998 and Varga et al. Genetics 147:755-764 1997) and cattle (Grobet et al. Nature Genetics 17:71-74 1997; Grobet et al. Mammalian Genome 9:210-213 1998; Kambadur et al. Genome Research 7:910-915 1997 and McPherron et al.

PNAS USA 94:12457-12461 1997) which are homozygous for naturally occurring Mst loss-of-function mutations share this phenotype commonly referred to as "double-muscling."

Myostatin Overexpression in Adult

One report has tested Mst overexpression directly in adult mice, by injecting a CHO cell line expressing recombinant Mst into the thighs of athymic nude mice, which resulted in a dramatic weight loss (33% of total body weight), partially due to a global decline in skeletal muscle mass. Morphometric analysis revealed that fiber diameter was reduced by 25% in Mst overexpressing animals. The question remains as to whether these wasting effects occurred as a result of Mst secretion into the circulation, or as an unspecific response either to cytokines produced by the Mst-transformed cell line, or as a B-cell immunogenic reaction.

Conditional Mst Inactivation

In the mdx mouse model of muscle dystrophy, inactivation of Mst with an antibody, and also crossing the mdx with the Mst knockout animals resulted in an increase in skeletal muscle mass and a reduction of muscle degeneration.

US20040158884 discloses a transgenic mouse model for conditional inactivation, as opposed to conditional overexpression, of Mst in an adult mouse. This model utilized a non-tissue specific cre-lox system to conditionally inactivate Mst in the mouse, to effect muscular hypertrophy. Conditional inactivation of Mst in mice has demonstrated that early postnatal inactivation of the Mst gene causes generalized muscular hypertrophy, of a magnitude similar to that observed for constitutive Mst knock out (KO) mice, primarily due to muscle fiber hypertrophy. But when adult mice (7-8 weeks old) were treated with an antibody against Mst, they also showed increased muscle mass as a result of fiber hypertrophy, and increased grip strength. No sex differences were detected in this study although others have suggested that Mst has a more prominent effect on male than on female muscle.

Thus, these studies looking at Mst expression levels in adult skeletal muscle suggest that regulation of muscle mass is controlled by Mst at the level of fiber size and/or at the level of cell growth, and that inactivating Mst in adult animals also increases muscle mass. However, these studies do not provide direct evidence that Mst is a negative regulator of adult muscle, but, rather, merely provide an indication that inactivating Mst causes muscle hypertrophy. It still remains to be demonstrated whether or not the presence of Mst is responsible for muscle atrophy or waste.

Such gaps have impaired the ability to develop appropriate treatments to improve muscle size and strength, and muscle atrophy-related conditions which continue to pose a substantial burden to patients as well as to public health. Understanding Mst and its effect in altered physiological conditions is crucial to advance discovery towards much-needed treatments of diseases associated with muscle wasting.

There is thus a need in the art for animal models for studying Mst activation and the associated effects on skeletal muscle.

SUMMARY OF THE INVENTION

Provided herein are novel nucleic acid sequences, vectors comprising such nucleic acid sequences, host cells comprising such vectors, and transgenic animals comprising such nucleic acid sequences, and related molecules and methods relating thereto.

In an embodiment, a conditional eukaryotic gene expression system may comprise two separate constructs:

a regulatory construct which includes a promoter sequence and a transactivation protein sequence with a polyA tail at the 3' end; and a response construct which includes a promoter such as a transactivator response element (TRE) and the gene of interest with a polyA tail at the 3' end.

In exemplary embodiments of a conditional myostatin overexpression system these two essential, basic structure may have the following parts:

the regulatory construct has a tissue (muscle) specific promoter MCK (muscle specific creatine kinase) and a doxycyclin inducible reverse transactivation protein sequence rtTA (also called Tet-ON): 5'-MCK-rtTA-polyA-3'; and the response construct has the TRE promoter and the mouse myostatin sequence: 5'-TRE-Mst-polyA-3'.

When the two constructs apply separately, it is called monocistronic version. When the two constructs put together in one, it is called bicistronic version. In the bicistronic version, the order and orientation of the elements (e.g., the order and/or orientation of the two constructs) is not critical, and may be altered or re-arranged in any suitable manner. For example, any of the possible structure/order of the bicistronic model listed below are suitable for the practice of the invention:

a. 5'-MCK-rtTA-polyA//TRE-Mst-polyA-3'
b. 5'-MCK-rtTA-polyA//polyA-Mst-TRE-5'
c. 3'-polyA-rtTA-MCK//TRE-Mst-polyA-3'
d. 5'-TRE-Mst-polyA//MCK-rtTApolyA-3'
e. 5'-TRE-Mst-polyA//polyA rtTA-MCK-5'
f. 3'-polyA-Mst-TRE//MCK-rtTA-polyA-3'

In some embodiments, it may be desirable to include or append a label and/or a tags to either or to both sequences. For example, in an embodiment of the conditional myostatin overexpressing system, the structure example "f" from the above list, may be labeled as follows:

3'-polyA-EGFP/IRES-Mst/HA-TRE//MCK-rtTA/BFP-polyA-3'

(where EGFP stands for a nucleic acid sequence encoding "enhanced green fluorescent protein"; IRES stands for a nucleic acid sequence encoding an "internal ribosome entry site" sequence; Mst stands for a nucleic acid sequence encoding myostatin; HA stands for a nucleic acid sequence encoding hemagglutinin; TRE stands for a nucleic acid sequence encoding a tetracycline response element; MCK stands for a nucleic acid sequence encoding muscle creatine kinase; rtTA stands for a nucleic acid sequence encoding reverse tetracycline transactivator; and BFP stands for a nucleic acid sequence encoding blue fluorescence protein).

For example, in a construct such as the one disclosed above, the BFP (blue fluorescence protein) and the IRES/EGFP (green fluorescence protein) were used for easy detection of gene expression, and HA (hemagglutinin) sequence was used to tag the Mst and to detect/quantify Mst expression on western blot. It will be understood that labels and tags are not an essential part of the system, but may be useful, and that any suitable label, tag, or other identifiable element may be used in the practice of the invention.

In further embodiments, transgenic animals are provided. Transgenic animals of the instant application provide tissue specific, conditional overexpression of Mst at any stage of development, allowing normal embryonic development, if desired, before triggering Mst overexpression, while allowing external manipulation of Mst levels and of muscle mass in the animals when desired. These transgenic animals having increased Mst expression provide decreased muscle mass compared to wild-type animals, and may be used to elucidate the functional role of myostatin in the regulation of skeletal muscle mass and muscle performance in the adult animal. Trangenic animals having features of the invention provide a conditional increase-of-function animal model that keeps Mst levels under physiological control via administration or withdrawal of a pharmacological modulator that can modify recombinant Mst expression in skeletal muscle. Specifically, the invention provides muscle tissue specific expression of Mst. Expression of Mst may be regulated, for example, by a control sequence such as a promoter, which may be a conditional promoter. A control sequence may be regulated by administration or by withdrawal of a control factor that affects the action of the control sequence. For example, Mst expression in a transgenic animal having features of the invention may be regulated by an rtTA-TRE2 regulatory and response sequence controlled via administration and withdrawal of doxycycline or tetracycline. Transgenic animals having features of the invention may be induced, upon administration or withdrawal of a control factor or control factors, to increase Mst expression. Such controlled increase in Mst expression leads to decreased muscle mass. In embodiments, transgenic animals having features of the invention may be induced, upon administration or withdrawal of a control factor or control factors, to increase Mst expression in a particular target tissue or multiple particular target tissues. Such controlled increase in Mst expression in the particular tissue(s) leads to decreased muscle mass in the particular tissue(s) as a result of the administration or withdrawal of a control factor or control factors.

Transgenic animals having features of the invention and having increased Mst expression, at least at some time during their life, may be used to provide animals with decreased muscle mass, or decreased muscle strength, and may provide animals with decreased muscle mass or strength in one or more target muscle(s). In alternative embodiments, transgenic animals having features of the invention and having decreased Mst expression, at least at some time during their life, may be used to provide animals with enhanced muscle mass, or increased muscle strength, and may provide animals with enhanced muscle mass or strength in one or more target muscle(s). Transgenic animals having features of the invention may be used for investigating whether the transient increase of Mst level reduces muscle mass and function, and whether ageing affects this process, as well as restoring physiological level of Mst corrects and/or normalizes the changes, and whether or not there are sex differences in Mst effects. Because the expression of Mst during embryogenesis is not affected in the conditionally Mst overexpressing transgenic (CMOT) animal, such as a CMOT mouse, the animals develop normally. Since the Mst gene may be allowed to function normally during development, transgenic animals of the instant application thus do not have some of the problems associated with overexpression, or knocking out, of a regulatory protein during embryogenesis. Alternatively, administering or withdrawing a control factor during embryogenesis or other developmental stage allows manipulation of Mst levels during development if desired.

Embodiments, Aspects and Variations of the Invention

The present application provides multiple embodiments, aspects and variations, including, but not limited to, the following embodiments, aspects and variations:

The application provides a transgenic non-human animal for conditionally overexpressing Mst. These animals comprise cells comprising a DNA transgene. The DNA transgene may comprise SEQ ID NO. 1, or variants thereof having greater than 80%, 90%, 95%, 99% sequence identity to SEQ ID No. 1, and may be operably linked to a tissue specific promoter. In one embodiment, the DNA transgene further comprises a regulatory sequence. The regulatory sequence may comprise, for example, reverse tetracycline transcription activator (rtTA). The transgene may further comprise a response sequence. In embodiments, the tissue specific promoter may comprise nucleic acid sequences encoding muscle creatine kinase (MCK), including a MCK promoter sequence (e.g., SEQ ID NO: 8) or Troponin I (e.g., TNNI1, found in slow twitch skeletal muscle, or TNNI2, found in fast-twitch skeletal muscle).

The application also provides a Mst expression response construct comprising a transgenic nucleotide sequence comprising SEQ ID NO. 1, or Mst cDNA (e.g., SEQ ID NO: 5), or variations thereof. For example, the transgene sequence SEQ ID NO: 1 includes a nucleic acid sequence encoding Mst (SEQ ID NO: 5).

The application also provides a bicistronic Mst expression construct comprising a regulatory sequence and a Mst response sequence. The application also provides a method of producing a Mst expression vector comprising cloning the Mst expression response construct for conditionally overexpressing Mst operably linked to a tissue specific promoter into a vector.

The application also provides a method of producing a bicistronic Mst expression vector comprising cloning a bicistronic Mst expression construct comprising a regulatory sequence and a Mst response construct into a vector.

The application also provides a method of producing a transgenic non-human animal comprising introducing the conditional monocistronic Mst expression response construct of any of the above embodiments into a non-human animal.

The application also provides a method of producing a double-transgenic non-human animal comprising i) introducing a conditional monocistronic Mst expression response construct of any of the previous embodiments into a non-human animal and ii) introducing a regulatory sequence in a second non-human animal and iii) crossing the first and second non-human animals to produce an offspring having both the regulatory and the response sequences.

The application also provides a method of producing a transgenic non-human animal comprising introducing a bicistronic Mst expression construct into a non-human animal.

In one embodiment, the vector comprises a fluorescent marker coding sequence. In variations of the above embodiment, the fluorescent marker coding sequence is selected from the group consisting of GFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1, luciferase, and aequorin, and other fluorescent marker polypeptides. Fluorescent proteins are disclosed in, for example, U.S. Pat. Nos. 5,981,200; 6,054,321; 6,077,707; 6,172,188; 6,194,548; 6,172,188; 6,803,188; 7,022,826; 7,091,31; 7,157,566; 7,314,915; 7,329,735; and 7,332,598.

The application also provides a method of transfecting cells with the construct of any of the above embodiments by electroporation or injection. The application also provides a construct of any of the above embodiments further comprising a fluorescent marker coding sequence. The fluorescent marker coding sequence may be, for example, a coding sequence coding for GFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1, luciferase, aequorin, or other fluorescent marker polypeptide.

The application also provides a construct of any of the above embodiments in a vector. In one embodiment, the vector is pEGFP-1; an EGFP sequence is found within the CMOT transgene exemplified in SEQ ID NO: 1; for example, an EGFP sequence is found in the IRES/EGFP sequence SEQ ID NO: 4 and in the blue fluorescent protein sequence SEQ ID NO: 10. The application also provides a construct of any of the above embodiments wherein the transgenic nucleotide sequence comprises SEQ ID NO. 1 or SEQ ID NO: 13 or Mst cDNA (e.g., SEQ ID NO: 5) operably linked to a promoter. The promoter may be, for example, a TRE2 promoter. In another embodiment, the application provides a bicistronic Mst expression construct such as, for example, SEQ ID NO: 13 wherein the transgenic nucleotide sequence may comprise SEQ ID NO. 1 or SEQ ID NO: 13 or Mst cDNA operably linked to a promoter, such as a TRE2 promoter.

In one embodiment, the application provides a transgenic nucleotide sequence comprising SEQ ID NO. 1 or SEQ ID NO: 13 or Mst cDNA (e.g., SEQ ID NO: 5) operably linked to a TRE2 promoter, in cells engineered to express rtTA protein in the presence of tetracycline or doxycycline. In another embodiment, the application provides a method of decreasing Mst expression in a cell comprising withdrawal or removal of tetracycline or doxycycline from a cell comprising the Mst expression response construct of any of the above embodiments. In another embodiment, the application provides a method of decreasing Mst expression in a cell comprising withdrawal or removal of tetracycline or doxycycline from a cell comprising the bicistronic Mst expression response construct of any of the above embodiments.

In another embodiment the application provides a Mst expression response construct wherein the nucleotide sequence comprises SEQ ID NO. 1 or SEQ ID NO: 13 or Mst cDNA (e.g., SEQ ID NO: 5) operably linked to TRE2. In one embodiment, the application provides a bicistronic Mst expression construct wherein the nucleotide sequence comprises SEQ ID NO. 1 or SEQ ID NO: 13 or Mst cDNA (e.g., SEQ ID NO: 5) operably linked to TRE2.

In another embodiment, the application provides a Mst expression regulatory construct wherein the nucleotide sequence comprises SEQ ID NO. 1 or SEQ ID NO: 13 or Mst cDNA (e.g., SEQ ID NO: 5) operably linked to MCK or Troponin I. For example, MCK is discussed in Shield et al., "E-box sites and a proximal regulatory region of the muscle creatine kinase gene differentially regulate expression in diverse skeletal muscles and cardiac muscle of transgenic mice" *Mol Cell Biol* 16:5058-5068 (1996).

In another embodiment, the application provides a bicistronic Mst expression construct wherein the nucleotide sequence comprises SEQ ID NO. 1 or SEQ ID NO: 13 or Mst cDNA (e.g., SEQ ID NO: 5) and is operably linked to MCK or Troponin I.

In another embodiment, the application provides a Mst expression regulatory construct further comprising a tissue specific promoter. In another embodiment, the application provides a bicistronic Mst expression construct further comprising a tissue specific promoter. In another embodiment, the application provides a Mst expression construct wherein the tissue specific promoter is skeletal muscle specific. In another embodiment, the application provides a bicistronic Mst expression construct wherein the tissue specific promoter is skeletal muscle specific.

In another embodiment, the application provides a Mst expression regulatory construct wherein the promoter is an MCK promoter. In another embodiment, the application provides a bicistronic Mst expression construct wherein the promoter is an MCK promoter. In another embodiment, the application provides a Mst expression response construct further comprising Mst regulating promoter TRE2. In another embodiment, the application provides a bicistronic Mst expression construct further comprising Mst regulating promoter TRE2.

In another embodiment, the application provides a Mst expression regulatory construct further comprising reverse tetracycline transactivator (rtTA) e.g., SEQ ID NO: 9. In another embodiment, the application provides a bicistronic Mst expression construct further comprising reverse tetracycline transactivator (rtTA) e.g., SEQ ID NO: 9.

In another embodiment, the application provides a method of modulating the expression of Mst (e.g., SEQ ID NO. 5) in a non-human animal comprising the construct of any of the above embodiments by increasing or decreasing the concentration of doxycycline in the non-human animal. In another embodiment, the application provides a transgenic non-human animal comprising a transgenic nucleotide sequence that comprises SEQ ID NO. 1 or SEQ ID NO: 13 or Mst cDNA (e.g., SEQ ID NO: 5) that is operably linked to a muscle tissue specific promoter. In one embodiment, the animal is a mouse. In one embodiment, the transgenic nucleotide sequence comprising SEQ ID NO. 1 or SEQ ID NO: 13 or Mst cDNA (e.g., SEQ ID NO: 5) integrated into the genome of the animal.

The application also provides the above embodiment wherein the transgenic nucleotide sequence comprising SEQ ID NO. 1 or SEQ ID NO: 13 or Mst cDNA (e.g., SEQ ID NO: 5) is operably linked to MCK promoter. The application also provides the above embodiment wherein the animal is a mouse. The application also provides a transgenic non-human animal of any of the above embodiments wherein the transgenic nucleotide sequence comprising SEQ ID NO. 1 or SEQ ID NO: 13 or Mst cDNA (e.g., SEQ ID NO: 5) is operably linked to a reverse transcription activator.

The application also provides a transgenic non-human animal of any of the above embodiments wherein the animal exhibits a Mst associated phenotype in the presence of a transcription activator.

The application also provides a transgenic non-human animal of any of the above embodiments wherein the phenotype can be reversed or ameliorated upon decrease or removal of said transcription activator. The application also provides a transgenic non-human animal of any of the above embodiments wherein the nucleotide sequence comprises SEQ ID NO, 1 or SEQ ID NO: 13 or Mst cDNA (e.g., SEQ ID NO: 5) is regulated by a transactivator. The application also provides a transgenic non-human animal of any of the above embodiments wherein the nucleotide sequence comprises SEQ ID NO. 1 or SEQ ID NO: 13 or Mst cDNA (e.g., SEQ ID NO: 5) is linked to a promoter. The application also provides a transgenic non-human animal of any of the above embodiments wherein the promoter is a tissue specific promoter. The application also provides a transgenic non-human animal of any of the above embodiments wherein the tissue specific promoter is skeletal muscle specific.

The application also provides a transgenic non-human animal of any of the above embodiments wherein the Mst phenotype is a skeletal muscle phenotype. The application also provides a transgenic non-human animal of any of the above embodiments wherein the skeletal muscle phenotype is aplasia. The application also provides a transgenic non-human animal of any of the above embodiments wherein the promoter is an MCK promoter.

The application also provides a transgenic non-human animal of any of the above embodiments wherein the transactivator is reverse tetracycline transactivator (rtTA) (e.g., SEQ ID NO: 9). The application also provides a transgenic non-human animal of any of the above embodiments wherein the transcription activator is tetracycline or doxycycline.

The application also provides a transgenic non-human animal of any of the above embodiments wherein the animal is a mouse. The application also provides a transgenic non-human animal of any of the above embodiments wherein the transcription activator is doxycycline.

The application also provides a method for screening for therapeutic agents that inhibit Mst activity comprising (a) administering test agents to a transgenic animal of any of the above embodiments, (b) evaluating the effects of the test agent on the muscular phenotype of the transgenic animal.

The application also provides a transgenic non-human animal produced by: (a) crossing a first transgenic non-human animal comprising a first construct that expresses rtTA operably linked to promoter MCK with a second non-human animal comprising a second construct comprising Mst or Mst cDNA operably linked to a promoter TRE2 and (b) selecting from the first generation offspring a transgenic non-human animal having a genome comprising both the first construct and the second construct.

The application also provides any of the above embodiments wherein the transgenic non-human animal is a mouse.

IN THE DRAWINGS

FIG. 1A. Structure of the fragments carrying the transgene for generating transgenic animals expressing EGFP and overexpressing myostatin, respectively, in the skeletal muscle. A: MCK1.3/EGFP-1 construct, B: MCK1.3/mMst construct. Asterisks show the position of 5' and 3' primers used. FIG. 1B. top: myostatin overexpressing construct (prior art); bottom: novel bicistronic conditional myostatin overexpressing construct. A novel bicistronic conditional myostatin overexpressing construct as disclosed herein may thus have a regulatory sequence comprising, e.g., polyA, rtTA and MCK; and a response sequence comprising TRE, Mst/IRES-EGFP, polyA. In a novel bicistronic conditional myostatin overexpressing construct having features of the invention, nucleic acids encoding a fluorescent protein, (e.g., blue fluorescent protein (BFP), tag (e.g., hemagglutinin (HA) or other marker may be inserted or included between the polyA and rtTA regions and/or between the TRE and Mst/IRES-EGFP regions. For example, a BFP-encoding sequence may be inserted between the polyA and rtTA regions, and an HA-encoding sequence may be inserted between the TRE and MstIRES-EGFP regions.

Figures 1, 1A, 2:
Figures 1, 1B:
Figures 1, 1B, 2:

FIG. 2. EGFP expression in C2C12 cells and skeletal muscle, A: Myoblast, B: Myotube, C: Control tissue, D: Transgenic animal muscle.

FIG. 3. Genotyping of transgenic and control mice. A: PCR, B: Southern blot.

FIG. 4: Muscle weight of transgenic and control mice, A: male, B: female.

FIG. 5. RT-PCR results of transgenic and control mice. A: agarose gel, B: densitometry FIG. 6. Western blot analysis of mice, A) male, B) female, C) densitometry FIG. 7. Histomorphometry results from transgenic and control mice. A: cross-sectional area of fibers, B: myonuclei numbers mice' skeletal muscle.

Figure 8:
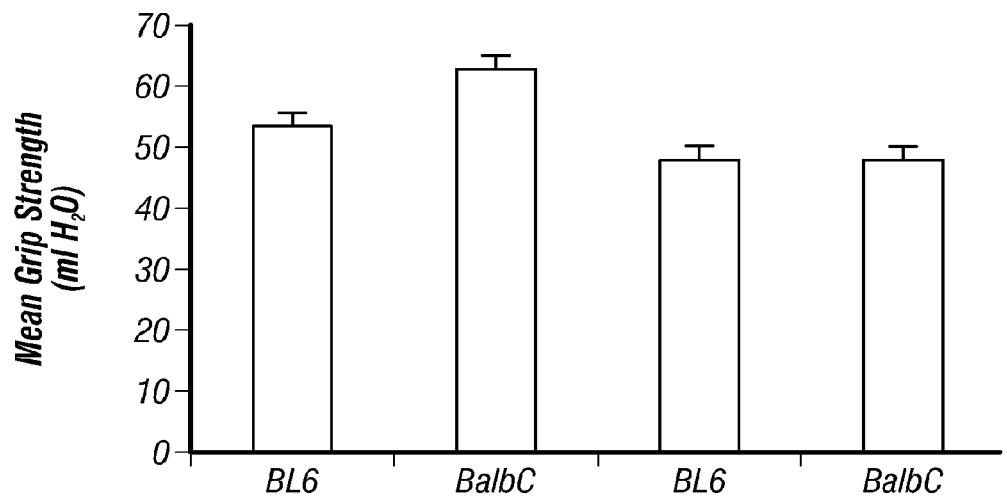

FIG. 8. Comparison of grip strength between mouse strains and gender

Figure 9:
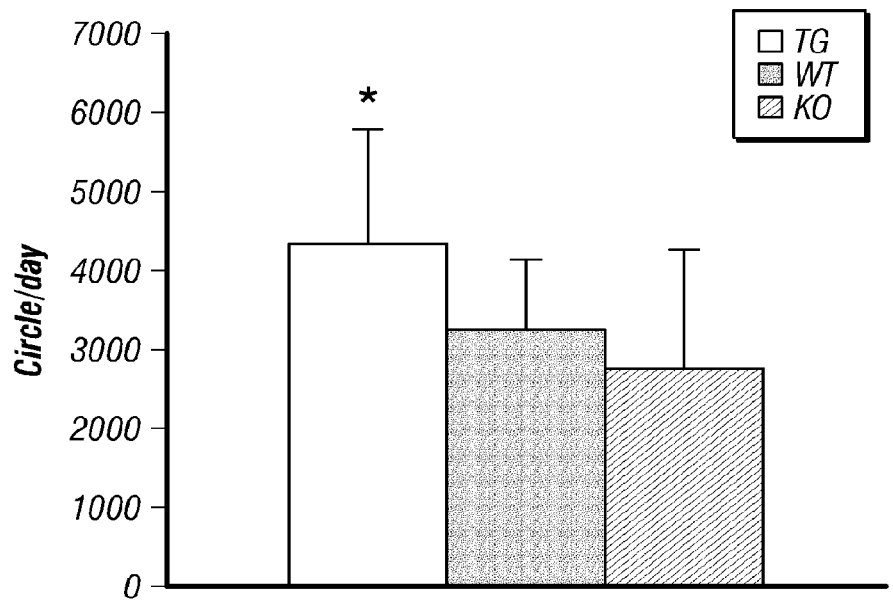

FIG. 9. Spontaneous daily activity measured by rodent activity wheel.

Figure 10A:
Figure 10B:
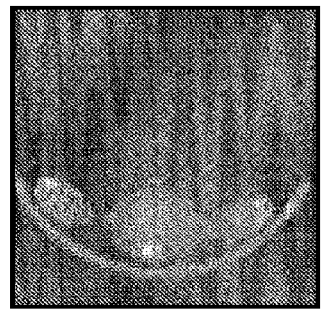
Figure 10C:
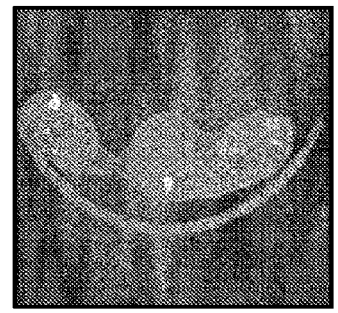

FIG. 10. CT scan images of 6 months-old male mice. A: Whole body 3D reconstructed image of a WT animal; B: a representative slice from raw data of Tg mouse; C: a representative slice from raw data of KO mouse.

Figure 11:
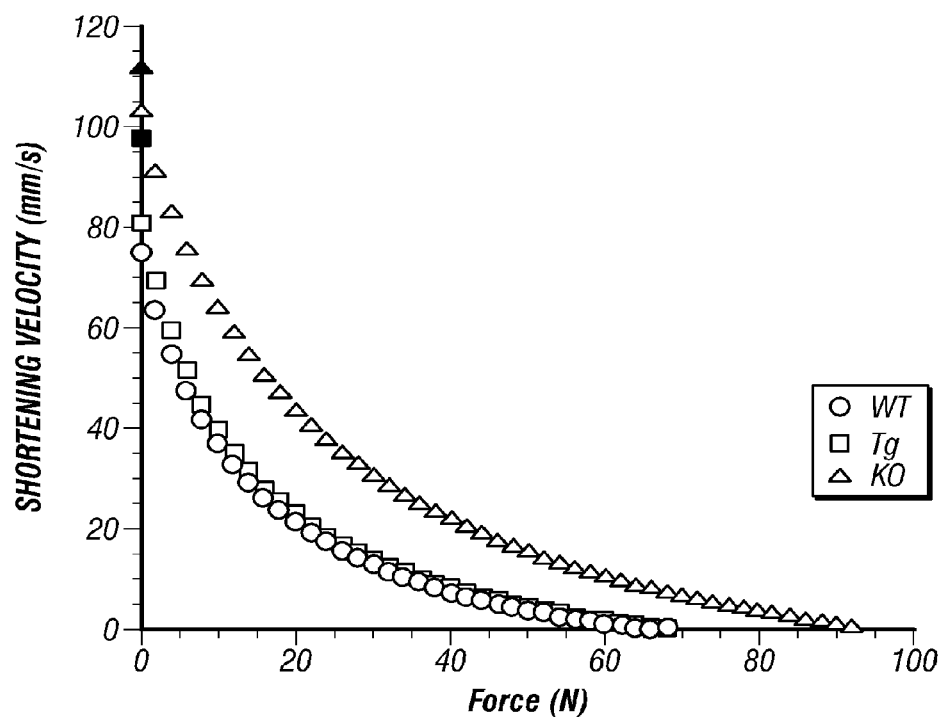

FIG. 11. Force-velocity relationship measured in Mst Tg, KO and WT mice on gastrocnemius muscle.

Figure 12:
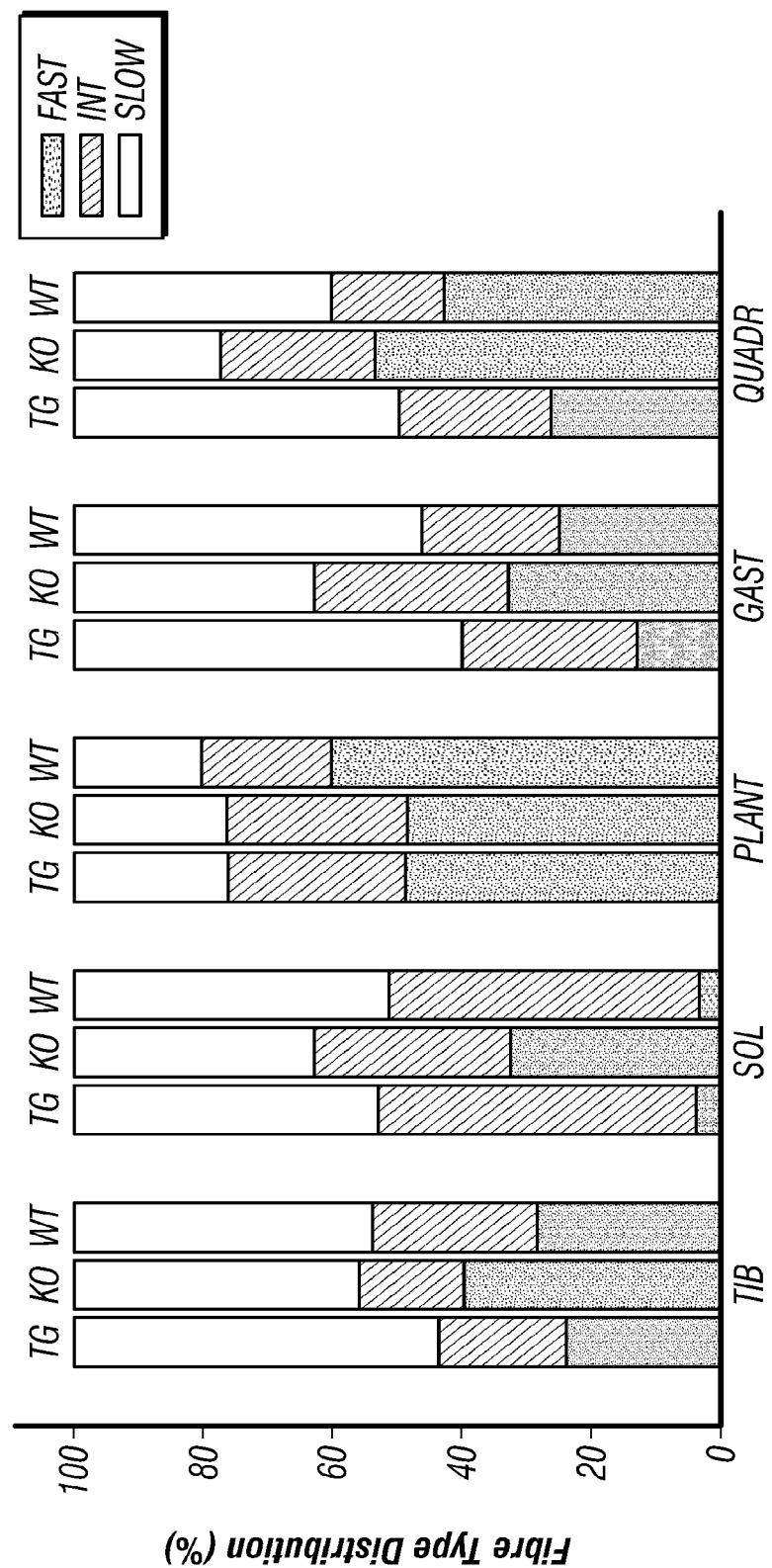

FIG. 12. Fiber type distribution in skeletal muscles.

Figure 13:
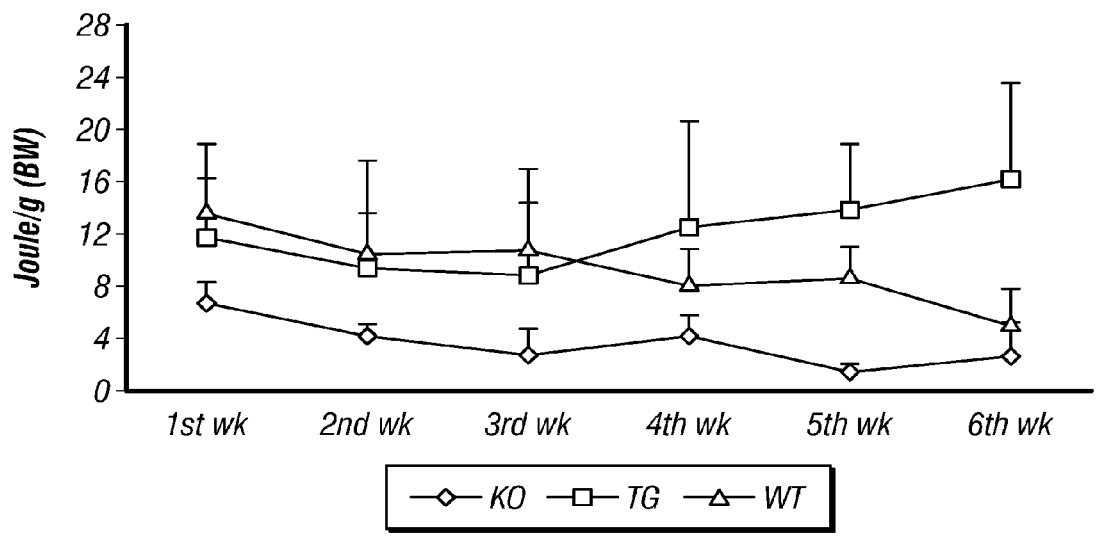

FIG. 13. Treadmill exercise tolerance.

Figure 14:
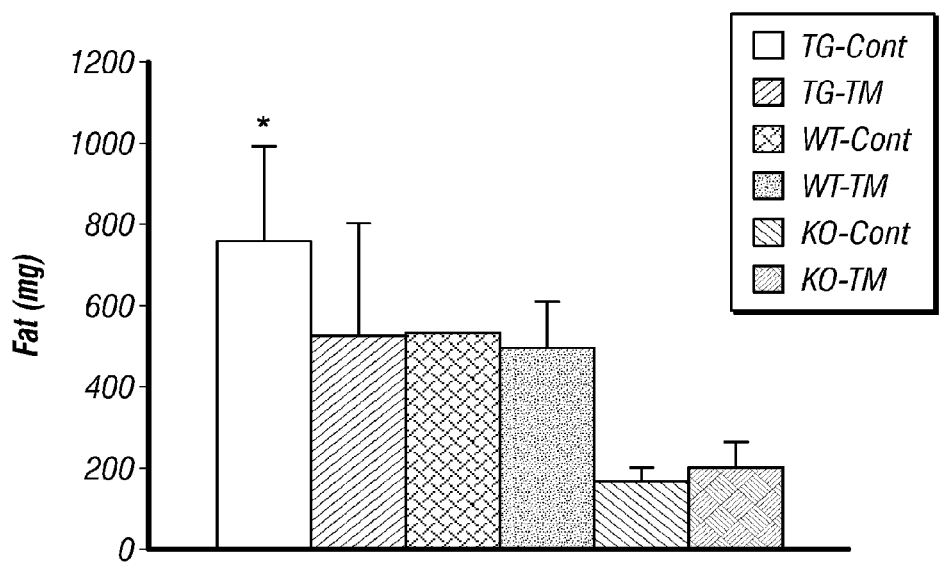

FIG. 14. Changes in abdominal fat mass followed by 8 weeks treadmill exercise test on Mst Tg, KO and WT mice compared with non-treadmill tested animals.

Figure 15A:
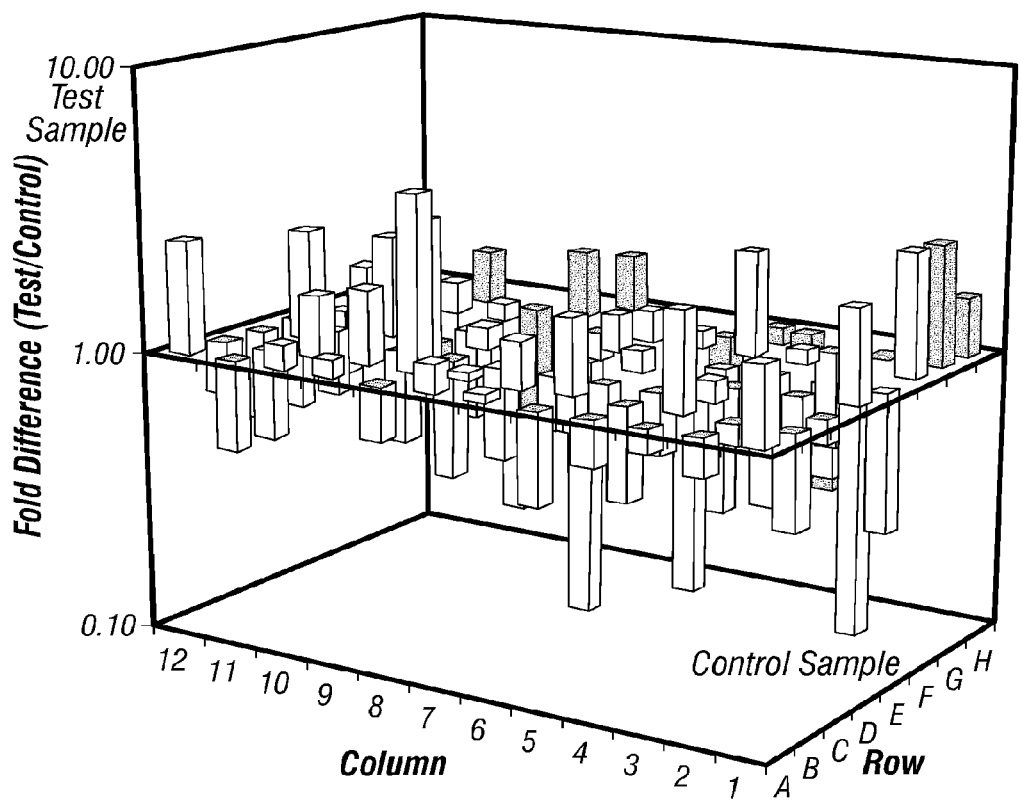
Figure 15B:
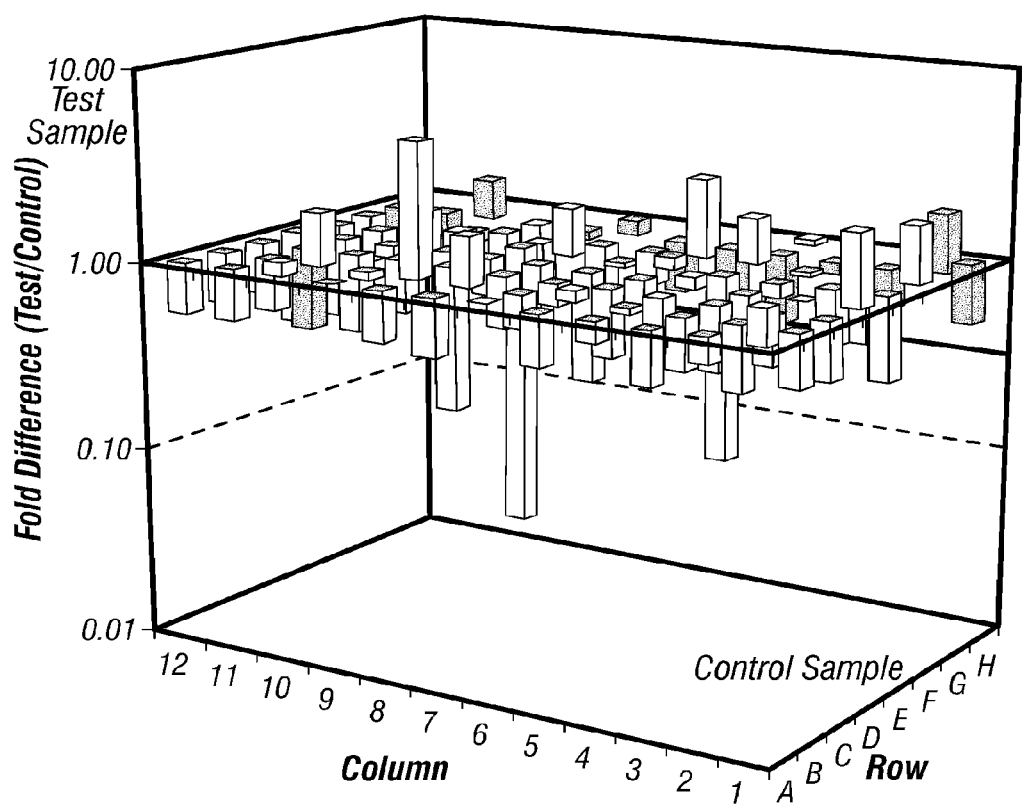

FIG. 15. Superarray pathway analysis data show changes in gene expression influenced by Mst. A: Tg mice; B: KO mice relative to WT controls.

Figure 16A:
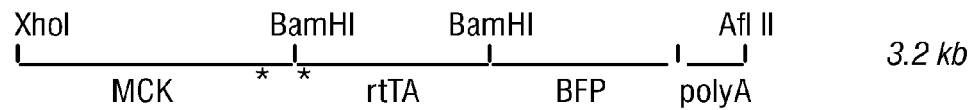
Figure 16B:
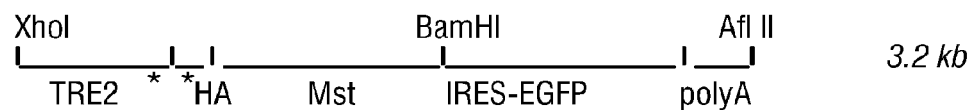

FIG. 16. Structure of the Tet-ON gene expression system carrying the sequences for conditional Mst overexpressing transgenic animals. A: MCK1.3/TetON/Blue construct, B: TRE2/HA-mMst/IRES-EGFP construct. Asterisks show the position of 5' and 3' primers used.

Figure 17:
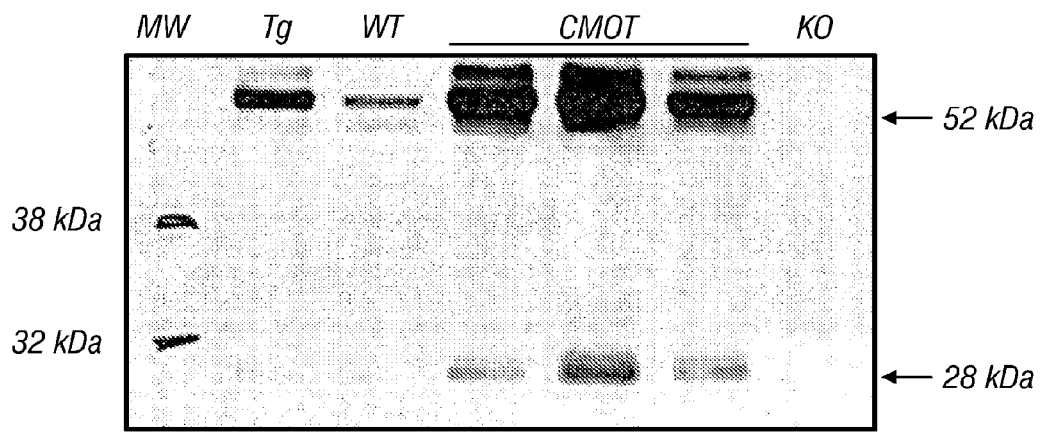

FIG. 17. Western blot of Mst expression in CMOT mice quadriceps muscle followed by Doxycylin induction (200 mg/kg Dox in chow) for 8 weeks.

FIG. 18. CMOT Transgene (SEQ ID NO: 1), including NICK promoter, Tet-ON (rtTA), ECFP (Blue FP), SV40 polyA, Plasmid backbone sequences (including pUC, HSV TK/polyA, Kan/Neo, SV40 ori, fl ori) SV40 polyA, IRES/EGFP, Myostatin (Mst), HA-tag on Mst, and TRE. The two "bold" sequences are the Afl II restriction site that was used to release the sequence from the plasmid.

FIG. 19. CMOT=pFin plasmid sequence (SEQ ID NO: 13); note that "Tet-on polyA." in the figure refers to SEQ ID NO: 9 (tet-on) and SEQ ID NO: 11 (polyA).

FIG. 20. CMOT plasmid (10273 base pairs) (SEQ ID NO: 13) Graphic map and Table by enzyme name.

FIG. 21. Schematic of Plasmid

FIG. 22. CMOT transgene (6786 base pairs) (SEQ ID NO: 1) Graphic map and Table by enzyme name.

DETAILED DESCRIPTION

All publications, patents, and patent applications cited herein, both supra and infra, are hereby incorporated by reference herein in their entireties.

The present application includes a listing of sequences following the abstract of the invention.

As used in the present specification the following terms have the meanings indicated:

The abbreviation "Tg" as used herein means transgenic.

The term "transgenic non-human animal" as used herein means a non-human animal, for example a mouse, having a cell or cells that contain a transgene, which transgene is either introduced into the animal or an ancestor of the animal. Such introduction of a transgene may be at a prenatal stage, for example, an embryonic stage.

The term "mouse" is used herein to include an individual mouse in all stages of development, including embryonic and fetal stages.

A "transgenic mouse" is any mouse containing one or more cells bearing genetic information altered or received, directly or indirectly, by deliberate genetic manipulation at a subcellular level, such as by targeted recombination or microinjection or infection with recombinant virus. The term "transgenic mouse" is intended to encompass classical cross-breeding or in vitro fertilization, as well as meant to encompass mice in which one or more cells are altered by, or receive, a recombinant DNA molecule. This recombinant DNA molecule may be specifically targeted to a defined genetic locus, may be randomly integrated within a chromosome, or it may be extrachromosomally replicating DNA.

The alteration or genetic information may be foreign to the animal (e.g. species of mouse) to which the recipient belongs, or foreign only to the particular individual recipient, or may be genetic information already possessed by the recipient. In the last case, the altered or introduced gene may be expressed differently that the native gene, or not expressed at all. Various types of nucleotide sequences can be used to generate transgenic animals, for example, mutant sequences and heterologous sequences, "Knock out" animals can also be generated, wherein entire genes or parts of genes are deleted or "knocked-out" to discern function. Methods for generating transgenic animals, particularly animals such as mice, have become conventional in the art and are described, for example, in U.S. Pat. No. 4,736,866.

The term "Mst" as used herein means myostatin protein. A nucleic acid encoding Mst is disclosed as SEQ ID NO: 5.

The terms "control sequences" and "regulatory sequences" refer to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer. A control sequence may be or include, for example, a rtTA-TRE2 regulatory and response sequence (which may interact, for example with tetracycline or a tetracycline derivative such as doxocycline).

The terms "control factor" and "regulatory factor" refer to a factor that affects a control sequence (also termed a regulatory sequence). A control factor may be administered, or may be withdrawn, in order to affect a control sequence. A control factor may be, for example, tetracycline or a tetracycline derivative such as doxocycline (e.g., for use with a rtTA-TRE2 regulatory and response sequence).

Control sequences may be modified, for example by the addition of further transcriptional regulatory elements to make the level of transcription directed by the control sequences more responsive to transcriptional modulators. Control sequences operably linked to sequences encoding a polypeptide described herein include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Thus, the terms "control sequence" and "regulatory sequence" as used herein means nucleotide sequences located upstream (T), within, and/or downstream (Y) to a coding sequence or "response sequence," which control the transcription and/or expression of the coding sequences or "response sequences," potentially in conjunction with the protein biosynthetic apparatus of the cell. These nucleotide sequences include a promoter sequence, a translation leader sequence, a transcription termination sequence, and a polyadenylation sequence.

The term "promoter" as used herein means a nucleic acid sequence which may be effective at increase transcription of nearby nucleic acid coding sequences, which are functional in mammalian cells, although prokaryotic promoters and promoters functional in other eukaryotic cells, such as insect cells, may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner or, alternatively, a tissue-specific manner, such as the "tissue specific promoter" NICK which is the gene for muscle creatine kinase, as disclosed herein. Viral promoters may also be used, for example the Moloney murine leukaemia virus long terminal repeat (MMLV LTR) promoter, the roes sarcoma virus (RSV) LTR promoter or the human cytomegalovirus (CMV) IE promoter.

Promoters are untranslated sequences located upstream from the start codon of a structural gene (generally within about 100 to 1000 base pairs (bp)) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for trk receptor is not usable. However, heterologous promoters generally will result in greater transcription and higher yields of expressed trk receptor as compared to the native trk receptor promoter.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT (SEQ ID NO: 14) region where X may be any nucleotide. At the 3' end of most eukaryotic genes is an AATAAA (SEQ ID NO: 15) sequence that may be the signal for addition of the poly A tail to the 3' end of the coding sequence. All of these sequences are suitably inserted into mammalian expression vectors.

Transcription from vectors in mammalian host cells may be, for example, controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the trk receptor sequence, provided such promoters are compatible with the host cell systems.

The early and late promoters of the SV40 virus are conveniently obtained as an SV40 restriction fragment which also contains the SV40 viral origin of replication [Fiers et al., Nature 273:113 (1978), Mulligan and Berg, Science 209, 1422-1427 (1980); Pavlakis et al., Proc. Natl. Acad. Sci. USA 78, 7398-7402 (1981)]. The immediate early promoter of the human cytomegalovirus is conveniently obtained as a HindIII E restriction fragment [Greenaway et al., Gene 18, 355-360 (1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., Nature 295, 503-508 (1982) on expressing cDNA encoding human immune interferon in monkey cells; Reyes et al., Nature 297, 598-601 (1982) on expressing human .beta.-interferon cDNA in mouse cells under the control of a thymidine kinase promoter from herpes simplex virus; Canaani and Berg, Proc. Natl. Acad. Sci, USA 79, 5166-5170 (1982) on expression of the human interferon β1 gene in cultured mouse and rabbit cells; and Gorman et al., Proc. Natl. Acad. Sci., USA 79, 6777-6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter. The actual plasmid used in the course of cloning the murine trk receptor contains the promoter of the murine 3-hydroxy-3-methylglutaryl coenzyme A reductase gene [Gautier et al., Nucleic Acids Res. 17, 8389 (1989)], whereas the reporter plasmid [pUMS $(GT)_8$-Tac] used during expression cloning contained an artificial multimerized trk recepto-inducible promoter element [McDonald et al., Cell 60, 767-779 (1990)].

The term "operably linked" as used herein means that the components described are in a relationship permitting them to function in their intended manner. A regulatory sequence "operably linked" to a coding sequence is ligated in such a way that expression of the coding sequence is achieved under conditions compatible with the control sequences.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

The term "vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized. Expression vectors, unlike cloning vectors, should contain a promoter which is recognized by the host organism and is operably linked to the nucleic acid encoding the desired polypeptide.

The term "variants" as used herein indicates a molecule, such as a polypeptide or polynucleotide, that has substantial sequence identity to a different (parent) molecule, but differs from the parent sequence by one or more different residues (e.g., different amino acids for polypeptides, or different nucleotides, for nucleic acids). Variants may be, for example, substitution, insertion, or deletion variants, in which one or more residue(s) is/are replaced by (an)other residue(s) (substitution variants), or in which one or more additional residue(s) is/are included in the sequence (an insertion variant), or in which one or more residue(s) is/are lacking (a deletion variant).

A substitution variant in a polypeptide may be a conservative substitution variant, in which an amino acid is replaced by a different amino acid with similar properties. Standard amino acid naming terminology is used herein. For example, conservative substitutions for the amino acid Ala (A) include: val, leu, ile, val. Conservative substitutions for the amino acid Arg (R) include: lys, gln, asn, lys. Conservative substitutions for the amino acid Asn (N) include: gln, his, asp, lys, arg, gln. Conservative substitutions for the amino acid Asp (D) include: glu, asn, glu. Conservative substitutions for the amino acid Cys (C) include ser, ala, ser. Conservative substitutions for the amino acid Gln (Q) include: asn, glu, asn. Conservative substitutions for the amino acid Glu (E) include: asp, gln, asp. Conservative substitutions for the amino acid Gly (G) include: ala. Conservative substitutions for the amino acid His (H) include: asn, gln, lys, arg. Conservative substitutions for the amino acid Ile (I) include: leu, val, met, ala, len phe, norleucine. Conservative substitutions for the amino acid Leu (L) include: norleucine, ile, val, ile, met, ala, phe. Conservative substitutions for the amino acid Lys (K) include: arg, gln, asn, arg. Conservative substitutions for the amino acid Met (M) include: leu, phe, ile, leu. Conservative substitutions for the amino acid Phe (F) include: leu, val, ile, ala, tyr. Conservative substitutions for the amino acid Pro (P) include: ala. Conservative substitutions for the amino acid Ser (S) include thr. Conservative substitutions for the amino acid Thr (T) include: ser. Conservative substitutions for the amino acid Trp (W) include: tyr, phe. Conservative substitutions for the amino acid Tyr (Y) include: trp, phe, thr, ser, phe. Conservative substitutions for the amino acid Val (V) include: ile, leu, met, phe, leu, ala, norleucine.

Variants that maintain (a) the structure of the polypeptide backbone in the area of the substitution, for example, as a sheet or helical conformation, (b) the charge or hydrophobicity of the molecule at the target site, or (c) the bulk of the side chain are expected to substantially maintain the properties of the parent polypeptide. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions will typically entail exchanging a member of one of these classes for another of the same class. Any cysteine residue not involved in maintaining the proper conformation of the parent polypeptide also may be substituted, generally with serine, to improve the oxidative stability of the molecule and prevent aberrant crosslinking. Conversely, cysteine bond(s) may be added to the polypeptide to improve its stability.

As used herein, "tetO" means a tetracycline operator comprising sequence which can be present in a promoter. Thus, a "tetO promoter" means a promoter having one or more such sequences.

As used herein, "tTA" means a fusion protein comprising the repressor of the Tn10 tetracycline-resistance operon of *Escheria coli* and a C-terminal portion of protein 16 of herpes simplex virus that functions as a strong transcriptional activator. This fusion protein is a tetracycline-controlled transactivator. For example, tTA will bind to the tetO region of a promoter and function as a strong activator of transcription in the absence of doxycycline. Doxycycline may therefore be used to suppress transcription from a promoter having tetO sequences.

As used herein, "rtTA" means a protein that is a variant of the tTA protein, and plays a role opposite that of tTA, i.e., rtTA protein requires doxycycline in order to activate transcription from a tetO promoter such as TRE2. Doxycycline can thus be used as an activator of transcription in conjunction with rtTA and a transgene operatively linked to a tetO-containing promoter such as TRE2, to effect controlled transactivation. SEQ ID NO: 9 provides an example of a rtTA.

The term "TRE2" as used herein means tetracycline response element.

As used herein "tetracycline controlled transactivation" refers to the tetracycline (Tc)-controlled gene expression system which permits the at will control of individual gene activities quantitatively and reversibly. In the reverse Tc-controlled transactivator (rtTA) system, Tc or doxycycline (Dox) acts as an inducer of transcription that works well in vitro, with reported induction levels of gene expression (like luciferase reporter gene, erythropoietin, ecdysone receptor, retinoid X receptor, etc.) ranging from 3 to 4 orders of magnitude above basal level.

It is well known that in transgenic and knock-out (KO) animals the irreversibility of genetic transfer may lead to compensatory upregulation, developmental defects, embryonic mortality, and others. Such limitations could be overcome by utilizing a "genetic switch" system, such as the rtTA-TRE2 system, that can be operated at will and permit the control of individual gene activities quantitatively and reversibly, in a temporal and spatial manner.

Several reports have successfully demonstrated how a drug-regulated gene expression system can be used to study gene function, and can be operated in a quantitative way in cell culture and transgenic mice. In many of these studies, the expression system is driven by the cytomegalovirus (CVM) promoter, which frequently causes leakiness in gene expression due to lack of tissue specificity, which can be overcome by using a strong muscle-specific promoter such as MCK.

The term "MCK" as used herein means muscle creatine kinase. Tissue-specific gene expression requires a well-characterized, strong, tissue specific promoter. Many muscle-specific regulatory sequences have been mapped, such as α-skeletal actin, α-cardiac actin, troponin I, myosin light chain 2, myosin heavy chain (MHC) and muscle creatine kinase (MCK). Both MCK and troponin I have high expression levels in muscle, and their promoter/enhancer regions are small enough to make them suitable for gene transfer. Within the mouse MCK gene, several regions are required for muscle-specific expression in myocytes and cardiomyocytes. Of particular interest is a 206 bp enhancer located approximately 1 kb upstream of the transcription start site which contains two E-box sequences. The 1 kb region immediately 3' of the 206 bp enhancer (called proximal regulatory region) has an E-box sequence as well, and plays an important role in tissue-specific gene expression. Simultaneous mutation of the three E-boxes in the 1,256 bp region of MCK promoter resulted in a substantial loss of reporter gene activity in cardiac and tongue muscle. SEQ ID NO: 8 provides an example of MCK promoter. To date, this mutated version of the MCK promoter is the only one which is truly skeletal muscle-specific, the E-box mutations had not dramatically affected transgene expression in fast muscles in CAT-transgenic mice.

The term "cDNA" as used herein means complementary deoxyribonucleic acid.

The term "construct" as used herein means a recombinant nucleic acid, generally recombinant DNA, that has been generated for the purpose of the expression of a specific nucleotide sequence(s), or is to be used in the construction of other recombinant nucleotide sequences.

The term "monocistronic myostatin expression" as used herein refers to a myostatin expression system wherein the regulatory sequence is not ligated into the same construct as the myostatin coding response element. Conditional eukaryote gene expression system requires a regulatory construct sequence and a response construct sequence. If the two sequences are used separately to generate transgenic animals, then they are termed the monocistronic gene expression system that further requires breeding the two transgenic animals. If their offsprings are genotyped as double transgenic, these animals can be used to test the conditional gene expression system in vivo.

The term "bicistronic myostatin expression construct" as used herein refers to a myostatin expression system wherein the regulatory sequence has been ligated into the same construct as the myostatin coding response element. Thus, in vivo, the method for bicistronic gene expression system requires that the regulatory and response sequences to be located on the same DNA fragment that is used to generate the transgenic animal. Once the animal is genotyped positively for the transgene, it can be used for testing the conditional gene expression without any further breeding with another transgenic animal.

The term "expression vector" as used herein means a plasmid comprising a transcriptional unit. The unit comprises (a) a genetic element or elements having a regulatory role in gene expression, for example, promoters or enhancers, (b) a structural or coding sequence which is transcribed into mRNA and translated into protein, and (c) appropriate transcription and translation initiation and termination sequences. Structural elements used in yeast expression systems preferably include a leader sequence enabling extracellular secretion of translated protein by a host cell.

The term "double-transgenic" as used herein is used to describe a non-human animal, for example a mouse, having a cell or cells that contain two transgenes, which transgenes are either introduced into the animal or an ancestor of the animal at a prenatal stage, for example, an embryonic stage.

The term "fluorescent marker coding sequence" as used herein means the nucleic acid sequence that codes for fluorescent and/or luminescent markers such as GET, EGFP, dsRed, dsRed2, CFP, ECFP, YFP, EYFP, BFP, dsRed 1, dsRed2, DsRed-Express, AsRed2, HcRed1, AmCyan, ZsYellow, ZsGreen, AcGFP-1. luciferase, aequorin, and other fluorescent and/or luminescent polypeptides. Fluorescent proteins are disclosed in, for example, U.S. Pat. Nos. 5,981,200; 6,054,321; 6,077,707; 6,172,188; 6,194,548; 6,172,188; 6,803,188; 7,022,826; 7,091,317; 7,157,566; 7,314,915; 7,329,735; and 7,332,598.

The term "transfecting" as used herein means causing the nucleic acid to be taken up by the cell.

The term "electroporation" as used herein means the temporary creation of holes or aqueous pores in the surface of a cell membrane by an applied electrical potential and through which therapeutic agents may pass into the cell. Electroporation is now widely used in biology, particularly for transfection studies, where plasmids, DNA fragments and other genetic material are introduced into living cells. During electroporation pulsing, molecules which are not normally membrane permeant are able to pass from the extracellular environment into the cells during the period of induced reversible membrane permeabilization. The permeabilized state is caused by the generation of an electrical field in the cell suspension or tissue of sufficient field strength to perturb the cell surface membrane's proteolipid structure. This perturbation (sometimes referred to as dielectric breakdown) is believed to be due to both a constituent charge separation and the effect of viscoelastic compression forces within the membrane and its sub-adjacent cytoskeletal structures. The result is a localized membrane thinning. At a critical external field strength, pores or small domains of increased permeability are formed in the membrane proteolipid bi-layer.

The term "Mst associated phenotype" as used herein means any of one or more characteristics of an organism, tissue, or cell associated with the expression of Mst.

The term "transcription activator" as used herein means any substance capable of inducing the transcription of a gene.

The term "transactivator" as used herein means a protein that binds to regulatory regions of DNA and enhances the expression of its associated gene.

The term "aplasia" as used herein means a decrease in muscle fiber number compared to a normal fiber number or a previously determined fiber number.

The term "atrophy" as used herein means is the partial or complete wasting away of a part of the body.

The term "test agent" as used herein means any compound or agent that is being examined for the ability to modulate myostatin expression. A test agent can be any type of molecule, including, for example a peptide, a polynucleotide (including antisense or RNAi), an antibody, a glycoprotein, a carbohydrate, a small organic molecule, or a peptidomimetic.

Exemplary Embodiments

The invention comprises, in part, constructs, transgenic animals, and methods, some of which are listed in the following exemplary list of embodiments. It is noted that this exemplary list of embodiments is not restrictive, but provides examples of the embodiments of the invention disclosed herein.

1. A conditional bicistronic myostatin expression construct comprising polyA-EGFP/IRES-Mst/HA-TRE//MCK-rtTA/BFP-polyA, where MCK is a promoter selected from MCK and MCK-3E.
2. A conditional bicistronic myostatin expression construct comprising polyA-BFP/rtTA-MCK//TRE-HA/Mst-IRES/EGFP-polyA.
3. A conditional bicistronic myostatin expression construct comprising TRE-HA/Mst-IRES/EGFB-polyA//MCK-rtTA/BFP-polyA.
4. A conditional bicistronic myostatin expression construct comprising MCK-rtTA/BFP-polyA//TRE-HA/Mst-IRES/EGFP-polyA.
5. A conditional monocistronic construct of any of embodiments 1-4 comprising two sequences: a: the regulatory construct MCK-rtTA/BFP-polyA, and b: the response construct TRE-HA/Mst-IRES/EGFP-polyA.
6. A conditional bicistronic myostatin expression construct comprising a construct of any of claims 1-4 lacking a HA tag at the 5' end of Mst sequence.
7. A conditional monocistronic construct of embodiment 6 where the response construct lacks a HA tag on Mst sequence.
8 A conditional bicistronic myostatin expression construct comprising a construct of any of claims 1-4 lacking an IRES/EGFP sequence downstream of Mst sequence.
9. A conditional monocistronic construct of embodiment 8 where the response construct has no IRES/EGFP sequence.
10. A conditional bicistronic myostatin expression construct comprising a construct of any of embodiments 1-4 lacking BFP fusion to the rtTA sequence.
11. A conditional monocistronic construct of embodiment 10 wherein the regulatory construct lacks a BFP fusion at the 3' end of the rtTA sequence.
12. A construct of any of embodiments 1-11 wherein said construct comprises a plasmid.
13. A method of producing a transgenic non-human animal comprising introducing the construct of any of embodiments 1-11 into a non-human animal.
14. A transgenic non-human animal for conditionally over-expressing Mst comprising cells comprising a construct of any of embodiments 1-11.
15. A transgenic non-human animal produced by: (a) crossing a first transgenic non-human animal comprising a first (regulatory) construct that expresses rtTA operably linked to promoter MCK or MCK-3E with a second non-human animal comprising a second (response) construct comprising Mst or Mst cDNA operably linked to a promoter TRE and (b) selecting from the first generation offspring a transgenic non-human animal having a genome comprising both the first regulatory construct and the second response construct.
16. A method for screening for therapeutic agents that inhibit Mst activity comprising (a) administering test agents to the transgenic animal of embodiments 14 or 15, (b) evaluating the effects of the test agent on the Mst associated phenotype of the animal.
17. A conditional bicistronic myostatin expression construct comprising a regulatory sequence and a myostatin (Mst) response sequence, wherein said bicistronic myostatin expression construct comprises a DNA transgene, said DNA transgene comprising SEQ ID NO. 13, or variants thereof with greater than 80%, 90%, 95%, 99% sequence identity operably linked to the TRE promoter, as a response sequence, and a regulatory sequence comprising a tissue specific promoter.
18. The conditional bicistronic myostatin expression construct of embodiment 1-4, 6, 8 and 10 wherein the regulatory sequence comprises reverse tetracycline transcription activator (rtTA).
19. The conditional bicistronic myostatin expression construct of embodiment 1-4, 6, 8 and 10 wherein the response sequence comprises TRE promoter.
20. The conditional bicistronic myostatin expression construct of embodiment 1-4, 6, 8 and 10 wherein the tissue specific promoter is selected from MCK, MCK-3E and Troponin I.
21. A transgenic non-human animal for conditionally over-expressing Mst comprising cells comprising a bicistronic myostatin expression construct comprising a regulatory sequence and a myostatin response sequence, wherein said bicistronic myostatin expression construct comprises a DNA transgene, said DNA transgene comprising SEQ ID NO. 13; or variants thereof with greater than 80%, 90%, 95%, 99% sequence identity operably linked to the TRE promoter, as a response sequence, and a regulatory sequence comprising a tissue specific promoter.
22. The transgenic non-human animal of embodiment 21 wherein the regulatory sequence comprises reverse tetracycline transcription activator (rtTA).
23. The transgenic non-human animal of embodiment 21 wherein the response sequence comprises TRE.
24. The transgenic non-human animal of embodiment 21 wherein the tissue specific promoter is MCK, MCK-3E or Troponin I.
25. A conditional bicistronic myostatin expression vector comprising the myostatin expression response construct of embodiment 17 cloned into a vector.
26. A method of producing a conditional bicistronic myostatin expression vector comprising cloning the myostatin expression construct of any of embodiments 1-4, 6, 8 and 10 into a vector.

27. A method of producing a transgenic non-human animal comprising introducing the conditional bicistronic myostatin expression construct of embodiment 17 into a non-human animal.

28. A conditional monocistronic myostatin expression construct comprising polyA-EGFP/IRES-Mst/HA-TRE//MCK-rtTA/BFP-polyA, where MCK is a promoter selected from MCK and MCK-3E.

29. A conditional monocistronic myostatin expression construct comprising polyA BFP/rtTA-MCK//TRE-HA/Mst-IRES/EGFP-polyA.

30. A conditional monocistronic myostatin expression construct comprising TRE-HA/Mst-IRES/EGFP-polyA//MCK-rtTA/BFP-polyA.

31. A conditional monocistronic myostatin expression construct comprising MCK-rtTA/BFP-polyA//TRE-HA/Mst-IRES/EGFP-polyA.

32. A conditional monocistronic construct of any of embodiments 28-31 comprising sequences: a: the regulatory construct MCK-rtTA/BFP-polyA, and b: the response construct TRE-HA/Mst-IRES/EGFP-polyA.

33. A conditional monocistronic myostatin expression construct comprising any of embodiments 28-31 lacking a HA tag at the 5' end of Mst sequence.

34. A construct of embodiment 33 wherein the response construct lacks an HA tag on Mst sequence.

35. A conditional monocistronic myostatin expression construct comprising a construct of any of embodiments 28-31 lacking IRES/EGFP sequence downstream of Mst sequence.

36. A conditional monocistronic construct of embodiment 35 wherein the response construct lacks a IRES/EGFP sequence.

37. A conditional monocistronic myostatin expression construct comprising a construct of any of embodiments 28-31 lacking a BFP fusion to the rtTA sequence.

38. A conditional monocistronic construct of embodiment 37 wherein the regulatory construct lacks a BFP fusion at the 3' end of the rtTA sequence.

39. A construct of any of embodiments 28-38 wherein said construct comprises a plasmid.

40. A method of producing a double-transgenic non-human animal comprising introducing the monocistronic myostatin expression constructs of embodiment 28-39 into a non-human animal.

41. A myostatin expression vector of any of the preceding embodiments, further comprising a fluorescent marker coding sequence selected from the group consisting of CFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1. luciferase, and aequorin.

42. The method of embodiment 13 or 26 wherein the vector comprises the conditional bicistronic myostatin expression vector of any of the preceding embodiments.

43. The conditional bicistronic myostatin expression vector of any of the preceding embodiments wherein the vector is pEGFP-1.

44. The conditional bicistronic myostatin expression response construct of embodiment 1 wherein the transgenic nucleotide sequence comprises SEQ ID NO. 5 or Mst cDNA operably linked to a TRE2 promoter in cells engineered to express rtTA protein in the presence of tetracycline or doxycycline.

45. A method of decreasing Mst expression in a cell comprising withdrawal or removal of tetracycline or doxycycline from a cell comprising a myostatin expression response construct of a preceding embodiment.

46. The conditional bicistronic myostatin expression response construct of embodiment 1 wherein the tissue specific promoter is skeletal muscle specific.

47. The conditional bicistronic myostatin expression response construct of a preceding embodiment wherein the promoter is an MCK-3E promoter.

48. A method of modulating the expression of Mst (SEQ ID NO. 5) in a non-human animal comprising inserting the construct of a preceding embodiment into cells of said animal and further by increasing or decreasing the concentration of doxycycline in the non-human animal.

49. A transgenic non-human animal comprising a transgenic nucleotide sequence of embodiment 1, wherein said tissue specific promoter comprises a muscle tissue specific promoter.

50. The transgenic non-human animal of embodiment 49 wherein the transgenic nucleotide sequence comprising SEQ ID NO. 5 or Mst cDNA is integrated into the genome of the animal.

51. The transgenic non-human animal of embodiment 50 wherein the transgenic nucleotide sequence comprising SEQ ID NO, 5 or Mst cDNA is operably linked MCK-3E promoter.

52. The transgenic non-human animal of embodiment 51 wherein the transgenic nucleotide sequence comprising SEQ ID NO. 5 or Mst cDNA operably linked to a reverse transcription activator.

53. The transgenic non-human animal of embodiment 52 wherein the animal exhibits an Mst associated phenotype in the presence of a transcription activator.

54. The transgenic non-human animal of embodiment 53 wherein the phenotype can be reversed or ameliorated upon decrease or removal of said transcription activator 55. The transgenic non-human animal of embodiment 53 wherein the nucleotide sequence comprises SEQ ID NO. 5 or Mst cDNA is regulated by a transactivator.

56. The transgenic non human animal of embodiment 55 wherein the nucleotide sequence comprises SEQ ID NO. X or Mst cDNA is linked to a promoter.

57. The transgenic non-human animal of embodiment 53 wherein the Mst associated phenotype is a muscular phenotype selected from aplasia and atrophy.

58. The transgenic non-human animal of embodiment 55 wherein the transactivator is reverse tetracycline transactivator (rtTA).

59 A method for screening for therapeutic agents that inhibit Mst activity comprising (a) administering test agents to the transgenic animal of any of the above embodiments, (b) evaluating the effects of the test agent on the Mst associated phenotype of the animal.

60. A transgenic non-human animal produced by: (a) crossing a first transgenic non-human animal comprising a first construct that expresses rtTA operably linked to promoter MCK-3E with a second non-human animal comprising a second construct comprising Mst or Mst cDNA operably linked to a promoter TRE2 and (b) selecting from the first generation offspring a transgenic non-human animal having a genome comprising both the first construct and the second construct.

61. A method of producing a double-transgenic non-human animal comprising introducing the conditional monocistronic Mst expression response construct of any of embodiments 28-31 into a non-human animal.

62. The transgenic non-human animal of embodiment 49 or 60 wherein the animal is a mouse.

63. A method for screening for therapeutic agents that inhibit Mst activity comprising (a) administering test agents to a transgenic mouse of any of the above embodiments, (b) evaluating the effects of the test agent on the Mst associated phenotype of the mouse.

The following examples provide further disclosure and illustration of the embodiments of the invention disclosed herein.

EXAMPLES

Example 1

The following experiments were done to investigate the role of Mst in processes that result in muscle atrophy and hypertrophy. The data support the following conclusions: 1.) an Mst overexpressing construct allows the quantification of Mst expression levels in myoblasts and myotubes in vitro, using a muscle-specific MCK promoter; 2.) the Mst overexpressing transgenic mouse is a good model for muscle atrophy, and has been characterized using: (a) PCR and Southern blot techniques to genotype the mouse; (b) RT-PCR and western blotting to quantify Mst expression levels in skeletal muscle; (c) CT scanning to quantify the muscle mass; (d) force-velocity, grip strength and activity wheel measurements to quantify muscle power; (e) SDS-PAGE to quantify the relative MHC composition of muscle; (f) immunohistochemistry to identify changes in muscle fiber distribution and structure; and (g) forced exercise test to evaluate muscle function.

Mst Overexpression Construct Expresses High Levels of Mst In Vitro

Preparation of EGFP and Myostatin Expression Constructs:
  pMCK1.3/EGFP-1 Plasmid:
  Generation of this construct has been described (Reisz-Porszasz, S. et al. Am. J. Physiol. Endocrinol. Metab. 285(4): E876-888, 2003) and may be accomplished as follows: A muscle specific creatine kinase (MCK) enhancer/promoter containing the region from −1354 to +1 bp from the transcription initiation site, cloned into the pEGFP-1 vector (Clontech) was used (FIG. 1A/A). The MCK fragment (1.3 kb) was released from pMCKG plasmid by restriction digest with SpeI/EcoRI. The vector was digested with HindIII. The two DNA fragments were blunt end ligated. A 2.2 kb construct containing the MCK, the EGFP and the SV40 polyA sequence was released by XhoI/Afl II digestion for animal pronuclei injection (FIG. 1A). Larochelle et al., "Efficient muscle-specific transgene expression after adenovirus-mediated gene transfer in mice using a 1.35 kb muscle creatine kinase promoter/enhancer" *Gene Ther* 4:465-472 (1997).
  pMCK-3E/EGFP-1 Plasmid:
  Another construct for generating the MCK promoter with the three point mutations was also used. The MCK promoter (from −1256 to −1 nucleotide) harbors three point mutations in its three conserved E-box site. The locations of the point mutations are: nt−1178, −1153 and −249 (Donoviel et al., "Analysis of muscle creatine kinase gene regulatory elements in skeletal and cardiac muscles of transgenic mice" Mol Cell Biol. 16:1649-1658 (1996)). These mutations prevent gene expression in the heart muscle and have been shown to restrict the expression of the protein to the skeletal muscle. A 2.2 kb fragment containing the mutated version of the MCK promoter and EGFP sequences was released with BglII/AflII restriction digest and used for pronuclei injection.
  pMCK-3E/mMst Plasmid:
  The mMst sequence was PCR amplified in order to introduce 5' AgeI site and 3' NotI site. Primers for mMst cloning: forward 5'-atg atg caa aaa ctg caa atg tat-3' (SEQ ID NO: 16); reverse 5'-tca tga gea ccc aca-3' (SEQ ID NO: 17). The PCR product and the pMCK-3E/EGFP-1 plasmid were restriction digested with AgeI/NotI enzymes, and ligated. A 2.6 kb fragment was released with Bgl II/Afl II digestion and used for pronuclei injection.
  pMCK1.3/mMst Plasmid:
  Mst cDNA from the mouse skeletal muscle was cloned and sequenced. This 1.1 kb sequence was subcloned into the pEGFP-1 vector by substituting the EGFP (725 bp) sequence to mMst sequence (FIG. 1A/B). The MCK promoter was cloned into this construct in a similar way as described above. The MCK promoter-Mst cDNA-polyA construct (2.6 kb) was released with KpnI/Afl II digestion and used for mouse pronuclei injection.

Figure 2A:
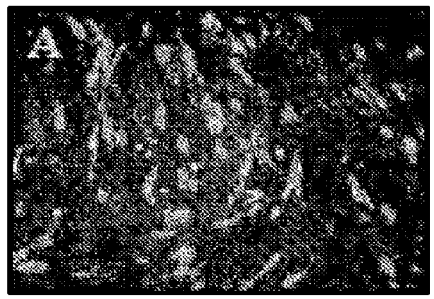
Figure 2B:
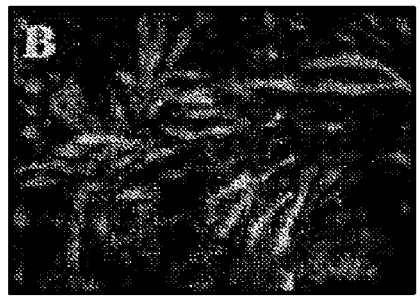

In Vitro Expression of Construct:
  The C3H murine myoblast cell line C2C12 was propagated in DME medium with 10% fetal bovine serum. For differentiation into myotubes, myoblasts were allowed to grow to approx. 90-100% confluence. After 2 days the medium was changed to DMEM with 5% horse serum. Myotubes began to form after 3 or 4 days. Cells were transiently transfected with 2 μg of the using Lipofectamine according to the manufacturer's protocol. Green fluorescence protein synthesis was monitored every day under fluorescence microscopy (FIGS. 2A and 2B).

Transfection experiment was repeated by using the bicistronic conditional Mst overexpressing transgene (FIG. 1B bottom) and Mst/EGFP expression was able to be switched on and off by adding (2.5 μg/ml doxycyclin as the optimized concentration) or withdrawing doxycycline from the media. When the gene was turned on, EGFP expression was observed in 5 days, while turning off the gene resulted in zero EGFP expression during one week. This experiment was repeated several times, showing that the gene induction system is unlikely to be leaking. Stable transfectants are maintained in G418 selection media. After 48 hours of infection we got high expression level of GFP in both myoblasts and myotubes. The mutated MCK promoter (MCK-3E) provided higher expression level in vitro, than the wild type (pMCK-3E/EGFP-1: 57%; versus pMCK1.3/EGFP-1: 25%).

Mst Overexpressing Transgenic Mice as a Model for Muscle Atrophy

Generation and identification of transgenic animals: Purified MCK1.3/EGFP and MCK1.3/mMst transgene sequences were sent to UC Irvine Transgenic Facility, and 300-300 pronuclei were injected with each DNA construct and transplanted into CB6F1 mice. Transgenic animals were identified by PCR reaction of ear (or tail) DNA. The size of the PCR product was 290 bp using the 5' primer located at −209 bp upstream, and the 3' primer located at +60 bp downstream of the transcriptional start site as shown in FIG. 1A (asterisks show primer locations). Primers for the ear DNA genotyping: forward 5'-aac cag tga gca agt cag cc-3' (SEQ ID NO: 18); reverse 5'-gcc agc agc aat cag cat-3' (SEQ ID NO: 19). These primers overlap the joint sequences of the MCK promoter 3' end and the EGFP or Mst gene 5' end. Female and male animals carrying the transgene and their age-matched controls were sacrificed at 7 weeks of age, 10 animals in each group. Genotyping of mice was performed by PCR (FIG. 3A) and Southern blot analysis (FIG. 3B) of 30 μg EcoRI digested genomic DNA prepared from liver (representative samples are shown).

Figure 2C:
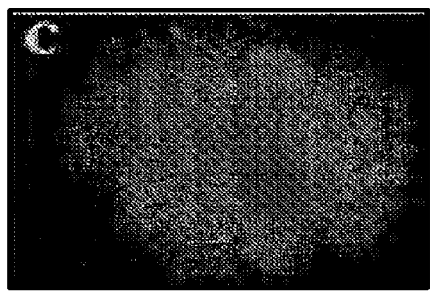
Figure 2D:
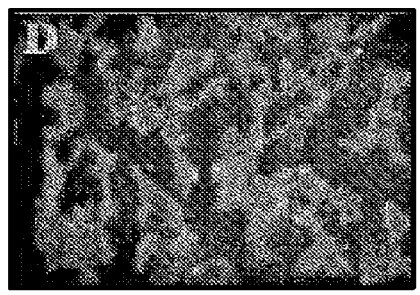
Figure 4A:
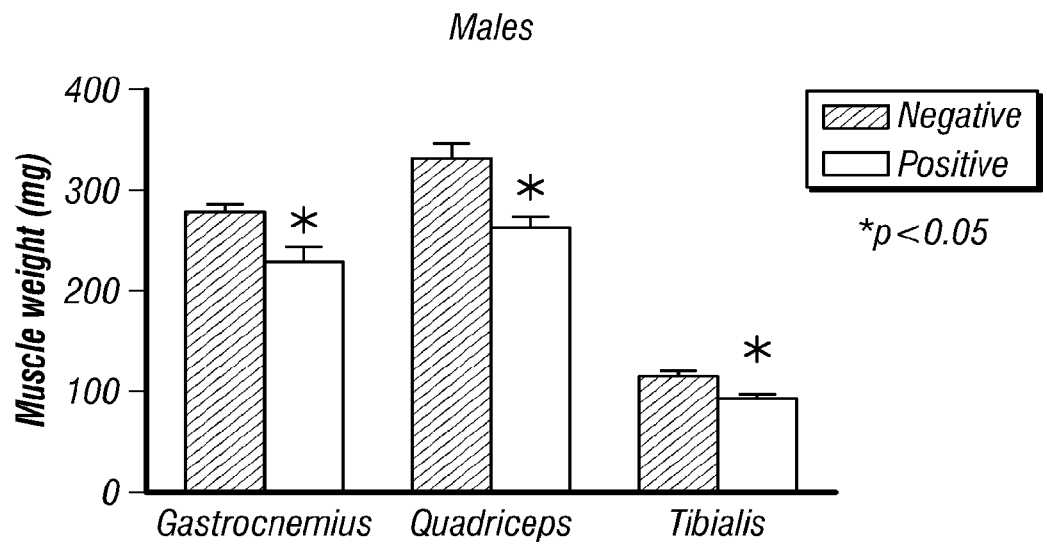
Figure 4B:
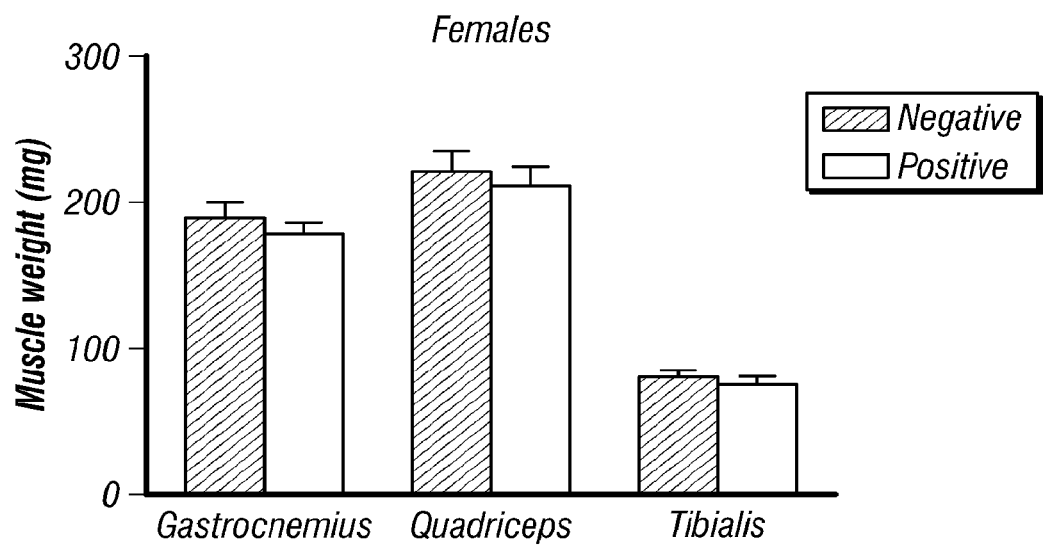

Skeletal muscles (tibialis, gastrocnemius, quadriceps, diaphragm, biceps, forearm muscle) were collected, and selected tissues were used for further investigation. Transgenic animals carrying the EGFP transgene showed green fluorescence only in muscles (FIGS. 2C and 2D). Results of different muscle weights collected from myostatin overexpressing and wild type animals are shown in FIG. 4. Although there was no significant difference between the body weights of transgenic and control males (22.3±2.1 and 24.8±2 g, respectively), there was a 17% decrease in gastrocnemius weight, a 21% decrease in quadriceps weight, and an 18% decrease in tibialis muscle weight (FIG. 4A). Significant differences in body weights (19.1±1.1 and 19.3±2.1 g), or in muscle weights between transgenic and control females were not found (FIG. 4B).

Determination of EGFP and Myostatin Expression

Transgenic animals show 2.2 fold increase in Mst expression in skeletal muscle: Mst expression was analyzed by RT-PCR, northern and western blotting. Total RNA was extracted from gastrocnemius, tibialis and quadriceps of transgenic and control mice. Aliquots were submitted to RT PCR reaction. Two primer sets for Mst were chosen. A first primer set for endogenous Mst included: forward 5'-aga caa aac acg agg tact c-3' (SEQ ID NO: 20) and reverse 5'-tgg att cag gct gtt tga gc-3' (SEQ ID NO: 21). A second primer set for Mst transgene included: forward 5'-gtc tcc cat taa tat gct at-3' (SEQ ID NO: 22) and reverse 5'-atc ata ccc tcc taa ctc ag-3' (SEQ ID NO: 23).

Figure 6B:
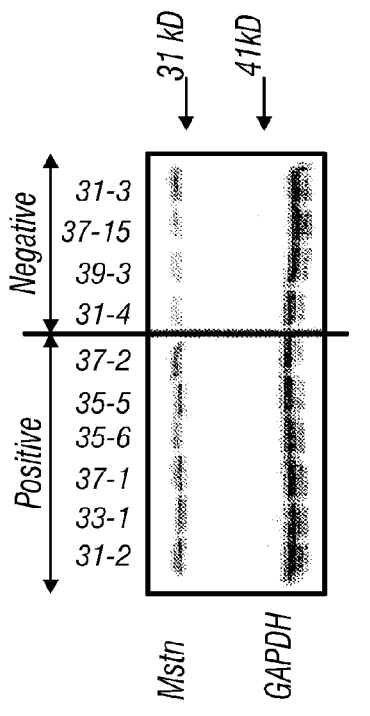
Figure 6C:
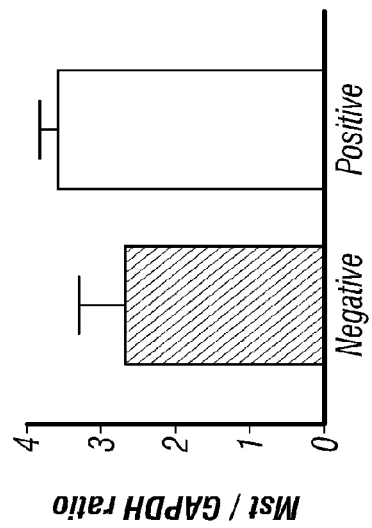
Figure 6A:
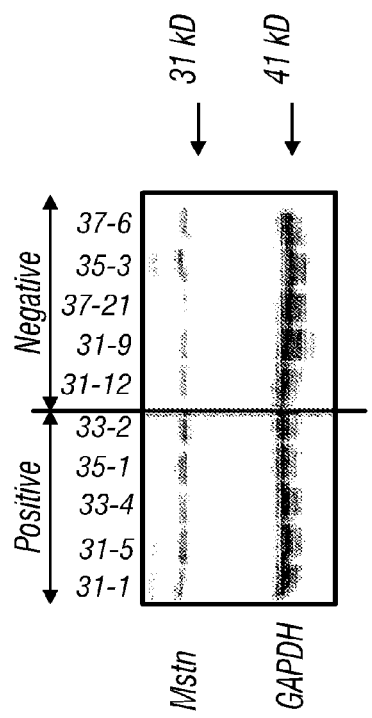

The first primer set was used to measure the total Mst present, but to avoid possible cross-reaction with GDF-11 mRNA, the second was used to differentiate the endogenous and exogenous Mst. The housekeeping gene GAPDH was employed, and was evenly expressed in all samples. There was a significant increase (37%) in Mst mRNA expression in transgenic animals (FIG. 5). Protein was extracted from the same muscles mentioned above. Denatured proteins were separated on SDS gel, transferred to NC membrane, and immunodetected with costume made Mst monoclonal antibody. This antibody recognizes the full length, unprocessed 52 kDa Mst protein and the 28 kDa biologically active Mst protein. Quantification of the Western blot results indicated a significantly higher (2.2 fold) Mst protein levels in transgenic animals' skeletal muscle. The relative expression levels within each animal followed this order: gastrocnemius>quadriceps>tibialis anterior. No detectable Mst protein was found in Mst KO animals. Mst proteins were also immunodetected with myostatin polyclonal antibody that recognized the 38 kDa form of Mst (FIG. 6). Significantly lower (41%) Mst protein was detectable in male skeletal muscle, than in female's (25%). The figure shows the western blot from gastrocnemius, but similar results were found in other muscles.

Quantification of muscle atrophy: Groups of animals of different ages (2 months, 6 months, 12 months and 18 months) were anaesthetized and scanned in CT scanner (MicroCAT II). The Xray source, Xray detector and video camera were mounted to a rotating stage that moved around the animal 360 degrees. The exposure time was about 29 minutes per animal. Amira 3.1 version software was used to obtain a 3D image from the raw data. Skeletal tissue and fat mass were quantified on the images. A significant reduction (24%) in hind limb muscle mass and an increase in abdominal fat (1.7 fold) in transgenic animals at age 6 months or older compared to control was identified. Representative 3D images and cross sections are shown on FIG. 10. Detailed quantification of the data is in progress.

Comparison of Muscle Strength Measurements:

A pulley apparatus was constructed in which one end of the pulley system consisted of a weight container, while the other end attached to the base of the animal tail. Mice were dangled over a horizontal pull bar assembly, and were allowed to grasp the bar. Once the grasp was secure, a steady stream of water flowed into the weight container. The volume of water required for the mouse to release the pull bar was measured. The difference in grip strength between females and males in two different mouse strains, C57B16 and BalbC, was measured (FIG. 8). Gender differences within the strains (B16: p=0.02193; BalbC: p=7.9E-07), differences between males (first two columns) of the two strains (p=0.00377), but not between female (last two columns, p=0.393) were observed.

The daily spontaneous activity was also analyzed on a rodent running wheel for four weeks and surprisingly found that Mst Tg mice had significantly greater daily activity compared KO and WT male animals as shown on FIG. 9.

Modified Mst expression does not change single fiber tension: Contractile measurements on 7 week-old male WT, transgenic and KO animals, 10 mice in each group were performed. Under anesthesia, the tendon of the plantaris muscle was attached to a computer controlled Cambridge 305B ergometer. The optimal muscle length (i.e., $L_0$) was determined from measurements of isometric tension made at various muscle lengths. All subsequent measurements were made with the muscle starting at an initial length of $L_0$. The muscle was then tested at a minimum of 15 different afterload conditions (3 to 100% of $P_0$) so that the force-velocity relationship could be determined. The afterload of the ergometer was controlled using the DAC-08 digital-to-analog board of the computer. Specific-tension was determined by normalizing maximal isometric tension to the cross-sectional area of the muscle. Force-velocity data was fitted using a linear version of the Hill equation. Using this equation, $V_{max}$ was estimated by determining the y-intercept of the force-velocity relationship. All of the above contractile measurements were made with a rest interval of 1 min. between each contraction. FIG. 11 shows the results of the force-velocity measurements. Plantaris muscle of the KO mice produced 40% more force than the WT and transgenic mice. Specific-tension provides insight regarding the physiology of the system, and, in this case, demonstrated that the muscles in both the transgenic and KO groups were capable of producing a normal amount of specific tension. No differences were found in isometric tension normalized to cross-sectional area and isometric twitches.

Fast type whole muscle MHC protein isoform composition in transgenic animals is not altered: Proteins were isolated from plantaris muscle from the same animals used for the contractile measurements. Approximately 0.1 μg of myofibrillar protein from each muscle sample were electrophoresed using a constant voltage of 275 V for 5 hrs. The four MHC isoforms, type I, type IIA, IIX and IIB proteins were stained using a silver staining kit and scanned for quantification using a laser densitometer. We found significant differences in MHC isoform composition in KO animals where the MHC type IIB protein levels were significantly higher by 17.5±1.7% compared to WT, and the type IIA protein levels were decreased by 10.5±1.3% in plantaris muscles. Transgenic animal's plantaris muscle MHC isoform composition was not significantly different from WT.

Histomorphometry

The cross-sectional area of the muscle fibers was determined by point counting. A minimum of 30 type II fibers was analyzed in each muscle specimen. The fields were randomly selected to measure the fiber area, and all of the fibers encompassed in those fields were evaluated. Significant differences were observed between myostatin overexpressing and control animals in gastrocnemius, as well as in quadriceps (FIG. 7A). The number of myonuclei were counted in 20 randomly selected muscle fibers of each type in gastrocnemius and quadriceps samples. Myonuclei numbers are summarized in FIG. 7B. Statistically significant differences were observed between transgenic and control in gastrocnemius, and in quadriceps muscles as well. Gender differences were neither observed in cross-sectional area nor in myonuclei number.

Mst transgenic animals exhibit significant changes in fiber morphometry: A comprehensive analysis on fiber cross-sectional area (CSA), fiber number, and fiber type distribution in plantaris, gastrocnemius, soleus, quadriceps, tibialis and extensor digitorum longus (EDL) muscles isolated from WT, KO and transgenic animals (n=5/group) has been conducted. Muscle samples were frozen and sectioned in a cryostat. Tissue sections were probed with a monoclonal antibody specific to type JIB MHC isoform, 200-300 fibers per sample were analyzed and quantified applying image analysis (Table I and FIG. 12).

but they lost more fat compared to WT and KO. WT and KO mice fat mass did not change significantly during exercise.

Mechanical Overloading of the Plantaris Muscle:

Mechanical Overloading has been used on rats. Mechanical overloading produces substantial hypertrophy of the plantaris muscle (muscle mass increased by 63% compared to control), and substantial changes of MHC protein isoform distribution in female rats. The overloaded muscle showed a significant reduction in fast type IIB MHC isoform, both at the mRNA and protein levels. This technique is adopted for corresponding experiments with mice, Mst Changes Molecular Pathways in Muscle In order to identify the pathways involved in the Mst overexpression induced muscle atrophy, muscle samples were collected from five animals in each group (gastrocnemuis

TABLE I

MHC composition and fiber cross sectional area (CSA) analysis in Mst KO, Tg, and WT animals.

| | Plantaris | | | red gastrocnemius | | | Soleus | | | EDL | | |
|---|---|---|---|---|---|---|---|---|---|---|---|---|
| | CSA ($\mu m^2$) | | IIB/I | CSA ($\mu m^2$) | | IIB/I | CSA ($\mu m^2$) | | IIB/I | CSA ($\mu m^2$) | | IIB/I |
| | type IIB | Type I | Ratio | type IIB | type I | ratio | type IIB | type I | ratio | type IIB | type I | ratio |
| WT | 4432 ± 115 | 2271 ± 245 | 3.6 | 3772 ± 265 | 2234 ± 154 | 0.5 | 2118 ± 176 | 1970 ± 256 | 0.2 | 3577 ± 189 | 1848 ± 98 | 4.25 |
| KO | 6785 ± 221* | 3874 ± 211* | 2.0 | 5998 ± 326* | 3111 ± 319 | 0.9* | 2510 ± 152 | 2045 ± 344 | 1.1* | 5392 ± 137* | 1991 ± 119 | 6.4* |
| Tg | 3974 ± 153* | 2075 ± 237 | 2.0 | 3145 ± 105* | 2015 ± 167 | 0.16* | 1989 ± 187 | 1769 ± 233 | 0.2 | 2434 ± 121* | 1122 ± 197 | 1.8* |

*significant differences compared to WT when $P < 0.05$

The data show significant changes in CSA of Tg animal's fast and mixed type muscles, but not in slow type muscles. KO animals had more fast type fibers while Tg animals had more slow type fibers, compared to WT. Significant changes in the number of fibers were not detected.

Mst Tg animals exhibit significantly higher level of exercise tolerance: The exercise tolerance of these three groups of animals using treadmill to exhaustion were completed. Following a short training period, six months-old animals were forced to run on a flat treadmill at 8 m/min speed for 5 min. Then both the belt speed and the inclination angle were increased to 12 m/min, 5% increment for 5 min. The next step was at 16 m/min, 10% increment for 5 min, etc. Animals were forced to run with 1.5 mA electric shock, and the test ended when the animals did not avoid the electric shock. The test was performed every other day for six weeks. The work rate weekly (3 days, four animals in each groups) (WR=g*BW*v*sin(a), where WR=work rate (Watts), g=gravitation acceleration, BW=body weight (kg), v=speed (m/min), a=opening angle of the treadmill) was calculated. The results are shown on FIG. 13. Exercise tolerance for KO animals was significantly lower than for Tg animals each week. This difference started to increase on week 3, mainly because Tg animals begun to show increased exercise tolerance. The lower exercise tolerance in KO mice could be related to increased amount of fast type fibers, and the shift from oxidative to glycolytic metabolic activity in adult skeletal muscle.

Male mice overexpressing Mst in skeletal muscle showed increased levels of abdominal fat mass if older than 4 months. At the end of the treadmill exercise experiment described above, abdominal fat pads were collected from control (not running on treadmill) and experimental animals. As shown in FIG. 14, Mst Tg animals had significantly higher fat before exercise than WT. Following six weeks of treadmill, Tg animals not only ran longer and had higher exercise tolerance, muscles were used because it had mixed fiber types and were large enough to isolate RNA in sufficient quantities). The isolated RNAs were pooled and subjected to cDNA synthesis, then applied on superarray Pathway Finder analysis. FIG. 15 shows the changes in gene expression levels in TG and KO animals relative to WT. Mst Tg animals TGF-β, p53, NF-kappaB, LDL and PI3K/Akt pathways were upregulated significantly, while the Hedgehog, retinoic acid, insulin and CREB pathways were downregulated. In Mst KO animals, the only upregulated pathway was TGF-β, while insulin and androgen pathways were significantly downregulated. These changes indicate that Mst is involved in cell proliferation, differentiation, cell cycle regulation (as already known), and also in cell metabolism and cell fate decision. Further analysis is needed to elucidate the exact role of Mst in these processes, and this is one of the goal of this project.

Generation of the CMOT Mouse

The data presented above shows that the Mst overexpressing mouse is a good model for muscle wasting. However, this model does not allow testing the mechanism of Mst action in the regulation of muscle in the adult. The Tg animals we have generated have a "developmental disorder", since Mst is overexpressed before birth. A more appropriate model to mimic atrophic pathology would be a conditional overexpressing transgenic (CMOT) animal, in which Mst could be turned on and off in a reversible way at any time during adulthood.

Example 2

Generation of the DNA Construct for Conditional Mst Overexpression pMCK1.3/Tet-ON/Blue Plasmid:

To produce a conditional Mst overexpressing transgenic animal, we have used two constructs, one is the regulatory plasmid (pTet-ON), and the other is the response plasmid (pTRE2). Both are available from Clontech, Inc. In the regulatory plasmid, the reverse transactivator protein (rtTA), which is a fusion of Tc repressor protein and VP16 protein of herpes simplex virus activation domain, expresses under the control of CMV promoter. First, this promoter was changed to the muscle specific promoter (MCK, SEQ ID NO: 8) to obtain rtTA expression only in skeletal muscle. A fusion protein of rtTA with blue-fluorescence protein was created to detect rtTA expression level both in vitro and in vivo (FIG. 16-A).

pTRE2/HA-mMst/IRES-EGFP Plasmid:

The response plasmid contains a multiple cloning site immediately downstream of the Tet responsive $P_{hCMV-1}$ promoter. This site was used for cloning the Mst sequence (SEQ ID NO: 5), which was previously fused with hemagglutinin (HA) epitope on its 5' end (SEQ ID NO: 6). It is well-known that Mst goes through a posttranslational modification.[3] During this process, two C-terminal domains of the full length Mst protein form a dimer by covalent bond called the processed/mature Mst. This dimer was able to be detected with an antibody against the C-terminal domain. The N-terminal domain stays attached to the dimer, and has an inhibitory function on it. This complex is called latency associated protein. An antibody against the HA sequence allowed detection of and following of the path of the N-terminal domain, both within the muscle tissues and in the serum. An IRES (internal ribosome entry site) sequence with an EGFP sequence (SEQ ID NO: 4) was inserted to be able to express Mst and EGFP with the same promoter on a single transcript (FIG. 16-B).

Both constructs were tested in vitro on two different cell lines, the C2C12 mouse myoblast and the human skeletal muscle myoblast (HSMM) before use in producing transgenic animals. The regulatory and the response plasmids were co-transfected into the cells by electroporation. The transfected cell lines were used to determine the optimal doxycyclin concentration and the optimal time course for maximum EGFP expression. For in vivo application, this monocistronic model requires generation of two different transgenic animals (the regulatory and the response animals). Their offspring are genotyped, selected for the presence of the two transgenes, respectively, and cross-bred. The second generation is screened for double transgenic animals. Each step requires duplication, and more importantly, the number of the resulted double-transgenic animals is very low. The results of producing these animals are described below.

Bicistronic Model:

To increase the number of double-transgenic animals and decrease the time to generate offsprings, a novel, bicistronic gene expression system was developed where the regulatory and response sequences are cloned in the opposite orientation. The basic idea is similar to the one described above, but instead of using two constructs, only one fragment with the regulatory and the response sequences was used. A muscle creatine kinase (MCK) enhancer/promoter (SEQ ID NO: 8) containing the region from −1354 to +1 bp from the transcription initiation site was cloned into the pTet-ON vector carrying the rtTA sequence (Clontech). The MCK fragment (1.3 kb) was released from pMCKG plasmid by restriction digest with SpeI/EcoRI. The vector was digested with HindIII. Both fragments were filled up by Klenow polymerase reaction, and blunt end ligation was performed. Blue fluorescent protein sequence (SEQ ID NO: 10) was fused to the 3' end of the rtTA sequence in order to visualize the expression.

Next, the myostatin cDNA (SEQ ID NO: 5) from the mouse skeletal muscle was cloned and sequenced. Primers for mMst cloning were: forward 5'-atg atg caa aaa ctg caa atg tat-3' (SEQ ID NO: 16); reverse 5'-tca tga gca ccc aca-3' (SEQ ID NO: 17). This 1.1 kb sequence was subcloned into the pTRE/HA vector and then the TRA/HA-Mst sequence was subsequently cloned into the pIRES/EGFP vector.

Finally, the two sequences were cloned together in reverse orientation into a bicistronic gene expression system resulting the final construct named: pMCK/rtTA-BFP/SV40polyA//TRE/HA-Mst/IRES-EGFP/SV40polyA (SEQ ID NO: 13) (FIG. 1B).

The TRE promoter is silent in the absence of binding Tet-activated rtTA protein, and becomes activated upon binding the Doxycycline (Dox, also known as doxycyclin), and express HA-Mst and EGFP at the same time.

This construct (6.4 kb) has been developed, the in vitro tests are completed, and the construct was injected into pronuclei. Stable transfectant myoblast (C2C12) cells were isolated and experiments regarding to optimal Dox concentration and time course were repeated.

Example 3

CMOT Animals: For the generation of transgenic mice, the 6.5 kb long MCK/rtTA-BFP/SV40polyA//TRE/HA-Mst/IRES-EGFP/SV40polyA fragment was released by AflII restriction endonuclease digestion and this fragment was used for pronuclei injection. Pronuclei injection was successfully completed. Three hundred and five pronuclei were injected with the bicistronic construct, and 24 pups were born. Five were identified positive for the transgene.

Transgenic (positive genotype) animals were used for breeding, and following an eighth weeks of Dox treatment in their chow, Mst and EGFP expression were monitored via collection of biopsy samples. Mst protein expression levels were detected by Western blot using monoclonal anti-Mst antibody that recognized the two forms of Mst protein: the 52 kDa and the 28 kDa. The representative result is shown on FIG. 17. Mst conditional expression was successfully repeated on these animals three times already by Dox treatment and Dox withdrawal.

Other non-human transgenic animals, such as transgenic rats, hamsters, rabbits, gerbils, sheep, goat, horse, cow, dog, cat, other mammal, chicken, turkey, goose, pheasant, other bird, salmon, trout, halibut, other fish, oyster, shrimp, or other animal, whether a domestic animal, laboratory animal, a game animal, or other animal, may be prepared by the same or analogous methods.

It will be appreciated by those skilled in the art that changes could be made to the embodiments described above without departing from the broad inventive concept thereof. It is understood, therefore that this invention is not limited to the particular embodiments disclosed, but it is intended to cover modifications that are within the spirit and scope of the invention, as defined by the appended claims.

What is claimed is:

1. A method for screening for agents that inhibit Mst activity comprising:

(a) administering a test agent to a transgenic non-human mammal that has been administered a control factor selected from tetracycline and doxycycline and thereby conditionally overexpresses myostatin (Mst), said transgenic non-human mammal having a genome that comprises a conditional bicistronic myostatin expression nucleic acid construct selected from the group of nucleic acid constructs consisting of:

i) a) polyA-green fluorescence protein (EGFP)/internal ribosome entry site (IRES)-Mst/hemagglutinin (HA)-tetracycline response element (TRE)//MCK-rtTA/blue fluorescence protein (BFP)-polyA, b) polyA-BFP/rtTA-MCK//TRE-HA/Mst-IRES/EGFP-polyA, c) TRE-HA/Mst-IRES/EGFP-polyA//MCK-rtTA/BFP-polyA, d) MCK-rtTA/BFP-polyA//TRE-HA/Mst-IRES/EGFP-polyA, e) TRE-HA/Mst-IRES/EGFP-polyA//polyA-BFP/rtTA-MCK, or f) MCK-rtTA/BFP-polyA//polyA-EGFP/IRES-Mst/HA-TRE;

ii) any one of the constructs of a) lacking a HA tag;

iii) any one of the constructs of a) lacking an IRES/EGFP or EGFP/IRES; and iv) any one of the constructs of a) lacking a BFP fusion to the rtTA sequence;

wherein MCK is a promoter selected from muscle specific creatine kinase, MCK-3E, and
troponin I;
and wherein, in the absence of said test agent, said administration of said control factor results in Mst overexpression and decreased muscle mass as compared to control wild-type mammals;
(b) measuring skeletal muscle mass in said transgenic non-human mammal administered said test agent; and
(c) identifying the test agent as an agent that inhibits Mst activity based on the effects of the test agent on decreased skeletal muscle mass of the transgenic non-human mammal overexpressing Mst.

2. The method of claim 1, wherein said conditional bicistronic myostatin expression nucleic acid construct is selected from the group of nucleic acid constructs consisting of:
i) polyA-EGFP)/internal ribosome entry site (IRES)-Mst/hemagglutinin (HA)-tetracycline response element (TRE)//MCK-rtTA/blue fluorescence protein (BFP),
ii) polyA-BFP/rtTA-MCK//TRE-HA/Mst-IRES/EGFP-polyA,
iii) TRE-HA/Mst-IRES/EGFP-polyA//MCK-rtTA/BFP-polyA,
iv) MCK-rtTA/BFP-polyA//TRE-HA/Mst-IRES/EGFP-polyA,
v) TRE-HA/Mst-IRES/EGFP-polyA//polyA-BFP/rtTA-MCK, and
vi) MCK-rtTA/BFP-polyA//polyA-EGFP/IRES-Mst/HA-TRE,
where MCK is a promoter selected from muscle specific creatine kinase, MCK-3E, and troponin I.

3. A method for screening for agents that inhibit Mst activity comprising:
(a) administering a test agent to a transgenic non-human mammal that has been administered a control factor selected from tetracycline and doxycycline and thereby conditionally overexpresses Mst, said transgenic non-human mammal comprising cells comprising a bicistronic myostatin expression nucleic acid construct comprising a regulatory sequence and a myostatin response sequence, wherein said bicistronic myostatin expression nucleic acid construct comprises a DNA transgene, said DNA transgene comprising SEQ ID NO.: 13, or variants thereof with greater than 80%, 90%, 95%, or 99% sequence identity to SEQ ID NO: 13, operably linked to the tetracycline response element (TRE) promoter, as a response sequence, and to a regulatory sequence comprising a tissue specific promoter selected from muscle specific creatine kinase, MCK-3E, and troponin I, said tissue specific promoter being a conditional promoter influenced by a control factor selected from tetracycline and doxycycline,
wherein, in the absence of said test agent, said administration of said control factor results in Mst overexpression and decreased muscle mass as compared to control wild-type mammals;
(b) measuring skeletal muscle mass in said transgenic non-human mammal administered said test agent; and
(c) identifying the test agent as an agent that inhibits Mst activity based on the effects of the test agent on the decreased skeletal muscle mass of the transgenic non-human mammal overexpressing Mst.

4. The method of claim 3, wherein the regulatory sequence comprises reverse tetracycline transcription activator (rtTA).

5. The method of claim 3 wherein the response sequence comprises TRE.

6. The method of claim 3 wherein the tissue specific promoter is muscle specific creatine kinase, MCK-3E or Troponin I.

* * * * *